(12) United States Patent
Li et al.

(10) Patent No.: US 9,711,741 B2
(45) Date of Patent: Jul. 18, 2017

(54) METAL COMPOUNDS AND METHODS AND USES THEREOF

(71) Applicants: Jian Li, Tempe, AZ (US); Eric Turner, Chandler, AZ (US); Liang Huang, Mesa, AZ (US)

(72) Inventors: Jian Li, Tempe, AZ (US); Eric Turner, Chandler, AZ (US); Liang Huang, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/421,634

(22) PCT Filed: Aug. 23, 2013

(86) PCT No.: PCT/US2013/056426
§ 371 (c)(1),
(2) Date: Feb. 13, 2015

(87) PCT Pub. No.: WO2014/031977
PCT Pub. Date: Feb. 27, 2014

(65) Prior Publication Data
US 2015/0207086 A1    Jul. 23, 2015

Related U.S. Application Data

(60) Provisional application No. 61/692,937, filed on Aug. 24, 2012.

(51) Int. Cl.
| | |
|---|---|
| C07F 15/00 | (2006.01) |
| H01L 51/50 | (2006.01) |
| H01L 51/00 | (2006.01) |
| C09K 11/06 | (2006.01) |
| H05B 33/14 | (2006.01) |

(52) U.S. Cl.
CPC ........ *H01L 51/0087* (2013.01); *C07F 15/006* (2013.01); *C07F 15/0086* (2013.01); *C09K 11/06* (2013.01); *H01L 51/0083* (2013.01); *H01L 51/0084* (2013.01); *H05B 33/14* (2013.01); *C09K 2211/1007* (2013.01); *C09K 2211/1029* (2013.01); *C09K 2211/1044* (2013.01); *C09K 2211/1088* (2013.01); *C09K 2211/1092* (2013.01); *C09K 2211/1096* (2013.01); *C09K 2211/185* (2013.01); *C09K 2211/188* (2013.01); *H01L 51/5016* (2013.01)

(58) Field of Classification Search
USPC ............................................. 546/2; 313/504
See application file for complete search history.

(56) References Cited

U.S. PATENT DOCUMENTS

| | | |
|---|---|---|
| 4,769,292 A | 9/1988 | Tang et al. |
| 5,451,674 A | 9/1995 | Silver et al. |
| 5,641,878 A | 6/1997 | Dandliker et al. |
| 5,707,745 A | 1/1998 | Forrest et al. |
| 5,844,363 A | 12/1998 | Gu et al. |
| 6,303,238 B1 | 10/2001 | Thompson et al. |
| 6,780,528 B2 | 8/2004 | Tsuboyama et al. |
| 7,002,013 B1 | 2/2006 | Chi et al. |
| 7,037,599 B2 | 5/2006 | Culligan et al. |
| 7,064,228 B1 | 6/2006 | Yu et al. |
| 7,268,485 B2 | 9/2007 | Tyan et al. |
| 7,279,704 B2 | 10/2007 | Walters et al. |
| 7,332,232 B2 | 2/2008 | Ma et al. |
| 7,442,797 B2 | 10/2008 | Itoh et al. |
| 7,501,190 B2 | 3/2009 | Ise |
| 7,635,792 B1 | 12/2009 | Cella et al. |
| 7,655,322 B2 | 2/2010 | Forrest et al. |
| 7,947,383 B2 | 5/2011 | Ise et al. |
| 8,133,597 B2 | 3/2012 | Yasukawa et al. |
| 8,389,725 B2 | 3/2013 | Li et al. |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Jian et al. |
| 9,059,412 B2 | 6/2015 | Zeng et al. |
| 9,221,857 B2 | 12/2015 | Li et al. |
| 9,224,963 B2 | 12/2015 | Li et al. |
| 9,238,668 B2 | 1/2016 | Li et al. |
| 9,312,502 B2 | 4/2016 | Li et al. |
| 9,312,505 B2 | 4/2016 | Brooks et al. |
| 9,318,725 B2 | 4/2016 | Li |
| 9,324,957 B2 | 4/2016 | Li et al. |
| 9,382,273 B2 | 7/2016 | Li et al. |
| 9,385,329 B2 | 7/2016 | Li et al. |

(Continued)

FOREIGN PATENT DOCUMENTS

| | | |
|---|---|---|
| CN | 1680366 A | 10/2005 |
| CN | 1777663 A | 5/2006 |

(Continued)

OTHER PUBLICATIONS

Ayan Maity et al., "Room-temperature synthesis of cyclometalated iridium(III) complexes; kinetic isomers and reactive functionalities", Chem. Sci., vol. 4, 2013, pp. 1175-1181.

(Continued)

*Primary Examiner* — Charanjit Aulakh
(74) *Attorney, Agent, or Firm* — Ballard Spahr LLP

(57) ABSTRACT

Disclosed herein are metal compounds, compositions, and devices related thereto, such as full color displays or OLEDs.

14 Claims, 15 Drawing Sheets

(56) References Cited

U.S. PATENT DOCUMENTS

| | | |
|---|---|---|
| 9,425,415 B2 | 8/2016 | Li et al. |
| 9,550,801 B2 | 1/2017 | Li et al. |
| 2001/0019782 A1 | 9/2001 | Igarashi et al. |
| 2002/0068190 A1 | 6/2002 | Tsuboyama et al. |
| 2003/0062519 A1 | 4/2003 | Yamazaki et al. |
| 2004/0230061 A1 | 11/2004 | Seo et al. |
| 2005/0037232 A1 | 2/2005 | Tyan et al. |
| 2005/0170207 A1 | 8/2005 | Ma et al. |
| 2005/0260446 A1 | 11/2005 | Mackenzie et al. |
| 2006/0024522 A1 | 2/2006 | Thompson |
| 2006/0066228 A1 | 3/2006 | Antoniadis et al. |
| 2006/0073359 A1 | 4/2006 | Ise et al. |
| 2006/0094875 A1 | 5/2006 | Itoh et al. |
| 2006/0127696 A1 | 6/2006 | Stossel et al. |
| 2006/0182992 A1 | 8/2006 | Nii et al. |
| 2006/0202197 A1 | 9/2006 | Nakayama et al. |
| 2006/0210831 A1 | 9/2006 | Sano et al. |
| 2006/0255721 A1 | 11/2006 | Igarashi et al. |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0111476 A1 | 5/2008 | Choi et al. |
| 2008/0241518 A1 | 10/2008 | Satou et al. |
| 2008/0241589 A1 | 10/2008 | Fukunaga et al. |
| 2008/0315187 A1 | 12/2008 | Bazan et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0126796 A1 | 5/2009 | Yang et al. |
| 2009/0128008 A1 | 5/2009 | Ise et al. |
| 2009/0205713 A1 | 8/2009 | Mitra et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0043876 A1 | 2/2010 | Tuttle et al. |
| 2010/0093119 A1 | 4/2010 | Shimizu |
| 2010/0141127 A1 | 6/2010 | Xia et al. |
| 2010/0147386 A1 | 6/2010 | Benson-Smith et al. |
| 2010/0171111 A1 | 7/2010 | Takada et al. |
| 2010/0171418 A1 | 7/2010 | Kinoshita et al. |
| 2010/0270540 A1 | 10/2010 | Chung et al. |
| 2010/0297522 A1 | 11/2010 | Creeth et al. |
| 2010/0307594 A1 | 12/2010 | Zhu et al. |
| 2011/0049496 A1 | 3/2011 | Fukuzaki |
| 2011/0062858 A1 | 3/2011 | Yersin et al. |
| 2011/0132440 A1 | 6/2011 | Sivarajan et al. |
| 2011/0217544 A1 | 9/2011 | Young et al. |
| 2012/0024383 A1 | 2/2012 | Kaiho et al. |
| 2012/0039323 A1 | 2/2012 | Hirano et al. |
| 2012/0095232 A1 | 4/2012 | Li et al. |
| 2012/0181528 A1 | 7/2012 | Takada et al. |
| 2012/0199823 A1 | 8/2012 | Molt et al. |
| 2012/0204960 A1 | 8/2012 | Kato et al. |
| 2012/0215001 A1 | 8/2012 | Li et al. |
| 2012/0223634 A1 | 9/2012 | Xia et al. |
| 2012/0264938 A1 | 10/2012 | Li et al. |
| 2012/0273736 A1 | 11/2012 | James et al. |
| 2012/0302753 A1 | 11/2012 | Li et al. |
| 2013/0048963 A1 | 2/2013 | Beers et al. |
| 2013/0168656 A1* | 7/2013 | Tsai et al. ................ 257/40 |
| 2013/0203996 A1 | 8/2013 | Li et al. |
| 2013/0237706 A1 | 9/2013 | Li et al. |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0203248 A1 | 7/2014 | Zhou et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0228914 A1 | 8/2015 | Li et al. |
| 2015/0274762 A1 | 10/2015 | Li et al. |
| 2015/0287938 A1 | 10/2015 | Li et al. |
| 2015/0318500 A1 | 11/2015 | Li et al. |
| 2015/0349279 A1 | 12/2015 | Li et al. |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133861 A1 | 5/2016 | Li et al. |
| 2016/0133862 A1 | 5/2016 | Li et al. |
| 2016/0194344 A1 | 7/2016 | Li et al. |
| 2016/0197291 A1 | 7/2016 | Li et al. |
| 2016/0285015 A1 | 9/2016 | Li et al. |
| 2016/0359120 A1 | 12/2016 | Li |
| 2016/0359125 A1 | 12/2016 | Li et al. |
| 2017/0005278 A1 | 1/2017 | Li et al. |
| 2017/0012224 A1 | 1/2017 | Li et al. |
| 2017/0047533 A1 | 2/2017 | Li et al. |

FOREIGN PATENT DOCUMENTS

| | | |
|---|---|---|
| CN | 1894269 A | 1/2007 |
| CN | 101142223 A | 3/2008 |
| CN | 101667626 A | 3/2010 |
| CN | 102449108 A | 5/2012 |
| CN | 102892860 A | 1/2013 |
| CN | 102971396 A | 3/2013 |
| CN | 104232076 A | 12/2014 |
| CN | 104693243 A | 6/2015 |
| CN | 105367605 A | 3/2016 |
| CN | 105418591 A | 3/2016 |
| EP | 1808052 A1 | 7/2007 |
| EP | 1874893 A1 | 1/2008 |
| EP | 1874894 A1 | 1/2008 |
| EP | 1919928 A1 | 5/2008 |
| EP | 2036907 A1 | 3/2009 |
| EP | 2096690 A2 | 9/2009 |
| EP | 2112213 A2 | 10/2009 |
| EP | 2417217 A2 | 2/2012 |
| EP | 2711999 A2 | 3/2014 |
| JP | 2002105055 A | 4/2002 |
| JP | 2005267557 A | 9/2005 |
| JP | 2005310733 A | 11/2005 |
| JP | 2006047240 A | 2/2006 |
| JP | 2006232784 A | 9/2006 |
| JP | 2006242080 A | 9/2006 |
| JP | 2006242081 A | 9/2006 |
| JP | 2006256999 A | 9/2006 |
| JP | 2006257238 A | 9/2006 |
| JP | 2006261623 A | 9/2006 |
| JP | 2006290988 A | 10/2006 |
| JP | 2006313796 A | 11/2006 |
| JP | 2006332622 A | 12/2006 |
| JP | 2006351638 A | 12/2006 |
| JP | 2007019462 A | 1/2007 |
| JP | 2007031678 A | 2/2007 |
| JP | 2007042875 A | 2/2007 |
| JP | 2007053132 A | 3/2007 |
| JP | 2007066581 A | 3/2007 |
| JP | 2007073620 A | 3/2007 |
| JP | 2007073845 A | 3/2007 |
| JP | 2007073900 A | 3/2007 |
| JP | 2007080593 A | 3/2007 |
| JP | 2007080677 A | 3/2007 |
| JP | 2007088105 A | 4/2007 |
| JP | 2007088164 A | 4/2007 |
| JP | 2007096259 A | 4/2007 |

(56) References Cited

FOREIGN PATENT DOCUMENTS

| | | |
|---|---|---|
| JP | 2007110067 A | 4/2007 |
| JP | 2007110102 A | 4/2007 |
| JP | 2007258550 A | 10/2007 |
| JP | 2007324309 A | 12/2007 |
| JP | 2008010353 A | 1/2008 |
| JP | 2008091860 A | 4/2008 |
| JP | 2008103535 A | 5/2008 |
| JP | 2008108617 A | 5/2008 |
| JP | 2008109085 A | 5/2008 |
| JP | 2008109103 A | 5/2008 |
| JP | 2008116343 A | 5/2008 |
| JP | 2008117545 A | 5/2008 |
| JP | 2008160087 A | 7/2008 |
| JP | 2008198801 A | 8/2008 |
| JP | 2008270729 A | 11/2008 |
| JP | 2008270736 A | 11/2008 |
| JP | 2008310220 A | 12/2008 |
| JP | 2009016184 A | 1/2009 |
| JP | 2009016579 A | 1/2009 |
| JP | 2009032977 A | 2/2009 |
| JP | 2009032988 A | 2/2009 |
| JP | 2009076509 A | 4/2009 |
| JP | 2009266943 A | 11/2009 |
| JP | 2009267171 A | 11/2009 |
| JP | 2009267244 A | 11/2009 |
| JP | 2009272339 A | 11/2009 |
| JP | 2009283891 A | 12/2009 |
| JP | 2010135689 A | 6/2010 |
| JP | 2012222255 A | 11/2012 |
| JP | 5601505 B2 | 10/2014 |
| JP | 2014221807 A | 11/2014 |
| JP | 2015081257 A | 4/2015 |
| KR | 20060115371 | 11/2006 |
| KR | 20070061830 | 6/2007 |
| KR | 20070112465 | 11/2007 |
| KR | 20130043460 | 4/2013 |
| TW | 200701835 A | 1/2007 |
| TW | 201307365 A | 2/2013 |
| WO | WO-0070655 A2 | 11/2000 |
| WO | WO-2004/003108 A1 | 1/2004 |
| WO | WO-2004085450 A2 | 10/2004 |
| WO | WO-2004108857 A1 | 12/2004 |
| WO | WO-2005042444 A2 | 5/2005 |
| WO | WO-2005042550 A1 | 5/2005 |
| WO | WO-2005113704 A2 | 12/2005 |
| WO | WO-2006033440 A1 | 3/2006 |
| WO | WO-2006/067074 A1 | 6/2006 |
| WO | WO-2006098505 A1 | 9/2006 |
| WO | WO-2006115299 A1 | 11/2006 |
| WO | WO-2006115301 A1 | 11/2006 |
| WO | WO-2007034985 A1 | 3/2007 |
| WO | WO-2007069498 A1 | 6/2007 |
| WO | WO-2008066192 A1 | 6/2008 |
| WO | WO-2008066195 A1 | 6/2008 |
| WO | WO-2008066196 A1 | 6/2008 |
| WO | WO-2008/101842 A1 | 8/2008 |
| WO | WO-2008117889 A1 | 10/2008 |
| WO | WO-2008123540 A2 | 10/2008 |
| WO | WO-2008131932 A1 | 11/2008 |
| WO | WO-2009017211 A1 | 2/2009 |
| WO | WO-2010007098 A1 | 1/2010 |
| WO | WO-2010056669 A1 | 5/2010 |
| WO | WO-2010093176 A2 | 8/2010 |
| WO | WO-2010118026 A2 | 10/2010 |
| WO | WO-2011/064335 A1 | 6/2011 |
| WO | WO-2011070989 A1 | 6/2011 |
| WO | WO-2011137429 A2 | 11/2011 |
| WO | WO-2011137431 A2 | 11/2011 |
| WO | WO-2012112853 A1 | 8/2012 |
| WO | WO-2012142387 A1 | 10/2012 |
| WO | WO-2012162488 A1 | 11/2012 |
| WO | WO-2012163471 A1 | 12/2012 |
| WO | WO-2013130483 A1 | 9/2013 |
| WO | WO-2014/016611 A1 | 1/2014 |
| WO | WO-2014031977 A1 | 2/2014 |
| WO | WO-2014047616 A1 | 3/2014 |
| WO | WO-2014109814 A2 | 7/2014 |
| WO | WO-2015027060 A1 | 2/2015 |
| WO | WO-2015131158 A1 | 9/2015 |
| WO | WO-2016025921 A1 | 2/2016 |
| WO | WO-2016029186 A1 | 2/2016 |

OTHER PUBLICATIONS

Baldo et al., Highly Efficient Phosphorescent Emission from Organic Electroluminescent Devices, Nature, 395: 151-154 (1998).
Baldo et al., Very High-Efficiency Green Organic Light-Emitting Devices Based on Electrophosphorescence , Appl Phys Lett, 75(3):4-6 (1999).
Barry O'Brien et al., "High efficiency white organic light emitting diodes employing blue and red platinum emitters," Journal of Photonics for Energy, vol. 4, 2014, pp. 043597-1-043597-8.
Barry O'Brien et al.: White organic light emitting diodes using Pt-based red, green and blue phosphorescent dopants. Proc. SPIE, vol. 8829, pp. 1-6 Aug. 25, 2013.
Berson et al. (2007). "Poly(3-hexylthiophene) fibers for photovoltaic applications," Adv. Funct. Mat., 17, 1377-84.
Bettington et al. "Tris-Cyclometalated Iridium(III) Complexes of Carbazole(fluorenyl)pyridine Ligands: Synthesis, Redox and Photophysical Properties, and Electrophosphorescent Light-Emitting Diodes" Chemistry: A European Journal, 2007, vol. 13, pp. 1423-1431.
Bouman et al. (1994). "Chiroptical properties of regioregular chiral polythiophenes," Mol. Cryst. Liq. Cryst., 256, 439-48.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
C Ulbricht et al., "Synthesis and Characterization of Oxetane-Functionalized Phosphorescent Ir(III)-Complexes", Macromol. Chem. Phys. 2009, 210, pp. 531-541.
Campbell et al. (2008). "Low-temperature control of nanoscale morphology for high performance polymer photovoltaics," Nano Lett., 8, 3942-47.
Chi et al., "Transition-metal phosphors with cyclometalating ligands: fundamentals and applications", Chemical Society Reviews, vol. 39, No. 2, Feb. 2010, pp. 638-655.
Chi-Ming Che et al., "Photophysical Properties and OLED Applications of Phosphorescent Platinum(II) Schiff Base Complexes," Chem. Eur. J., vol. 16, 2010, pp. 233-247.
Coakley et al. (2004). "Conjugated polymer photovoltaic cells," Chem. Mater., 16, 4533-4542.
D Wang et al., "Carbazole and arylamine functionalized iridium complexes for efficient electro-phosphorescent light-emitting diodes", Inorganica Chimica Acta 370 (2011) pp. 340-345.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Dorwald, "Side Reactions in Organic Synthesis: A Guide to Successful Synthesis Design," Chapter 1, 2005 Wiley-VCH Verlag GmbH & Co. KGaA, Wienheim, 32 pages.
Eric Turner et al., "Cyclometalated Platinum Complexes with Luminescent Quantum Yields Approaching 100%," Inorg. Chem., 2013, vol. 52, pp. 7344-7351.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Finikova, M. A. et al., New Selective Synthesis of Substituted Tetrabenzoporphyris, Doklady Chemistry, 2003, vol. 391, No. 4-6, pp. 222-224.
Galanin et al. Synthesis and Properties of meso-Phenyl-Substituted Tetrabenzoazaporphines Magnesium Complexes. Russian Journal of Organic Chemistry (Translation of Zhurnal Organicheskoi Khimii) (2002), 38(8), 1200-1203.
Glauco Ponterini et al., "Comparison of Radiationless Decay Processes in Osmium and Platinum Porphyrins," J. Am. Chem. Soc., vol. 105, No. 14, 1983, pp. 4639-4645.

(56) References Cited

OTHER PUBLICATIONS

Gong et al., Highly Selective Complexation of Metal Ions by the Self-Tuning Tetraazacalixpyridine macrocycles, Tetrahedron, 65(1): 87-92 (2009).
Gottumukkala, V. et al., Synthesis, cellular uptake and animal toxicity of a tetra carboranylphenyl N-tetrabenzoporphyr in, Bioorganic&Medicinal Chemistry, 2006, vol. 14, pp. 1871-1879.
Guijie Li et al., "Efficient and stable red organic light emitting devices from a tetradentate cyclometalated platinum complex," Organic Electronics, 2014, vol. 15 pp. 1862-1867.
H Tang et al., "Novel yellow phosphorescent iridium complexes containing a carbazoleeoxadiazole unit used in polymeric light-emitting diodes", Dyes and Pigments 91 (2011) pp. 413-421.
H-J Seo et al., "Blue phosphorescent iridium(III) complexes containing carbazole-functionalized phenylpyridine for organic light-emitting diodes: energy transfer from carbazolyl moieties to iridium(III) cores", RSC Advances, 2011, 1, pp. 755-757.
Hansen (1969). "The universality of the solubility parameter," I & EC Product Research and Development, 8, 2-11.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Imre et al (1996). "Liquid-liquid demixing from solutions of polystyrene. 1. A review. 2. Improved correlation with solvent properties," J. Phys. Chem. Ref. Data, 25, 637-61.
International Preliminary Report on Patentability issued on Feb. 24, 2015 byt the International Searching Authority for International Patent Application No. PCT/US2013/056426, which was published as WO 2014/031977 on Feb. 27, 2014 (Inventor—Li et al.; Applicant—Arizona Technology Enterprises; (7 pages).
International Search Report and Written Opinion mailed on Jan. 20, 2014 by the International Searching Authority for International Patent Application No. PCT/US2013/056426, which was published as WO 2014/031977 on Feb. 27, 2014 (Inventor—Li et al.; Applicant—Arizona Technology Enterprises; (11 pages).
Jan Kalinowski et al., "Light-emitting devices based on organometallic platinum complexes as emitters," Coordination Chemistry Reviews, vol. 255, 2011, pp. 2401-2425.
Jeong et al. (2010). "Improved efficiency of bulk heterojunction poly(3-hexylthiophene):[6,6]-phenyl-C61-butyric acid methyl ester photovoltaic devices using discotic liquid crystal additives," Appl. Phys. Lett.. 96, 183305.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Ji Hyun Seo et al., "Efficient blue-green organic light-emitting diodes based on heteroleptic tris-cyclometalated iridium (III) complexes", Thin Solid Films, vol. 517, 2009, pp. 1807-1810.
Jw Levell et al., "Carbazole/iridium dendrimer side-chain phosphorescent copolymers for efficient light emitting devices", New J. Chem., 2012, 36, pp. 407-413.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Kim et al (2009). "Altering the thermodynamics of phase separation in inverted bulk-heterojunction organic solar cells," Adv. Mater., 21, 3110-15.
Kim et al. (2005). "Device annealing effect in organic solar cells with blends of regioregular poly(3- hexylthiophene) and soluble fullerene," Appl. Phys. Lett. 86, 063502.
Kroon et al. (2008). "Small bandgappolymers for organic solar cells," Polymer Reviews, 48, 531-82.
Lee et al. (2008). "Processing additives for improved efficiency from bulk heterojunction solar cells," J. Am. Chem. Soc., 130, 3619-23.

Li et al. (2005). " Investigation of annealing effects and film thickness dependence of polymer solar cells based on poly (3-hexylthiophene)," J. Appl. Phys., 98, 043704.
Li et al. (2007). "Solvent annealing effect in polymer solar cells based on poly(3-hexylthiophene) and methanofullerenes," Adv. Funct. Mater., 17, 1636-44.
Liang, et al. (2010). "For the bright future—bulk heterojunction polymer solar cells with power conversion efficiency of 7.4%," Adv. Mater. 22, E135-38.
Meso-Phenyltetrabenzoazaporphyrins and their zinc complexes. Synthesis and spectral properties, Russian Journal of General Chemistry (2005), 75(4), 651-655.
Morana et al. (2007). "Organic field-effect devices as tool to characterize the bipolar transport in polymer-fullerene blends: the case of P3HT-PCBM," Adv. Funct. Mat., 17, 3274-83.
Moule et al. (2008). "Controlling morphology in Polymer-Fullerene mixtures," Adv. Mater., 20, 240-45.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Nillson et al. (2007). "Morphology and phase segregation of spincasted films of polyfluorene/PCBM Blends," Macromolecules, 40, 8291-8301.
Notice of Allowance issued on Apr. 17, 2014 for U.S. Appl. No. 13/399,252, filed Feb. 17, 2012 and granted as U.S. Pat. No. 8,816,080 on Aug. 26, 2014 (Inventor—Li, et al.) (9 pages).
Notice of Allowance issued on Aug. 18, 2014 for U.S. Appl. No. 14/332,610, filed Jul. 16, 2014 and granted as U.S. Pat. No. 8,927,713 on Aug. 15, 2014 (Inventor—Li, et al.) (9 pages).
Notice of Allowance issued on Dec. 7, 2015 for U.S. Appl. No. 13/963,519, filed Aug. 9, 2013 and granted as U.S. Pat. No. 9,312,502 on Apr. 12, 2016 (Inventor—Li, et al.) (8 pages).
Notice of Allowance issued on Feb. 12, 2016 for U.S. Appl. No. 13/695,338, filed May 16, 2013 and granted as U.S. Pat. No. 9,324,957 on Apr. 26, 2016 (Inventor—Li, et al.) (5 pages).
Notice of Allowance issued on Feb. 29, 2016 for U.S. Appl. No. 14/380,719, filed Aug. 23, 2014 and granted as U.S. Pat. No. 9,318,725 on Apr. 19, 2016 (Inventor—Li, et al.) (35 pages).
Notice of Allowance issued on Jul. 7, 2016 for U.S. Appl. No. 14/589,599, filed Jan. 5, 2015 and granted as U.S. Pat. No. 9,425,415 on Aug. 23, 2016 (Inventor—Li, et al.) (9 pages).
Notice of Allowance issued on May 13, 2016 for U.S. Appl. No. 14/145,461, filed Dec. 31, 2013 and granted as U.S. Pat. No. 9,382,273 on Jul. 5, 2016 (Inventor—Li, et al.) (10 pages).
Notice of Allowance issued on May 19, 2016 for U.S. Appl. No. 14/513,506, filed Oct. 14, 2014 and granted as U.S. Pat. No. 9,385,329 on Jul. 5, 2016 (Inventor—Li, et al.) (11 pages).
Notice of Allowance issued on Nov. 24, 2015 for U.S. Appl. No. 13/479,921, filed May 24, 2012 and granted as U.S. Pat. No. 9,238,668 on Jan. 19, 2016 (Inventor—Li, et al.) (5 pages).
Notice of Allowance issued on Sep. 16, 2014 for U.S. Appl. No. 13/263,096, filed Jan. 3, 2012 and granted as U.S. Pat. No. 8,946,417 on Feb. 3, 2015 (Inventor—Li, et al.) (5 pages).
Notice of Allowance issued on Sep. 17, 2015 for U.S. Appl. No. 13/446,354, filed Apr. 13, 2012 and granted as U.S. Pat. No. 9,221,857 on Aug. 23, 2016 (Inventor—Li, et al.) (5 pages).
Olynick et al. (2009). "The link between nanoscale feature development in a negative resist and the Hansen solubility sphere," Journal of Polymer Science: Part B: Polymer Physics, 47, 2091-2105.
Peet et al. (2007). "Efficiency enhancement in low-bandgap polymer solar cells by processing with alkane dithiols," Nature Materials, 6, 497-500.
Pivrikas et al. (2008). "Substituting the postproduction treatment for bulk-heterojunction solar cells using chemical additives," Organic Electronics, 9, 775-82.
Rui Zhu et al., "Color tuning based on a six-membered chelated iridium (III) complex with aza-aromatic ligand," Chemistry Letters, vol. 34, No. 12, 2005, pp. 1668-1669.
Saricifci et al. (1993). "Semiconducting polymerbuckminsterfullerene heterojunctions: diodes photodiodes, and photovoltaic cells," Appl. Phys. Lett., 62, 585-87.

(56) References Cited

OTHER PUBLICATIONS

Satake et al., "Interconvertible Cationic and Neutral Pyridinylimidazole .eta.3-Allylpalladium Complexes. Structural Assignment by 1H, 13C, and 15N NMR and X-ray Diffraction, Organometallics", vol. 18, No. 24, 1999, pp. 5108-5111.
Saunders et al. (2008). "Nanoparticle-polymer photovoltaic cells," Advances in Colloid and Interface Science, 138, 1-23.
Shih-Chun Lo et al., "High-Triplet-Energy Dendrons: Enhancing the Luminescence of Deep Blue Phosphorescent Indium(III) Complexes," J. Am. Chem. Soc., vol. 131, 2009, pp. 16681-16688.
Shin et al. (2010). "Abrupt morphology change upon thermal annealing in Poly(3-hexathiophene)/soluble fullerene blend films for polymer solar cells," Adv. Funct. Mater., 20, 748-54.
Shiro Koseki et al., "Spin-orbit coupling analyses of the geometrical effects on phosphorescence in Ir(ppy)3 and its derivatives", J. Phys. Chem. C, vol. 117, 2013, pp. 5314-5327.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Stephen R. Forrest, "The path to ubiquitous and low-cost organic electronic appliances on plastic," Nature, vol. 428, Apr. 29, 2004, pp. 911-918.
Steven C. F. Kui et al., "Robust Phosphorescent Platinum(II) Complexes Containing Tetradentate O{circumflex over (0)}N{circumflex over (0)}C{circumflex over (0)}N Ligands: Excimeric Excited State and Application in Organic White-Light-EmittingDiodes," Chem. Eur. J., 2013, vol. 19, pp. 69-73.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Vanessa Wood et al., "Colloidal quantum dot light-emitting devices," Nano Reviews , vol. 1, 2010, 8 pages.
Wang et al. (2010). "The development of nanoscale morphology in polymer: fullerene photovoltaic blends during solvent casting," Soft Matter, 6, 4128-4134.
Wang et al., C(aryl)-C(alkyl) bond formation from Cu(ClO4)2-mediated oxidative cross coupling reaction between arenes and alkyllithium reagents through structurally well-defined Ar-Cu(III) intermediates, Chem Commun, 48: 9418-9420 (2012).
Wong; Challenges in organometallic research—Great opportunity for solar cells and OLEDs, Journal of Organometallic Chemistry, 2009, 694, 2644-2647.
Xiao-Chu Hang et al., "Highly Efficient Blue-Emitting Cyclometalated Platinum(II) Complexes," Angewandte Chemie, International Edition, vol. 52, No. 26, Jun. 24, 2013, pp. 6753-6756.
Xiaofan Ren et al., "Ultrahigh Energy Gap Hosts in Deep Blue Organic Electrophosphorescent Devices," Chem. Mater, vol. 16, 2004, pp. 4743-4747.
Yakubov,L.A. et al., Synthesis and Properties of Zinc Complexes of mesoHexadecyloxy-Substituted Tetrabenzoporphyrin and Tetrabenzoazaporphyrins, Russian Journal of Organic Chemistry, 2008, vol. 44, No. 5, pp. 755-760.
Yang et al. (2005). "Nanoscale morphology of high-performance polymer solar cells," Nano Lett., 5, 579-83.
Yao et al. (2008). "Effect of solvent mixture on nanoscale phase separation in polymer solar cells," Adv. Funct. Mater.,18, 1783-89.
Yao et al., Cu(ClO4)2-Mediated Arene C-H Bond Halogenations of Azacalixaromatics Using Alkali Metal Halides as Halogen Sources, The Journal of Organic Chemistry, 77(7): 3336-3340 (2012).
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Yu et al. (1995). "Polymer Photovoltaic Cells: Enhanced efficiencies via a network of internal donor-acceptor heterojunctions," Science, 270, 1789-91.
Z Liu et al., "Green and blue-green phosphorescent heteroleptic iridium complexes containing carbazole-functionalized beta-diketonate for non-doped organic light-emitting diodes", Organic Electronics 9 (2008) pp. 171-182.
Z Xu et al., "Synthesis and properties of iridium complexes based 1,3,4-oxadiazoles derivatives", Tetrahedron 64 (2008) pp. 1860-1867.
International Search Report and Written Opinion mailed on Jul. 31, 2014 by the International Searching Authority for International Patent Application No. PCT/US2013/066793, which was published as WO 2014/109814 on Jul. 17, 2014 (Inventor—Li, et al.) (11 pages).
International Preliminary Report on Patentability issued on Apr. 28, 2015 by the International Searching Authority for International Patent Application No. PCT/US2013/066793, which was published as WO 2014/109814 on Jul. 17, 2014 (Inventor—Li, et al.) (8 pages).
Restriction Requirement was issued on Jun. 10, 2016 by the U.S. Patent and Trademark Office for U.S. Appl. No. 14/437,963, filed Oct. 25, 2013 and published as US-2015-0274762-A1 on Oct. 1, 2015 (Inventor—Li, et al.) (9 pages).
Response to Restriction Requirement was mailed on Aug. 10, 2016 to the U.S. Patent and Trademark Office for U.S. Appl. No. 14/437,963, filed Oct. 25, 2013 and published as US-2015-0274762-A1 on Oct. 1, 2015 (Inventor—Li, et al.) (3 pages).
Non Final Rejection was issued on Aug. 26, 2016 by the U.S. Patent and Trademark Office for U.S. Appl. No. 14/437,963, filed Oct. 25, 2013 and published as US-2015-0274762-A1 on Oct. 1, 2015 (Inventor—Li, et al.) (7 pages).
Marc Lepeltier et al., "Efficient blue green organic light-emitting devices based on a monofluorinated heteroleptic ridium(III) complex," Synthetic Metals, (2015) 199:139-146.
Notice of Allowance was issued on Nov. 23, 2016 by the U.S. Patent and Trademark Office for U.S. Appl. No. 14/611,654, filed Feb. 2, 2015 and granted as 9,550,801 on Jan. 24, 2017 (Inventor—Jian Li, et al.) (7 pages).
Issue Notification was issued on Jan. 4, 2017 by the U.S. Patent and Trademark Office for U.S. Appl. No. 14/611,654, filed Feb. 2, 2015 and granted as 9,550,801 on Jan. 24, 2017 (Inventor—Jian Li, et al.) (1 pages).
Restriction Requirement was issued on Dec. 8, 2016 by the U.S. Patent and Trademark Office for U.S. Appl. No. 15/202,058, filed Jul. 5, 2016 and published as US 2017-0005278 A1 on Jan. 5, 2017 (Inventor—Jian Li, et al.) (9 pages).
Response to Restriction Requirement was mailed on Jan. 30, 2017 to the U.S. Patent and Trademark Office for U.S. Appl. No. 15/202,058, filed Jul. 5, 2016 and published as US 2017-0005278 A1 on Jan. 5, 2017 (Inventor—Li, et al.) (13 pages).
International Search Report and Written Report were mailed on Jun. 5, 2012 for International Application No. PCT/US2012/025588, filed Feb. 17, 2012 and published as WO 2012/112853 on Aug. 23, 2012 (Inventor—Li, et al.) (7 pages).
International Preliminary Report on Patentability was mailed on Aug. 21, 2013 for International Application No. PCT/US2012/025588, filed Feb. 17, 2012 and published as WO 2012/112853 on Aug. 23, 2012 (Inventor—Li, et al.) (5 pages).
Non Final Rejection was issued on Nov. 23, 2016 by the U.S. Patent and Trademark Office for U.S. Appl. No. 15/243,801, filed Aug. 22, 2016 and published as US 2017-0047533 A1 on Feb. 16, 2017 (Inventor—Jian Li, et al.) (6 pages).
Response to Non Final Rejection was mailed on Feb. 21, 2017 to the U.S. Patent and Trademark Office for U.S. Appl. No. 15/243,801, filed Aug. 22, 2016 and published as US 2017-0047533 A1 on Feb. 16, 2017 (Inventor—Jian Li, et al.) (1 page).
Notice of Allowance was issued on Jan. 18, 2017 by the U.S. Patent and Trademark Office for U.S. Appl. No. 14/980,518, filed Dec. 28, 2015 and Published as US 2016-0194344 A1 on Jul. 7, 2016 (Inventor—Jian Li, et al.) (7 pages).
Issue Notification was issued on Mar. 1, 2017 by the U.S. Patent and Trademark Office for U.S. Appl. No. 14/980,518, filed Dec. 28, 2015 and published as US 2016-0194344 A1 on Jul. 7, 2016 (Inventor—Jian Li, et al.) (1 page).
Notice of Allowance was issued on Feb. 7, 2017 by the U.S. Patent and Trademark Office for U.S. Appl. No. 14/300,832, filed Jun. 10,

(56) References Cited

OTHER PUBLICATIONS 2015 and published as US 2014-0364605 A1 on Dec. 11, 2014 (Inventor—Jian Li, et al.) (5 pages).

Restriction Requirement was issued on Dec. 5, 2016 by the U.S. Patent and Trademark Office for U.S. Appl. No. 14/913,306, filed Feb. 19, 2016 and published as US 2016-0285015 A1 on Sep. 29, 2016 (Inventor—Jian Li, et al.) (5 pages).

Response to Restriction Requirement was mailed on Jan. 30, 2017 to the U.S. Patent and Trademark Office for U.S. Appl. No. 14/913,306, filed Feb. 19, 2016 and published as US 2016-0285015 A1 on Sep. 29, 2016 (Inventor—Jian Li, et al.) (2 pages).

Restriction Requirement was issued on Dec. 27, 2016 by the U.S. Patent and Trademark Office for U.S. Appl. No. 15/202,111, filed Jul. 5, 2016 and published as US 2017-0012224 A1 on Sep. 29, 2016 (Inventor—Jian Li, et al.) (10 pages).

Response to Restriction Requirement was mailed on Feb. 24, 2017 to the U.S. Patent and Trademark Office for U.S. Appl. No. 15/202,111, filed Jul. 5, 2016 and published as US 2017-0012224 A1 on Sep. 29, 2016 (Inventor—Jian Li, et al.) (1 page).

Non Final Rejection was issued on Feb. 13, 2017 by the U.S. Patent and Trademark Office for U.S. Appl. No. 14/591,188 filed Jan. 7, 2015 and published as US 2015-0194616 A1 on Jul. 9, 2015 (Inventor—Jian Li, et al.) (8 pages).

\* cited by examiner

METAL COMPOUNDS AND METHODS AND USES THEREOF

CROSS-REFERENCE TO RELATED APPLICATIONS

The present application is a U.S. National Phase Application of International Application No. PCT/US2013/056426, filed Aug. 23, 2013, which claims priority to U.S. Application No. 61/692,937, filed Aug. 24, 2012, all of which applications are incorporated herein fully by this reference

STATEMENT OF GOVERNMENT SUPPORT

The present invention was made with financial support from the National Science Foundation (NSF) under Career Grant No. 0748867 and from a NSF GK-12 fellowship and from Department of Energy SSL Core Technology under Grant No. DE-EE0005075. The U.S. government has certain rights in this invention.

This invention was made with government support under CHE0748867, awarded by National Science Foundation. The government has certain rights in the invention.

TECHNICAL BACKGROUND

Compounds capable of hole and electron conduction and efficient energy transfer are ideally suited for use in a wide variety of applications, including optical and electro-optical devices, and photo-absorbing devices. Much research has been devoted to the discovery and optimization of organic and organometallic materials for use in such applications. Generally, research in this area aims to accomplish a number of goals, including improvements in hole and electron transport and energy level tuning, as well as improvements in processing ability, among others.

Despite significant advances in research devoted to optical and electro-optical materials, existing host materials have a number disadvantages, including poor processing ability, poor energy matching to certain emissive materials, poor charge carrier mobility, among others. Thus, a need exists for new materials which exhibit improved performance. This need and other needs are satisfied by the present invention.

Cyclometalated metal complexes can be used for many applications including host materials and emitters for OLEDs. One of most important factors dictating the quantum efficiency of emission, is proportional to the integral of wavefunction of ground state and excited state, which favors a small difference in their equilibrium geometry.

Despite significant advances in research devoted to optical, electro-optical, and marker materials, existing materials have a number disadvantages, including poor processing ability, inefficient emission or absorption, and less than ideal stability, among others. Thus, a need exists for new materials which exhibit improved performance in optical emitting and absorbing applications. This need and other needs are satisfied by the present invention.

SUMMARY

The present invention relates to, in one aspect, to metal compounds that can be useful as host materials in, for example, full color displays. The present invention also relates, in one aspect to metal compounds that can be useful as emitters for devices, such as OLEDs In one aspect, disclosed herein is a compound having the structure:

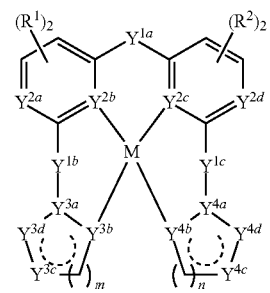

wherein M comprises Pt, Pd, Ir, Rh, or Au; wherein each of $R^1$ and $R^2$ independently are hydrogen, substituted or unsubstituted alkyl, alkenyl, alkynyl, aryl, heteroaryl, cycloalkane, cycloalkane, heterocyclyl, amino, nitro hydroxyl, halogen, thio, alkoxy, haloalkyl, arylalkane, or arylalkene; wherein each of $Y^{1a}$, $Y^{1b}$, and $Y^{1c}$ independently is O, $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to an adjacent ring structure, thereby forming a cyclic structure; wherein each of $Y^{2a}$, $Y^{2b}$, $Y^{2c}$, and $Y^{2d}$ independently is N, $NR^{6a}$, or $CR^{6b}$, wherein each of $R^{6a}$ and $R^{6b}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently is N, O, S, $NR^{6a}$, $CR^{6b}$, wherein each of $R^{6a}$ and $R^{6b}$ independently hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; or $Z(R^{6c})_2$, wherein Z is C or Si, and wherein each $R^{6c}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; wherein each of m and n independently are an integer 1 or 2; wherein each of independently is partial or full unsaturation of the ring with which it is associated.

In one aspect, disclosed herein is a compound having the structure:

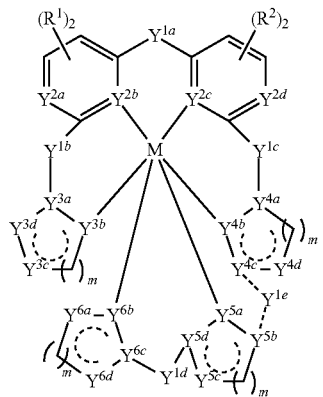

wherein M comprises Ir, Rh, Pt, Ru, or Os; wherein each of $R^1$ and $R^2$ independently are hydrogen, substituted or unsubstituted alkyl, alkenyl, alkynyl, aryl, heteroaryl, cycloalkane, cycloalkane, heterocyclyl, amino, nitro hydroxyl, halogen, thio, alkoxy, haloalkyl, arylalkane, or arylalkene; wherein each of $Y^{1a}$, $Y^{1b}$, $Y^{1c}$, $Y^{1d}$, and $Y^{1e}$ independently is O, $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to an adjacent ring structure, thereby forming a cyclic structure; wherein each of $Y^{2a}$, $Y^{2b}$, $Y^{2c}$, and $Y^{2d}$ independently is N, $NR^{6a}$, or $CR^{6b}$, wherein each of $R^{6a}$ and $R^{6b}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; wherein each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently is N, O, S, $NR^{6a}$, $CR^{6b}$, wherein each of $R^{6a}$ and $R^{6b}$ independently hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; or $Z(R^{6c})_2$, wherein Z is C or Si, and wherein each $R^{6c}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; wherein in each of each of $Y^{5a}$, $Y^{5b}$, $Y^{5c}$, $Y^{5d}$, $Y^{6a}$, $Y^{6b}$, $Y^{6c}$, and $Y^{6d}$ independently is N, O, S, $NR^{6a}$, or $CR^{6b}$; wherein each of m and n independently are an integer 1 or 2; wherein each of

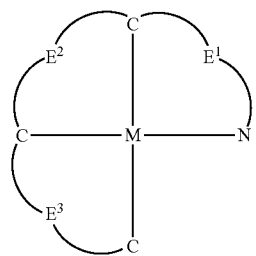

independently is partial or full unsaturation of the ring with which it is associated.

In one aspect, disclosed herein is a compound having the structure:

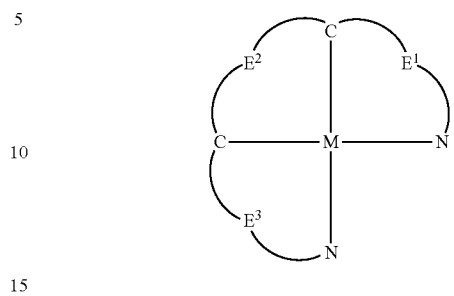

wherein the formula, M represent a metal cation with two positive charges, which include, but are not limited to Platinum(II) ($Pt^{2+}$), Palladium(II) ($Pd^{2+}$), wherein $E^1$, $E^2$, and $E^3$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, disclosed herein is a compound having the structure:

wherein M represents a metal cation with three positive charges, which include, but are not limited to Gold(III) ($Au^{3+}$), silver(III) ($Ag^{3+}$), wherein each $E^1$, $E^2$, and $E^3$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein N represents a substituted or unsubstituted aromatic ring or heterocyclic group with a nitrogen atom coordinated to the metal.

In one aspect, disclosed herein is a compound having the structure:

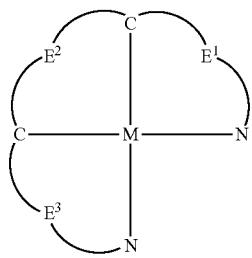

wherein M represent a metal cation with one positive charges, which include, but is not limited to, iridium (I) ($Ir^{1+}$), Rhodium (I) ($Rh^{1+}$), etc., wherein $E^1$, $E^2$, and $E^3$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein C represents a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, disclosed herein is a compound having the structure:

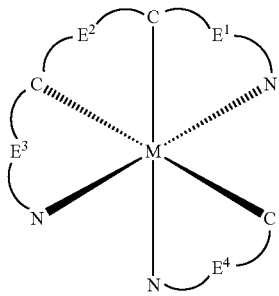

wherein M represent a metal cation with three positive charges, which include, but are not limited to, iridium (III) ($Ir^{3+}$), Rhodium(III) ($Rh^{3+}$), Cobalt (III) ($Co^{3+}$), Aluminum (III) ($Al^{3+}$), and Gallium(III) ($Ga^{3+}$), wherein $E^1$, $E^2$, $E^3$, and $E^4$ independently represent a linking atom, comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, disclosed herein is a compound having the structure:

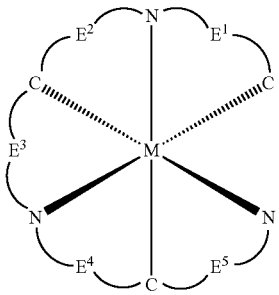

wherein M represent a metal cation with three positive charges, which include, but are not limited to, iridium (III) ($Ir^{3+}$), Rhodium(III) ($Rh^{3+}$), Cobalt (III) ($Co^{3+}$), Aluminum (III) ($Al^{3+}$), Gallium(III) ($Ga^{3+}$), wherein $E^1$, $E^2$, $E^3$, $E^4$, and $E^5$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, disclosed herein is a compound having the structure:

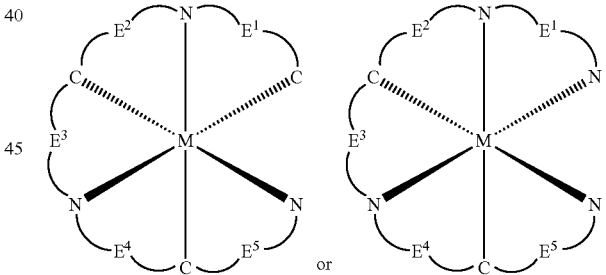

wherein M represent a metal cation with three positive charges, which include, but are not limited to, iridium (III) ($Ir^{3+}$), Rhodium(III) ($Rh^{3+}$), Cobalt (III) ($Co^{3+}$), Aluminum (III) ($Al^{3+}$), Gallium(III) ($Ga^{3+}$), wherein $E^1$, $E^2$, $E^3$, $E^4$, and $E^5$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, disclosed herein is a compound having the structure:

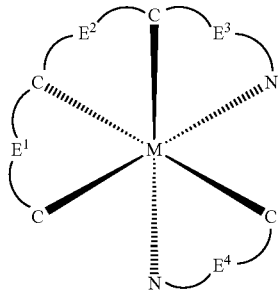

wherein M represent a metal cation with four positive charges, which include, but are not limited to, Palladium(IV) ($Pd^{4+}$), Platinum(IV) ($Pt^{4+}$), wherein $E^1$, $E^2$, $E^3$, and $E^4$, independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, disclosed herein is a compound having the structure:

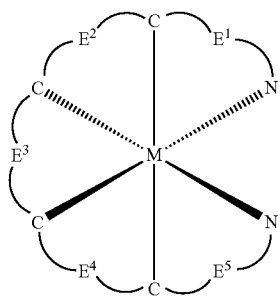

wherein M represent a metal cation with four positive charges, which include, but are not limited to, Palladium(IV) ($Pd^{4+}$), Platinum(IV) ($Pt^{4+}$), wherein $E^1$, $E^2$, $E^3$, $E^4$, and $E^5$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, disclosed herein is a compound having the structure:

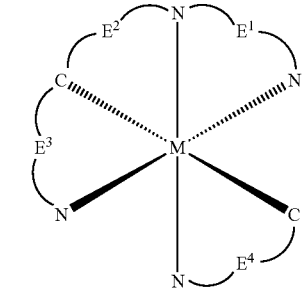

wherein M represent a metal cation with three positive charges, which include, but are not limited to, iridium (III) ($Ir^{3+}$), Rhodium(III) ($Rh^{3+}$), Cobalt (III) ($Co^{3+}$), Aluminum (III) ($Al^{3+}$), Gallium(III) ($Ga^{3+}$), wherein $E^1$, $E^2$, $E^3$, and $E^4$, independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, disclosed herein is a compound having the structure:

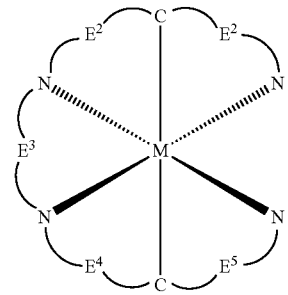

wherein M represent a metal cation with two positive charges, which include, but are not limited to, Ruthenium (II) ($Ru^{2+}$), Osmium (II) ($Os^{2+}$), wherein $E^1$, $E^2$, $E^3$, $E^4$, and $E^5$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

Also disclosed herein are compositions comprising one or more of the disclosed compounds.

Also disclosed herein are devices comprising one or more of the disclosed compounds. Suitable devices include, but are not limited to, OLEDs and full color displays.

BRIEF DESCRIPTION OF THE FIGURES

The accompanying figures, which are incorporated in and constitute a part of this specification, illustrate several aspects and together with the description serve to explain the principles of the invention.

Figure 1:
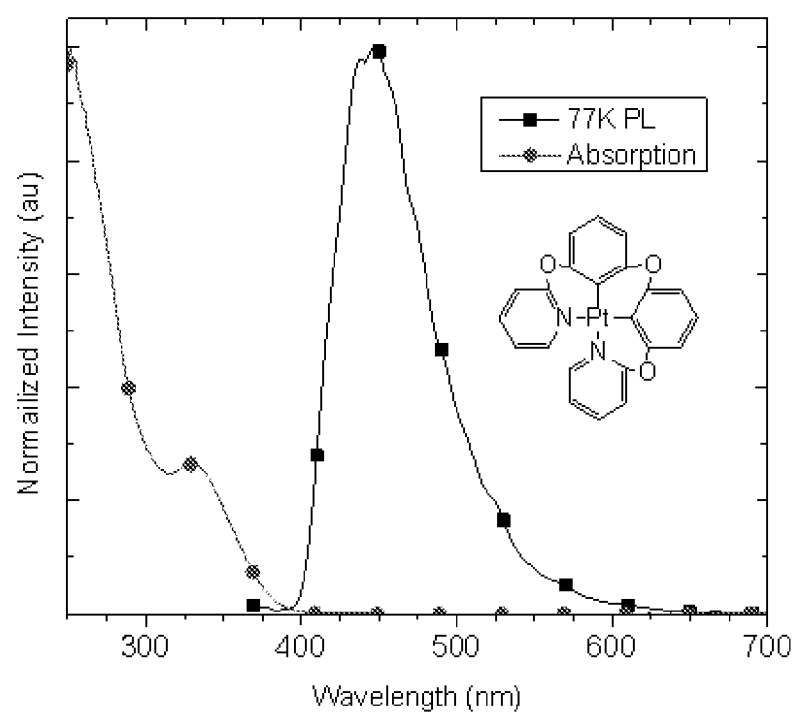
FIG. 1 shows the absorption spectra of the compound Pt—OOO (inset) in dichloromethane at room temperature, and the emission spectra at 77K in 2-methyltetrahydrofuran.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Definitions

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As referred to herein, a linking atom connect two groups such as, for example, a N and C group. The linking atom can, if valency permits, have other chemical moieties attached. For example, an oxygen would not have any other chemical groups attached as the valency is satisfied once it is bonded to the two groups (N and/or C groups). In another example, when carbon is the linking atom, two additional chemical moieties would be attached to the carbon as valency would require such. Suitable chemical moieties includes, but are not limited to, hydrogen, hydroxyl, alkyl, alkoxy, =O, halogen, nitro, amine, amide, thiol, aryl, heteroaryl, cycloalkyl, and heterocyclyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "nitrile" as used herein is represented by the formula —CN.

The term "thiol" as used herein is represented by the formula —SH.

The term "heterocyclyl" or the like terms refer to cyclic structures including a heteroatom. Thus, "heterocyclyl" includes both aromatic and non-aromatic ring structures with one or more heteroatoms. Non-limiting examples of heterocyclic includes, pyridine, isoquinoline, methylpyrrole and thiophene etc. "Heteroaryl" specifically denotes an aromatic cyclic structure including a heteroatom.

As used herein the terms "compound" and "complex" are used interchangeably.

Several structures herein show a nitrogen (N) coordinated to a metal. It is understood that the although the valency is indicated to be neutral in the structure it can if appropriate, as appreciated by those skilled in the art, be a cationic species having a net positive charge due to the coordination. Thus, nitrogen can be shown in the structures to have neutral charge or a positive charge and in some cases these structures can be used interchangeably as appropriate and as recognized by one skilled in the art.

The compounds and compositions disclosed herein are described as containing a "metal" or "metals." Examples of such "metal" components include, but are not limited to Pt, Pd, Ir, Rh, Au, Os, or Ru. It should be understood that references to such "metals" in this application does NOT imply a particular valence, chemical, or physical state of those elements, or that those elements are necessarily in a zero valent state, or metallic solid physical state or alloy (although they could be in such states), but rather that the term "metal" or "metals" can also be present in a compound with other elements or groups wherein the metal can be present in any energetically feasible positive oxidation state (i.e. cationic oxidation states). For example, a reference to platinum (Pt) includes the cationic form $Pt^{2+}$ of platinum or $Pt^{4+}$ of platinum.

Compounds

As briefly described above, the present invention is directed to metal compounds or complexes, such as platinum, palladium, gold, silver, ruthenium, iridium, rhodium, aluminum, gallium, cobalt, and osmium compounds. In one aspect, the compositions disclosed here can provide emission spectra of platinum, palladium, gold, silver, ruthenium, iridium, rhodium, aluminum, gallium, cobalt, and osmium. In another aspect, the compositions disclosed herein can provide tunable emission spectra.

In one aspect, the disclosed compounds are useful as host materials in devices, such as full color displays.

In another aspect, the disclosed compounds are useful as emitters in devices, such as OLEDs.

Cyclometalated metal complexes can be used for many applications including emitters for OLEDs. One of most important factors dictating the quantum efficiency of emission, is proportional to the integral of wavefunction of ground state and excited state, which favors a small difference in their equilibrium geometry. Typically, an efficient emitter requires a rigid planar chemical structure, which has 5-membered coordination rings (Scheme 1). On the other hand, emitters containing unplanar lumophore do not have strong emission at the room temperature due to their distorted molecular geometry, which has 6-membered coordination rings (Scheme 1b). This invention provides a materials design route which enables the emitters with 6-membered coordination rings to be efficient emitters and have tunable emission wavelength in the visible range. This class of emitters can be utilized as emitters for full color displays and lighting applications. To make this work, one condition needs to be satisfied: the molecular geometry needs to be very rigid. The molecular structure of four-coordinating ligands will be preferred which ensures the electrochemical and photophysical stability of metal complexes.

As illustrated in Scheme 1, PtNON is an emitter with 6-membered coordination rings, which has demonstrated an electron-to-photon conversion efficiency over 20% in the device settings

SCHEME 1

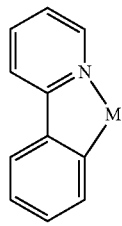

(a)

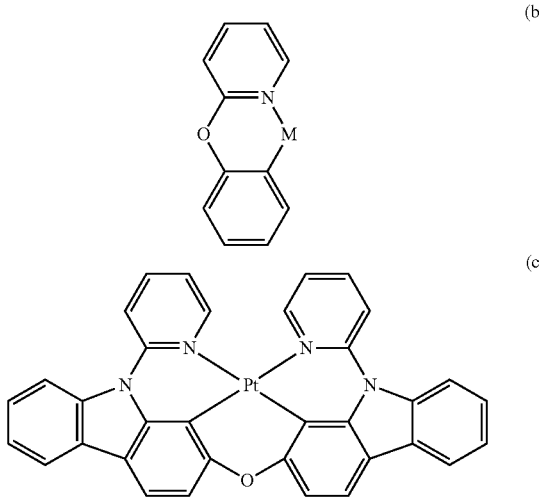

Accordingly, the invention also relates to metal compounds that can be useful as emitters in devices, such as OLEDs.

The emission (and absorption) profile of the compounds can be tuned by varying the structure of the ligand surrounding the metal center. For example, compounds having a ligand with electron withdrawing substituents will generally exhibit different optical properties, including emission and absorption, than compounds having a ligand with electron donating substituents. Generally, a chemical structural change affects the electronic structure of the compound, which thereby affects the absorption and emission of the compound. Thus, the compounds of the present invention can be tailored or tuned to a specific application that desires a particular emission or absorption characteristic.

In another aspect, the emission spectrum of any of the compositions of the present disclosure can be tuned to a desired and/or customized spectrum. In another aspect, the complexes disclosed herein can provide a narrow bandwidth, enabling their use in, for example, applications in which broad spectrum emitters are not suitable.

In one aspect, the excited state dynamics of the complex can be described by the scheme:

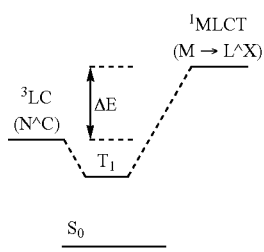

where $^3LC$ represents the energy of the ligand centered triplet state, $^1MLCT$ represents the energy of the metal-to-ligand charge transfer singlet state, $T_1$ represents the energy of the emissive triplet state, $S_0$ represents the energy of the ground state, and $\Delta E$ represents the difference in energy between $^1MLCT$ and $^3LC$.

In still another aspect, an expansion utilizing different emitting portions and linking groups should provide narrow emitting complexes covering a wide range of the visible spectrum. The emission energy of a certain complex can be tuned by modifying the ligand centered triplet state of the emitting fragment ($^3LC$). This can be accomplished through changes in structure that modify the energy of the donating or accepting portion of the emitting fragment.

In another aspect, the nature of the $^1MLCT$ transitions can be controlled by modifying the ancillary portion of the complex (L^X), through changes in the cyclometalating portion, the linking portions, or both.

In one aspect, the inventive compositions are useful as emitters for full color display application. In such an aspect, the geometry of cyclometalating ligands can be rigid. This rigidity can allow for similar geometry between the ground and excited state, resulting in a narrow emission spectra dominated by the transition from the lowest vibrational level in the excited state to the lowest vibrational level in the ground state.

In another aspect, complexes can be designed to tune the values of the emitting fragment centered $^3LC$ state and the metal to ancillary ligand $^1MLCT$ states independently. Reduction in the differences in energy between these states ($\Delta E$) will improve mixing between them, improve the radiative decay rate, and suppress transitions that occur from the emissive state ($T_1$) to excited vibrational levels in the ground state ($S_0$). As a consequence, the vibrational shoulders of the emission spectra can be reduced, resulting in a more narrow emission profile.

In a further aspect, the molecular structure having four coordinating ligands to a metal center can be preferred. In such an aspect, a four ligand coordinated structure can at least partially ensure the electrochemical and/or photophysical stability of the complex during, for example, fabrication and operation of a color display device.

In another aspect, the inventive compositions can provide improved efficiency and/or operational lifetimes in lighting devices, such as, for example, organic light emitting devices, such as OLEDs, as compared to conventional materials. Thus, also disclosed herein are devices comprising the complexes described herein. One application for phosphorescent emissive complexes, such as those described herein, is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

In one aspect, for the formulas described herein, M can comprise Pt. In another aspect, M can comprise Pd. In yet another aspect, M can comprise Rh. In yet another aspect, M can comprise Ir. In yet another aspect, M can comprise Au. In yet another aspect, M can comprise Ag. In yet another aspect, M can comprise Cu. In yet another aspect, M can comprise Zr. In yet another aspect, M can comprise Hg. In yet another aspect, M can comprise Ga. In yet another aspect, M can comprise Co. In yet another aspect, M can comprise Os. In yet another aspect, M can comprise Ru.

In one aspect, for the formulas described herein, each of $Y^{1a}$, $Y^{1b}$, and $Y^{1c}$ independently can be O, $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to an adjacent ring structure, thereby forming a cyclic structure.

In one aspect, for the formulas described herein, each of $Y^{1a}$, $Y^{1b}$, $Y^{1c}$, $Y^{1d}$, and $Y^{1e}$ independently is O, $NR^2$, CR²R³, S, AsR², BR², PR², P(O)R², or SiR²R³, or a combination thereof, wherein each of R² and R³ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or R² and R³ together form C=O, wherein each of R² and R³ independently is optionally linked to an adjacent ring structure, thereby forming a cyclic structure.

In one aspect, at least one of $Y^{1a}$, $Y^{1b}$, and $Y^{1c}$ is NR². In another aspect, at least two of $Y^{1a}$, $Y^{1b}$, and $Y^{1c}$ are NR². In yet another aspect, $Y^{1a}$, $Y^{1b}$ and $Y^{1c}$ are NR².

In one aspect, at least one of $Y^{1a}$, $Y^{1b}$, $Y^{1c}$, $Y^{1d}$, and $Y^{1e}$ is NR². In another aspect, at least two of $Y^{1a}$, $Y^{1b}$, $Y^{1c}$, $Y^{1d}$, and $Y^{1e}$ are NR². In yet another aspect, at least three of $Y^{1a}$, $Y^{1b}$, $Y^{1c}$, $Y^{1d}$, and $Y^{1e}$, are NR².

In one aspect, for the formulas disclosed herein, at least one of $Y^{1a}$, $Y^{1b}$, $Y^{1c}$, $Y^{1d}$, and/or $Y^{1e}$ can independently comprise O. In another aspect, at least one of $Y^{1a}$, $Y^{1b}$, $Y^{1c}$, $Y^d$, and/or $Y^{1e}$ can independently comprise NR². In yet another aspect, at least one of $Y^{1a}$, $Y^{1b}$, $Y^{1c}$, $Y^{1d}$, and/or $Y^{1e}$ can independently comprise CR²R³. In yet another aspect, at least one of $Y^{1a}$, $Y^{1b}$, $Y^{1c}$, $Y^{1d}$, and/or $Y^{1e}$ can independently comprise S. In yet another aspect, at least one of $Y^{1a}$, $Y^{1b}$, $Y^{1c}$, $Y^{1d}$, and/or $Y^{1e}$ can independently comprise BR². In yet another aspect, at least one of $Y^{1a}$, $Y^{1b}$, $Y^{1c}$, $Y^{1d}$, and/or $Y^{1e}$ can independently comprise PR². In yet another aspect, at least one of $Y^{1a}$, $Y^{1b}$, $Y^{1c}$, $Y^{1d}$ and/or $Y^{1e}$ can independently comprise P(O)R². In yet another aspect, at least one of $Y^{1a}$, $Y^{1b}$, $Y^{1c}$, $Y^{1d}$, and/or $Y^{1e}$ can independently comprise SiR²R³. In one aspect, $Y^{1a}$, $Y^{1b}$, $Y^{1c}$, $Y^{1d}$, and/or $Y^{1e}$ can be oxygen In one aspect, each of R² and R³ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or R² and R³ together form C=O, wherein each of R² and R³ independently is optionally linked to an adjacent ring structure, thereby forming a cyclic structure. In another aspect, each of R² and R³ independently is hydrogen, alkyl, alkenyl, alkynyl, aryl, heteroaryl, cycloalkane, cycloalkane, or heterocyclyl, wherein each R² and R³ independently is optionally linked to an adjacent ring structure, thereby forming a cyclic structure. In yet another aspect, each of R² and R³ independently is hydrogen, alkyl, aryl, heteroaryl, or heterocyclyl, wherein each of R² and R³ independently is optionally linked to an adjacent ring structure, thereby forming a cyclic structure. In yet another aspect, one of R² or R³ is aryl, wherein each of R² and R³ independently is optionally linked to an adjacent ring structure, thereby forming a cyclic structure. In one aspect, each of R² and R³ independently is optionally linked to an adjacent ring structure, thereby forming a cyclic structure.

For each structure shown herein, it is appreciated that if an R² or R³ group is shown to be linked to an adjacent ring structure, such as a six or five membered ring. In one aspect, each of $Y^{1a}$, $Y^{1b}$, $Y^{1c}$, $Y^{1d}$, and/or $Y^{1e}$ can independently comprise

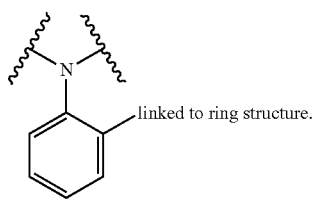
linked to ring structure.

Thus, forming a cyclic structure, for example

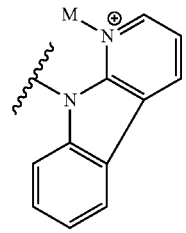

or. In another aspect, each of $Y^{1a}$, $Y^{1b}$, $Y^{1c}$, $Y^{1d}$, and/or $Y^{1e}$ can independently comprise

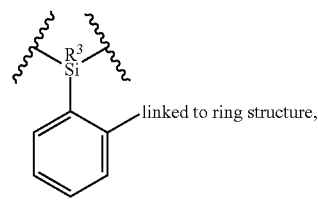
linked to ring structure, for example,

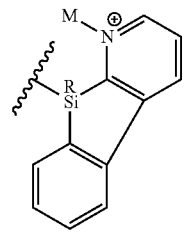

In another aspect, each of $Y^{1a}$, $Y^{1b}$, $Y^{1c}$, $Y^{1d}$, and/or $Y^{1e}$ can independently comprise

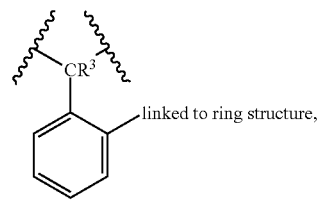
linked to ring structure, for example,

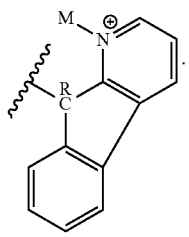

In yet another aspect, each of $Y^{1a}$, $Y^{1b}$, $Y^{1c}$, $Y^{1d}$, and/or $Y^{1e}$ can independently comprise

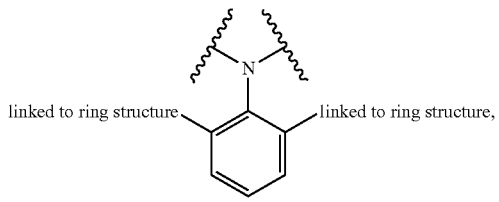

for example,

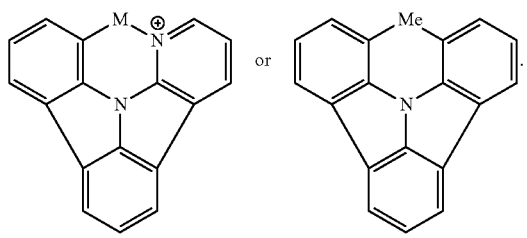

In yet another aspect, each of $Y^{1a}$, $Y^{1b}$, $Y^{1c}$, $Y^{1d}$ and/or $Y^{1e}$ can independently comprise

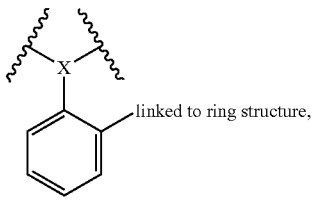

wherein X is N, B, P, or As. In yet another aspect, each of $Y^{1a}$, $Y^{1b}$, $Y^{1c}$, $Y^{1d}$, and/or $Y^{1e}$ can independently comprise

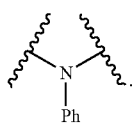 [SMILES: *N(*)c1ccccc1]

In yet another aspect, each of $Y^{1a}$, $Y^{1b}$ $Y^{1c}$, $Y^{1d}$, and/or $Y^{1e}$ can independently comprise

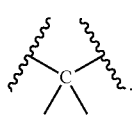 [SMILES: *C(*)(C)C]

In yet another aspect, each of $Y^{1a}$, $Y^{1b}$, $Y^{1c}$, $Y^{1d}$ and/or $Y^{1e}$ can independently comprise

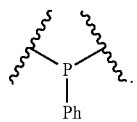 [SMILES: *P(*)c1ccccc1]

In yet another aspect, each of $Y^{1a}$, $Y^{1b}$, $Y^{1c}$, $Y^{1d}$, and/or $Y^{1e}$ can independently comprise

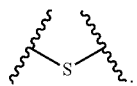

In yet another aspect, each of $Y^{1a}$, $Y^{1b}$, $Y^{1c}$, $Y^{1d}$, and/or $Y^{1e}$ can independently comprise

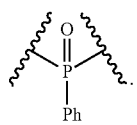 [SMILES: *P(*)(=O)c1ccccc1]

In one aspect, for the formulas described herein, each of $Y^{2a}$, $Y^{2b}$, $Y^{2c}$, and $Y^{2d}$ independently is N, $NR^{6a}$, or $CR^{6b}$, wherein each of $R^{6a}$ and $R^{6b}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene. In one aspect, at least one of $Y^{2a}$, $Y^{2b}$, $Y^{2c}$, and $Y^{2d}$ is $CR^{6b}$. In another aspect, at least two of $Y^{2a}$, $Y^{2b}$, $Y^{2c}$, and $Y^{2d}$ is $CR^{6b}$. In yet another aspect, at least three of $Y^{2a}$, $Y^{2b}$, $Y^{2c}$, and $Y^{2d}$ is $CR^{6b}$. In yet another aspect, at least one of $Y^{2a}$, $Y^{2b}$, $Y^{2c}$, and $Y^{2d}$ is $NR^{6a}$.

In one aspect, each of $Y^{3a}$, $Y^{3b}$, $Y^{3c}$, $Y^{3d}$, $Y^{3e}$, $Y^{4a}$, $Y^{4b}$, $Y^{4c}$, $Y^{4d}$ independently is N, O, S, $NR^{6a}$, $CR^{6b}$, wherein each of $R^{6a}$ and $R^{6b}$ independently hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; or $Z(R^{6c})_2$, wherein Z is C or Si, and wherein each $R^{6c}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene. In another aspect, at least four of $Y^{3a}$, $Y^{3b}$, $Y^{3c}$, and $Y^{3d}$ are $CR^{6b}$. In another aspect, at least three of $Y^{3a}$, $Y^{3b}$, $Y^{3c}$, and $Y^{3d}$ are $CR^{6b}$. In another aspect, at least one of $Y^{3a}$, $Y^{3b}$, $Y^{3c}$, and $Y^{3d}$ is N or $NR^{6a}$. In another aspect, at least four of $Y^{4a}$, $Y^{4b}$, $Y^{4c}$ and $Y^{4d}$ are $CR^{6b}$. In another aspect, at least three of $Y^{4a}$, $Y^{4b}$, $Y^{4c}$, and $Y^{4d}$ are $CR^{6b}$. In another aspect, at least one of $Y^{4a}$, $Y^b$, $Y^{4c}$, and $Y^{4d}$ is N or $NR^{6a}$.

In one aspect, of each of $Y^{5a}$, $Y^{5b}$, $Y^{5c}$, $Y^{5d}$, $Y^{6a}$, $Y^{6b}$, $Y^{6c}$ and $Y^{6d}$ independently is N, O, S, $NR^{6a}$, or $CR^{6b}$. In another aspect, at least four of $Y^{5a}$, $Y^{5b}$, $Y^{5c}$, and $Y^{5d}$ are $CR^{6b}$. In another aspect, at least three of $Y^{5a}$, $Y^{5b}$, $Y^{5c}$, and $Y^{5d}$ are $CR^{6b}$. In another aspect, at least one of $Y^{5a}$, $Y^{5b}$, $Y^{5c}$, and $Y^{5d}$ is N or $NR^{6a}$. In another aspect, at least four of $Y^{6a}$, $Y^{6b}$, $Y^{6c}$ and $Y^{6d}$, are $CR^{6b}$. In another aspect, at least three of $Y^{6a}$, $Y^{6b}$, $Y^{6c}$ and $Y^{6d}$ are $CR^{6b}$. In another aspect, at least one of $Y^{6a}$, $Y^{6b}$, $Y^{6c}$, and $Y^{6d}$ is N or $NR^{6a}$.

In one aspect, $R^{6b}$ hydrogen. In another aspect, at least one $R^{6b}$ is hydrogen. In another aspect, at least one $R^{6b}$ is alkyl or aryl.

In one aspect, $R^{6a}$ is hydrogen. In another aspect, at least one $R^{6a}$ is hydrogen. In another aspect, at least one $R^{6a}$ is alkyl or aryl.

In one aspect, m is 1. In another aspect, m is 2. In one aspect, at least one m is 1. In another aspect, at least one m is 2. In one aspect, n is 1. In another aspect, n is 2. In yet another aspect, at least one m is 1 and at least one m is 2. In yet another aspect, at least one m is 1 and n is 1. In yet another aspect, at least one m is 1 and n is 2. In yet another aspect, at least one m is 2 and n is 2. In yet another aspect, at least one m is 2 and n is 2.

In one aspect,

is partial unsaturation of the ring with which it is associated. In another aspect,

is full unsaturation of the ring with which it is associated. In another aspect, at least one

is full unsaturation of the ring with which it is associated and at least one

is partial unsaturation of the ring with which it is associated.

In one aspect, the compounds disclosed herein can have a structure where m is 2, n is 2, $Y^{2b}$ and $Y^{2c}$ is CH, $Y^{3b}$ and $Y^{4b}$ is N, at least one of $Y^{1b}$ and $Y^{1c}$ is $NR^2$, $CR^2R^3$, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to an adjacent ring structure, thereby forming a cyclic structure, and M is Pt or Pd.

In one aspect, the compounds disclosed herein can have a structure where m is 2, n is 2, $Y^{2b}$ is CH, $Y^{3b}$, $Y^{2c}$ and $Y^{4b}$ is N, $Y^{1b}$ is $NR^2$, $CR^2R^3$, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to an adjacent ring structure, thereby forming a cyclic structure, and M is Ir or Rh.

In one aspect, the compounds disclosed herein can have a structure where m is 2, n is 2, $Y^{2b}$, $Y^{2c}$ and $Y^{4b}$ is CH, $Y^{3b}$ is N, $Y^{1b}$ is $NR^2$, $CR^2R^3$, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to an adjacent ring structure, thereby forming a cyclic structure, and M is Au.

In one aspect, the compounds disclosed herein can have a structure where at least of one of $Y^{2a}$, $Y^{2d}$, $Y^{3d}$ and $Y^{4d}$ is C, at least one of $Y^{1b}$ and $Y^{1c}$ is $NR^2$, $CR^2R^3$, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, wherein $R^2$ is covalently linked to at least one of Yea, $Y^{2d}$, $Y^{3d}$ and $Y^{4d}$ thereby forming a cyclic structure, and M is Pt or Pd.

In another aspect, the compounds disclosed herein can have a structure where at least of one of $Y^{2a}$ and $Y^{3d}$ is C, $Y^{1b}$ is $NR^2$, $CR^2R^3$, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, wherein $R^2$ is covalently linked to at least one of Yea and $Y^{3d}$, thereby forming a cyclic structure, and M is Ir or Rh.

In another aspect, the compounds disclosed herein can have a structure where at least of one of $Y^{2a}$ and $Y^{3d}$ is C, $Y^{1b}$ is $NR^2$, $CR^2R^3$, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, wherein $R^2$ is covalently linked to at least one of Yea and $Y^{3d}$, thereby forming a cyclic structure, and wherein M is Au.

In another aspect, the compounds disclosed herein can have a structure where m is 2, $Y^{2b}$ and $Y^{2c}$ is CH, $Y^{3b}$ and $Y^{4b}$ is N, at least one of $Y^{1b}$ and $Y^{1c}$ is $NR^2$, $CR^2R^3$, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to an adjacent ring structure, thereby forming a cyclic structure, and M is Ir or Rh.

In another aspect, the compounds disclosed herein can have a structure where at least of one of $Y^{2a}$, $Y^{2d}$, $Y^{3d}$ and $Y^{4d}$ is C, at least one of $Y^{1b}$ and $Y^{1c}$ is $NR^2$, $CR^2R^3$, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, wherein $R^2$ is covalently linked to at least one of Yea, $Y^{2d}$, $Y^{3d}$ and $Y^{4d}$ thereby forming a cyclic structure, and M is Ir or Rh In another aspect, the compounds disclosed herein can have a structure where m is 2, n is 2, $Y^{2b}$ and $Y^{2c}$ is CH, $Y^{3b}$ and $Y^{4b}$ is N. In yet another aspect, the compounds disclosed herein can have a structure where m is 2, n is 2, and $Y^{2b}$ and $Y^{2c}$ is CH. In another aspect, the compounds disclosed herein can have a structure where m is 2, n is 2, and $Y^{3b}$ and $Y^{4b}$ is N.

In one aspect, for the formulas described herein, each of $E^1$, $E^2$, $E^3$, $E^4$, and/or $E^5$ can independently comprise O, $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure.

In one aspect, at least one of $E^1$, $E^2$, $E^3$, $E^4$, and/or $E^5$ can independently comprise O. In another aspect, at least one of $E^1$, $E^2$, $E^3$, $E^4$, and/or $E^5$ can independently comprise $NR^2$. In yet another aspect, at least one of $E^1$, $E^2$, $E^3$, $E^4$, and/or $E^5$ can independently comprise $CR^2R^3$. In yet another aspect, at least one of $E^1$, $E^2$, $E^3$, $E^4$, and/or $E^5$ can independently comprise S. In yet another aspect, at least one of $E^1$, $E^2$, $E^3$, $E^4$, and/or $E^5$ can independently comprise $BR^2$. In yet another aspect, at least one of $E^1$, $E^2$, $E^3$, $E^4$, and/or $E^5$ can independently comprise $PR^2$. In yet another aspect, at least one of $E^1$, $E^2$, $E^3$, $E^4$, and/or $E^5$ can independently comprise $P(O)R^2$. In yet another aspect, at least one of $E^1$, $E^2$, $E^3$, $E^4$, and/or $E^5$ can independently comprise $SiR^2R^3$. In one aspect, $E^1$, $E^2$, $E^3$, $E^4$, and $E^5$ can be oxygen.

In one aspect, at least one of $E^1$, $E^2$, $E^3$, $E^4$, and/or $E^5$ can independently can be absent from a structure recited herein, whereby a bond is then directly present between any Ns and/or Cs.

In one aspect, each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C and/or N, thereby forming a cyclic structure. In another aspect, each of $R^2$ and $R^3$ independently is hydrogen, alkyl, alkenyl, alkynyl, aryl, heteroaryl, cycloalkane, cycloalkane, or heterocyclyl, wherein each of $R^2$ and $R^3$ independently is optionally linked to a C and/or N, thereby forming a cyclic structure. In yet another aspect, each of $R^2$ and $R^3$ independently is hydrogen, alkyl, aryl, heteroaryl, or heterocyclyl, wherein each of $R^2$ and $R^3$ independently is optionally linked to a C or N, thereby forming a cyclic structure. In yet another aspect, one of $R^2$ or $R^3$ is aryl, wherein each of $R^2$ and $R^3$ independently is optionally linked to a C or N, thereby forming a cyclic structure. In one aspect, each of $R^2$ and $R^3$ independently is linked to a C or N, thereby forming a cyclic structure.

For each structure shown herein, it is appreciated that if an $R^2$ or $R^3$ group is shown to be linked to a N, then it can also be bound to C in a similar type structure. In one aspect, each of $E^1$, $E^2$, $E^3$, $E^4$, and/or $E^5$ can independently comprise

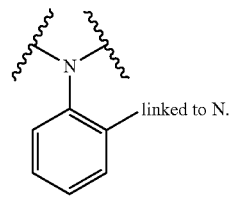
linked to N.

Thus, forming a cyclic structure, for example

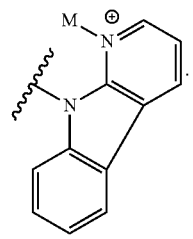

It is also understood that each of $E^1$, $E^2$, $E^3$, $E^4$, and/or $E^5$ can independently be linked to C in a similar manner, thereby forming, for example,

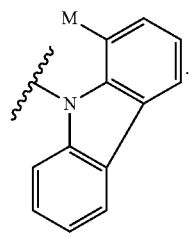

In another aspect, each of $E^1$, $E^2$, $E^3$, $E^4$, and/or $E^5$ can independently comprise

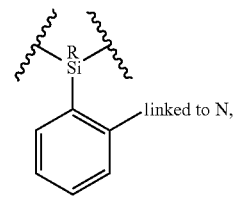
linked to N, for example,

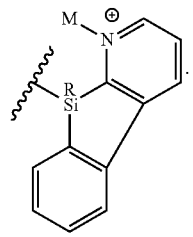

In another aspect, each of $E^1$, $E^2$, $E^3$, $E^4$, and/or $E^5$ can independently comprise

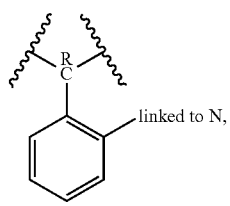
linked to N, for example,

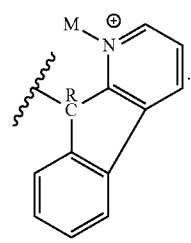

In yet another aspect, each of $E^1$, $E^2$, $E^3$, $E^4$, and/or $E^5$ can independently comprise

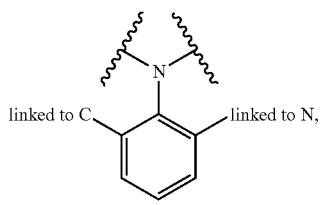

for example,

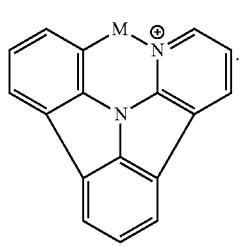

In yet another aspect, each of $E^1$, $E^2$, $E^3$, $E^4$, and/or $E^5$ can independently comprise

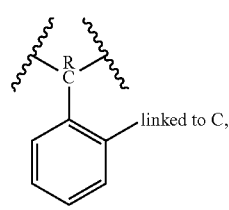

for example,

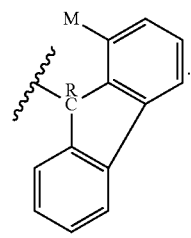

In yet another aspect, each of $E^1$, $E^2$, $E^3$, $E^4$, and/or $E^5$ can independently comprise

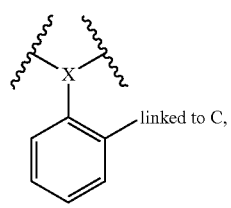

wherein X is N, B, P, or As. In yet another aspect, each of $E^1$, $E^2$, $E^3$, $E^4$, and/or $E^5$ can independently comprise

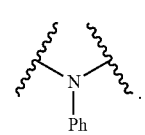

In yet another aspect, each of $E^1$, $E^2$, $E^3$, $E^4$, and/or $E^5$ can independently comprise

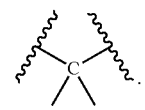

In yet another aspect, each of $E^1$, $E^2$, $E^3$, $E^4$, and/or $E^5$ can independently comprise

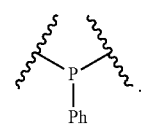

In yet another aspect, each of $E^1$, $E^2$, $E^3$, $E^4$, and/or $E^5$ can independently comprise

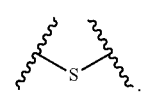

In yet another aspect, each of $E^1$, $E^2$, $E^3$, $E^4$, and/or $E^5$ can independently comprise

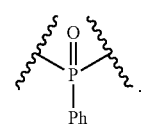

In yet another aspect, each of $E^1$, $E^2$, $E^3$, $E^4$, and/or $E^5$ can independently comprise

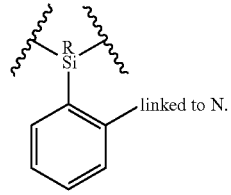
linked to N.

In one aspect, at least one of $E^1$, $E^2$, and $E^3$ is O. In another aspect, at least two of $E^1$, $E^2$, and $E^3$ are O. In one aspect, at least one of $E^1$, $E^2$, and $E^3$ is $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure.

In one aspect, $E^1$, $E^2$, and $E^3$ can be oxygen. In one aspect, $E^1$, $E^2$, and $E^3$ can comprise O, $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure. In another aspect, $E^1$ and $E^3$ can be oxygen. In yet another aspect $E^2$ comprise O, $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure.

In one aspect, at least one of $E^1$, $E^2$, and $E^3$ is

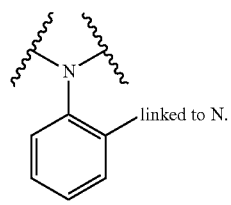
linked to N.

In another aspect, at least one of $E^1$, $E^2$, and $E^3$ is

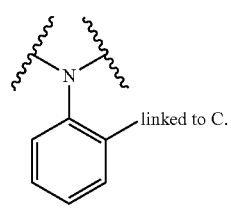
linked to C.

In yet another aspect, at least one of $E^1$, $E^2$, and $E^3$ is

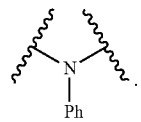

In yet another aspect, at least one of $E^1$, $E^2$, and $E^3$ is

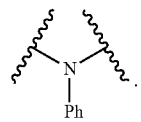

In yet another aspect, at least one of $E^1$, $E^2$, and $E^3$ is

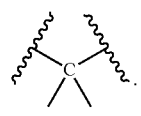 [SMILES: *C(*)(C)C]

In yet another aspect, at least one of $E^1$, $E^2$, and $E^3$ is

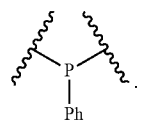

In yet another aspect, at least one of $E^1$, $E^2$, and $E^3$ is

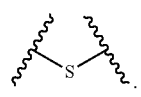

In yet another aspect, at least one of $E^1$, $E^2$, and $E^3$ is

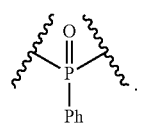

In one aspect, at least one of $E^1$, $E^2$, $E^3$, and $E^4$ is O. In another aspect, at least two of $E^1$, $E^2$, $E^3$, and $E^4$ are O. In yet another aspect, at least three of $E^1$, $E^2$, $E^3$, and $E^4$ are O. In yet another aspect, $E^1$, $E^2$, and $E^3$ can be oxygen. In yet another aspect, $E^1$, $E^2$, $E^3$, and $E^4$ can be oxygen. In yet another aspect, $E^1$, $E^2$, $E^3$, $E^4$, and $E^5$ can be oxygen.

In one aspect, at least one of $E^1$, $E^2$, $E^3$, and $E^4$ is $NR^2$. In another aspect, at least two of $E^1$, $E^2$, $E^3$, and $E^4$ are $NR^2$. In yet another aspect, at least three of $E^1$, $E^2$, $E^3$, and $E^4$ are $NR^2$. In yet another aspect, $E^1$, $E^2$, and $E^3$ can be $NR^2$. In yet another aspect, $E^1$, $E^2$, $E^3$, and $E^4$ can be $NR^2$. In yet another aspect, $E^1$, $E^2$, $E^3$, $E^4$, and $E^5$ can be $NR^2$.

In one aspect, at least one of $E^1$, $E^2$, $E^3$, and $E^4$ is $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure. In one aspect, at least two of $E^1$, $E^2$, $E^3$, and $E^4$ is $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure.

In one aspect, at least one N is

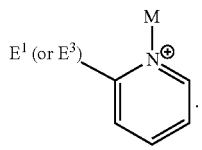

In another aspect, at least one N is

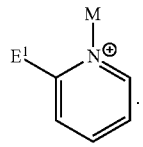

In yet another aspect, at least one N is

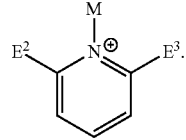

In yet another aspect, at least one N is

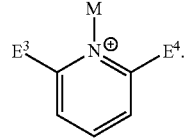

In yet another aspect, at least one N is

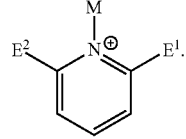

In yet another aspect, at least one N is

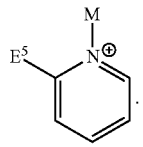

In another aspect, the N groups can be substituted heterocyclyl. In another aspect, the N groups can be unsubstituted heterocyclyl. In another aspect, the N groups can be pyridine.

In one aspect, at least one C is

In another aspect, at least one C is

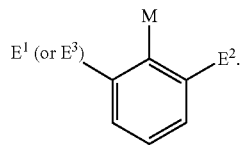

In yet another aspect, at least one C is

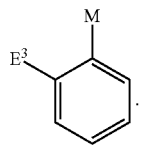

In yet another aspect, at least one C is

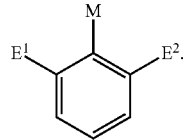

In yet another aspect, at least one C is

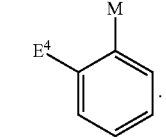

In yet another aspect, at least one C is

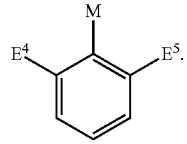

In yet another aspect, at least one C is

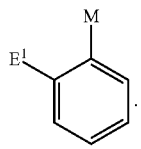

In one aspect, C can be an unsubstituted aromatic ring or heterocyclic group. In another aspect, C can be a unsubstituted aromatic ring or heterocyclic group. In another aspect, C can be a substituted aromatic ring or heterocyclic group. In one aspect, the C groups can be phenyl.

Some structures recited herein refer to "R" which can represent $R^2$ or $R^3$ as defined herein.

The following structures can as appropriate be a subgenus and/or individual compound of the disclosed generic structures disclosed herein. It is appreciated that some of these structures have different indicators, i.e. $R^1$, A, U etc. than those in the corresponding in the generic structure. For example, it is appreciated that X, A, and A in

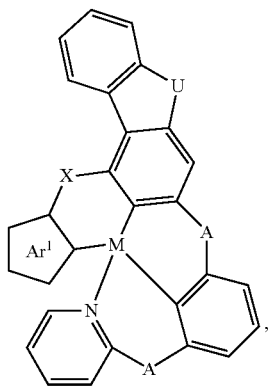

would correspond to $Y^{1b}$, $Y^{1a}$ and $Y^{1c}$ respectively in

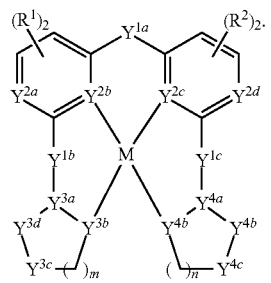

Thus, X, A, and A can have the meaning of $Y^{1b}$, $Y^{1a}$, and $Y^{1c}$ as described herein.

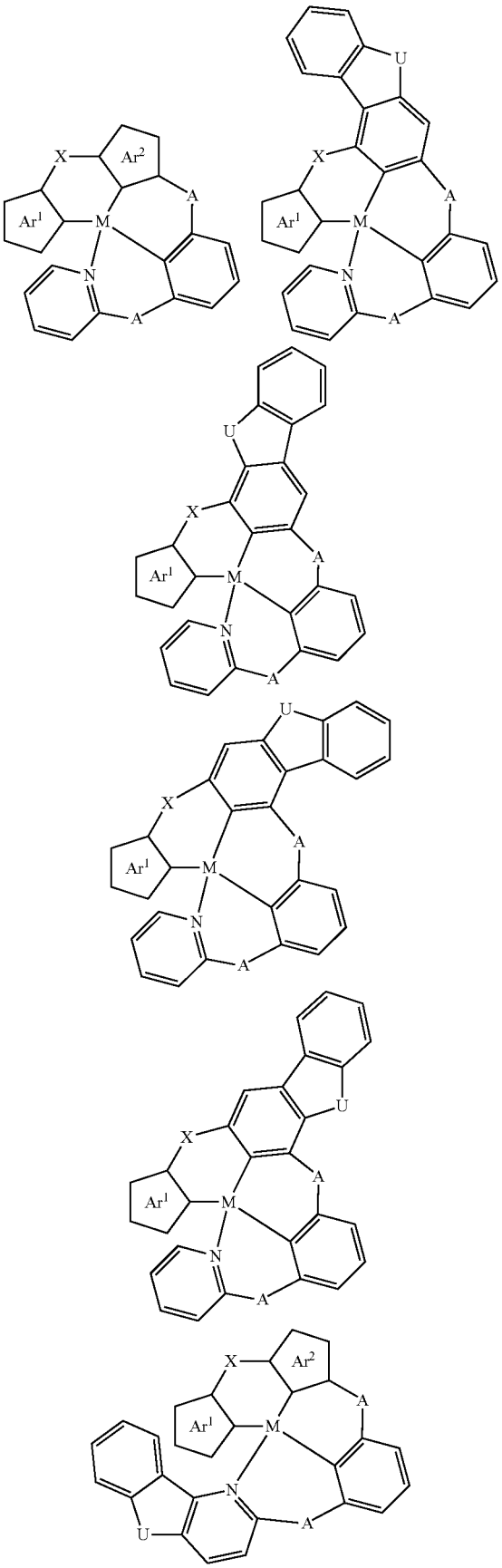

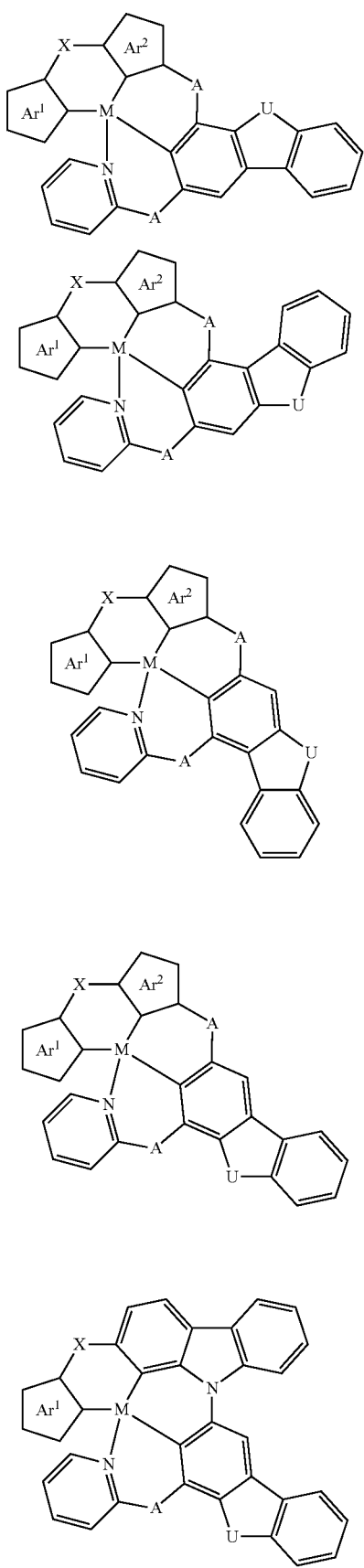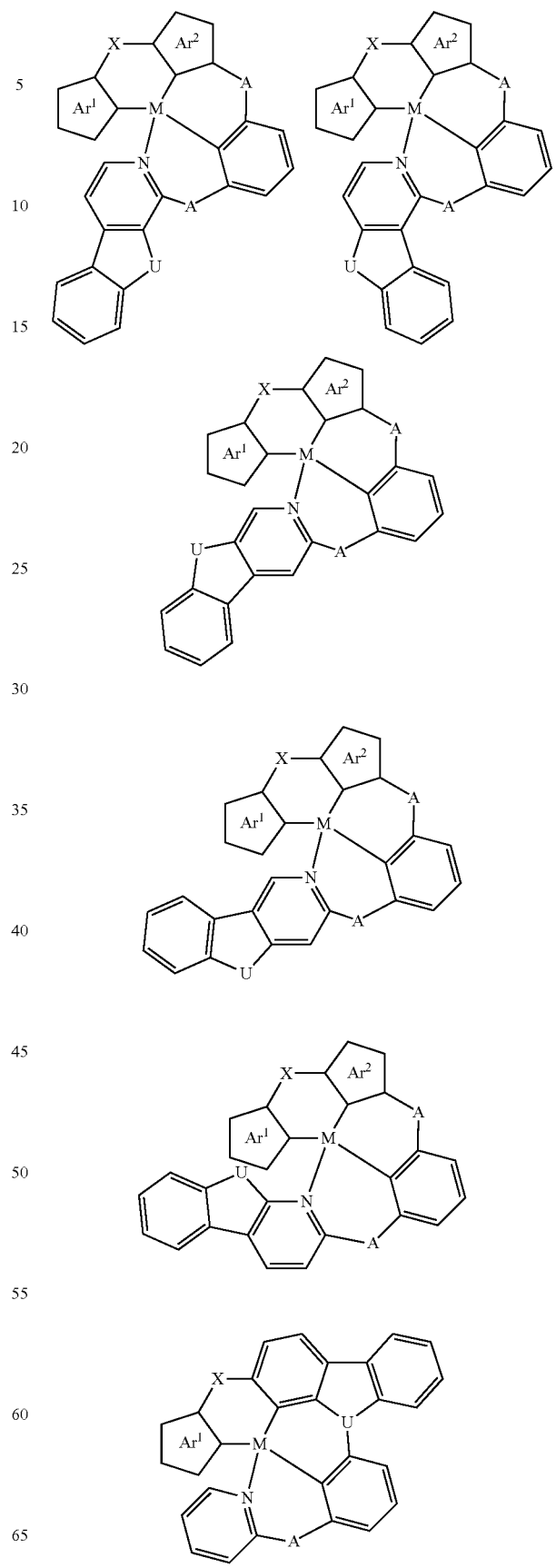

-continued
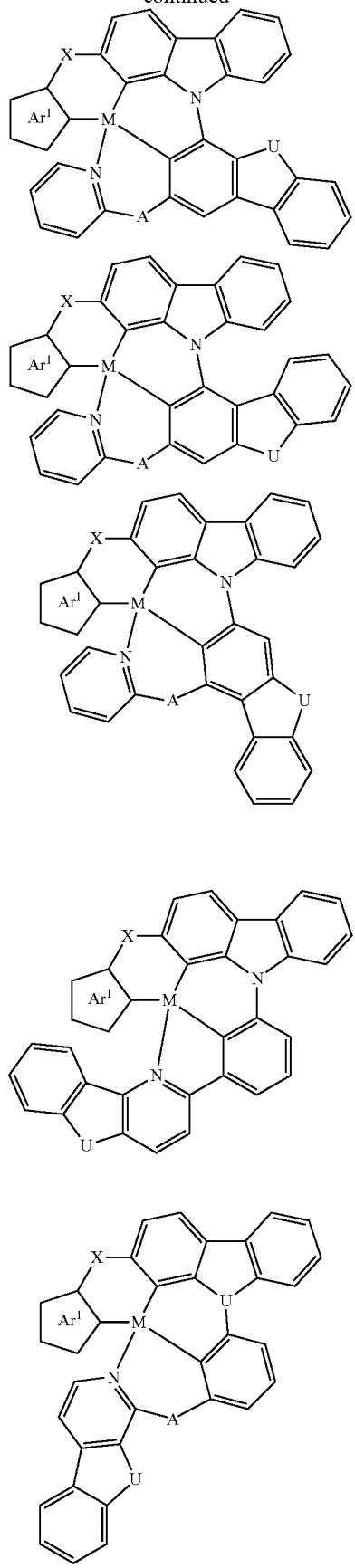
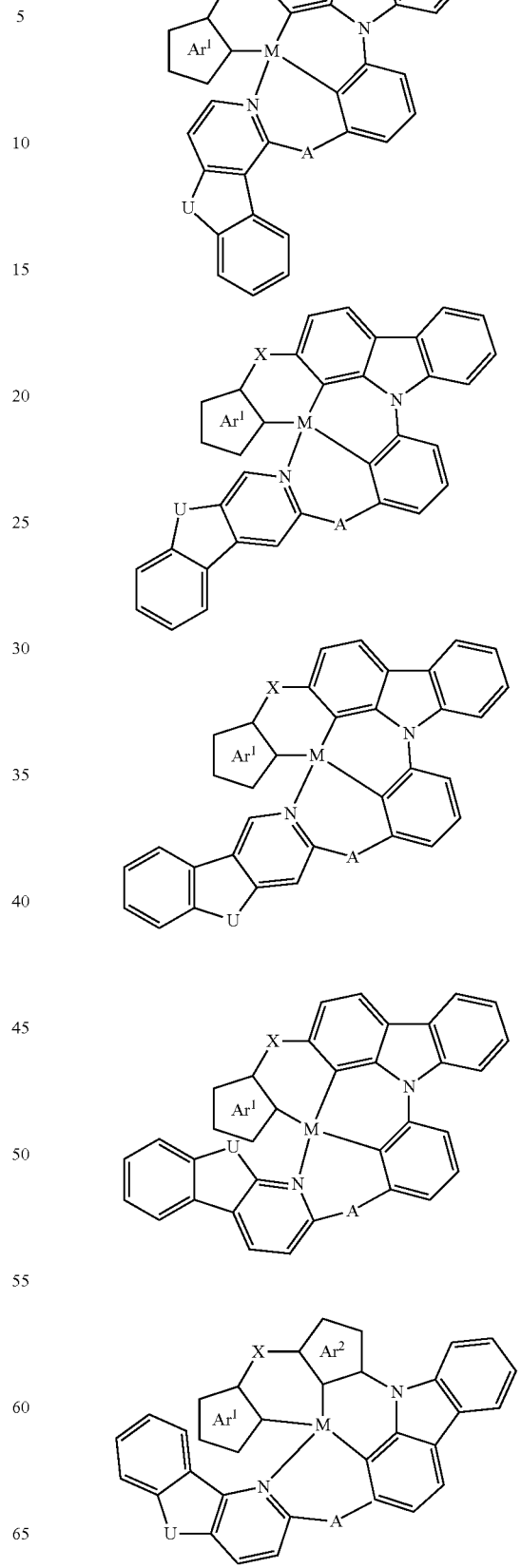

-continued
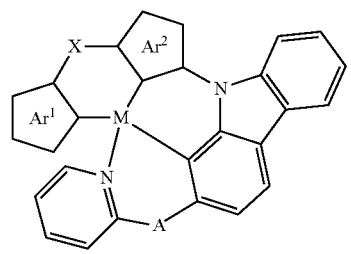
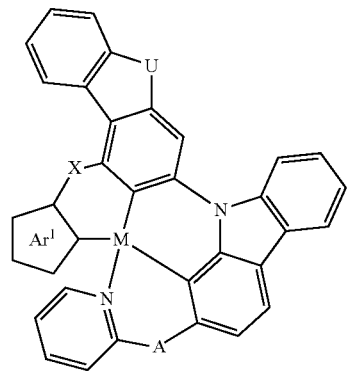
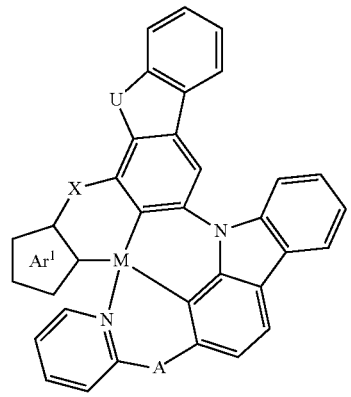
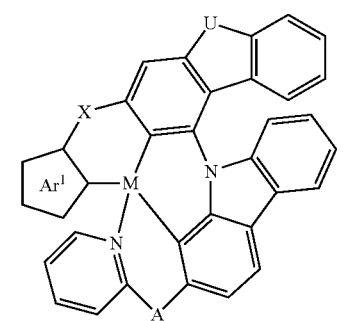
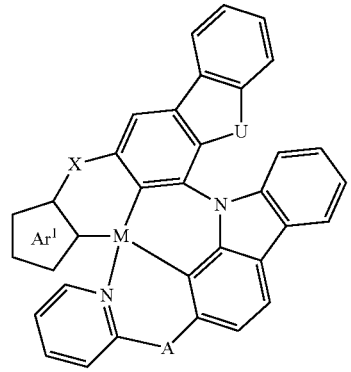
-continued
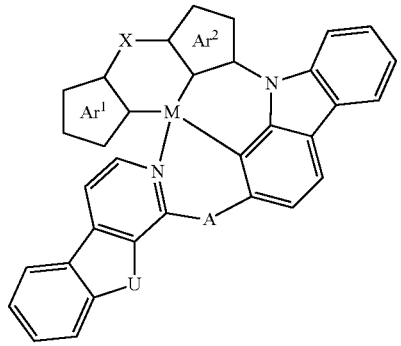
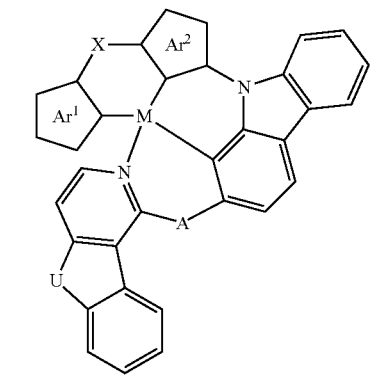
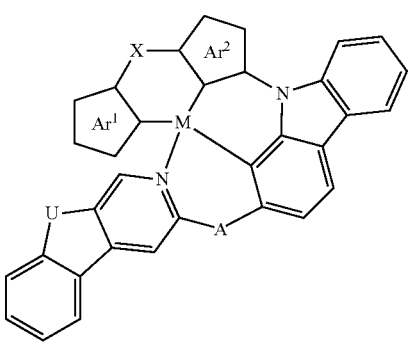
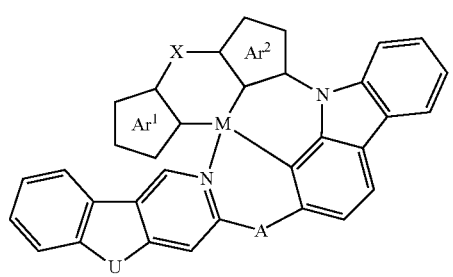
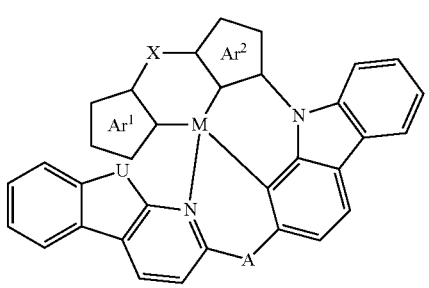

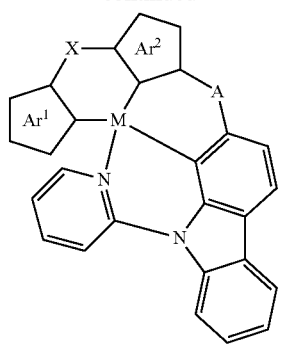
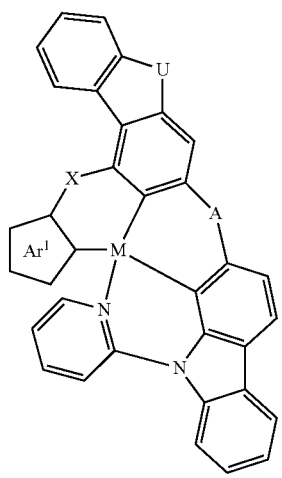
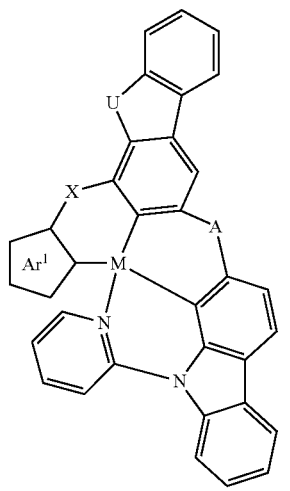
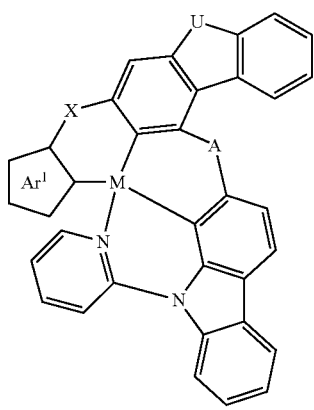
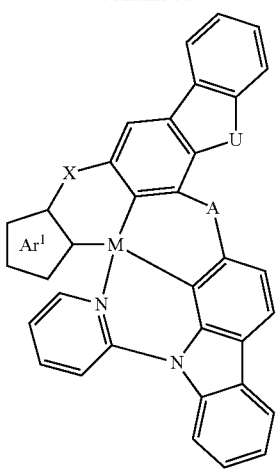
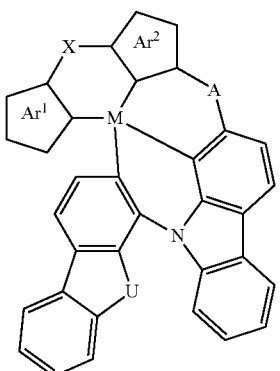
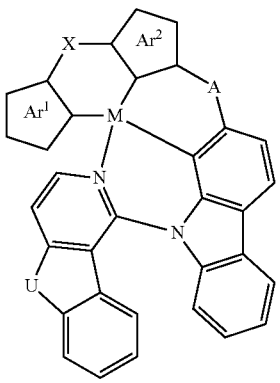
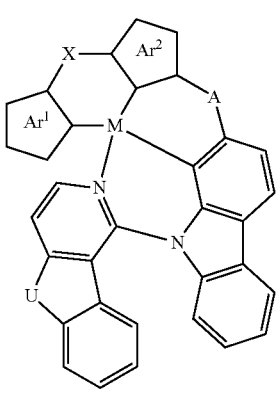
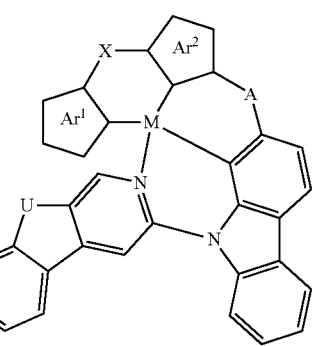

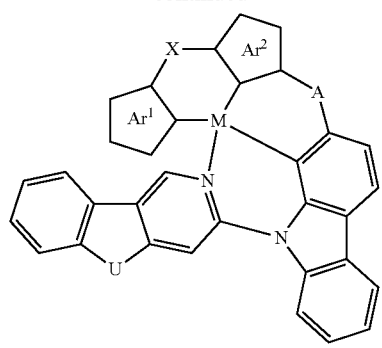
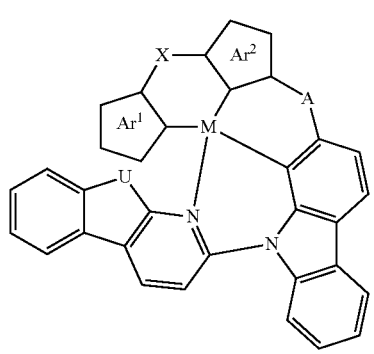
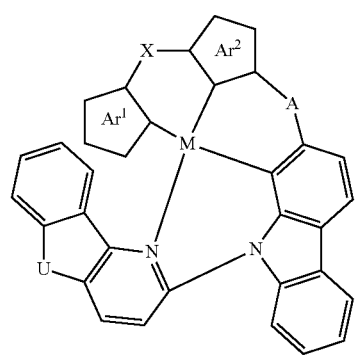
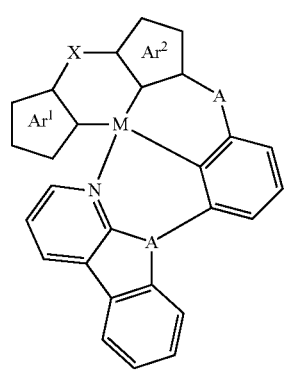
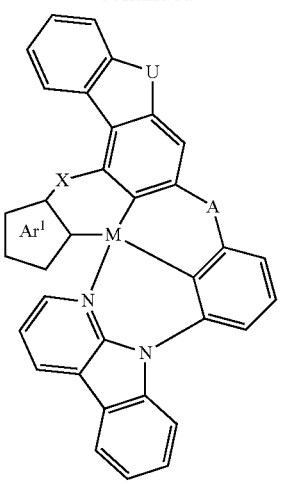
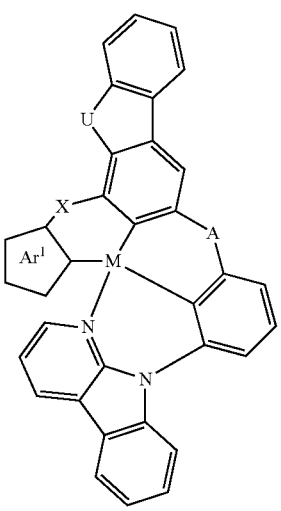
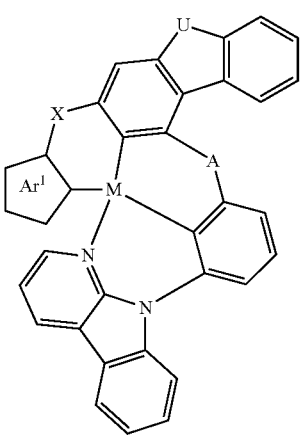

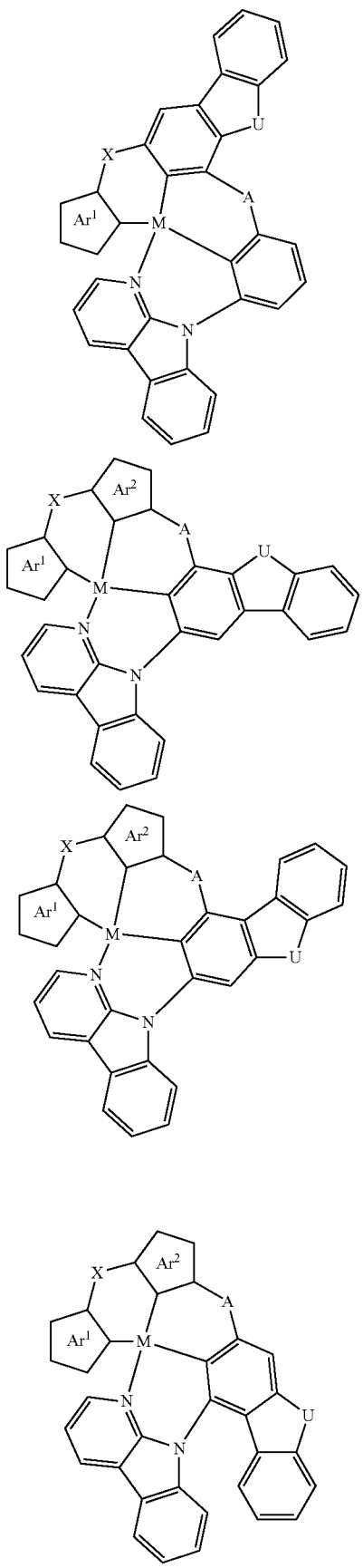
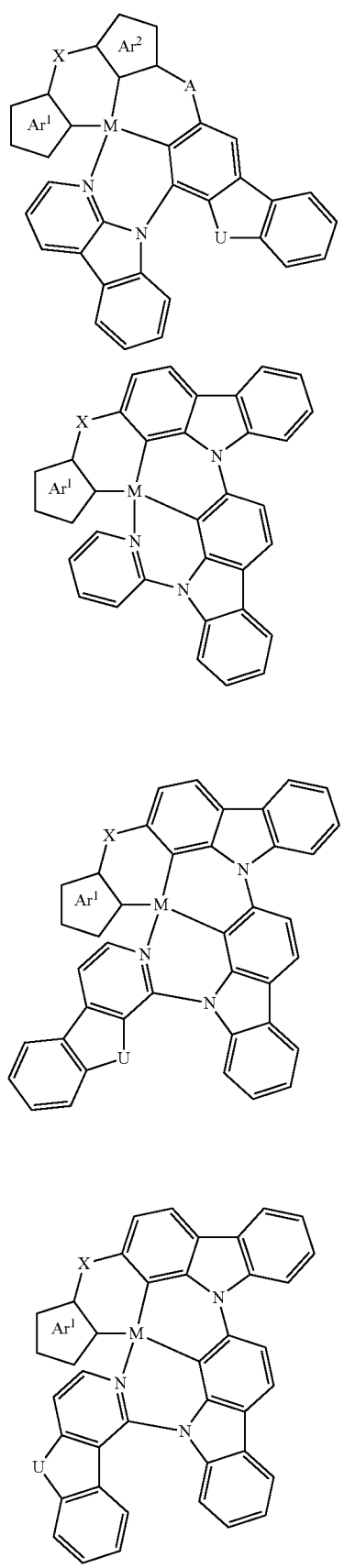

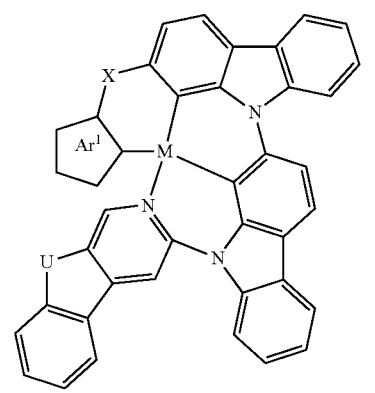
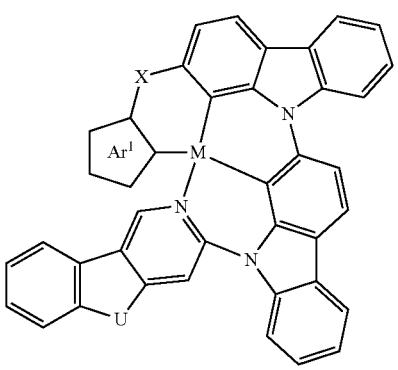
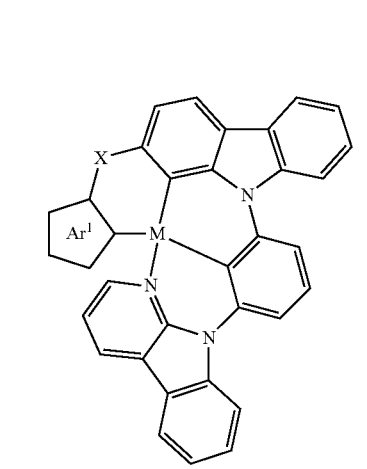
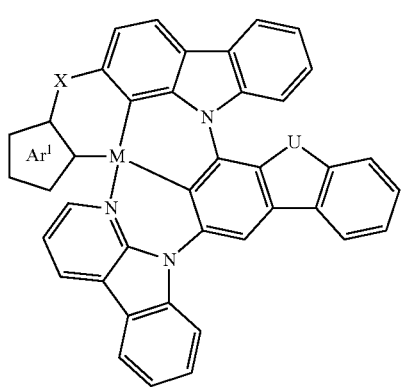
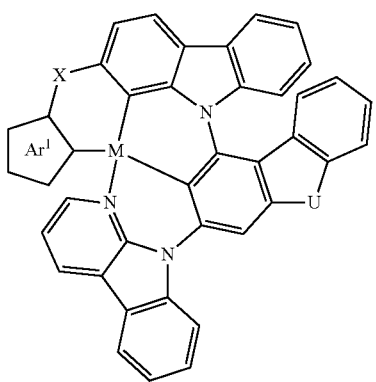
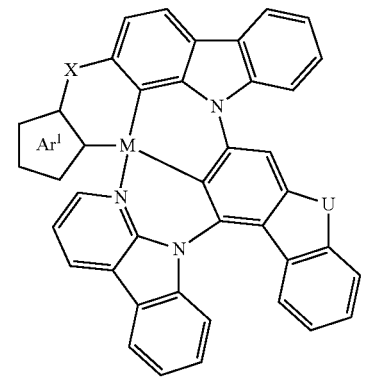
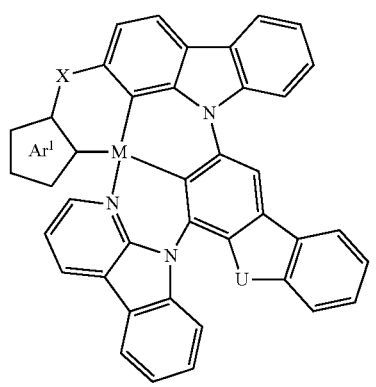
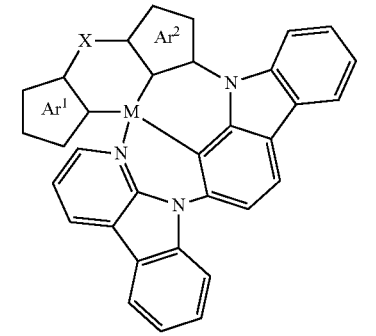

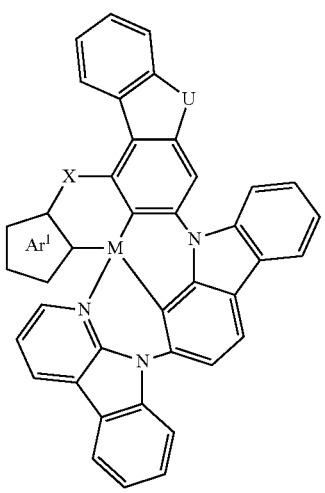
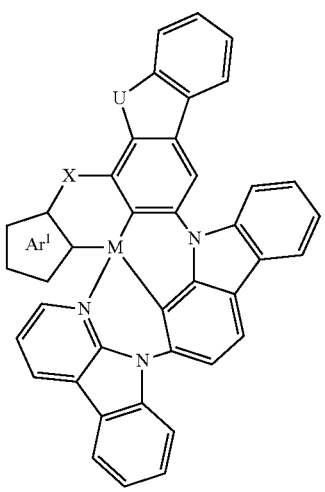
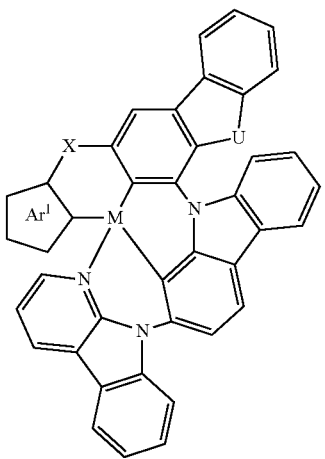
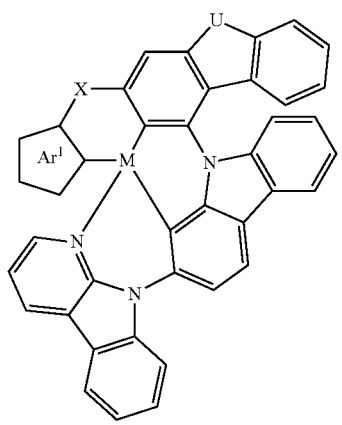
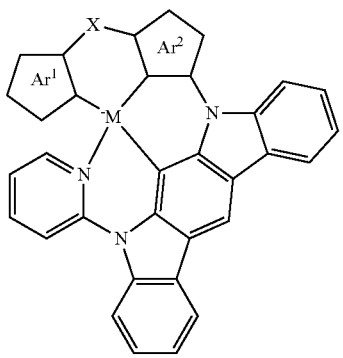
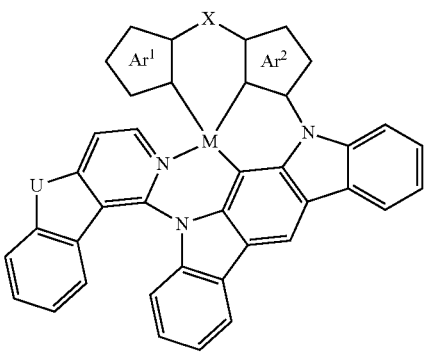
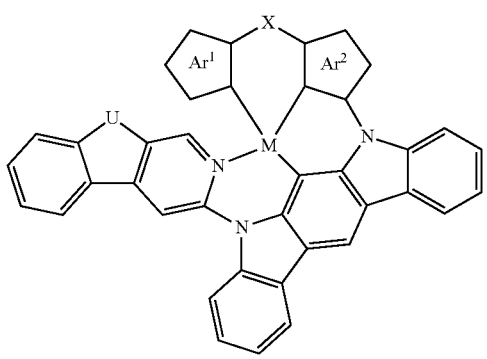

-continued
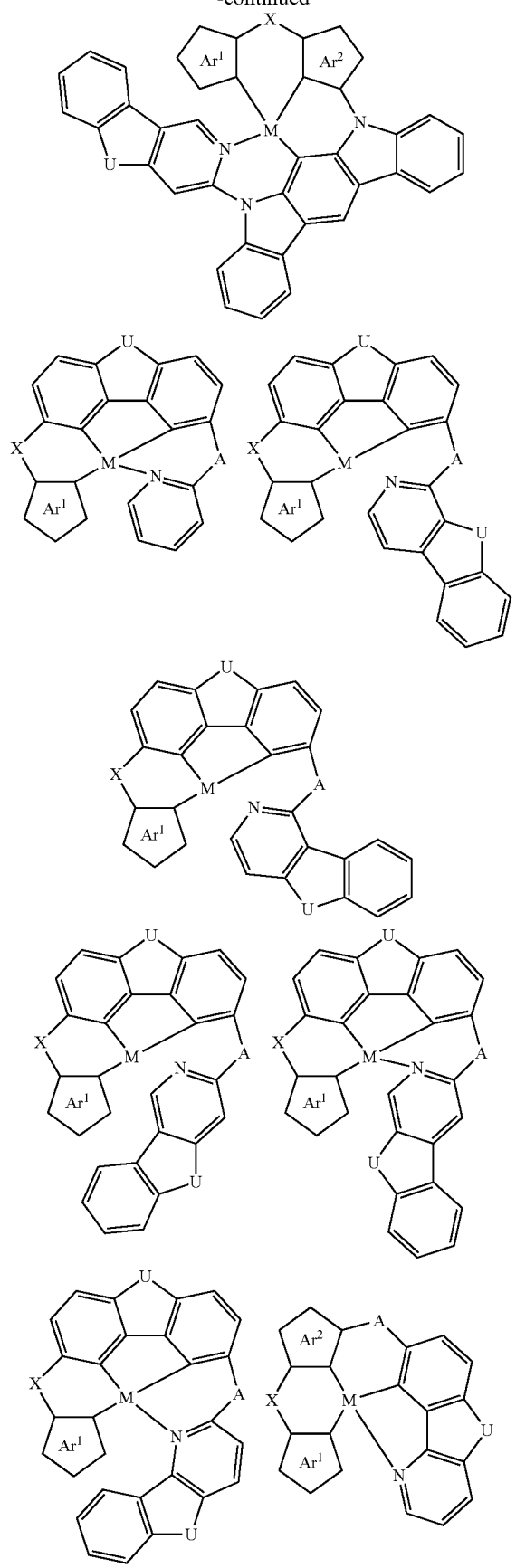
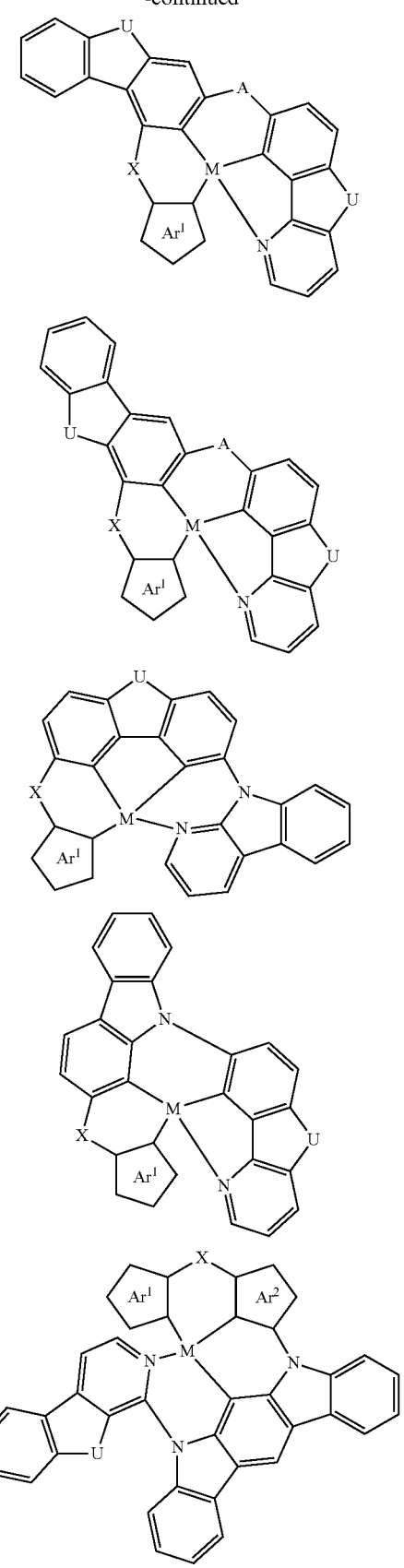

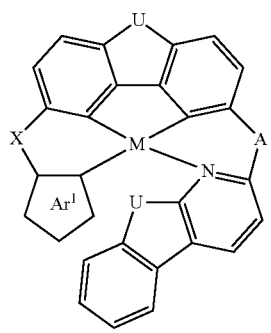
Specific compounds include but are not limited to:
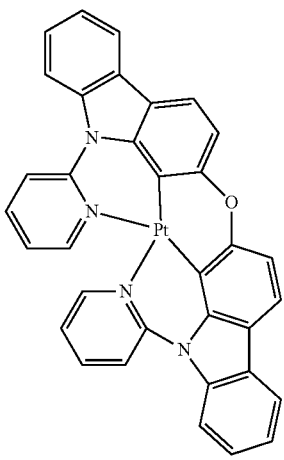
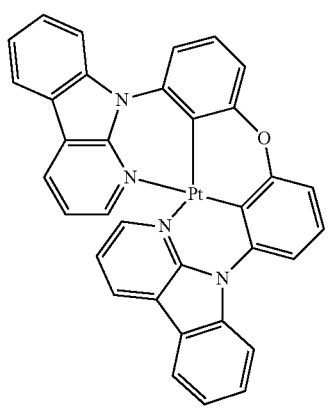
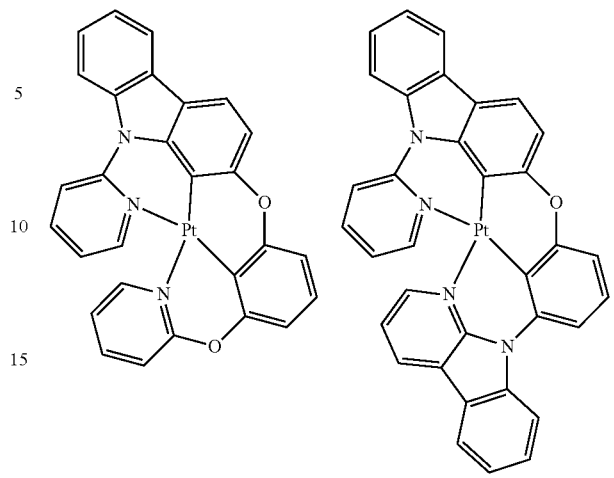
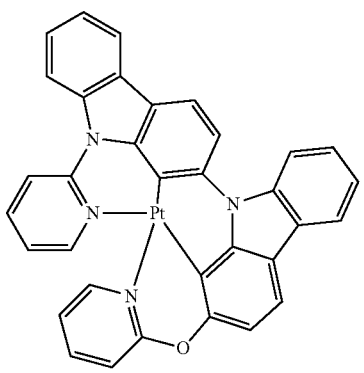
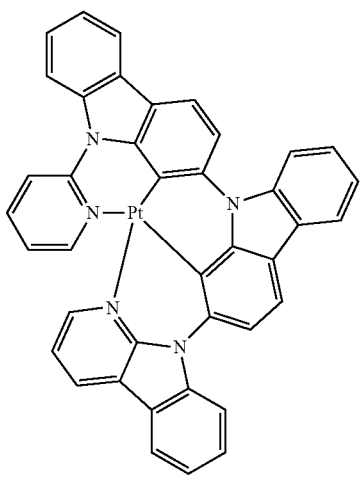

51
-continued
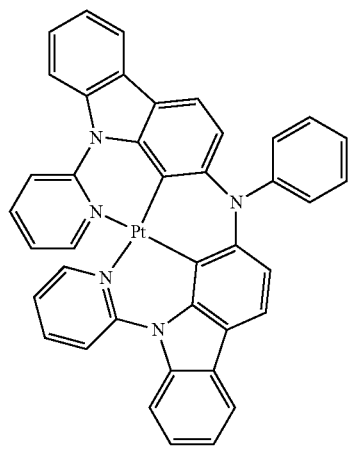
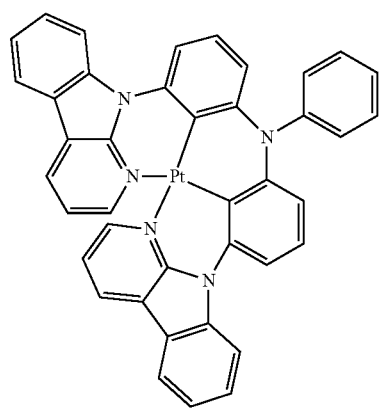
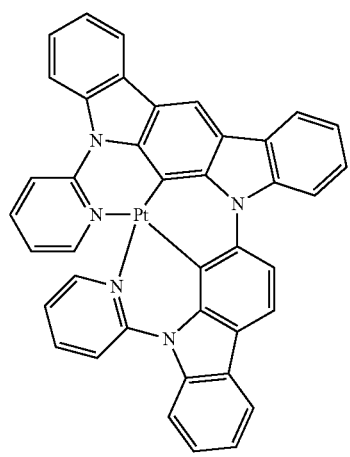
52
-continued
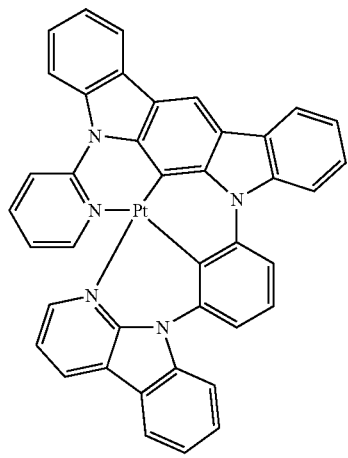
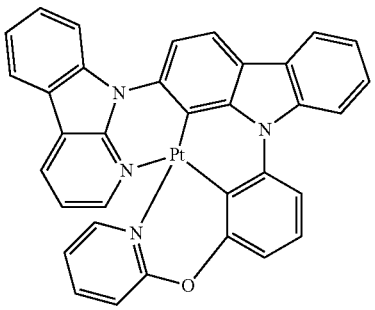
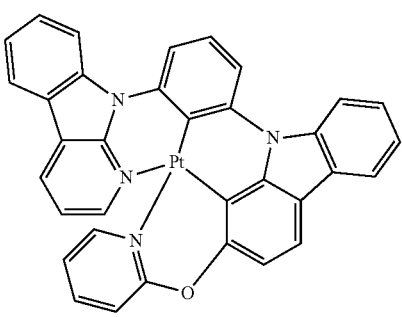
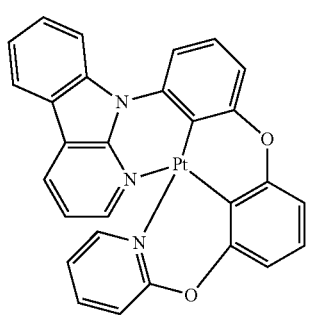

53
-continued

54
-continued

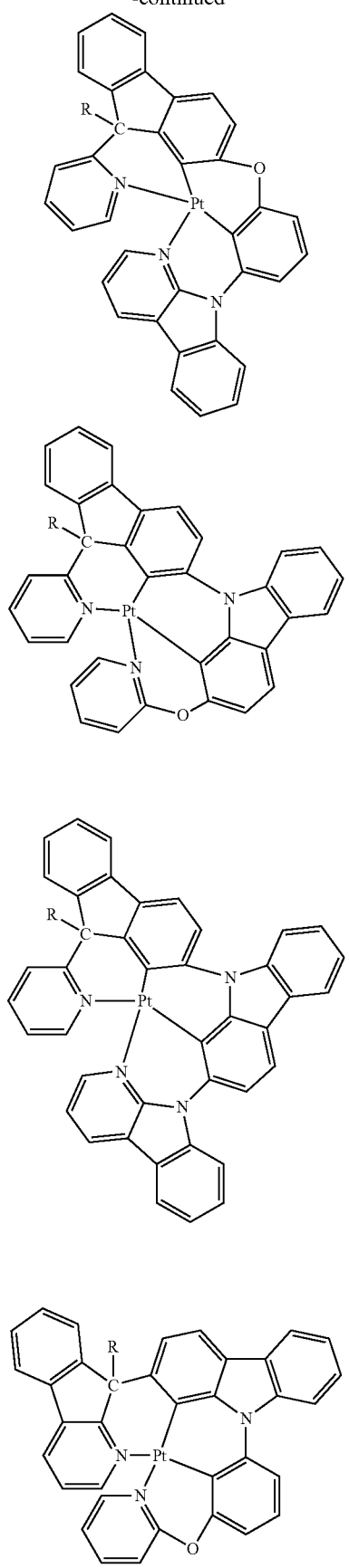
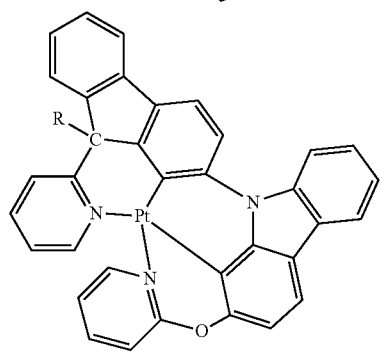
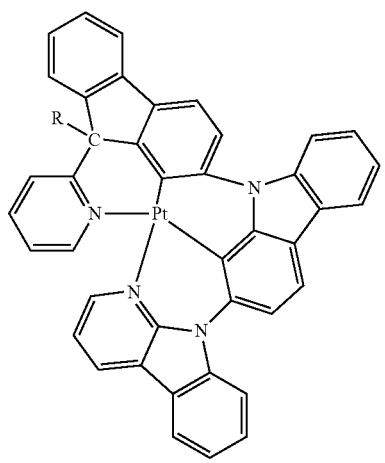
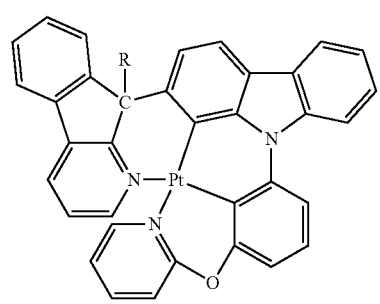
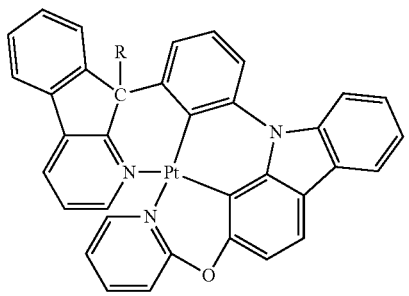
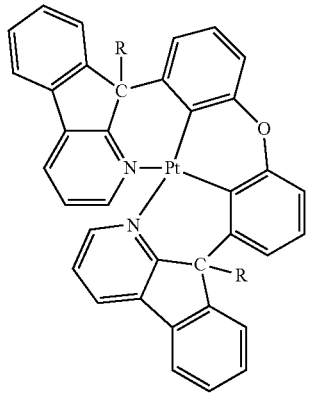
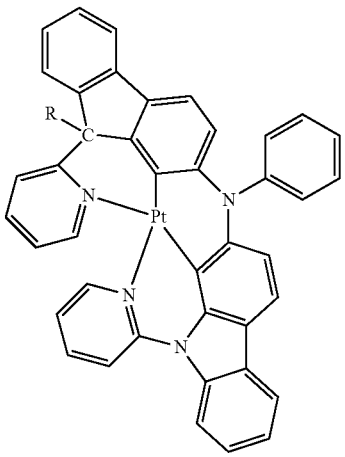
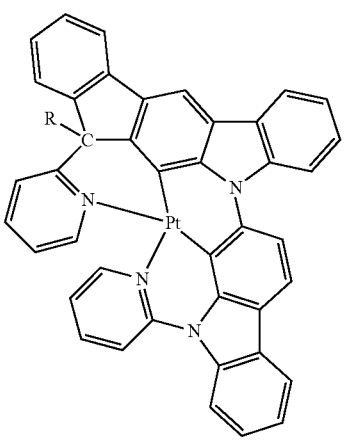

-continued
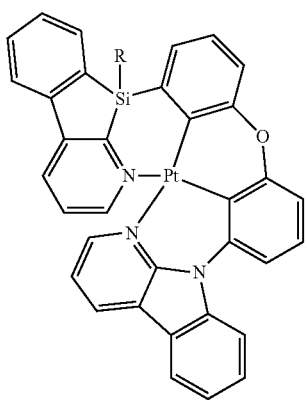
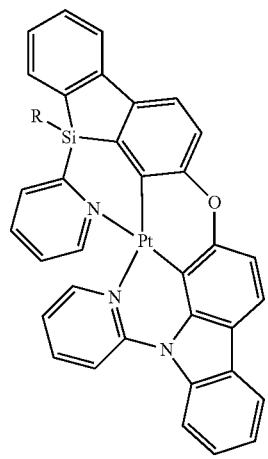
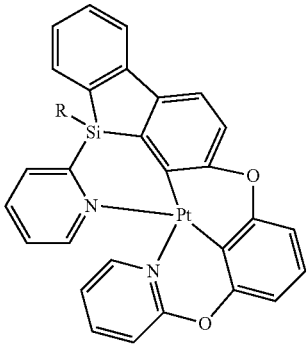
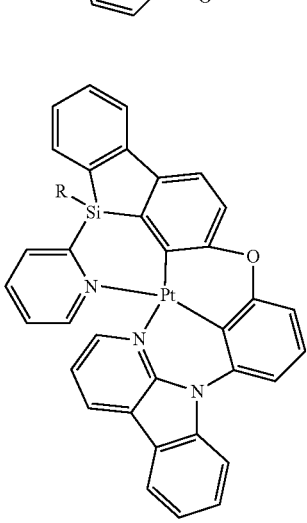
-continued
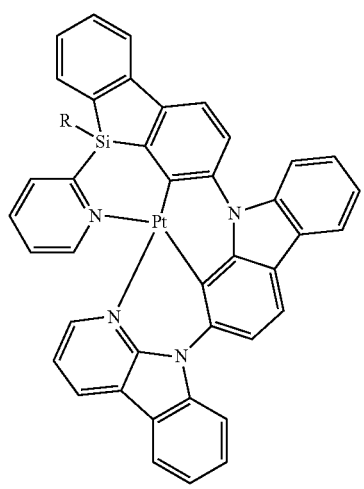
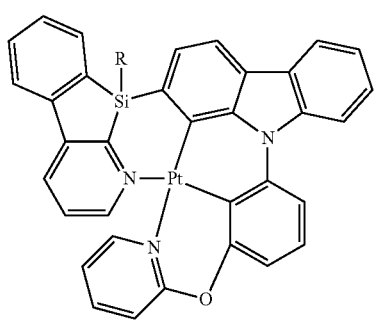
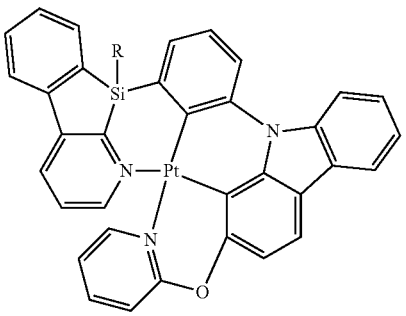
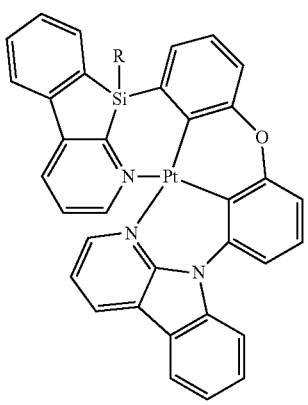

-continued
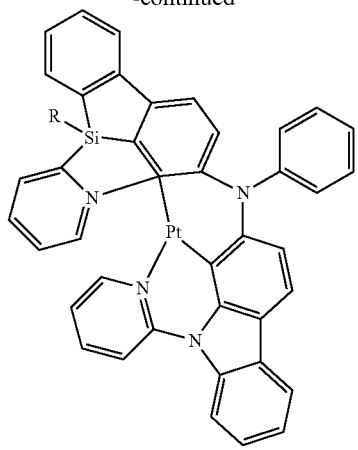
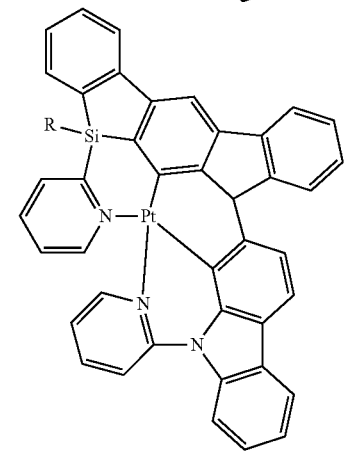
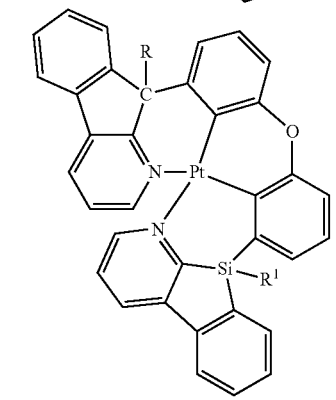
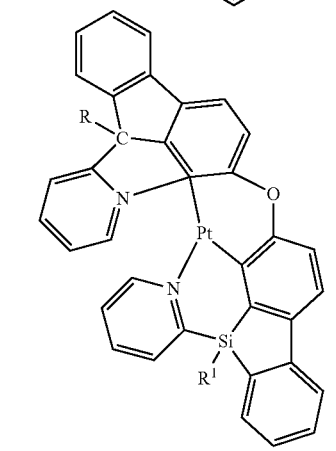
-continued
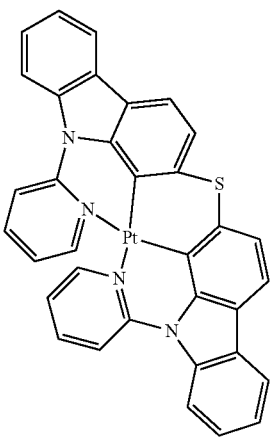
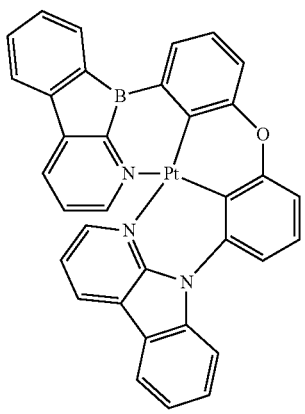
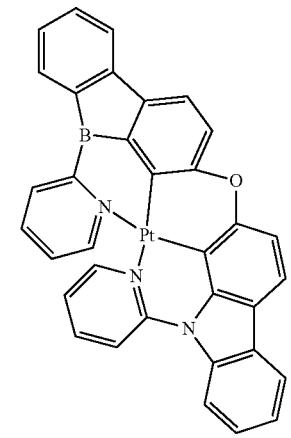

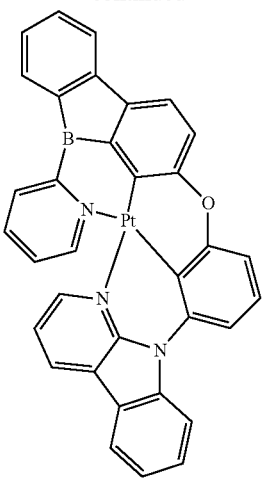
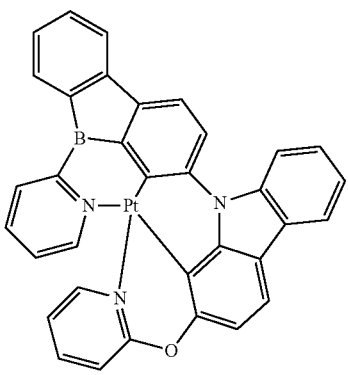
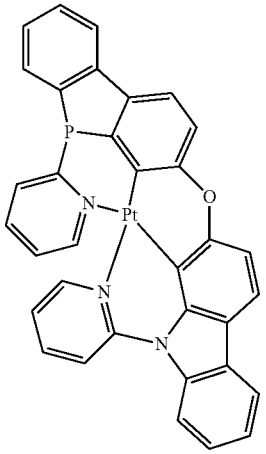
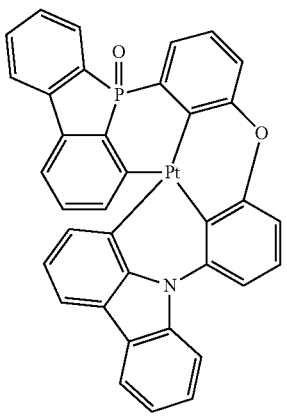
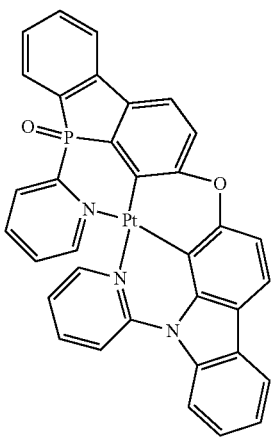
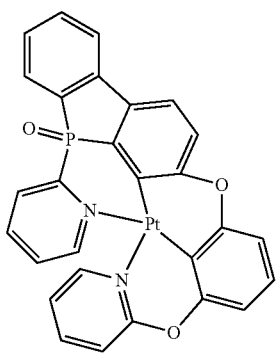
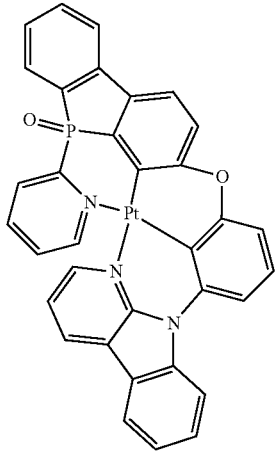
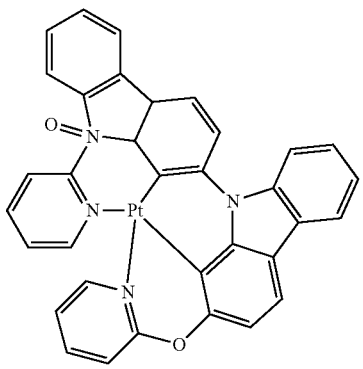

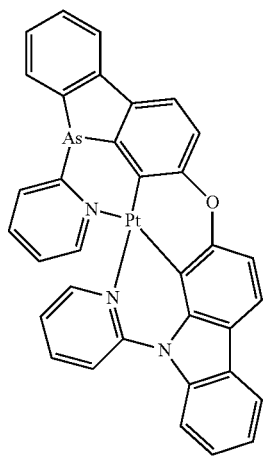
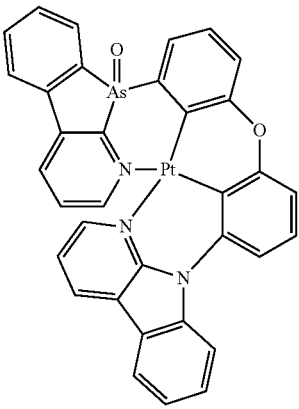
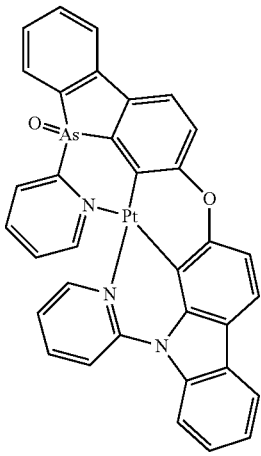
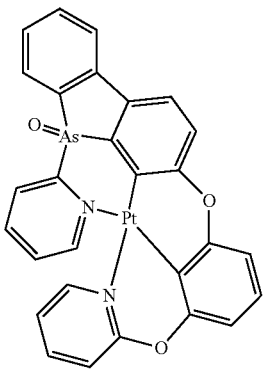
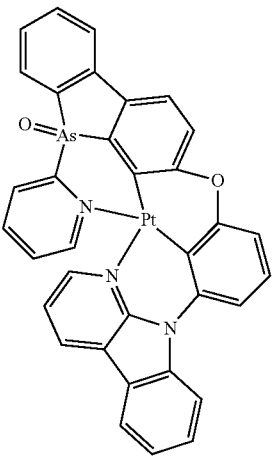
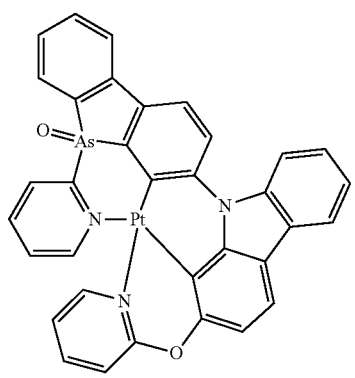
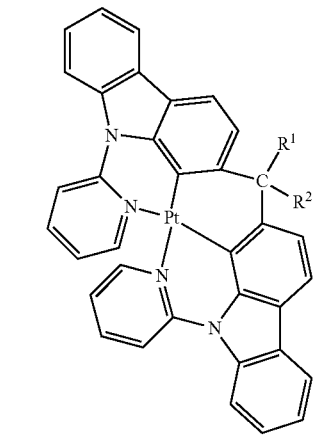
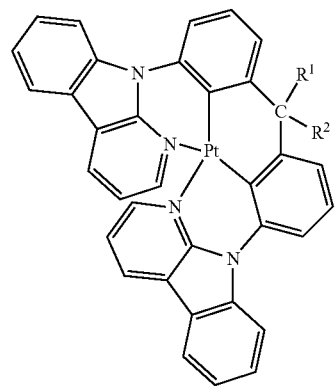

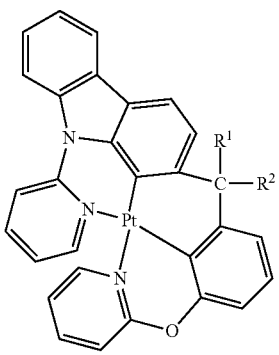
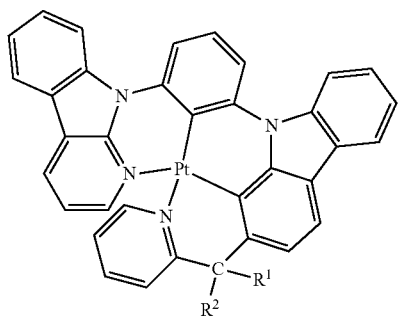
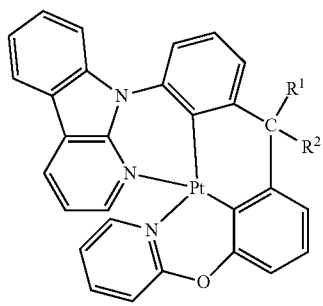
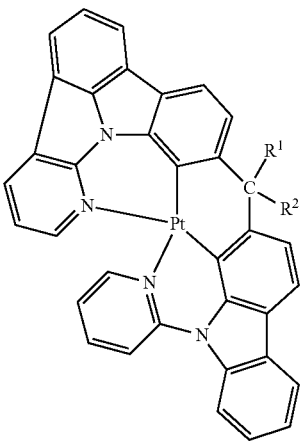
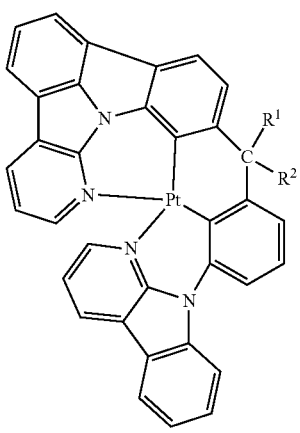

-continued
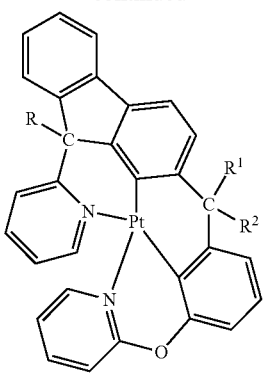
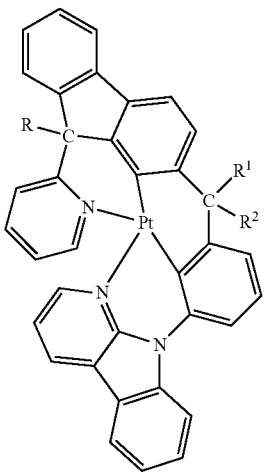
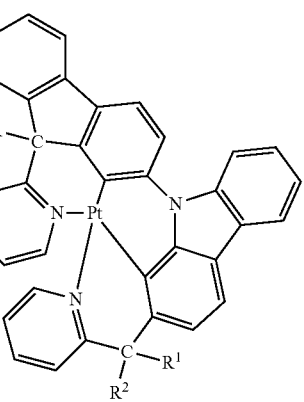
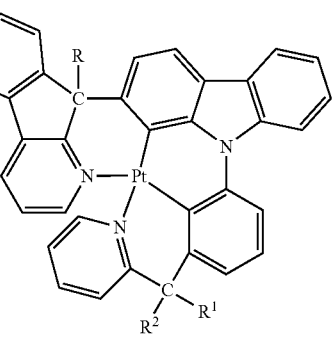
-continued
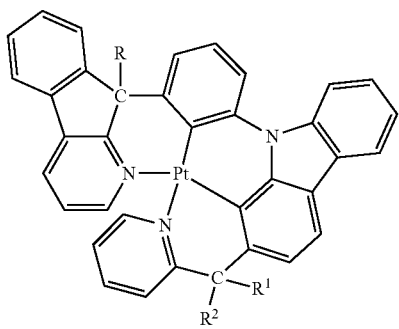
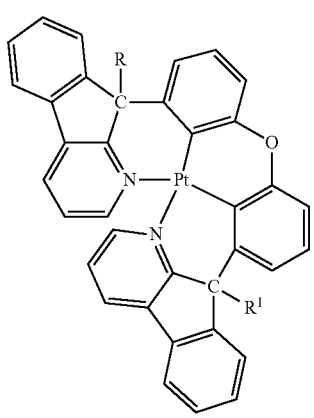
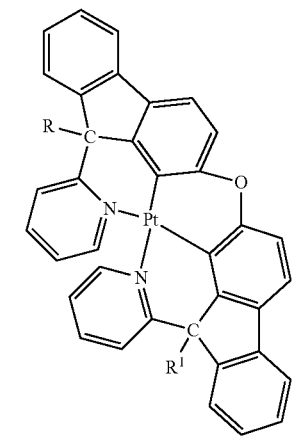

-continued
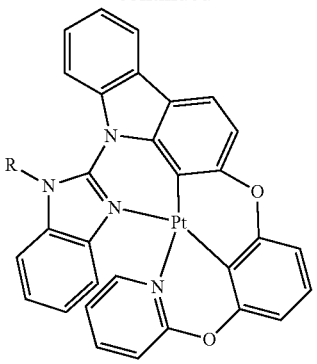
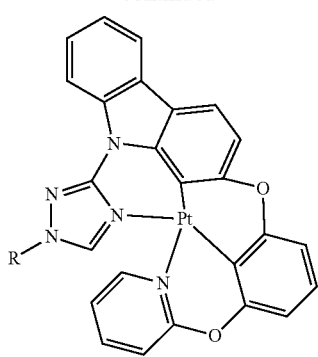
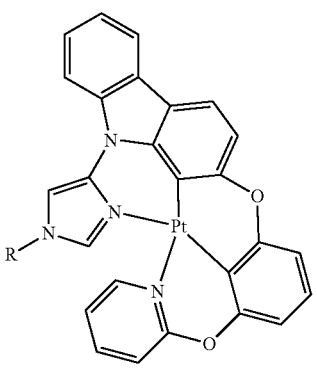
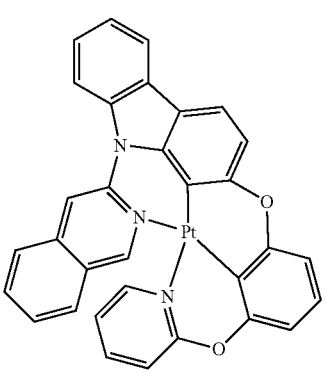
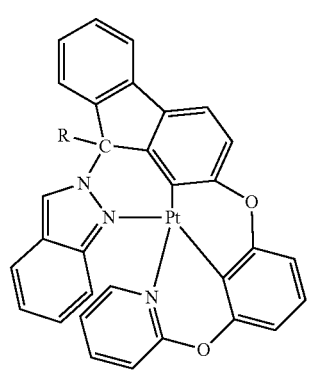
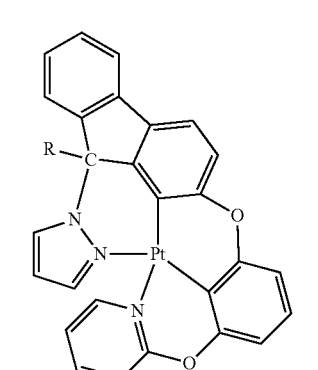
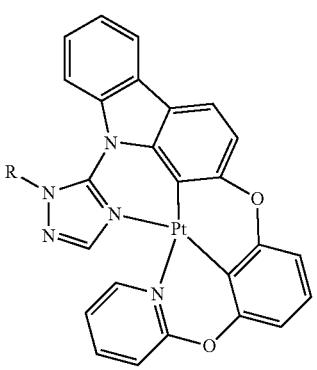
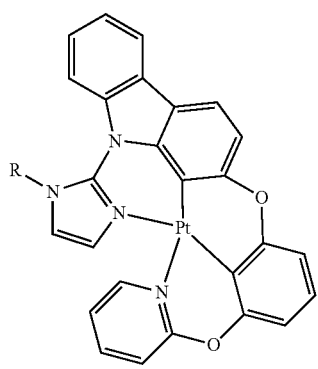

71
-continued
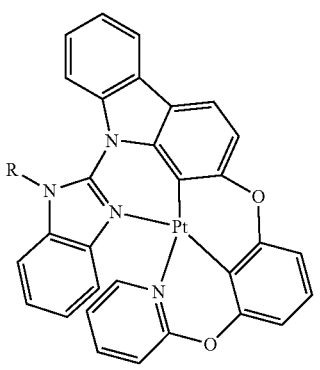
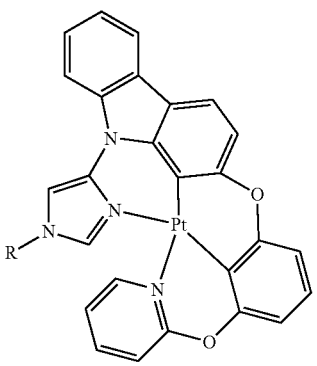
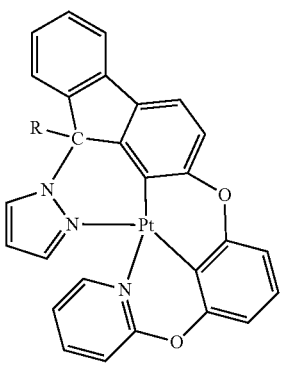
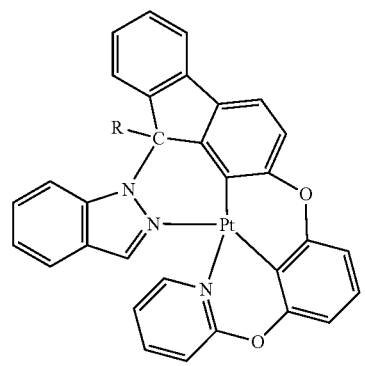
72
-continued
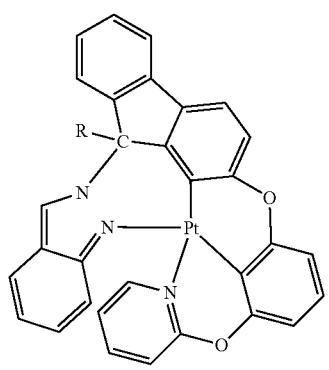
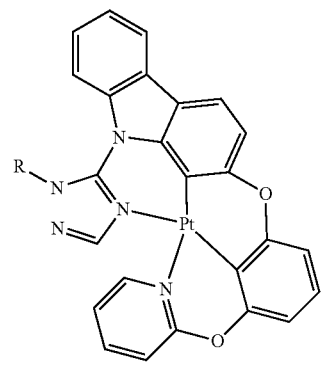
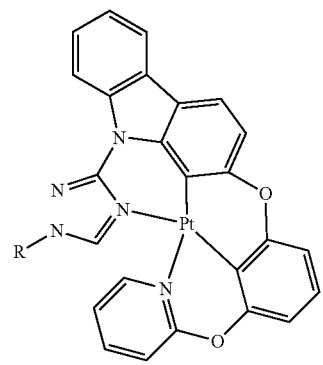
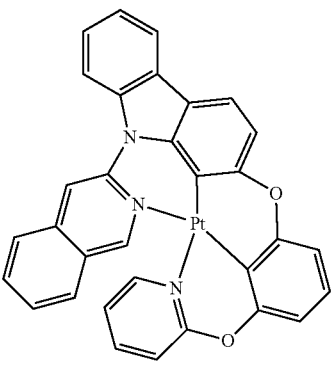

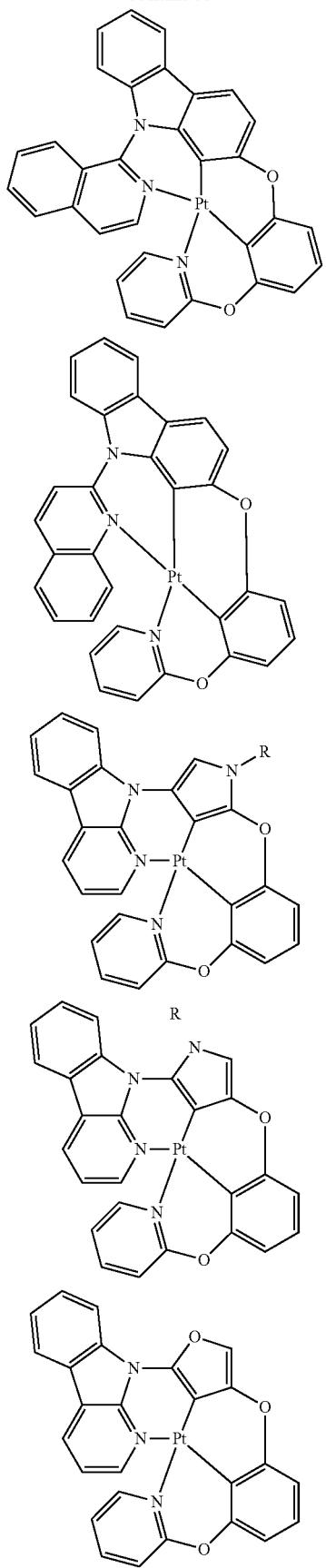
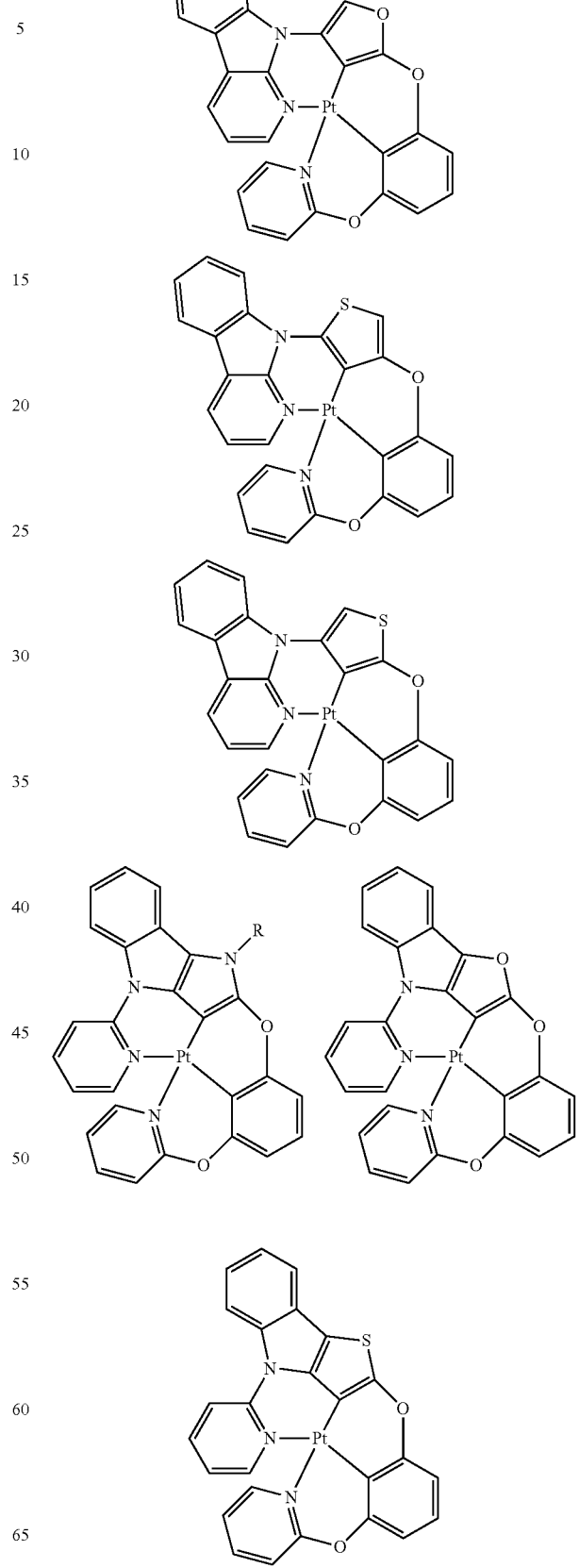

-continued
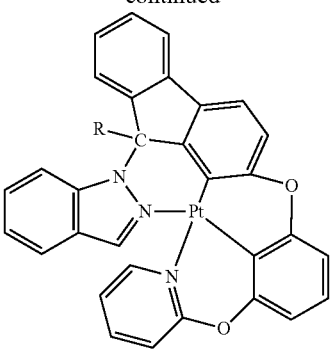
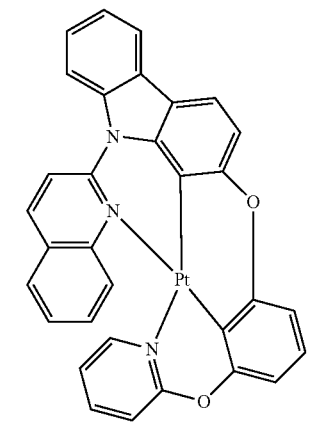
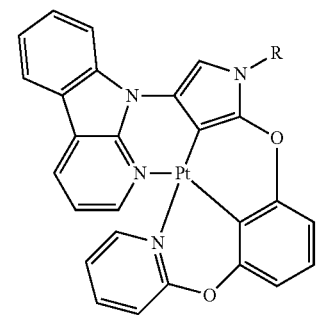
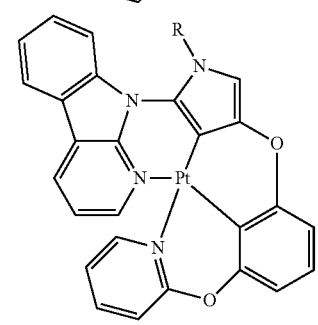
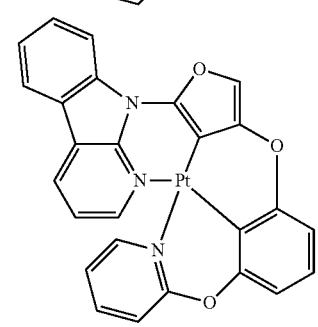
-continued
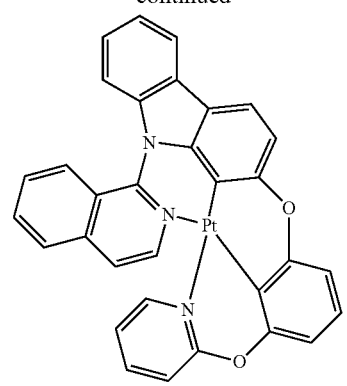
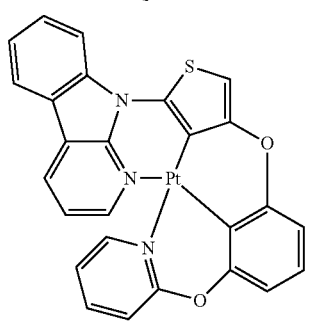
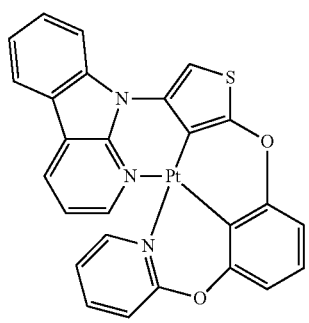
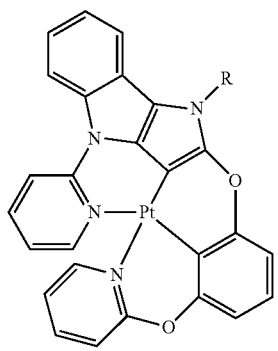
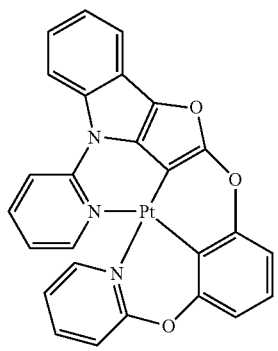

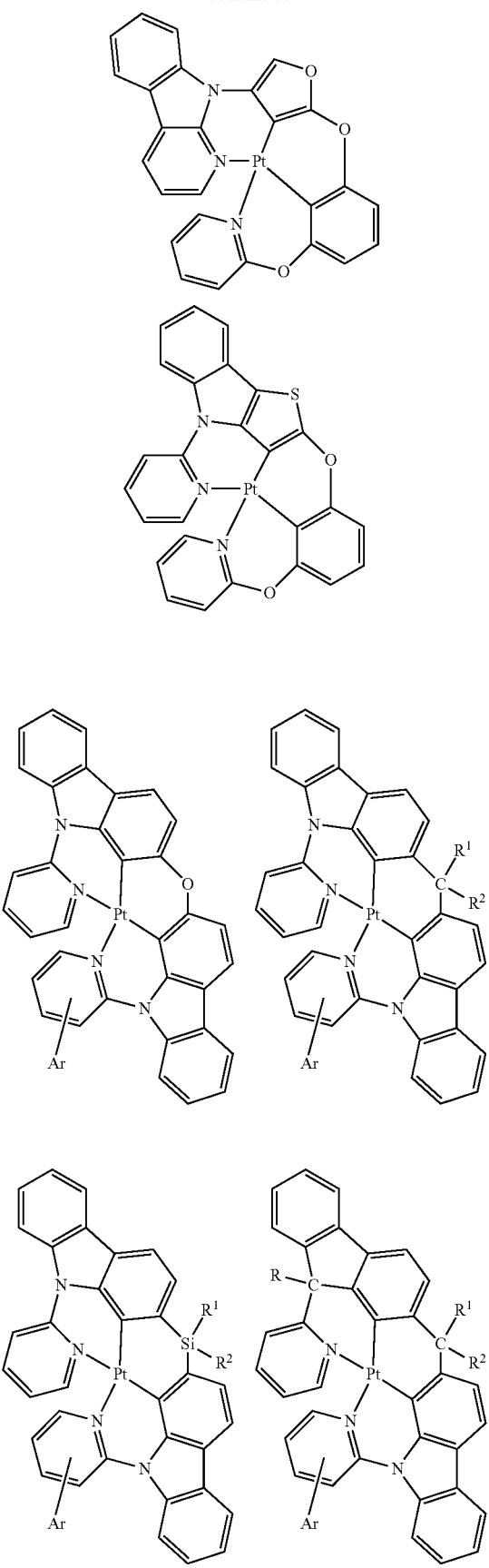
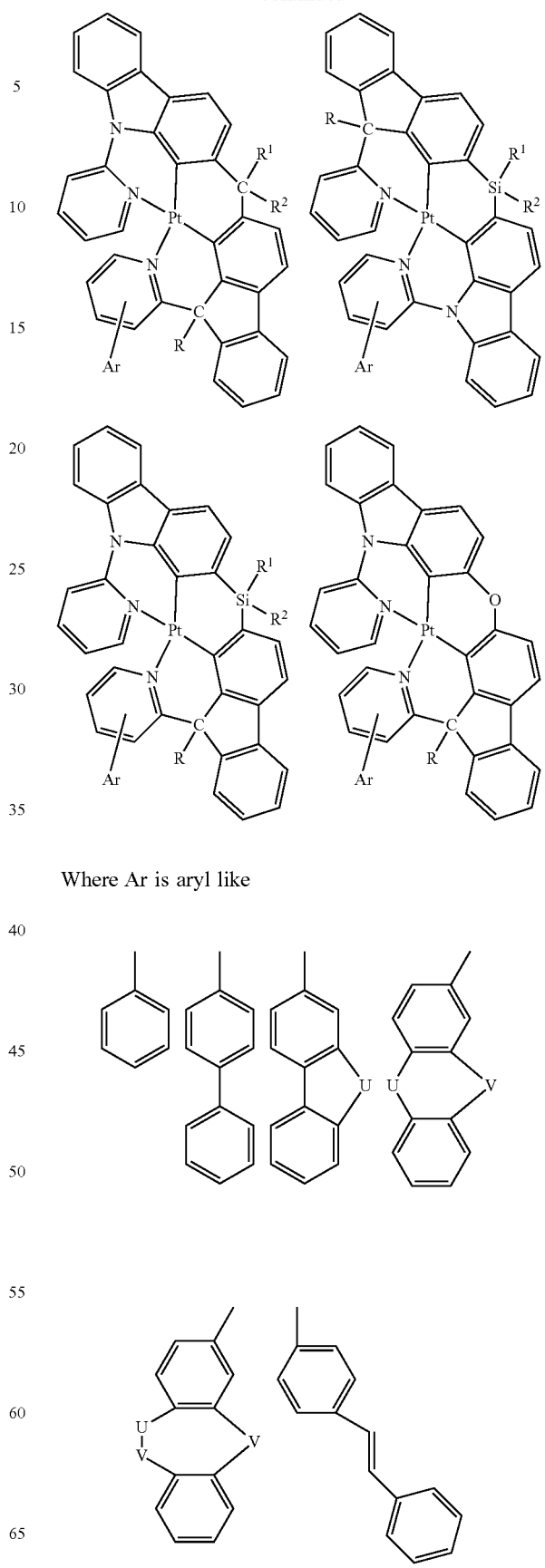
Where Ar is aryl like

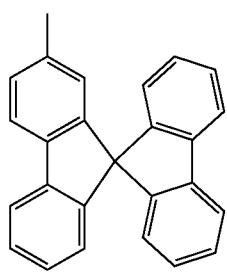
and their analogs.
Where U, V and W could be the same or different atoms like carbon (C), nitrogen (N), oxygen (O), sulfur (S), phosphorus (P), silicon (Si), boron (B) and others.
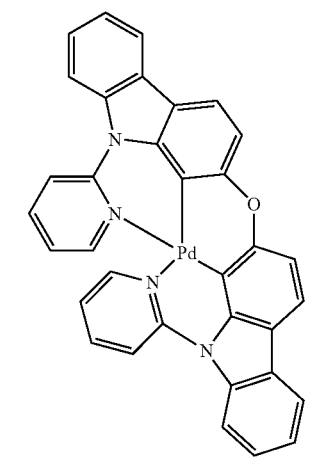
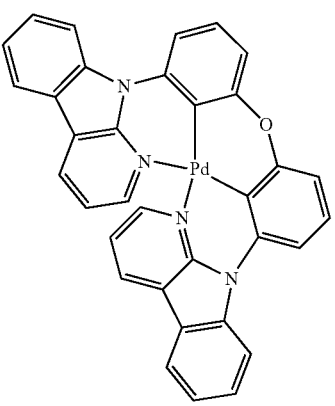
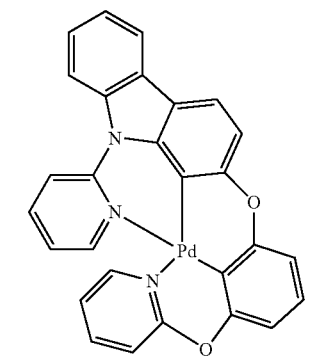
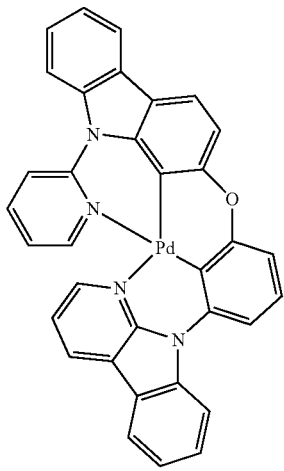
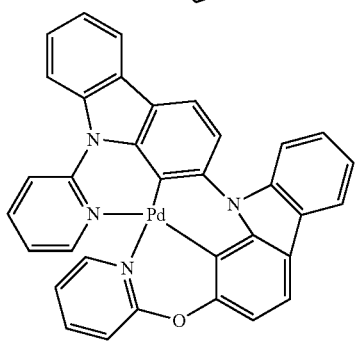
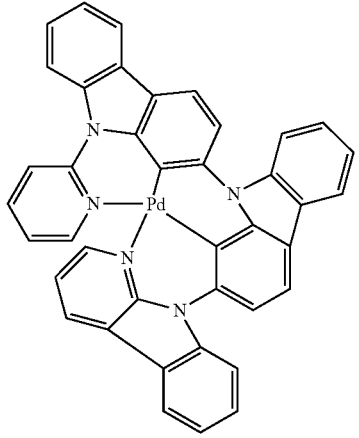
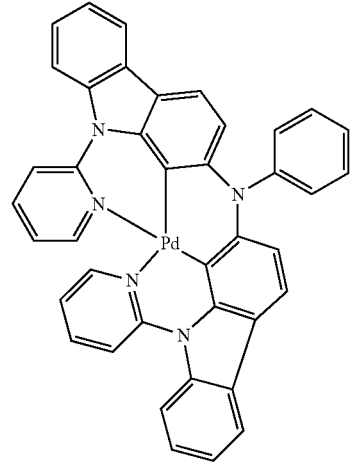

81
-continued
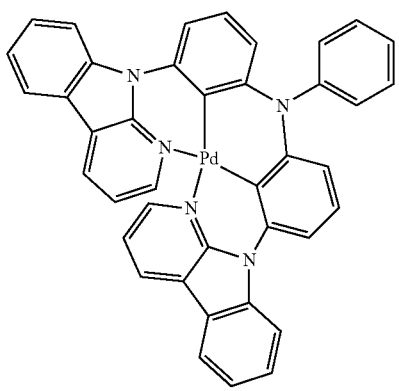
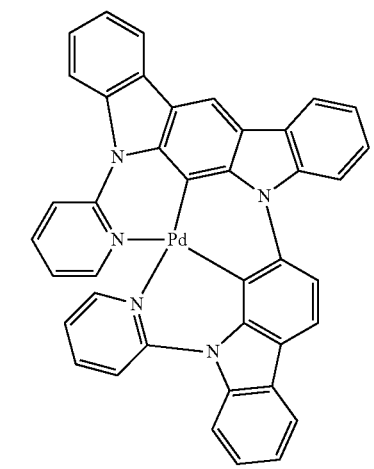
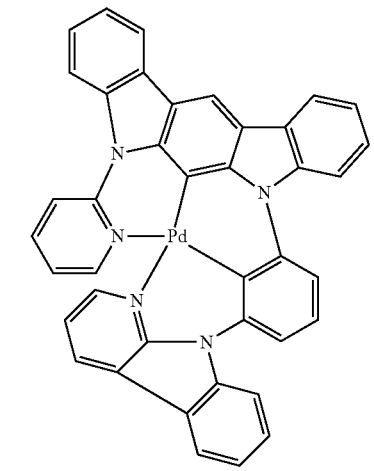
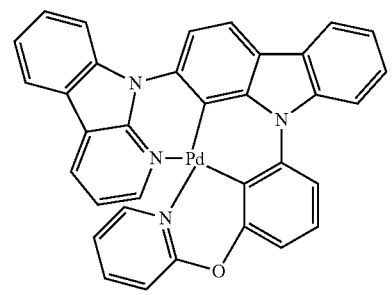
82
-continued
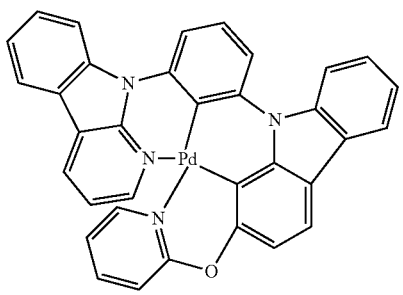
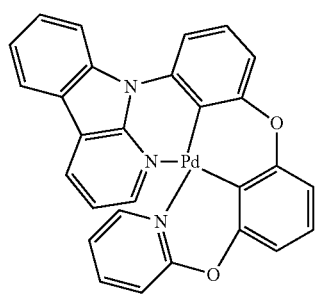
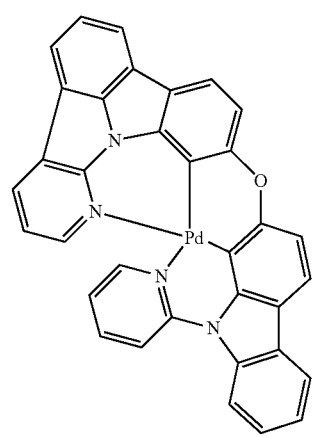
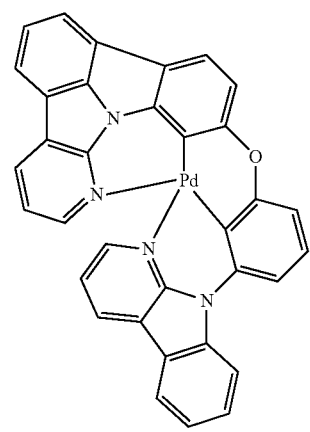

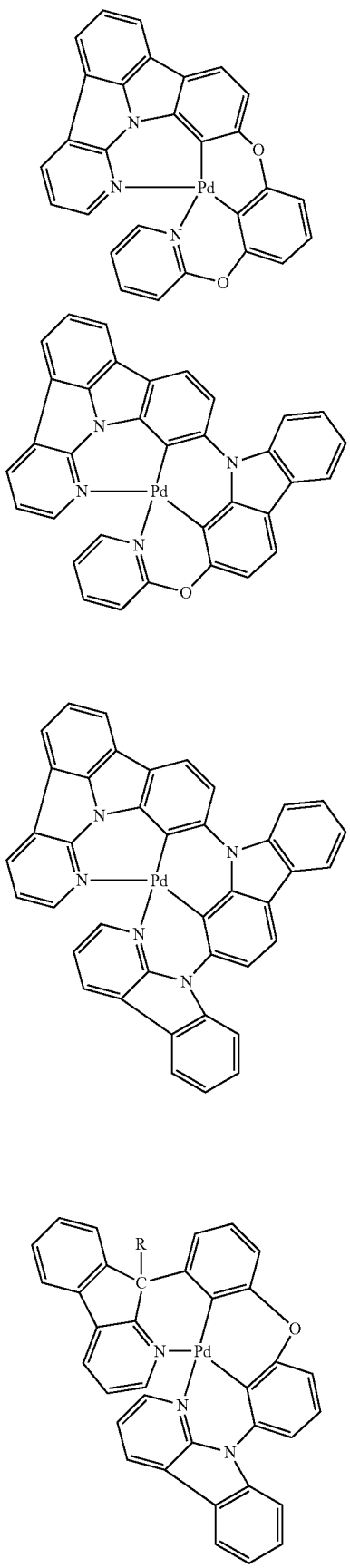
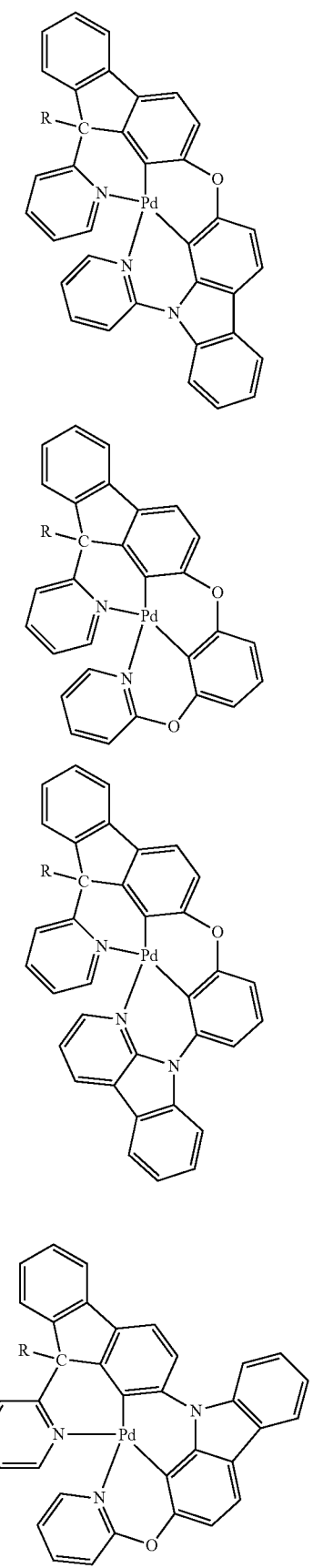

85
-continued
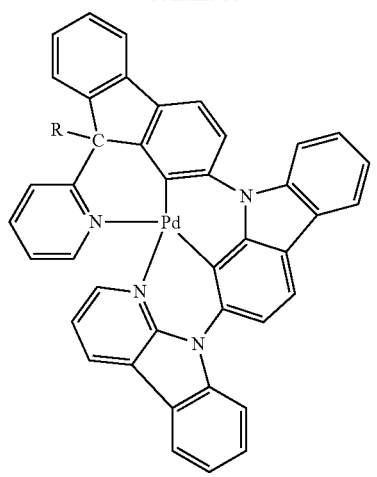
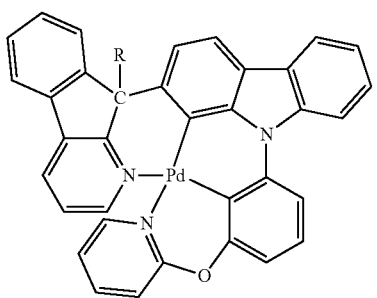
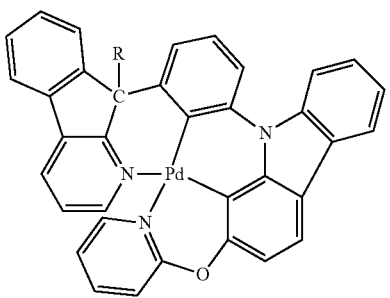
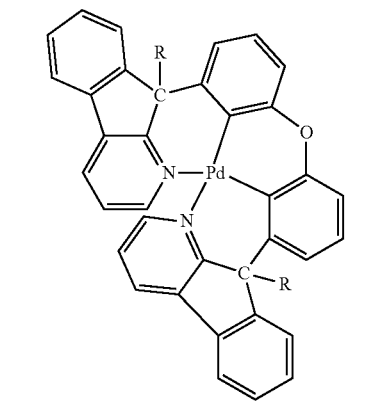
86
-continued
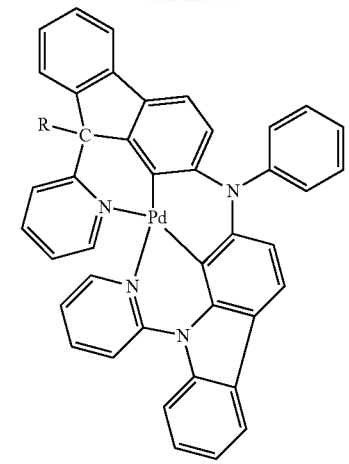
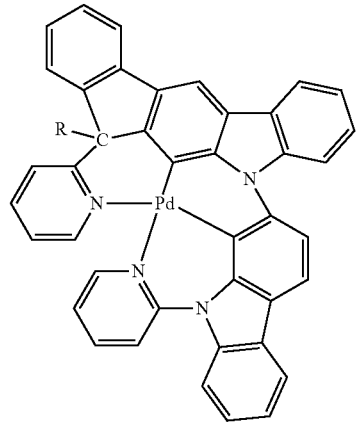
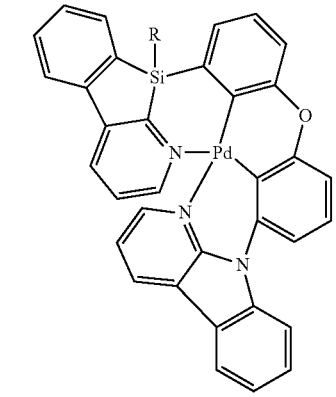
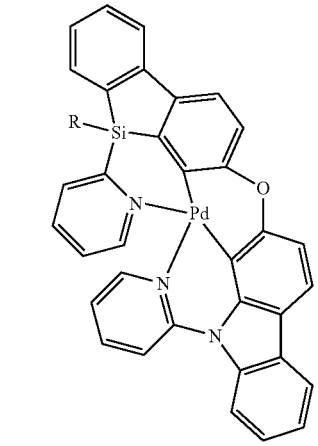

87
-continued
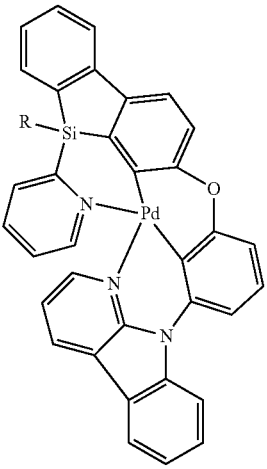
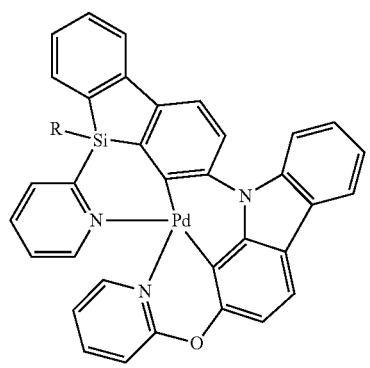
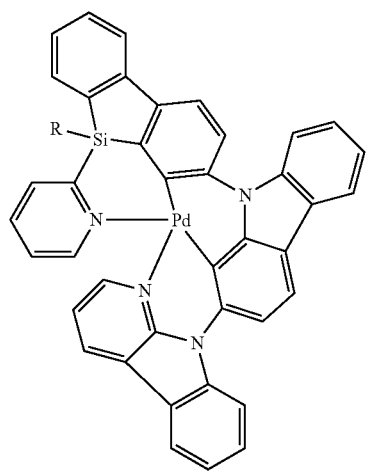
88
-continued
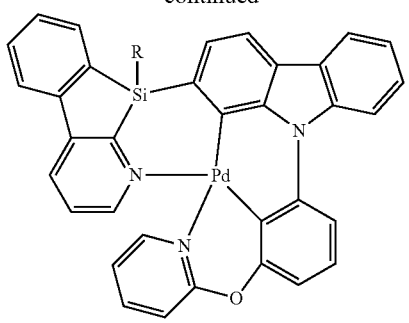
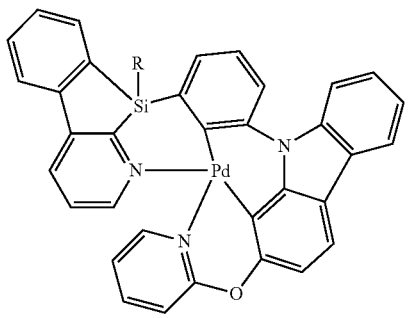
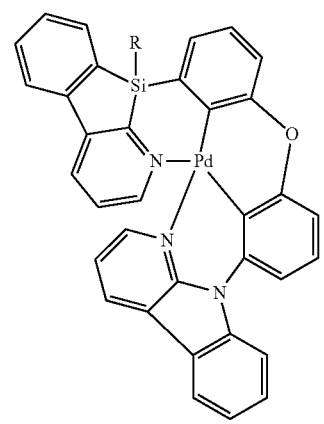
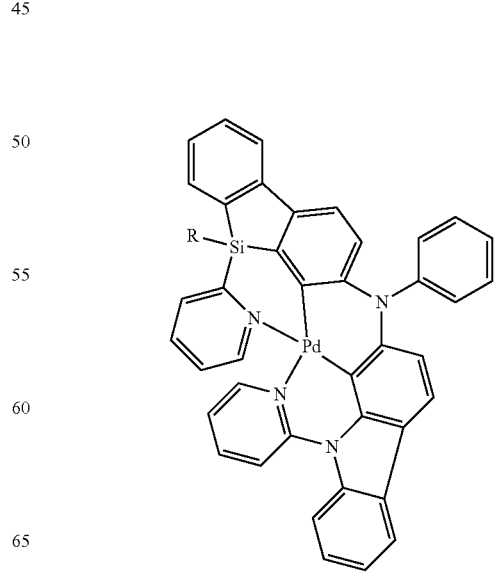

-continued
89
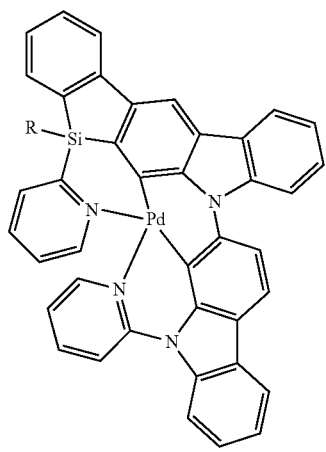
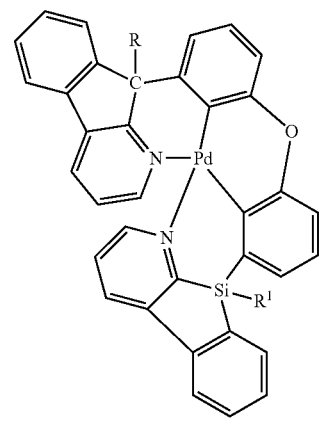
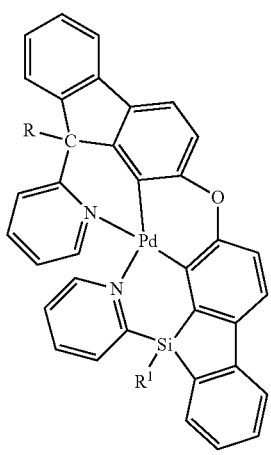
-continued
90
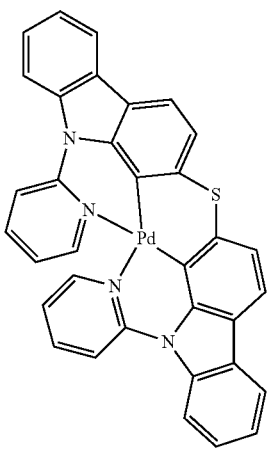
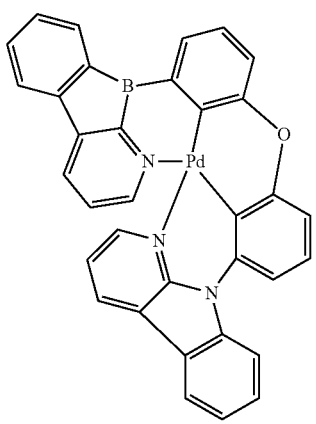
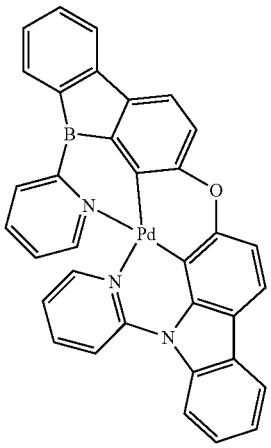
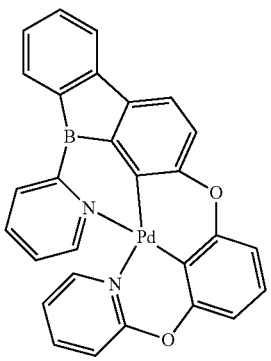

91
-continued
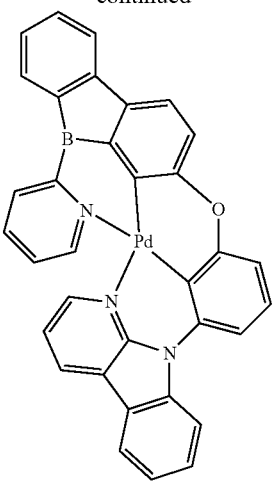
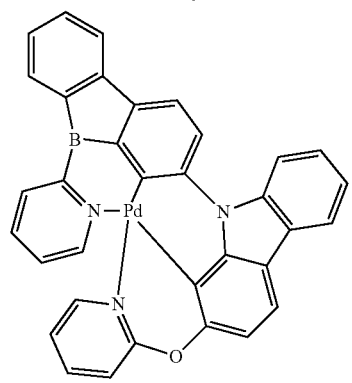
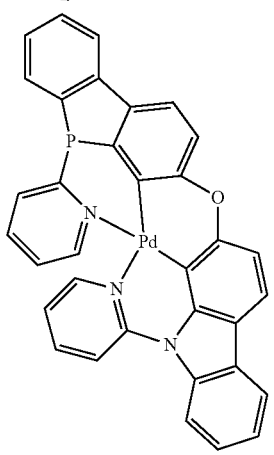
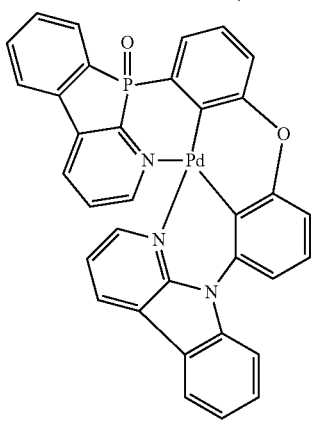
92
-continued
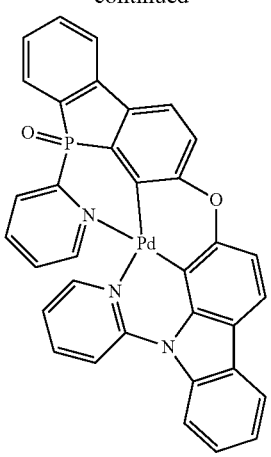
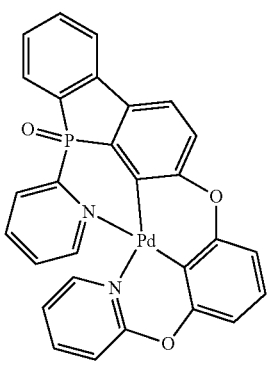
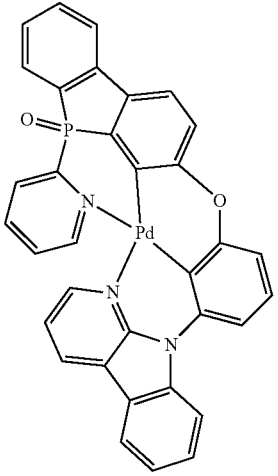
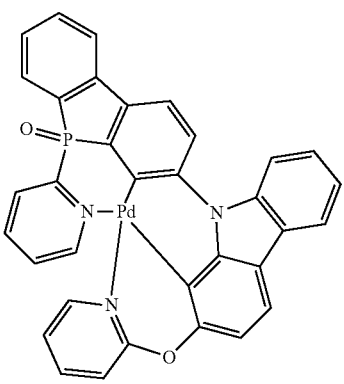

-continued
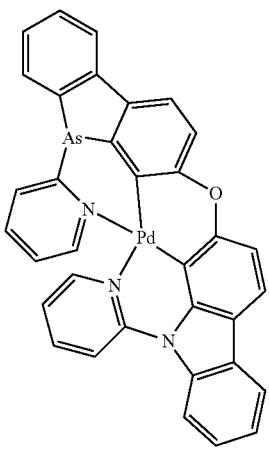
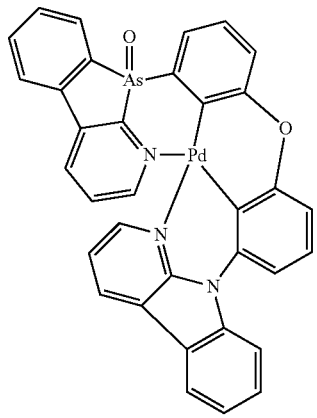
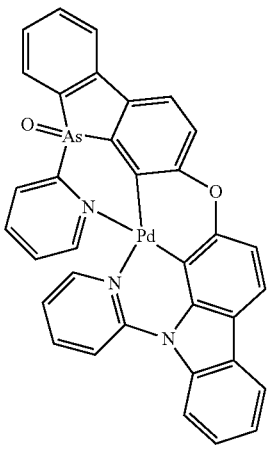
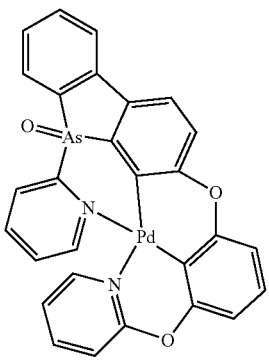
-continued
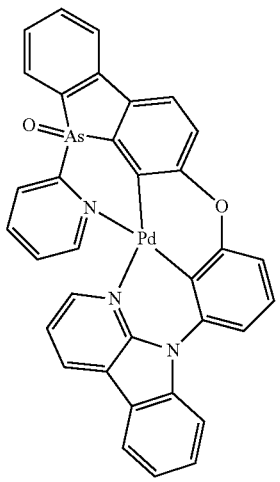
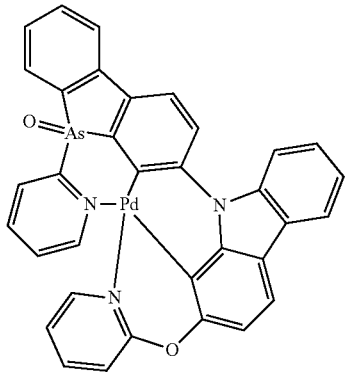
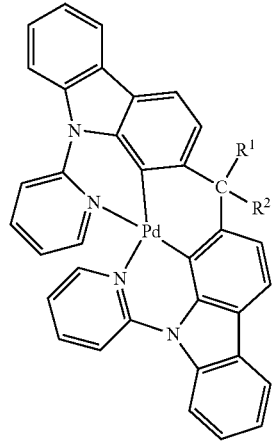
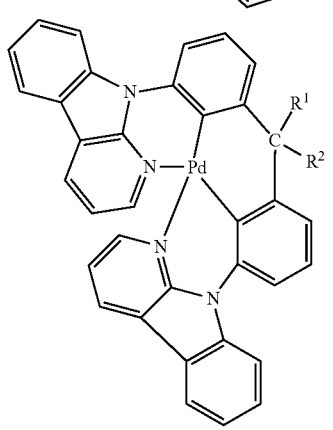

95
-continued
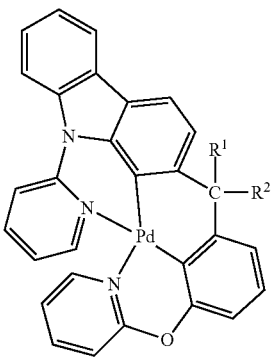
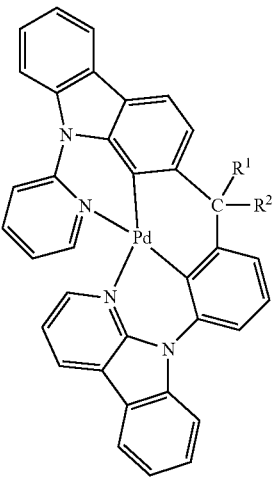
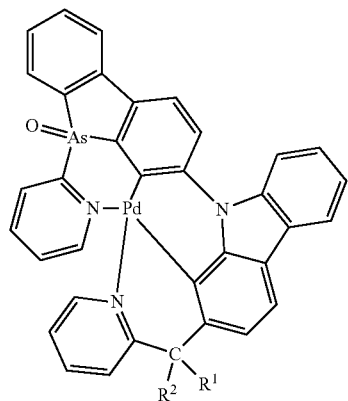
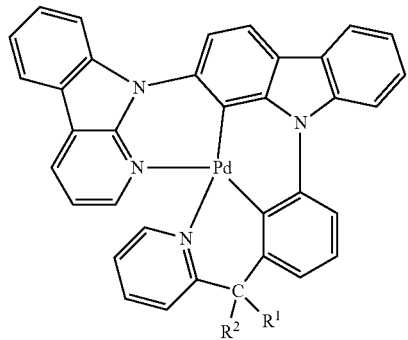
96
-continued
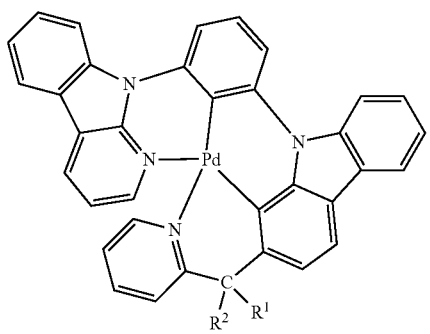
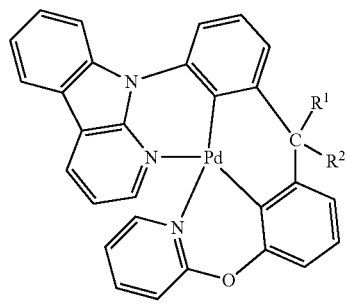
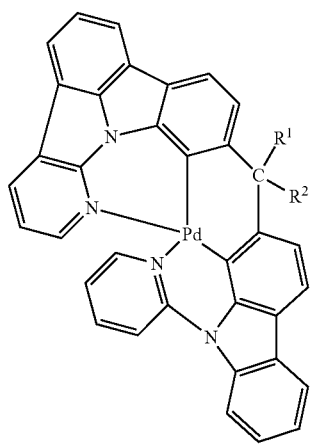
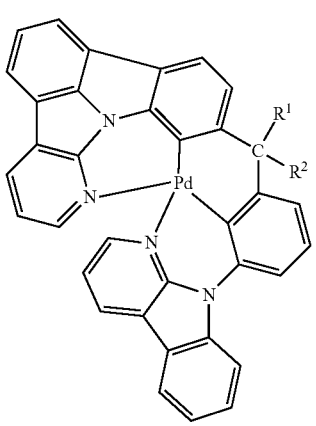

97
-continued
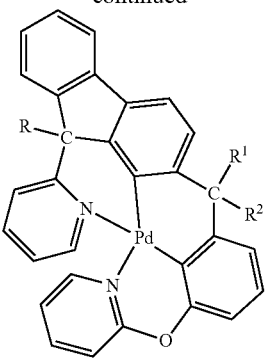
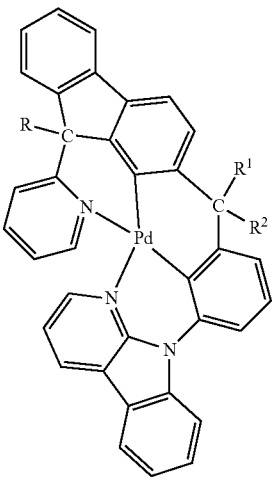
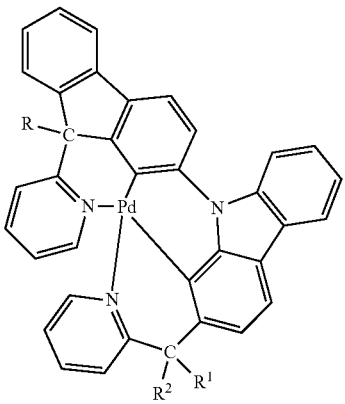
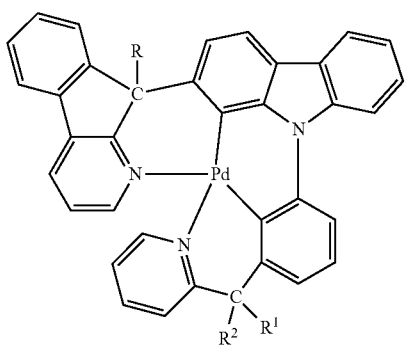
98
-continued
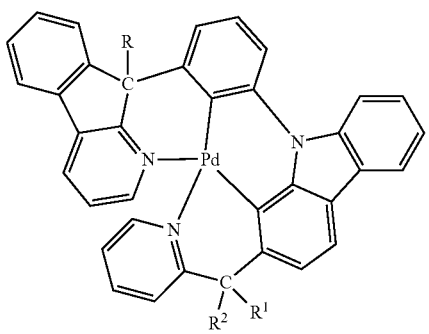
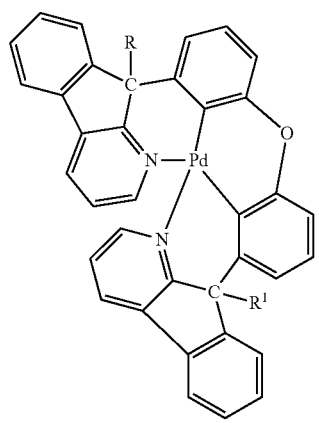
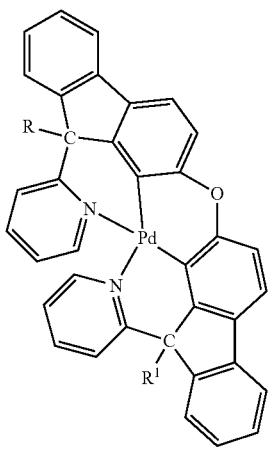
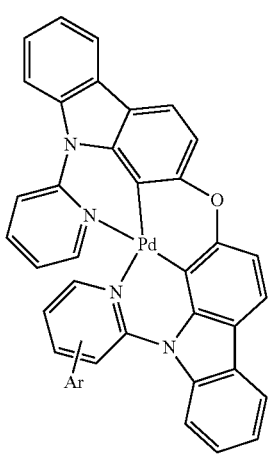

99
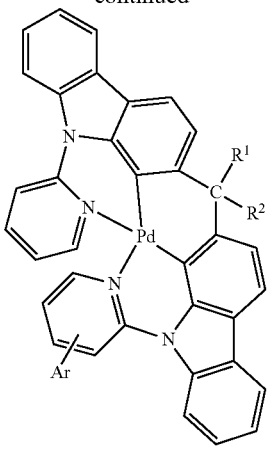
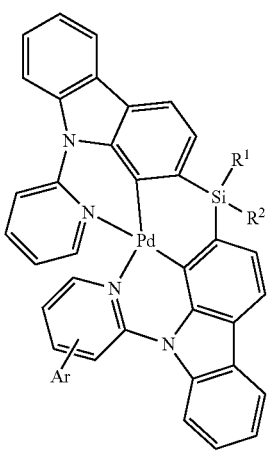
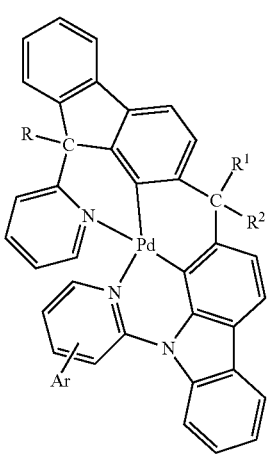
100
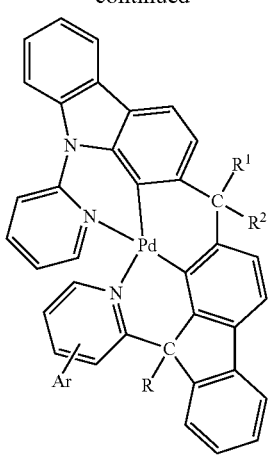
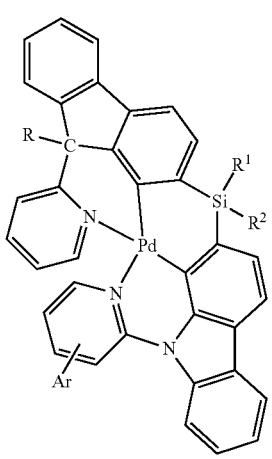
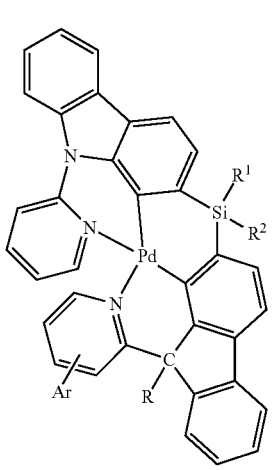

-continued
101
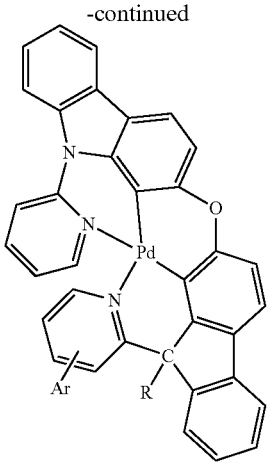
Where Ar is aryl functional group like
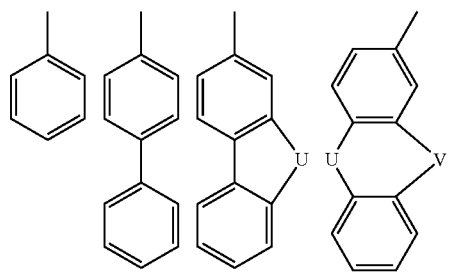
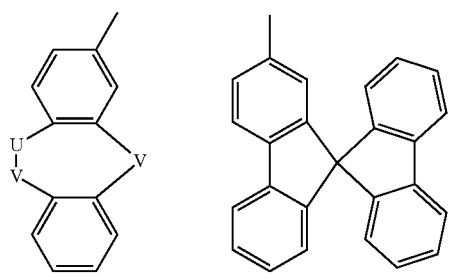
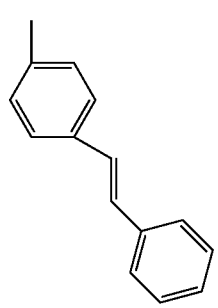
and their analogs.
Where U, V, W could be the same or different atoms like carbon (C), oxygen (O), nitrogen (N), phosphorus (P), silicon (Si)
102
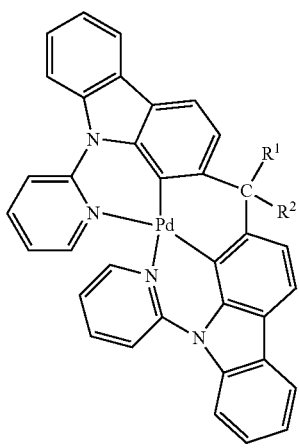
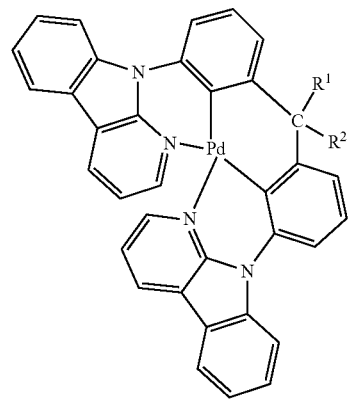
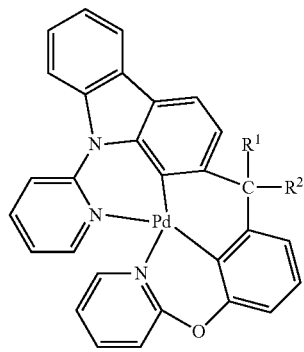
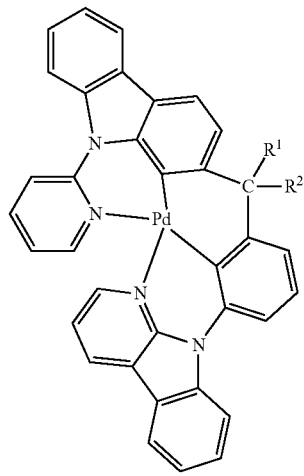

103
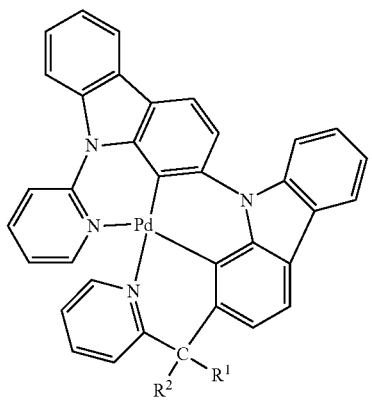
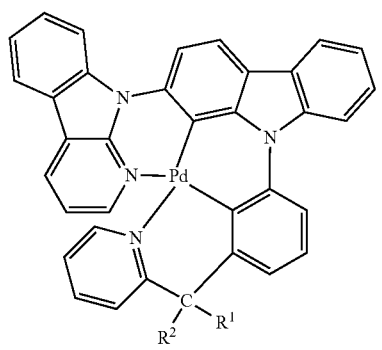
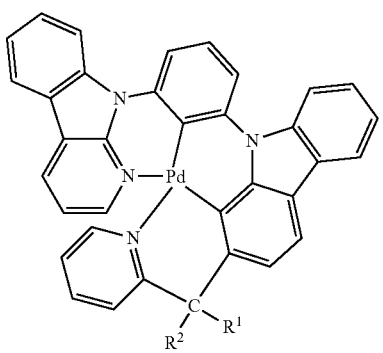
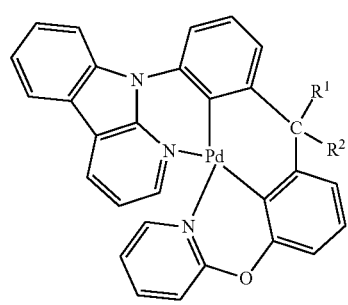
104
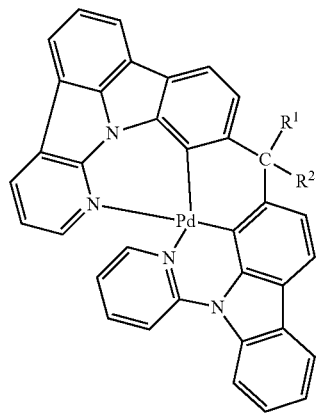
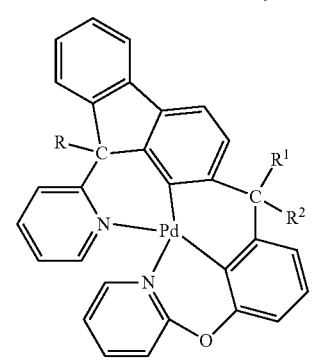
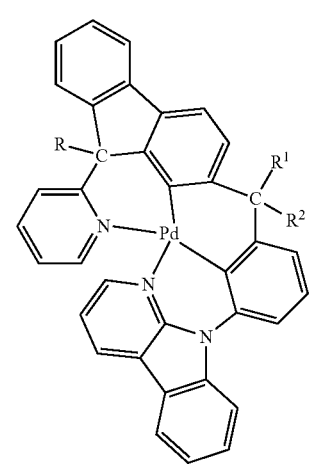
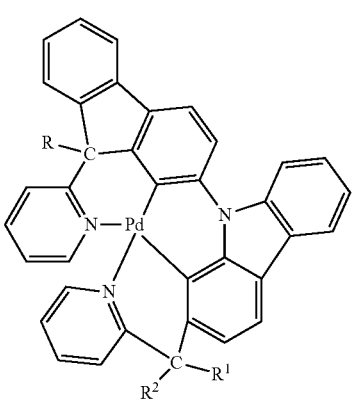

-continued
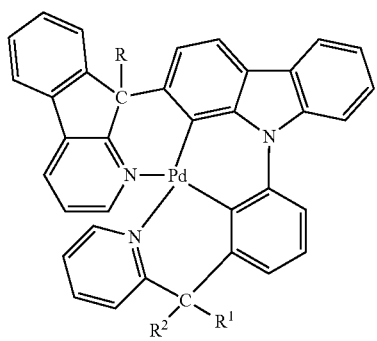
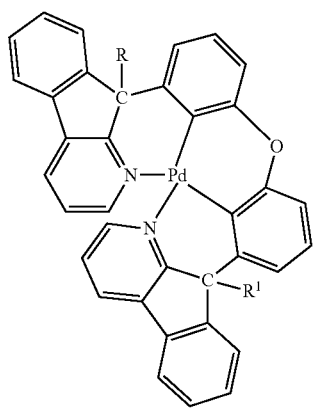
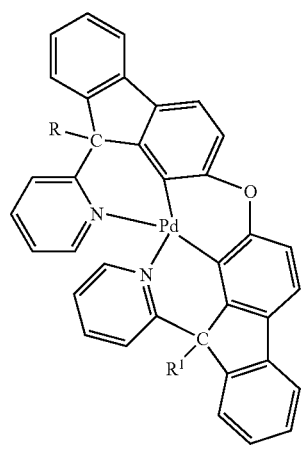
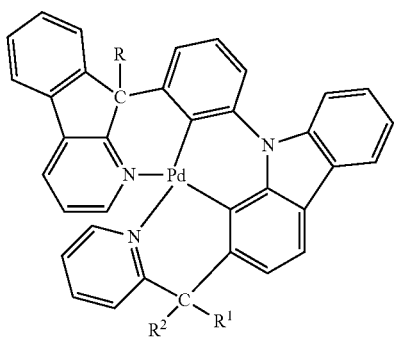
-continued
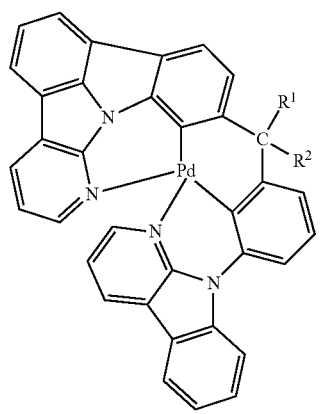
In one aspect, the compounds can have the structure:
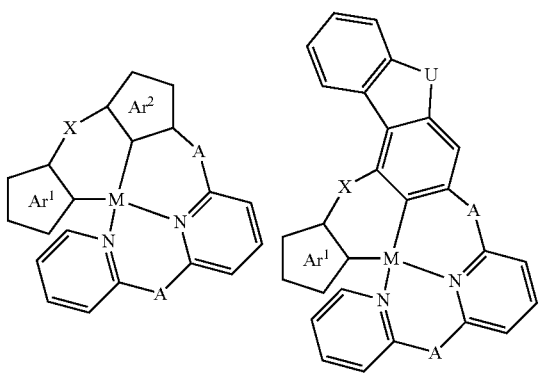
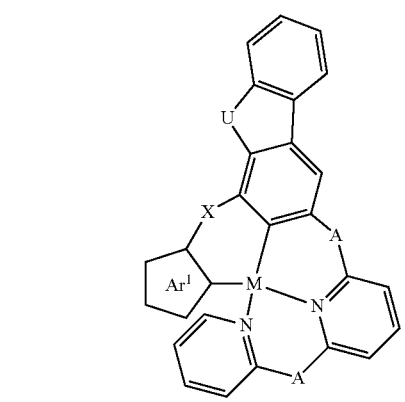
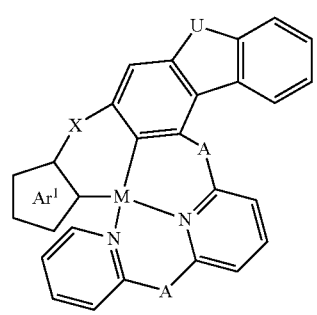

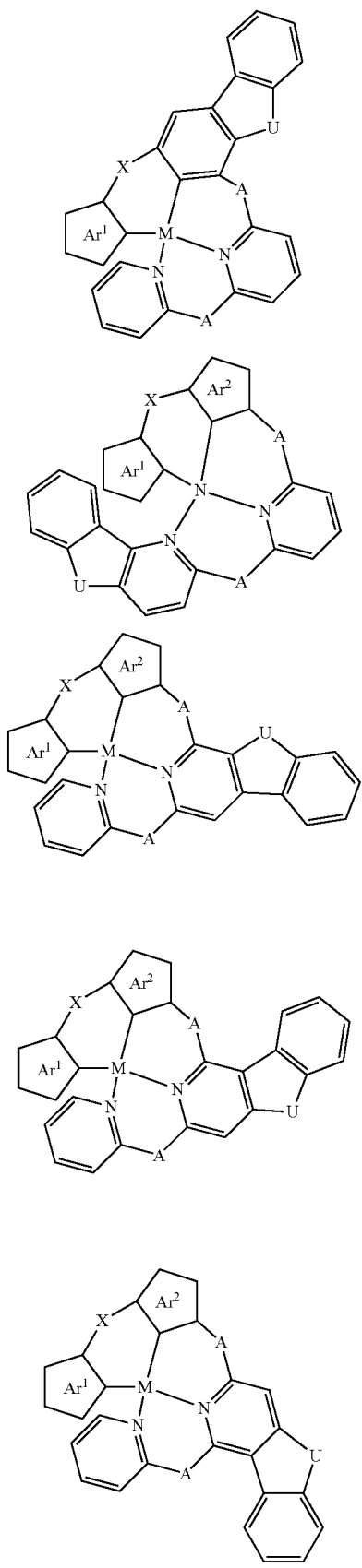
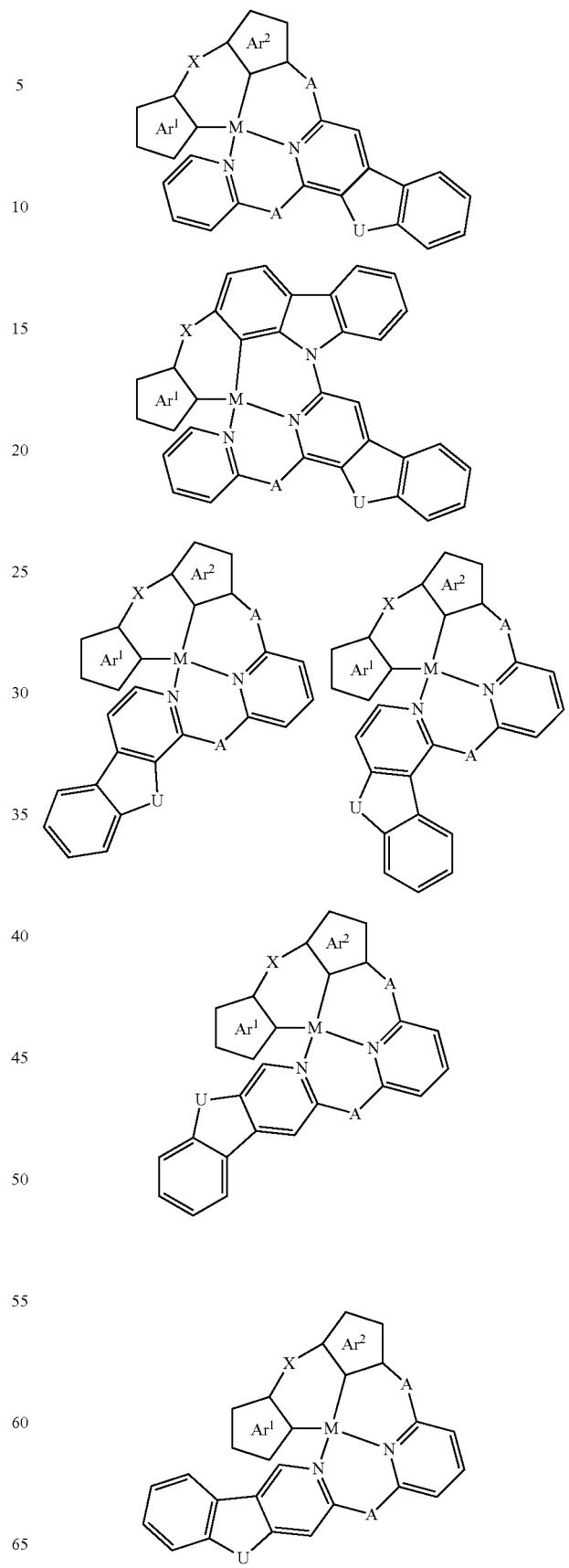

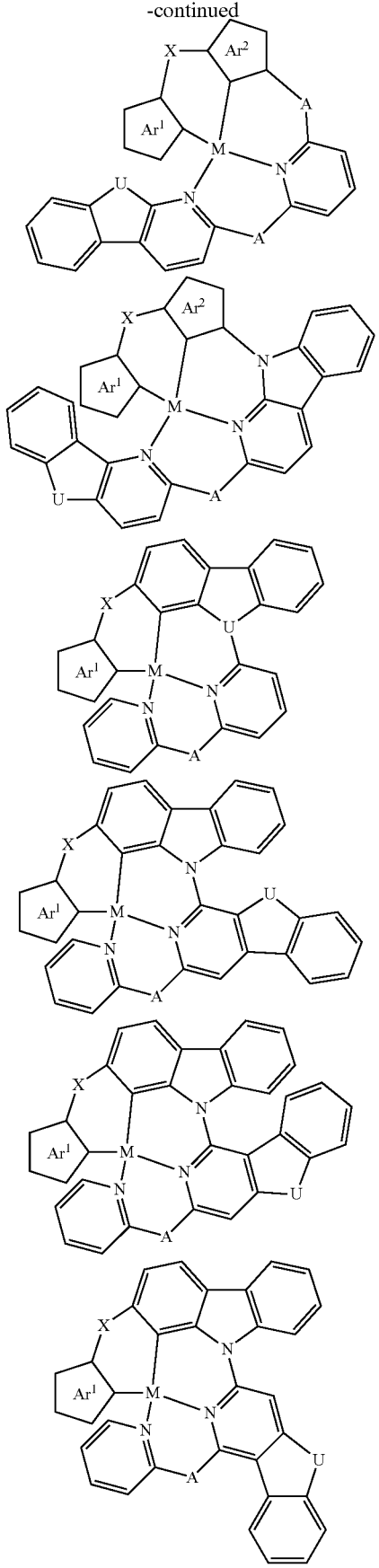
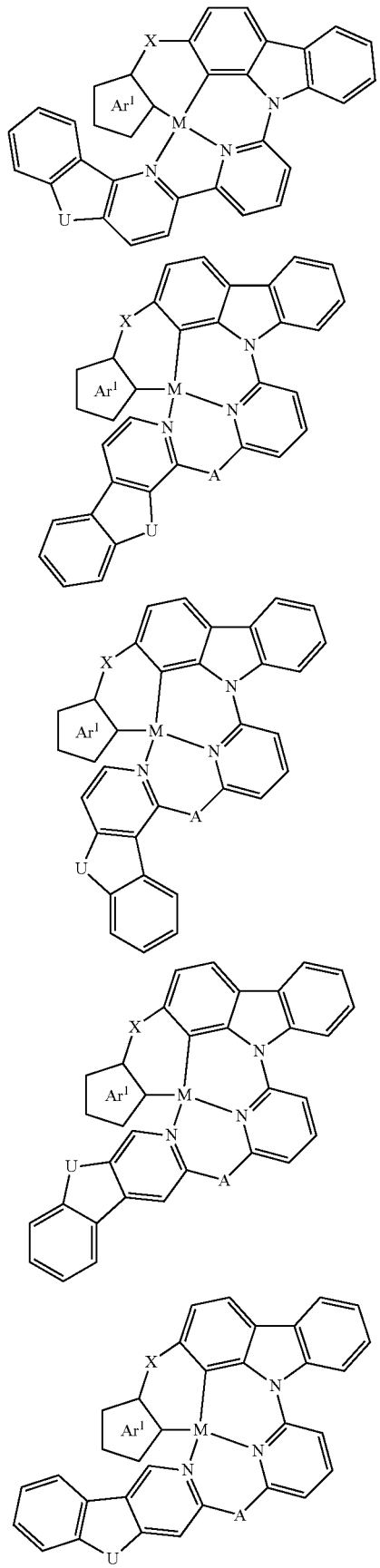

-continued
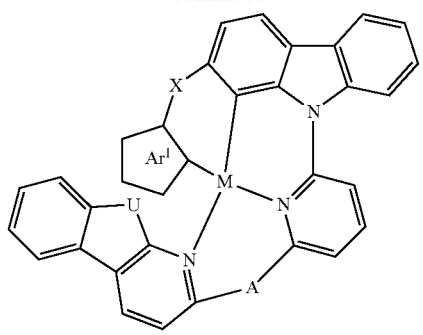
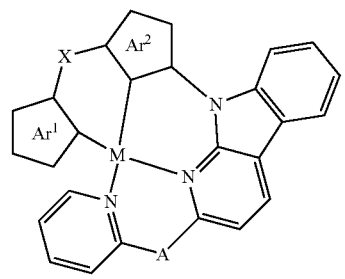
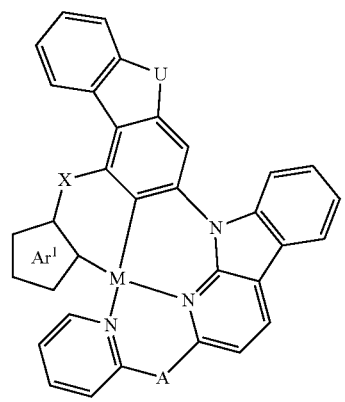
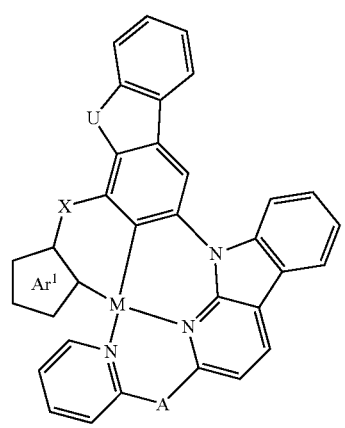
-continued
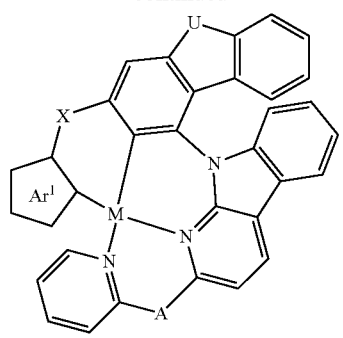
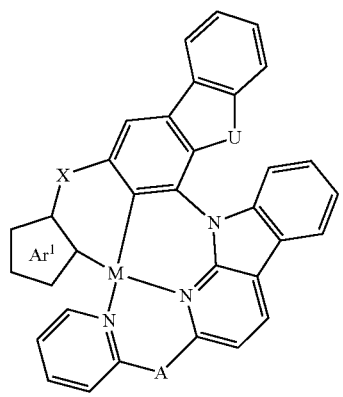
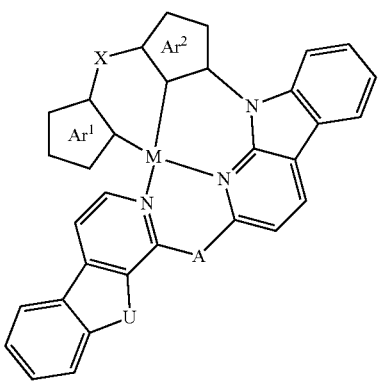
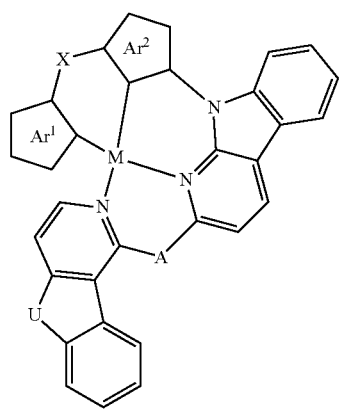

113
-continued
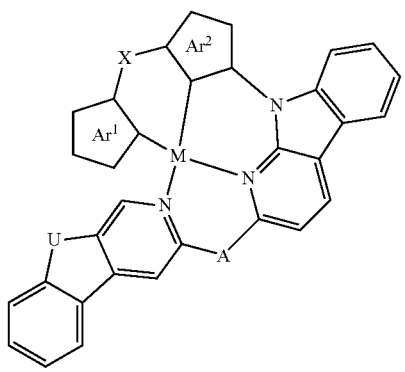
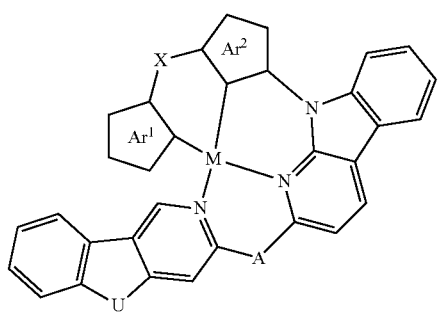
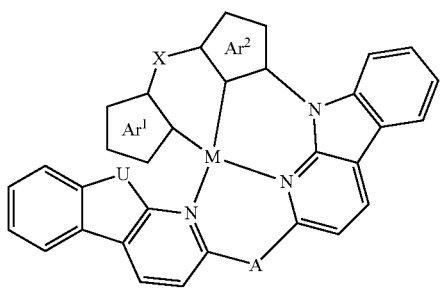
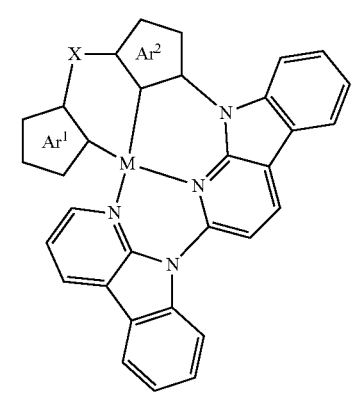
114
-continued
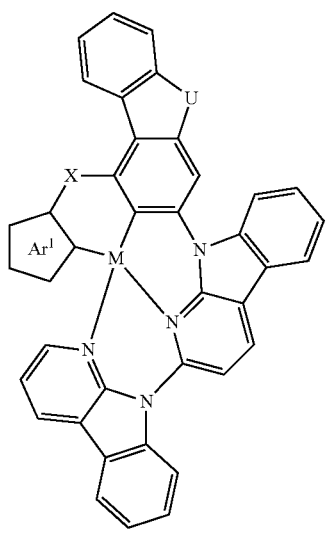
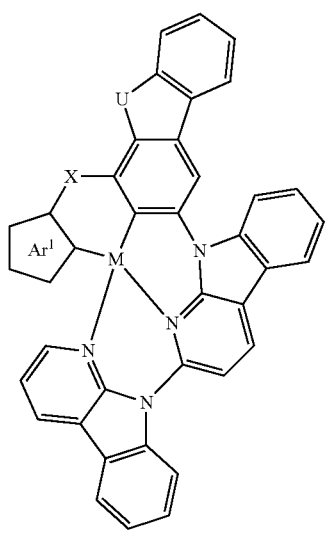
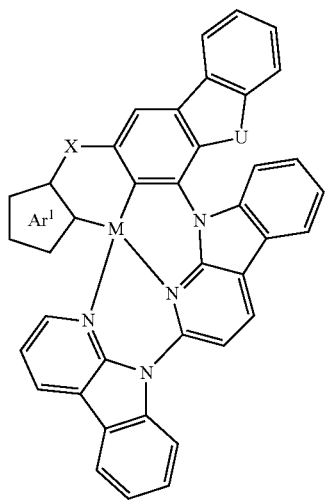

115
-continued
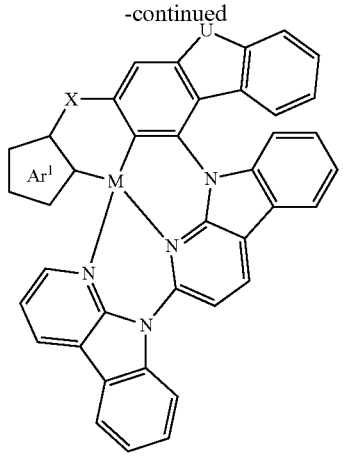
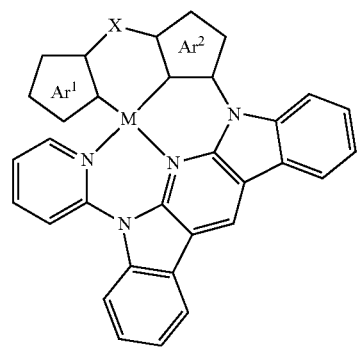
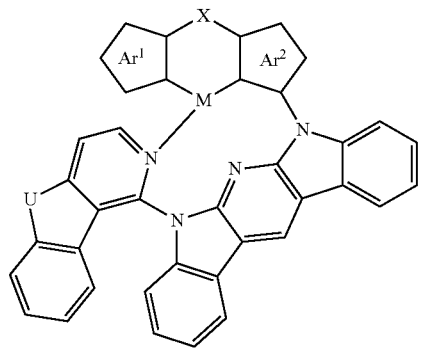
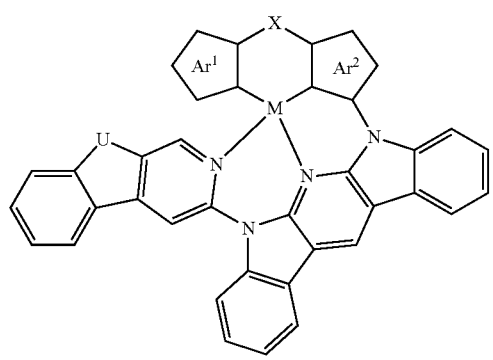
116
-continued
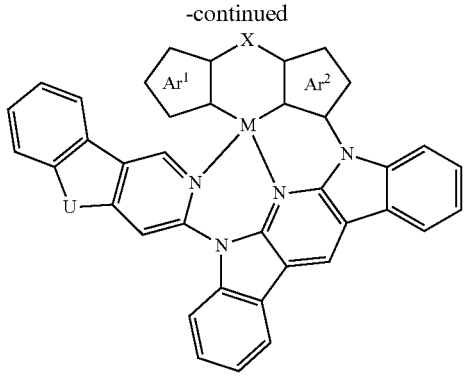
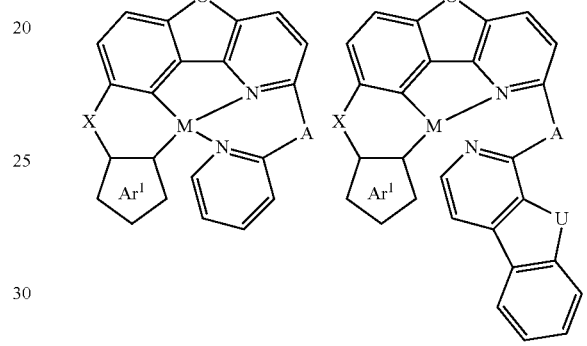
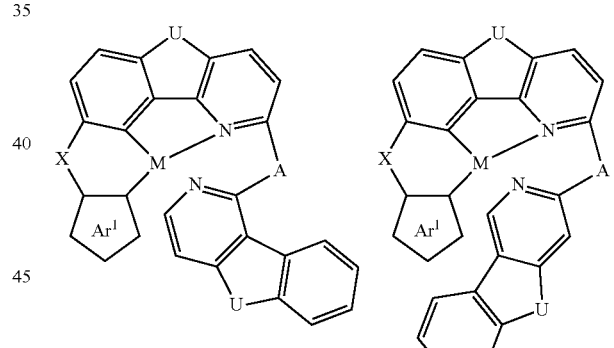
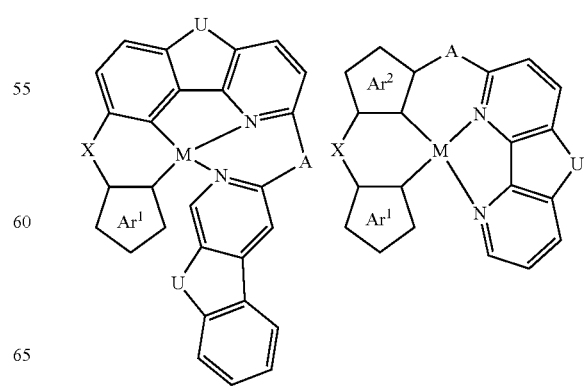

117
-continued
118
-continued
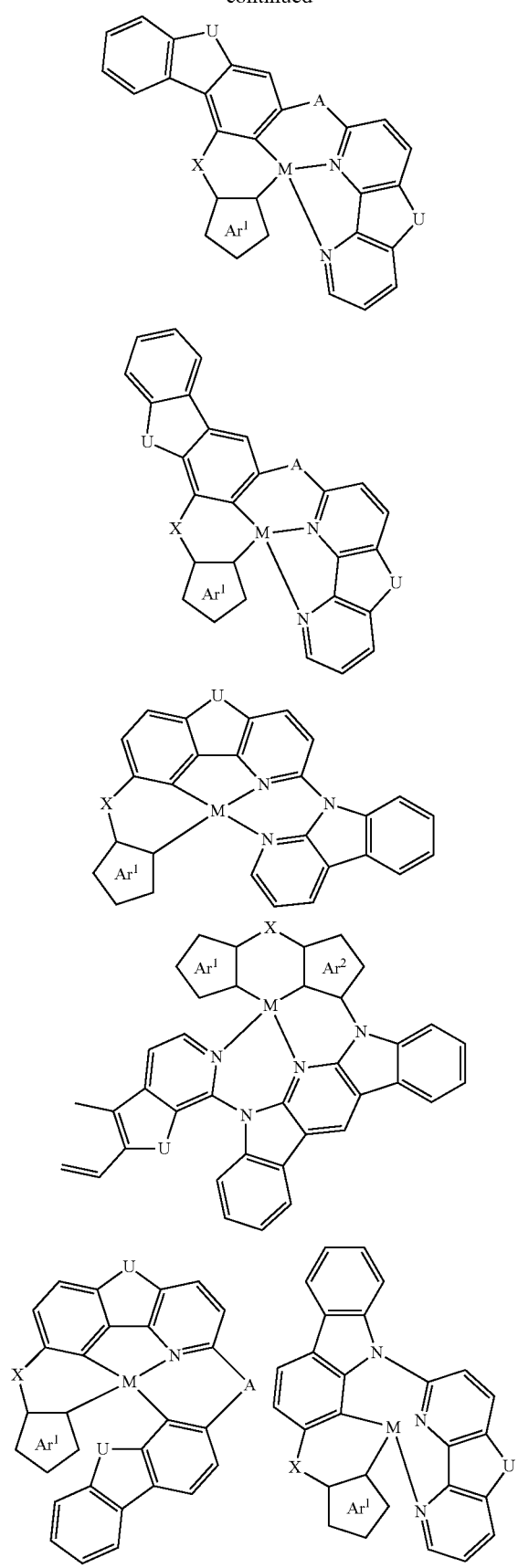
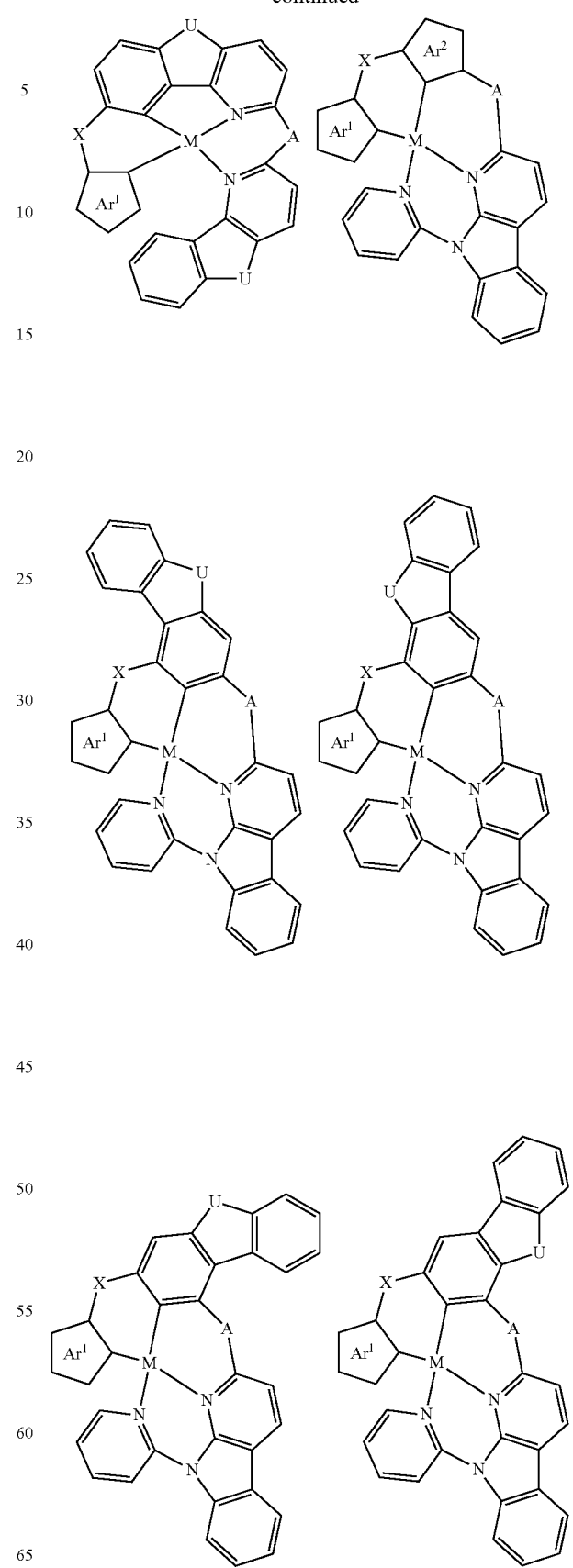

119
-continued
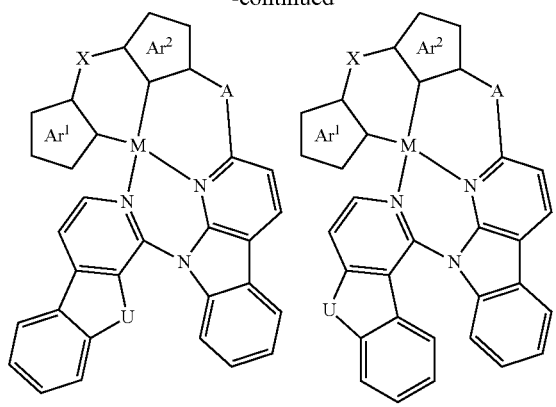
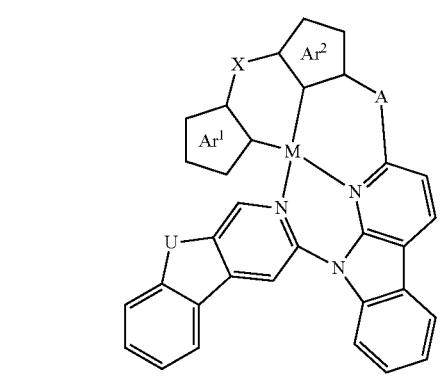
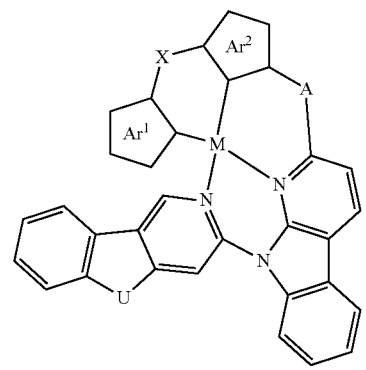
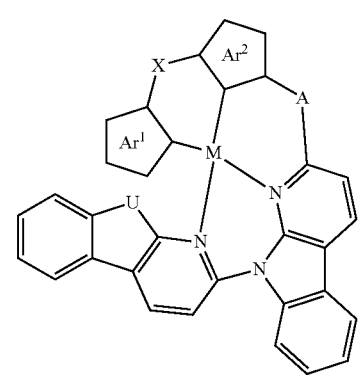
120
-continued
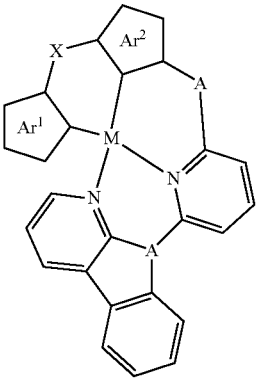
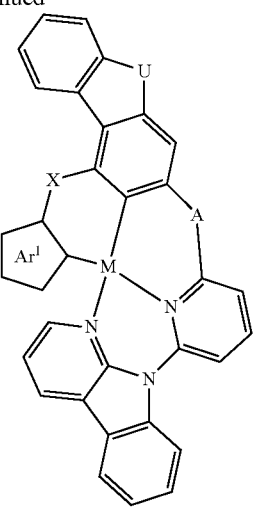
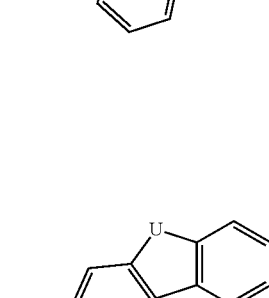
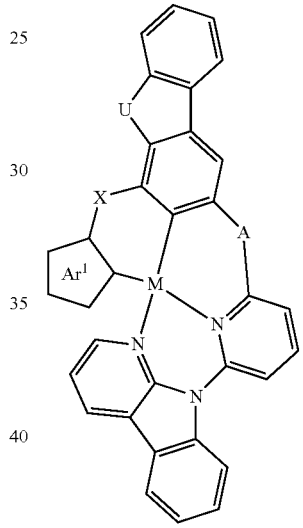
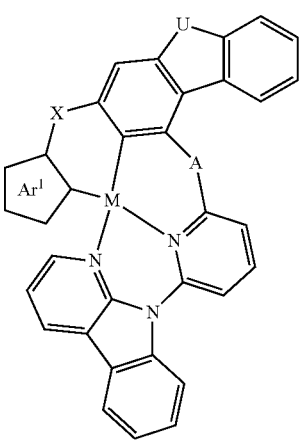
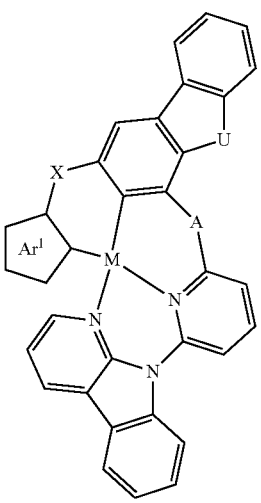

-continued
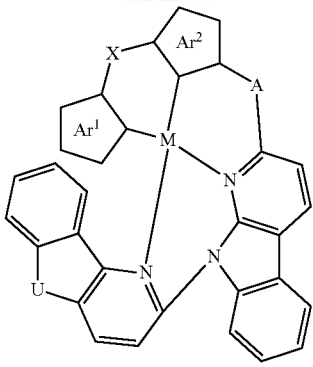
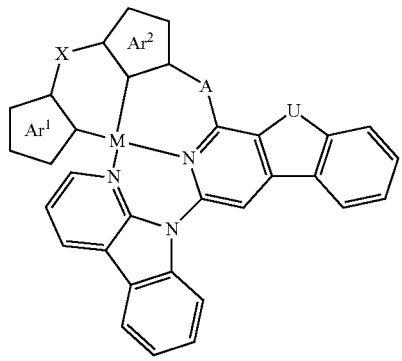
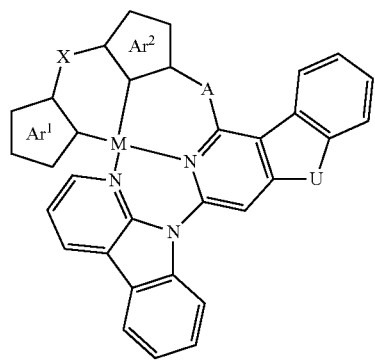
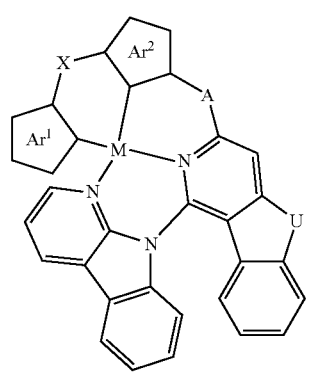
-continued
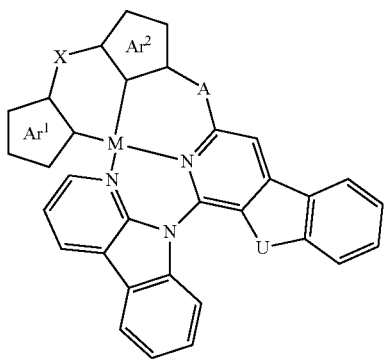
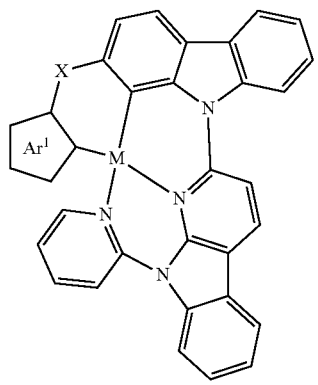
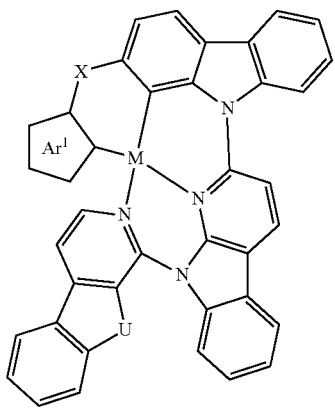
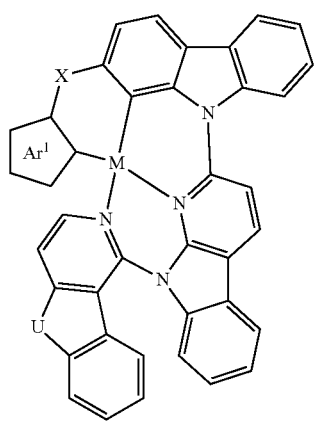

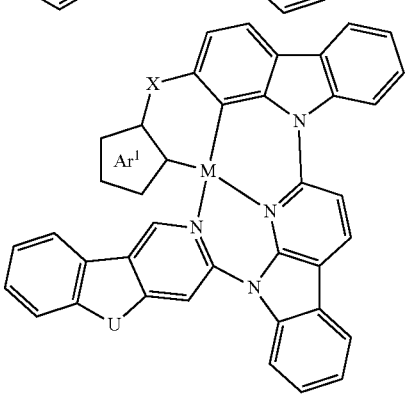
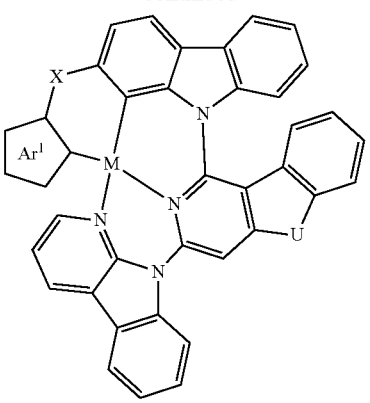
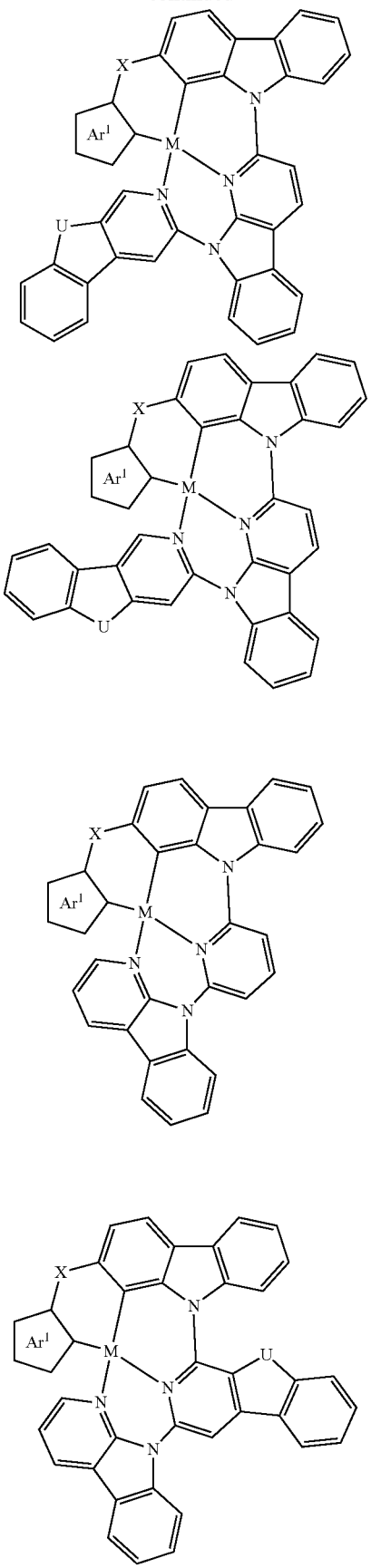
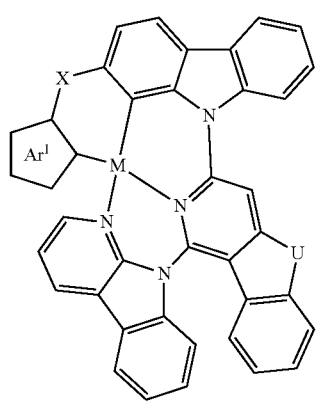
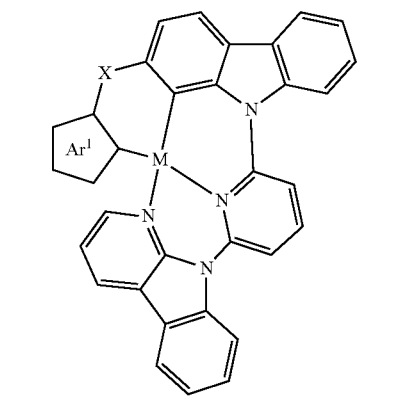
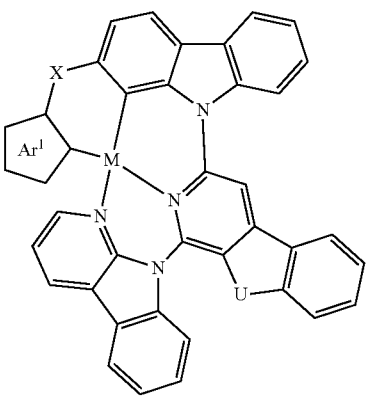

In one aspect, M is Ir or Rh.
Specific compounds include but are not limited to:
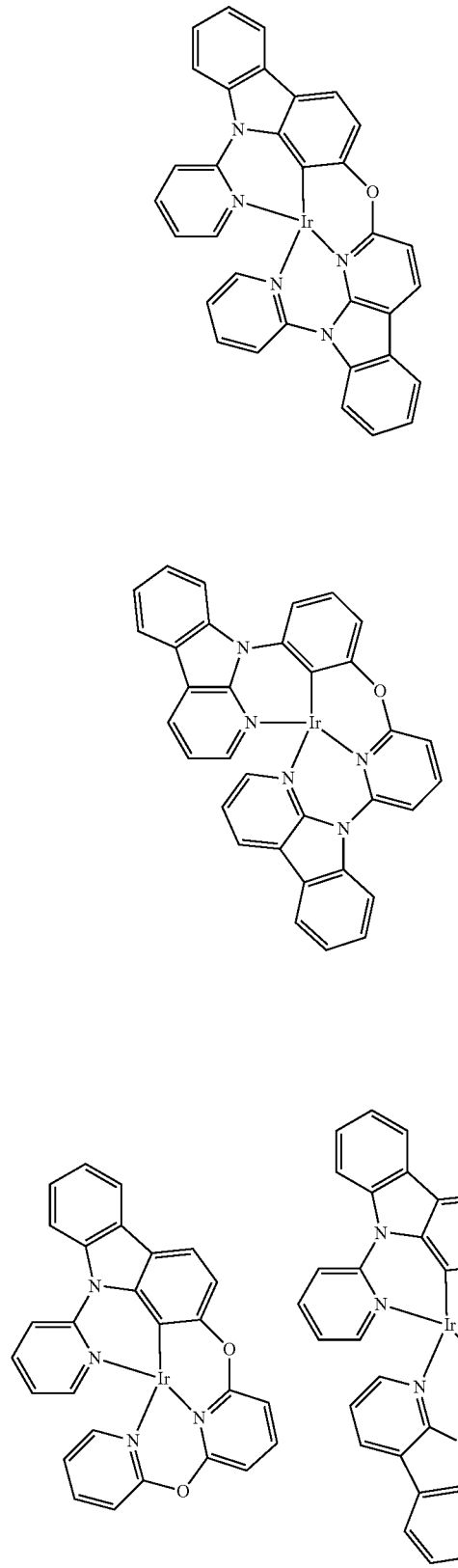
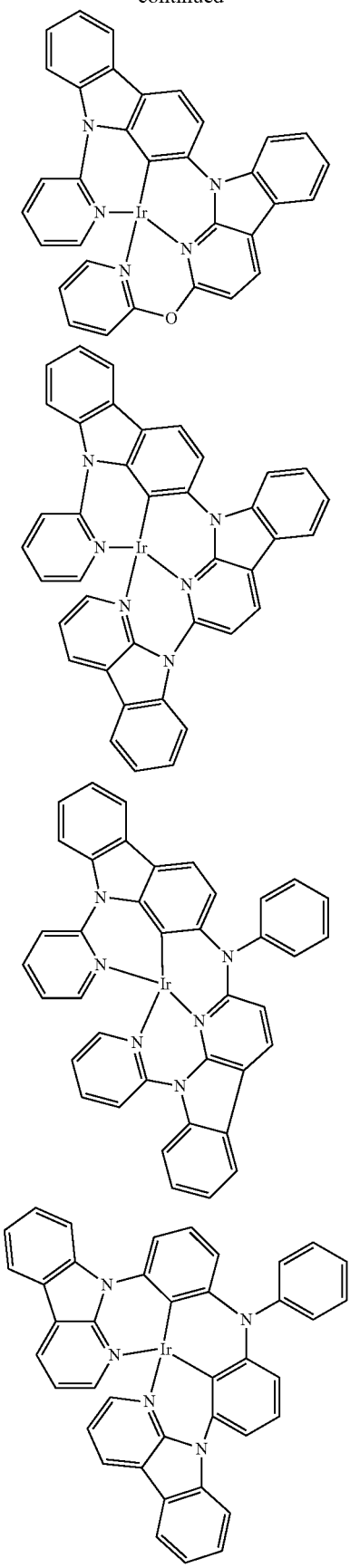

127
-continued
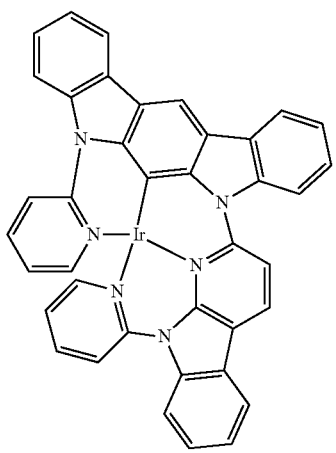
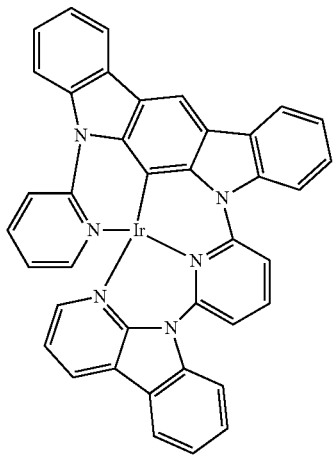
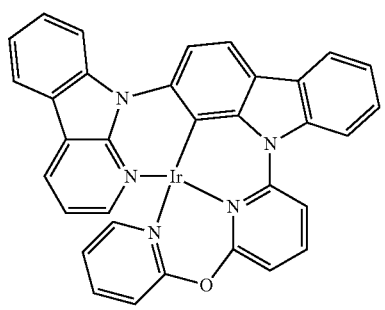
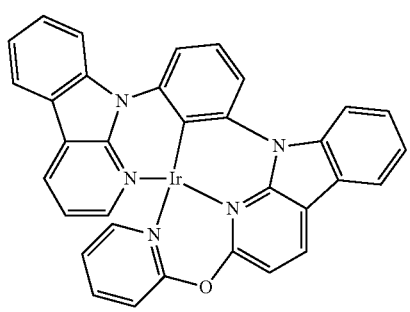
128
-continued
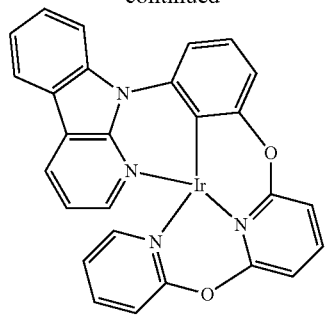
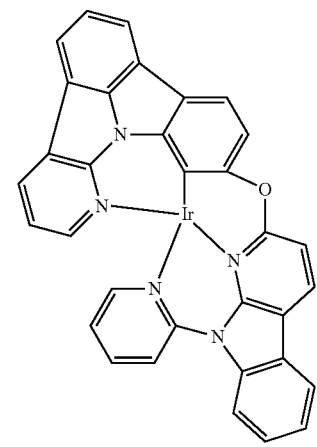
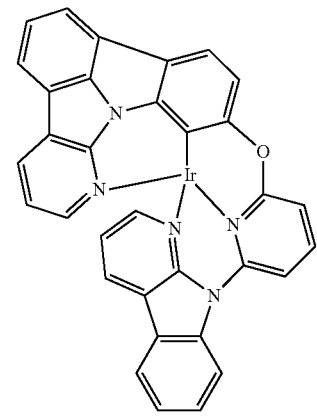
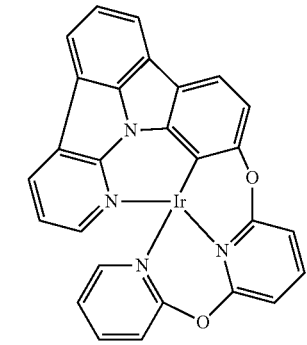

129
-continued
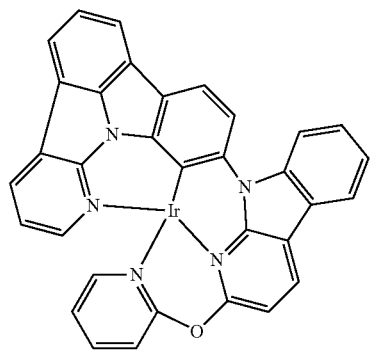
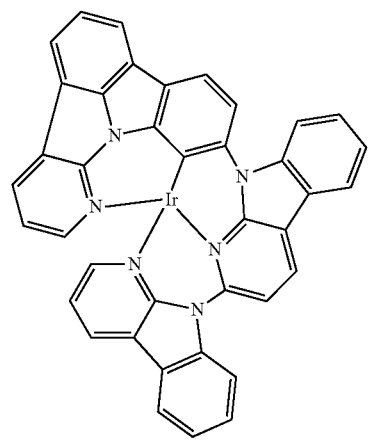
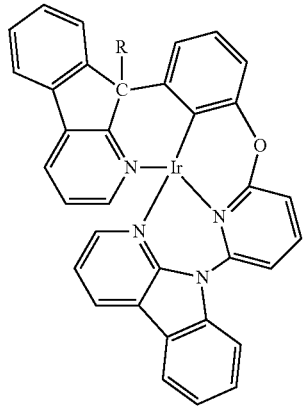
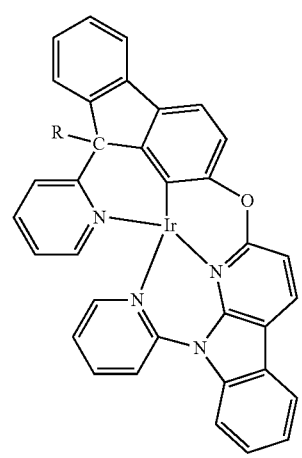
130
-continued
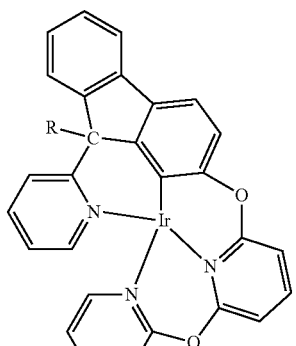
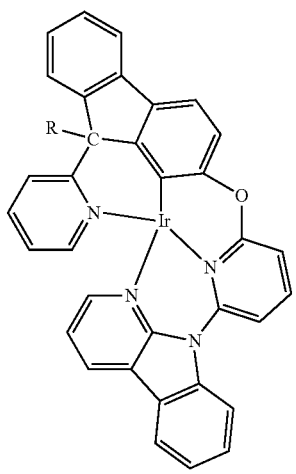
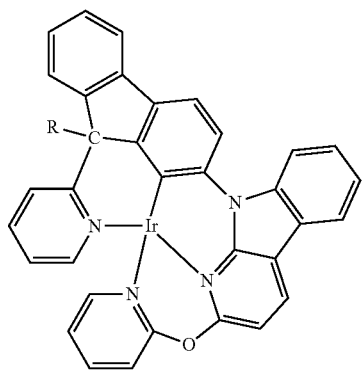
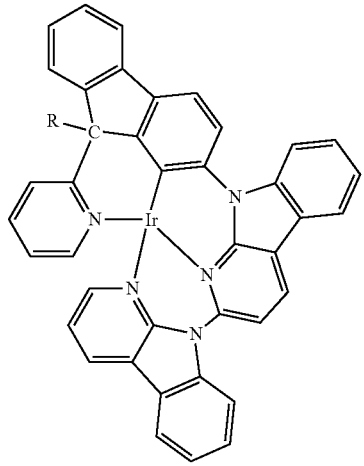

131
-continued
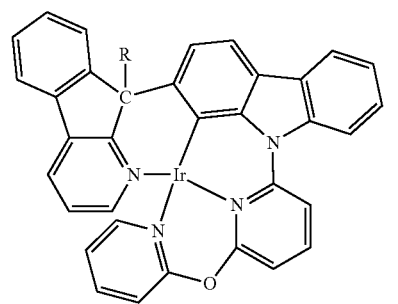
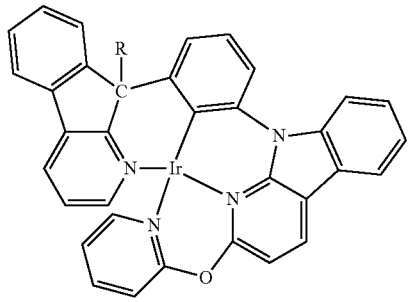
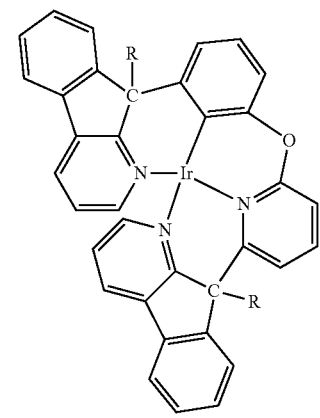
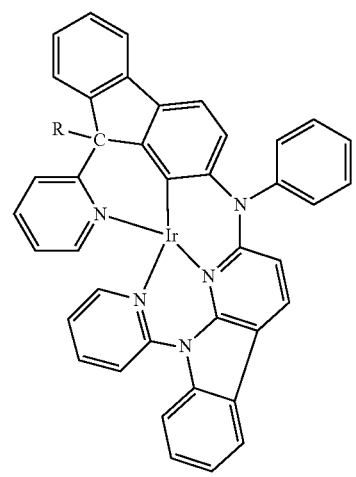
132
-continued
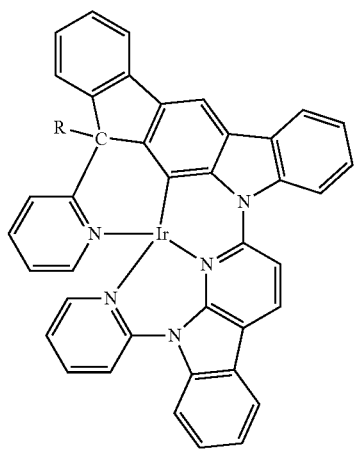
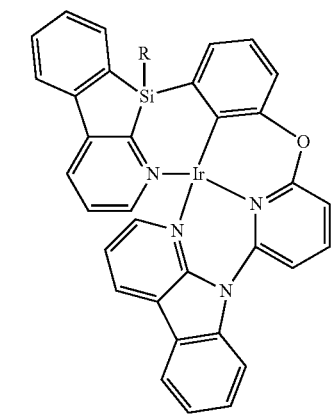
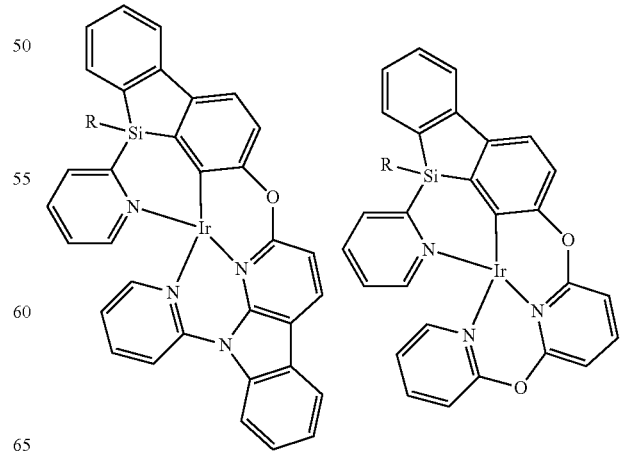

133
-continued
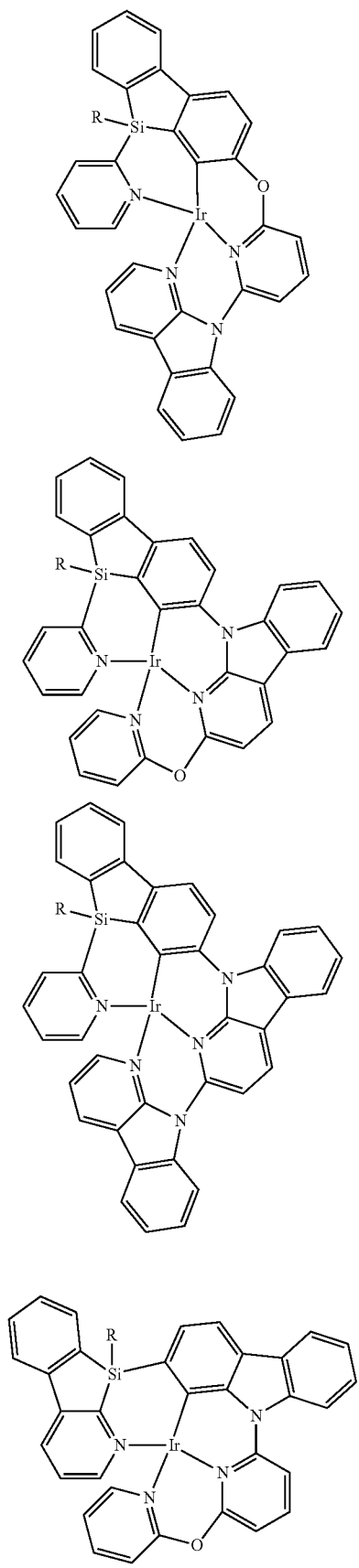
134
-continued
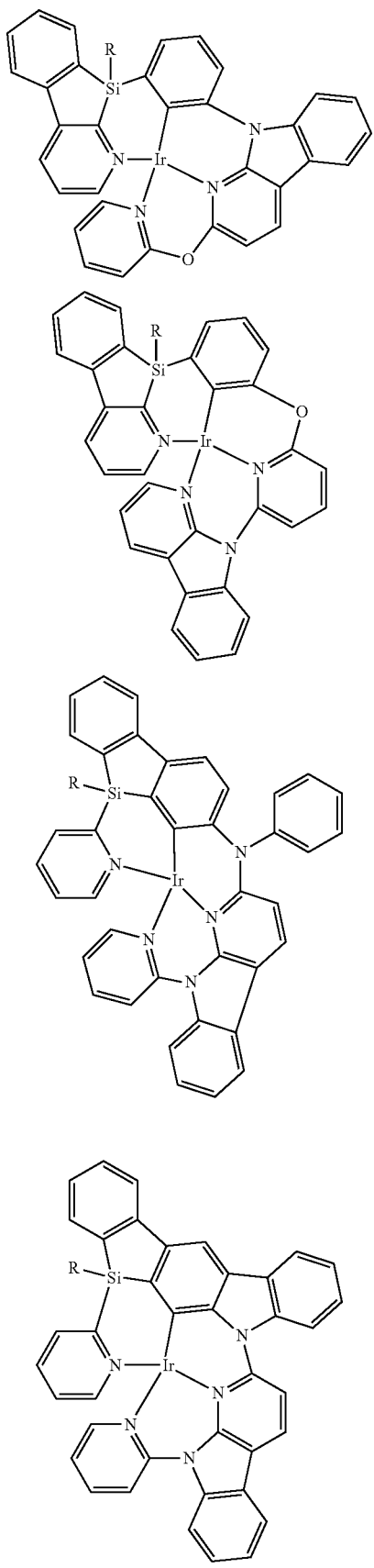

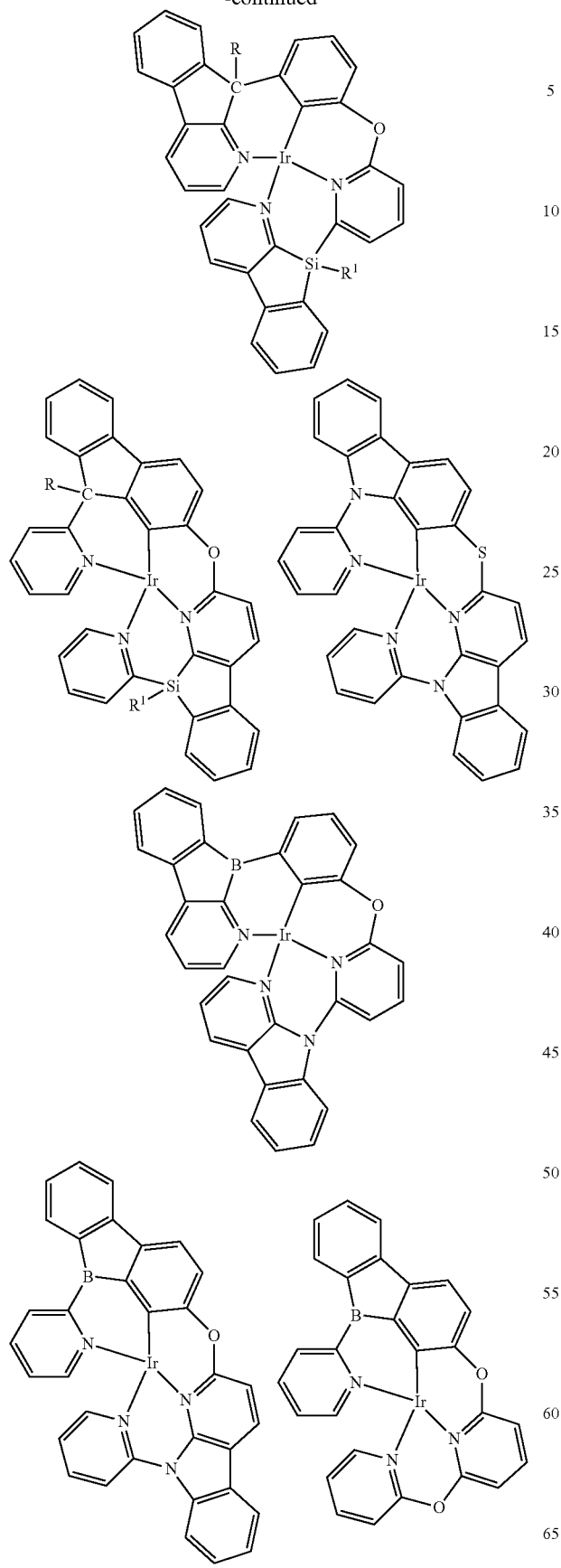
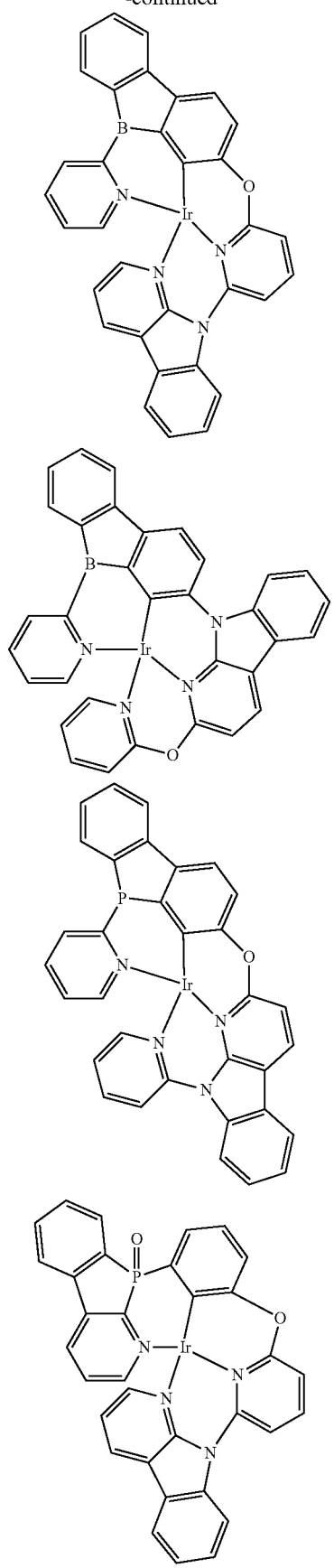

137
-continued
138
-continued
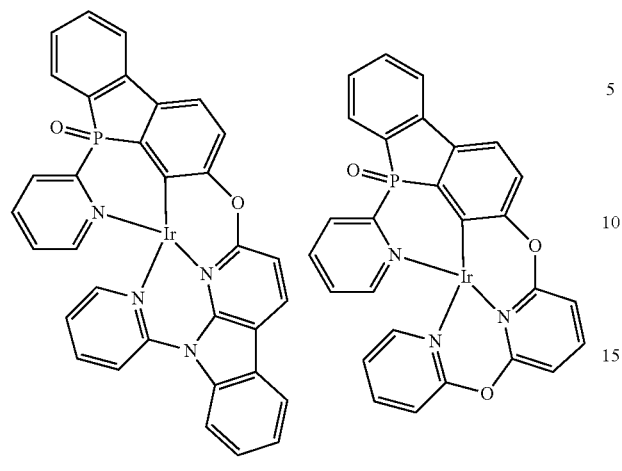
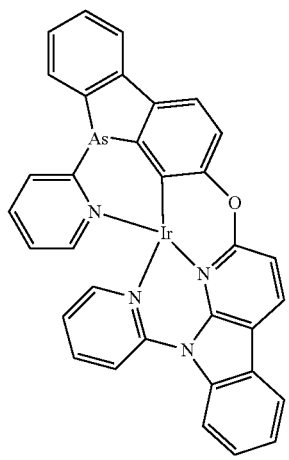
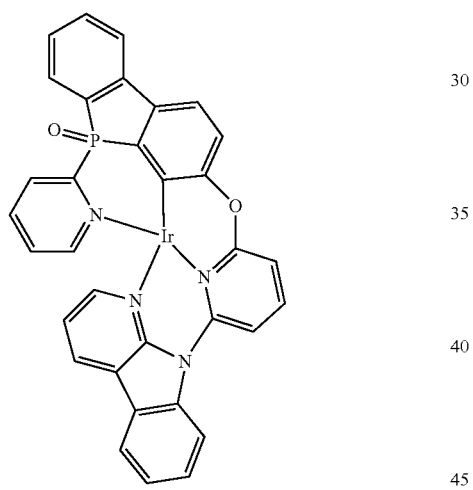
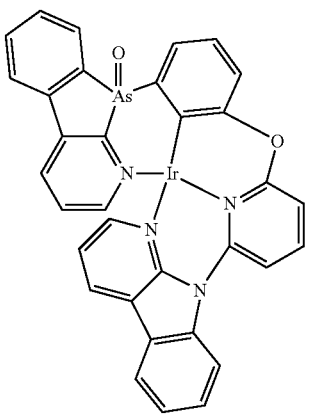
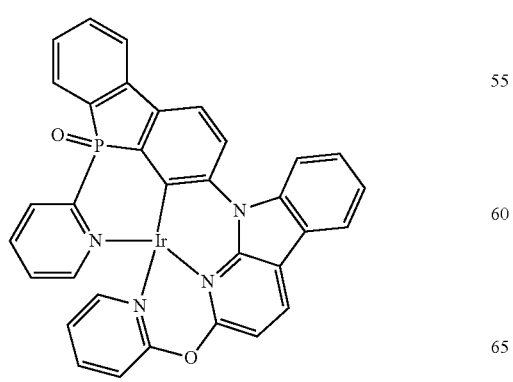
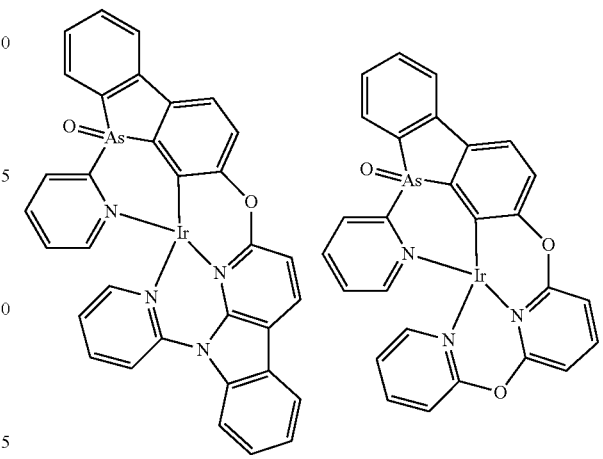

-continued
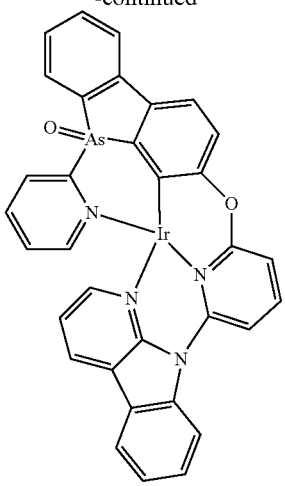
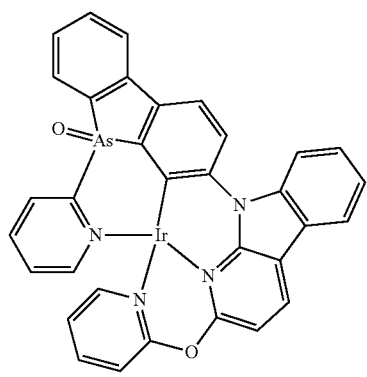
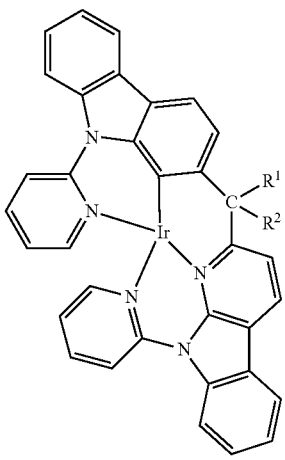
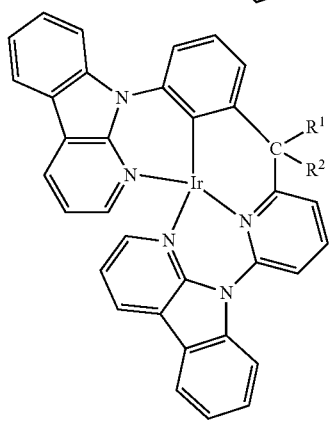
-continued
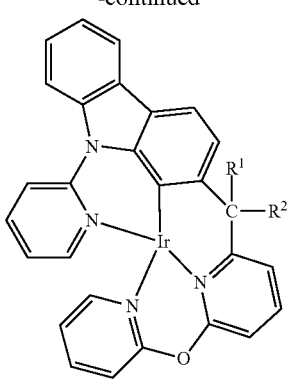
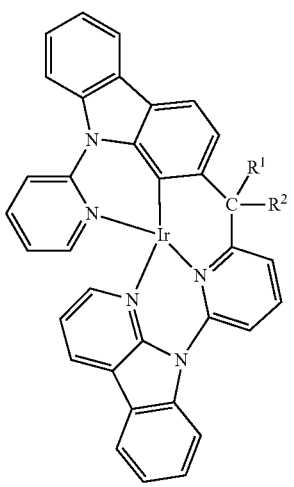
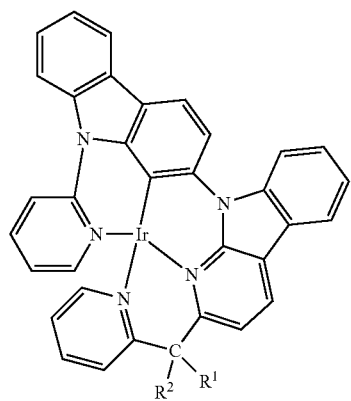
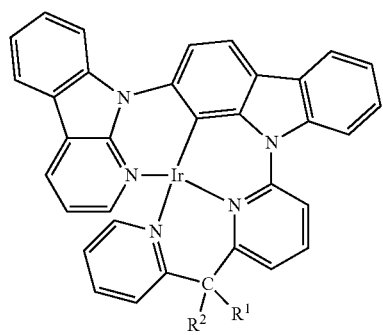

141
-continued
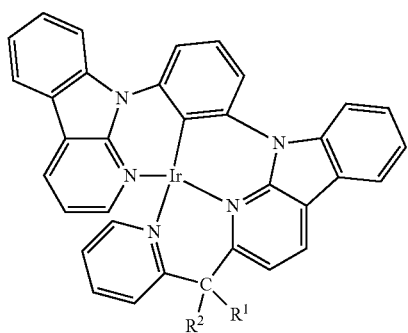
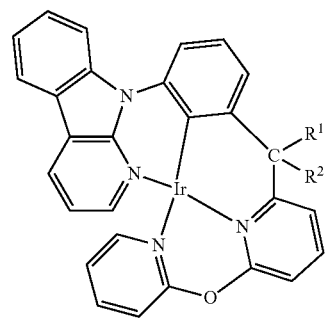
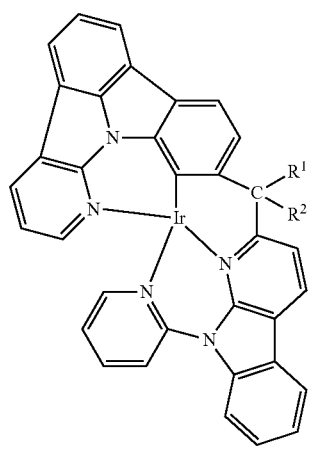
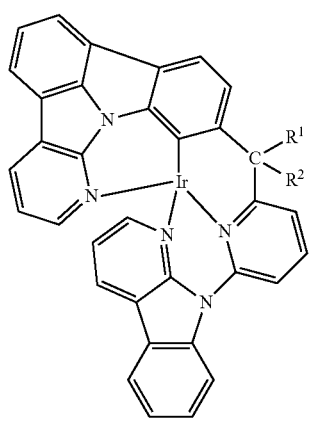
142
-continued
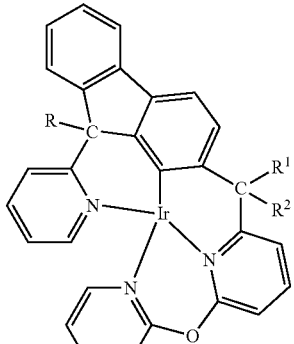
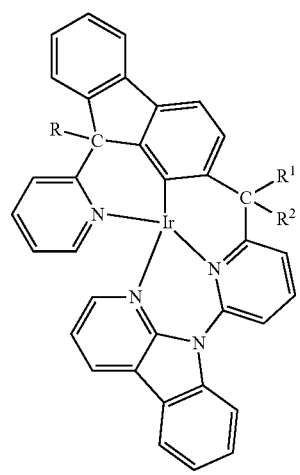
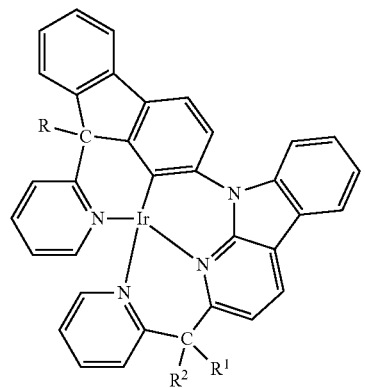
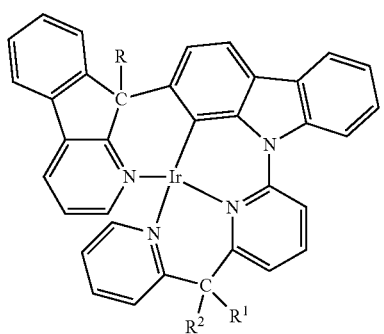

143
-continued
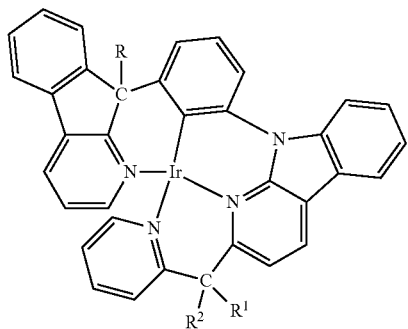
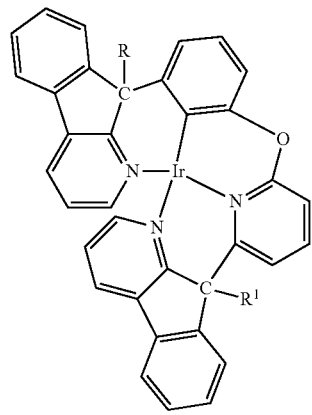
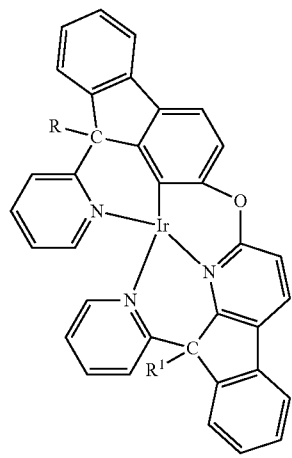
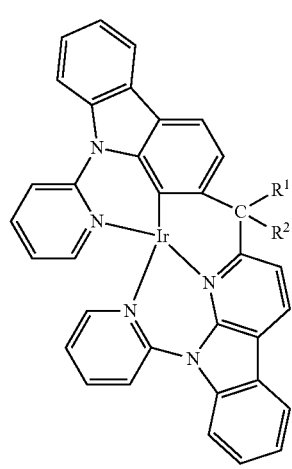
144
-continued
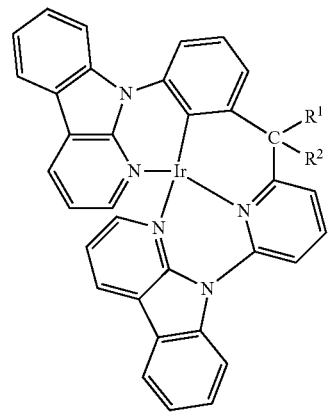
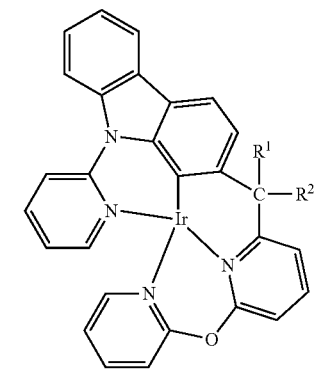
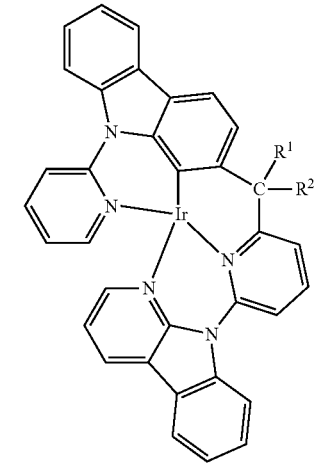
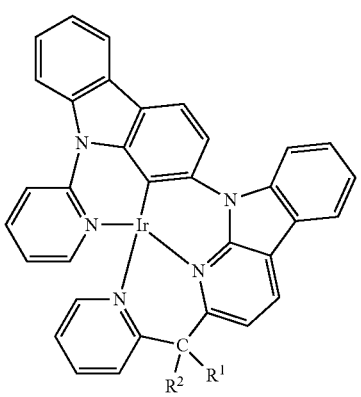

145
-continued
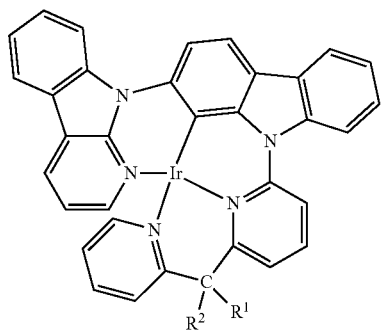
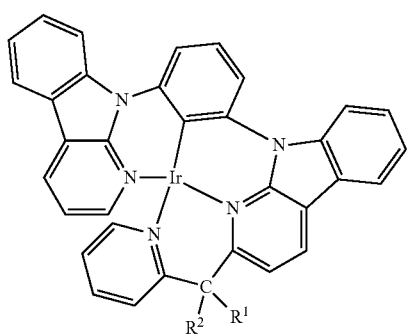
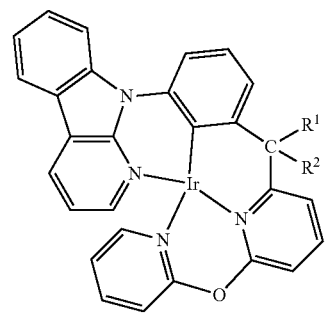
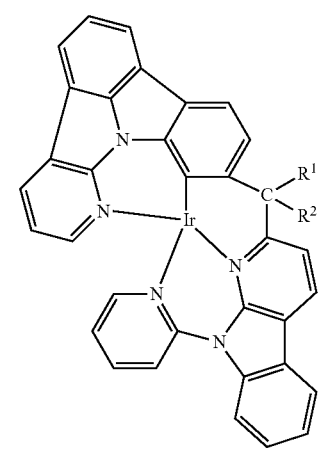
146
-continued
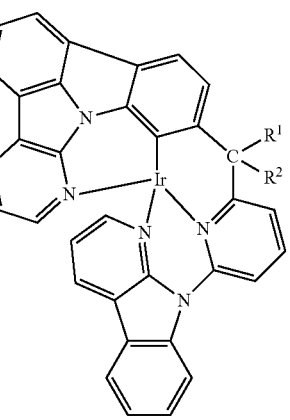
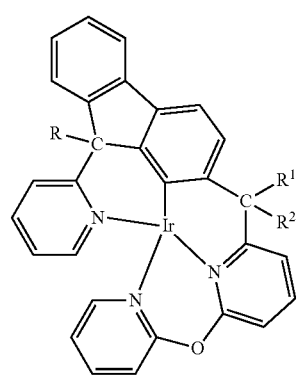
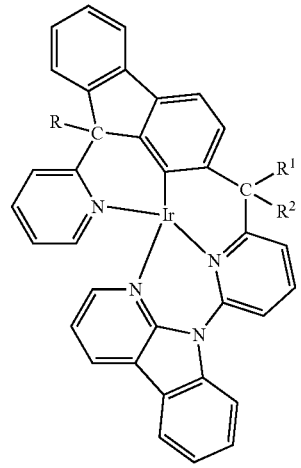
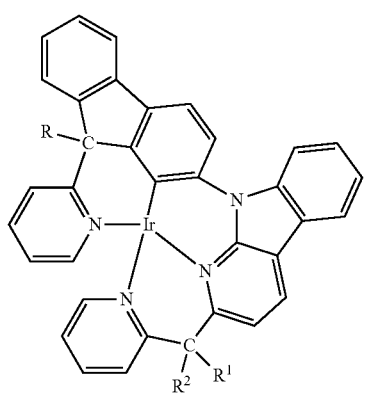

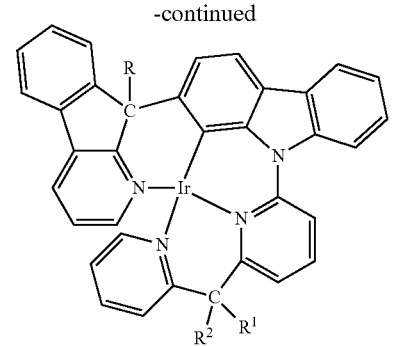
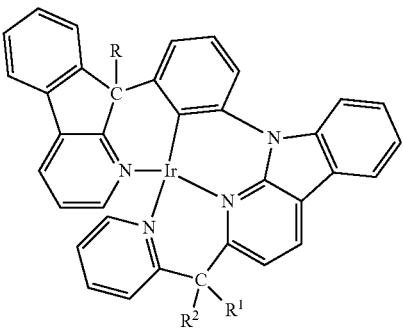
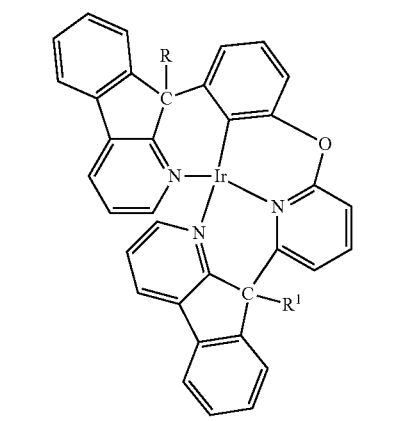
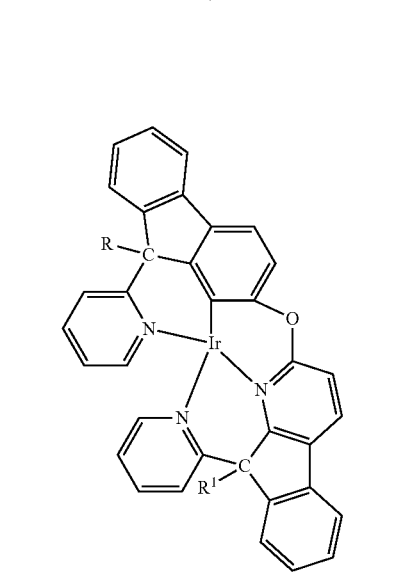
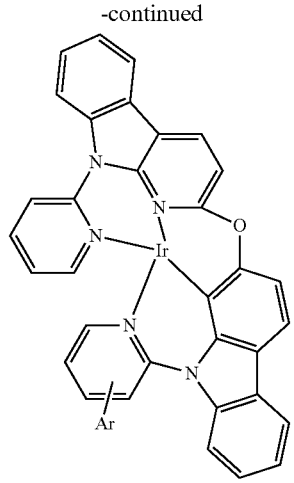
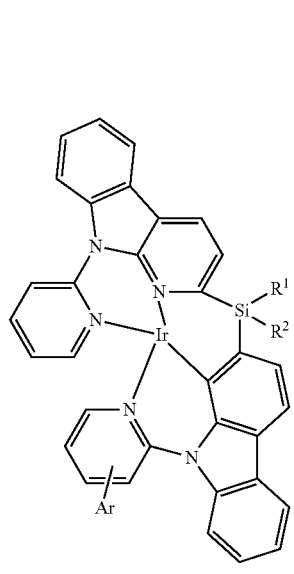
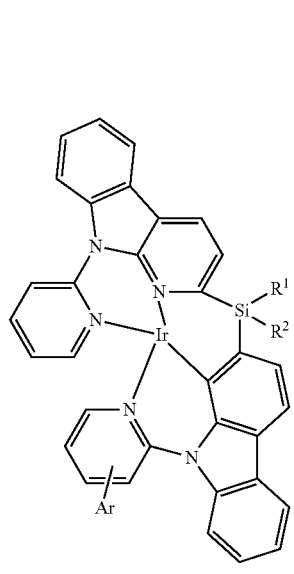

149
-continued
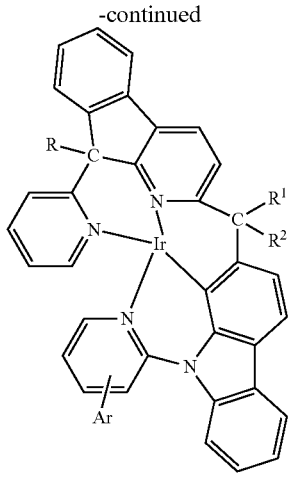
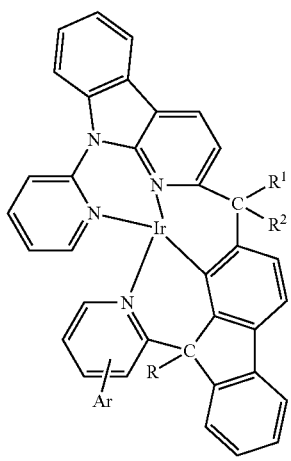
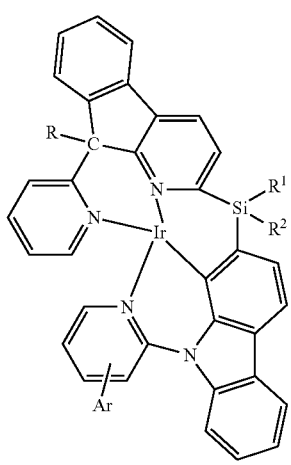
150
-continued
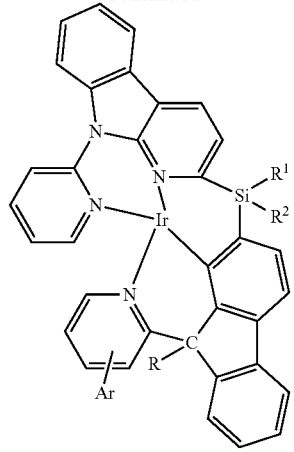
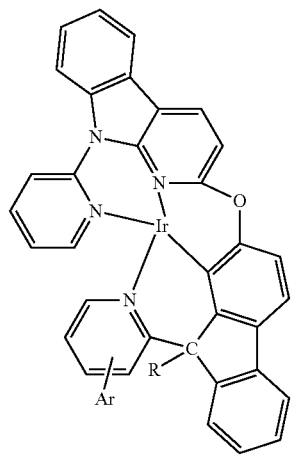
Where Ar is aryl functional group like
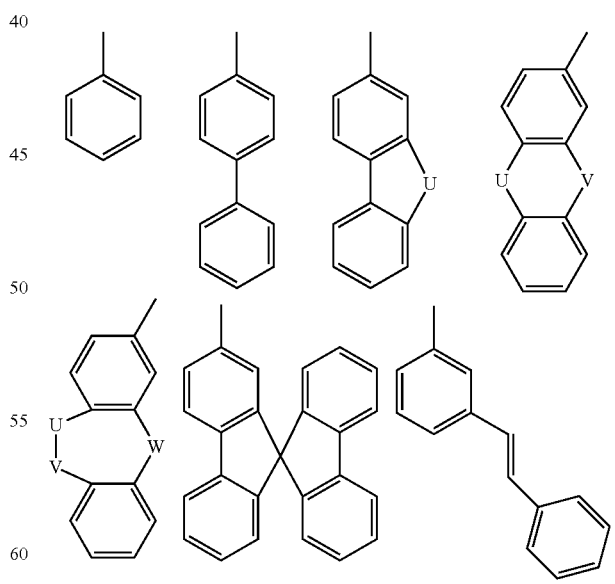
and their analogs.
Where U, V, W could be the same or different atoms like carbon (C), oxygen (O), nitrogen (N), phosphorus (P), silicon (Si), boron (B) and other atoms.

151
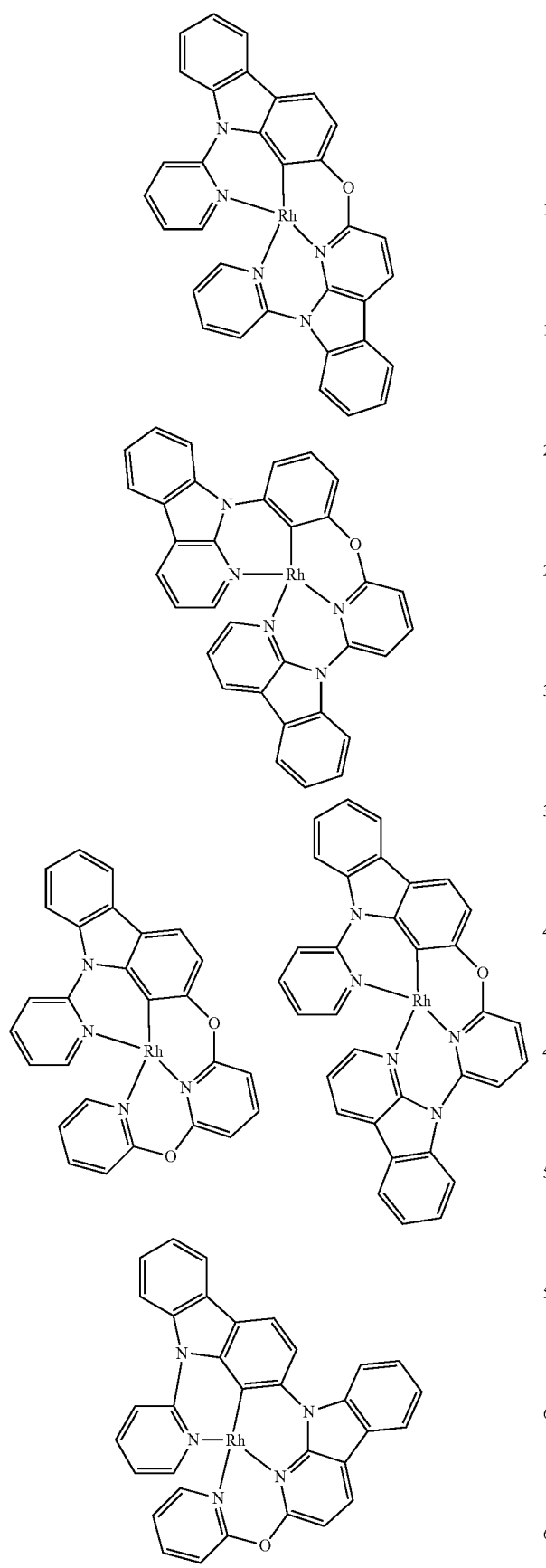
152
-continued
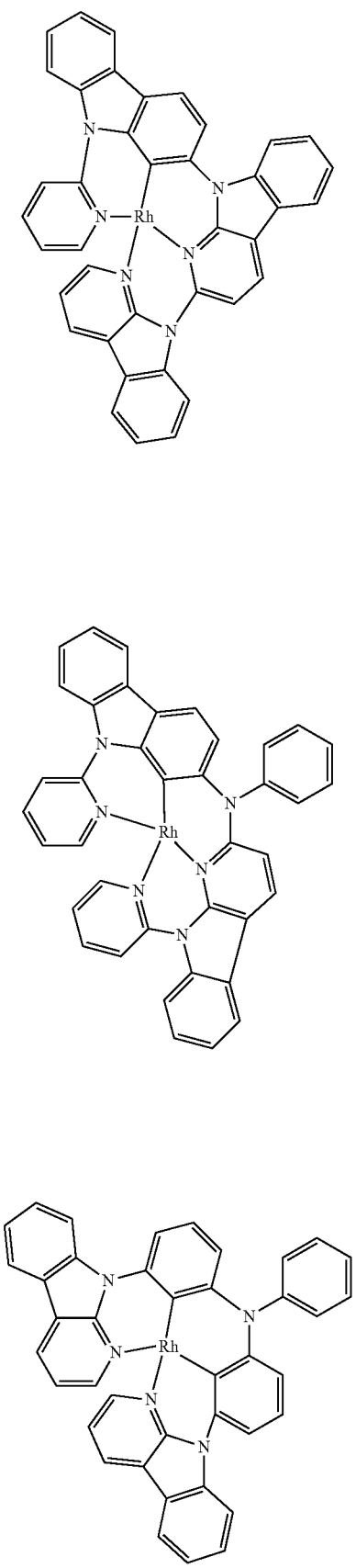

153
-continued
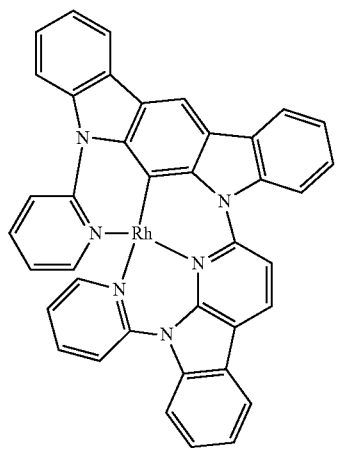
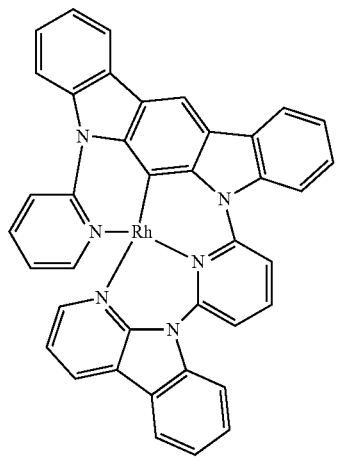
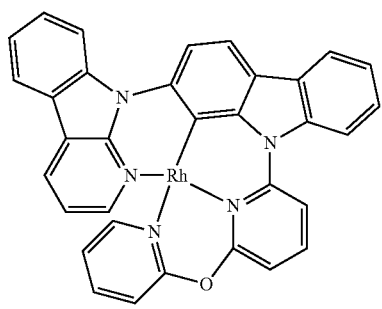
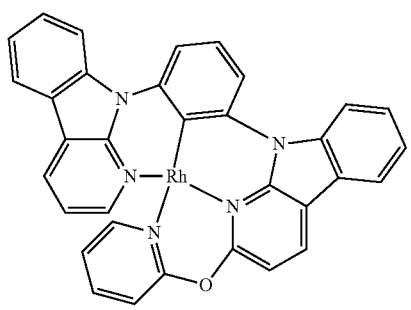
154
-continued
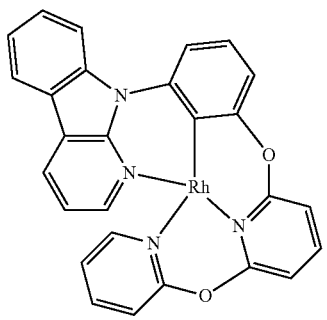
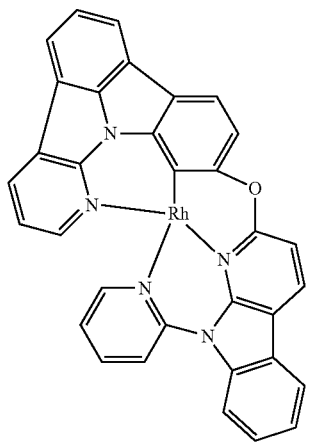
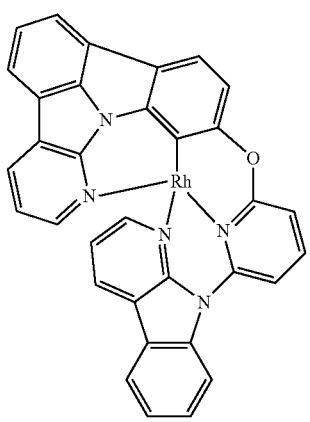
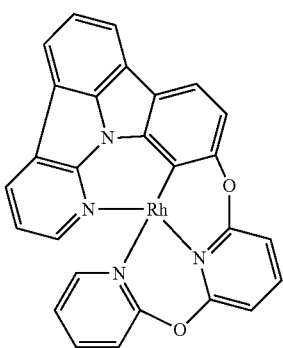

155
-continued
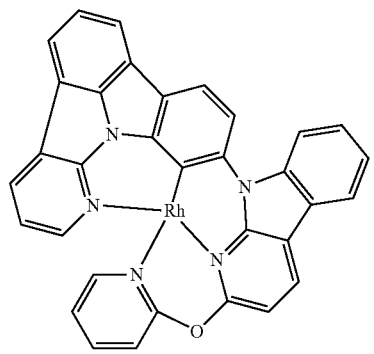
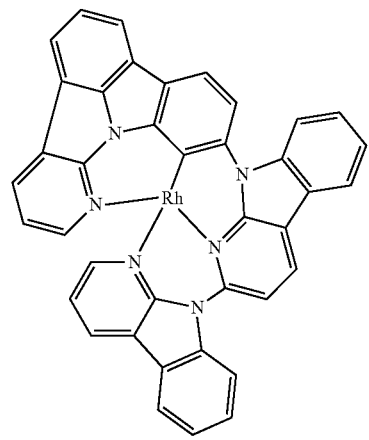
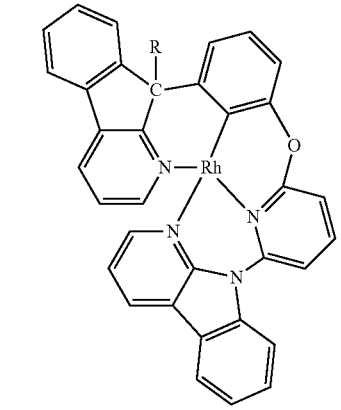
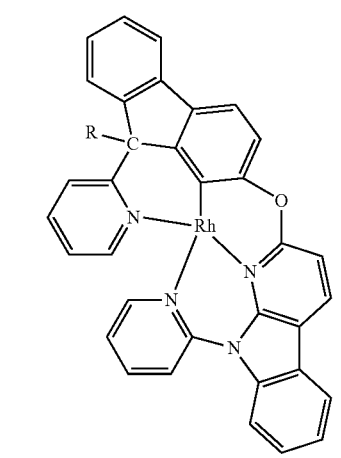
156
-continued
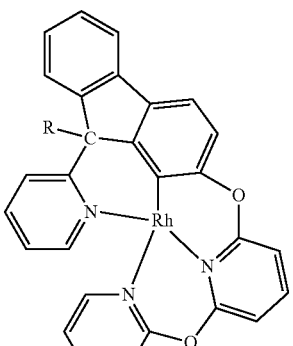
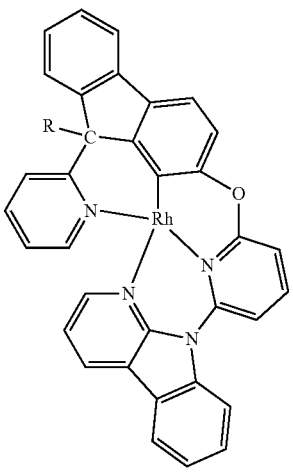
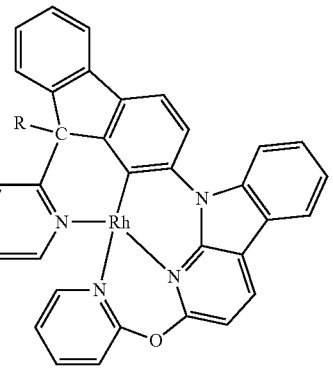
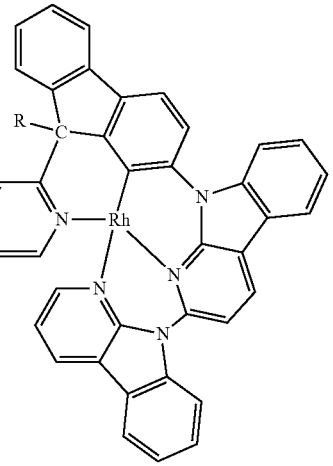

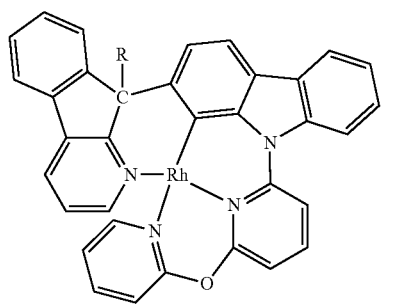
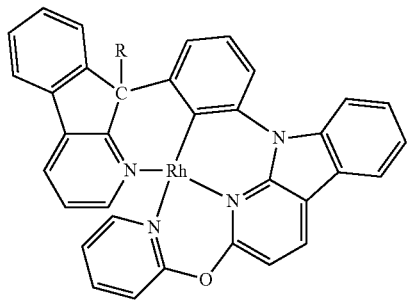
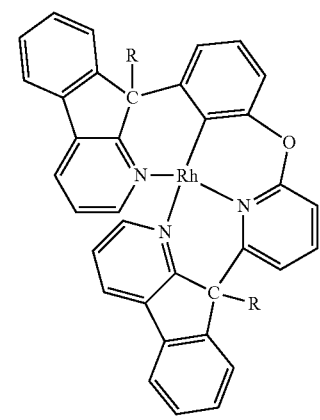
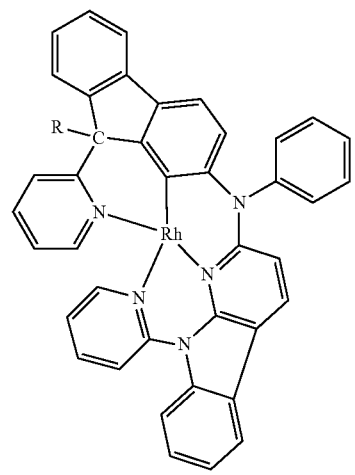
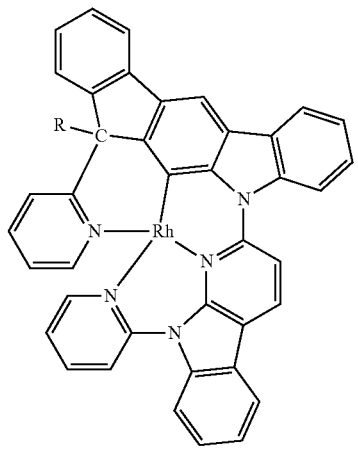
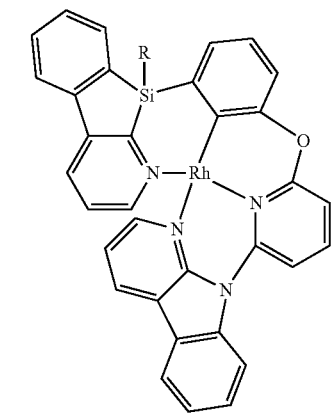

159
-continued
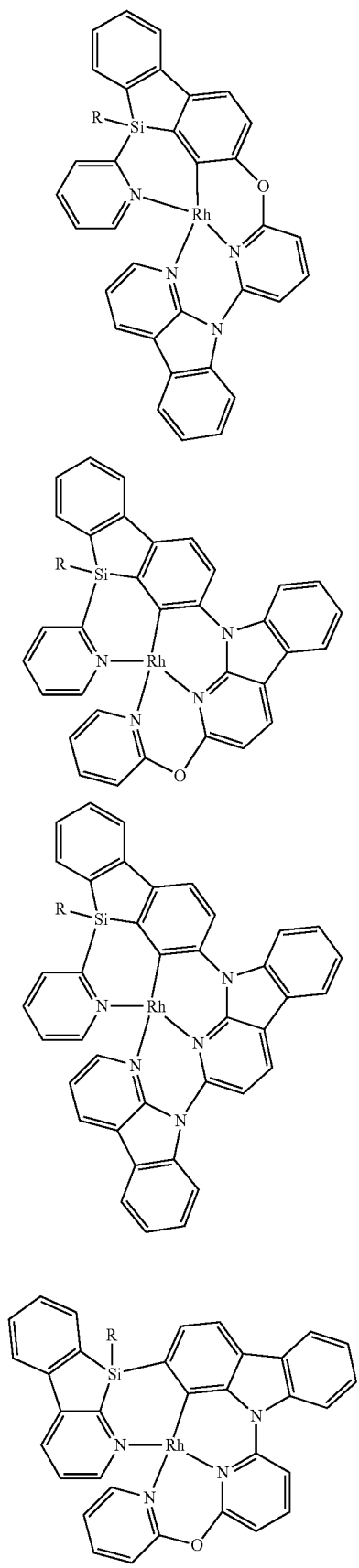
160
-continued
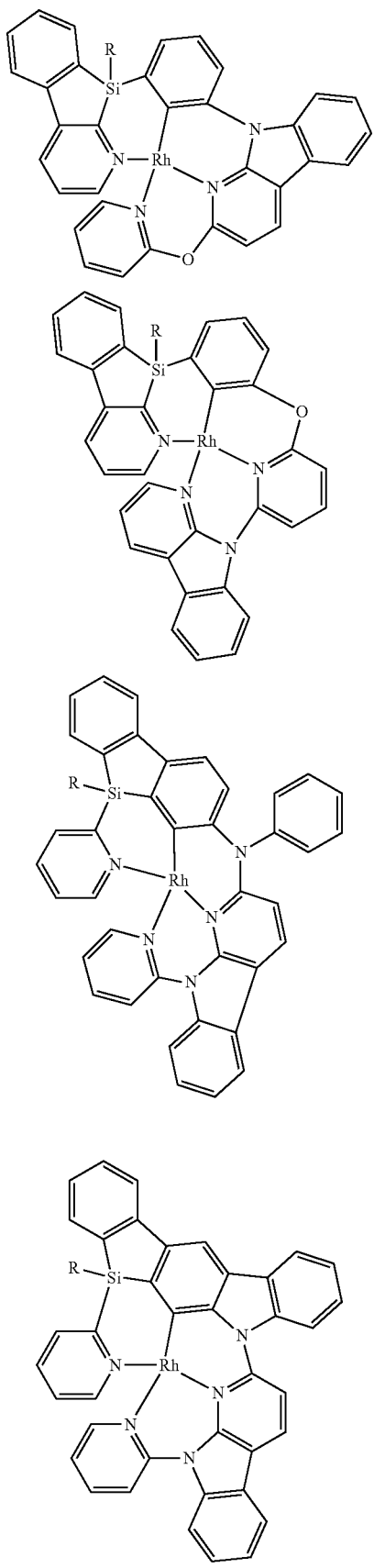

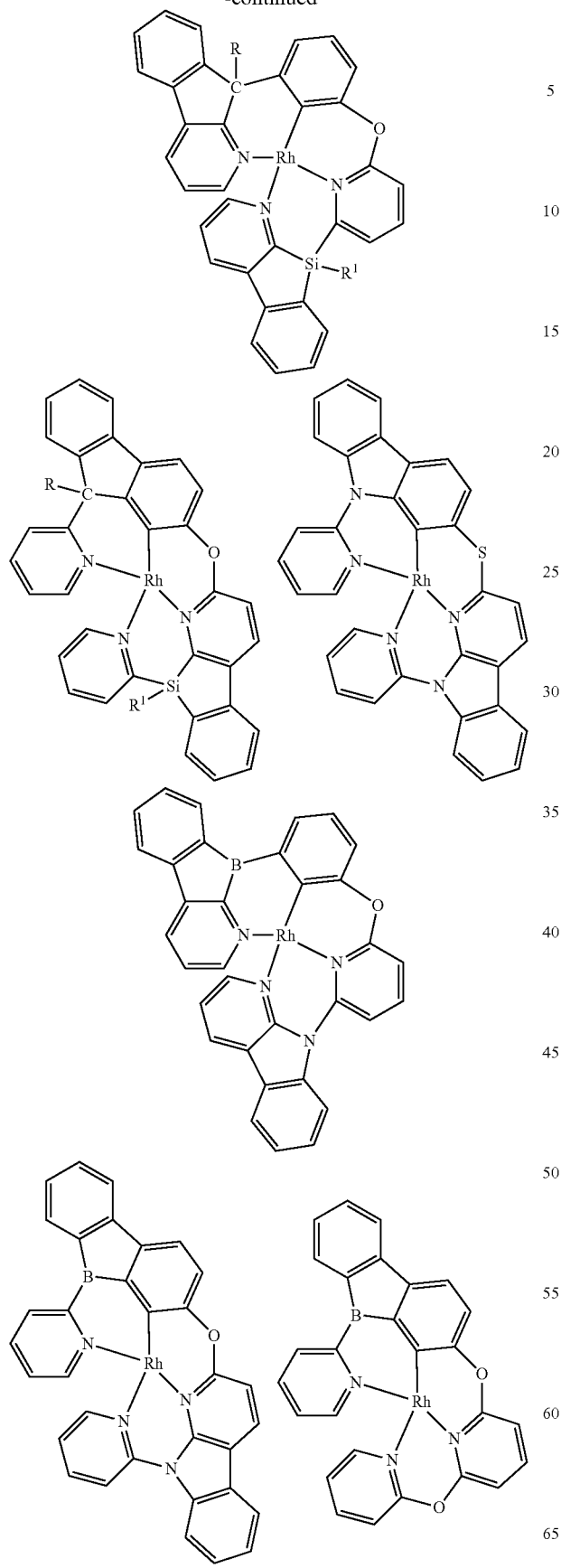
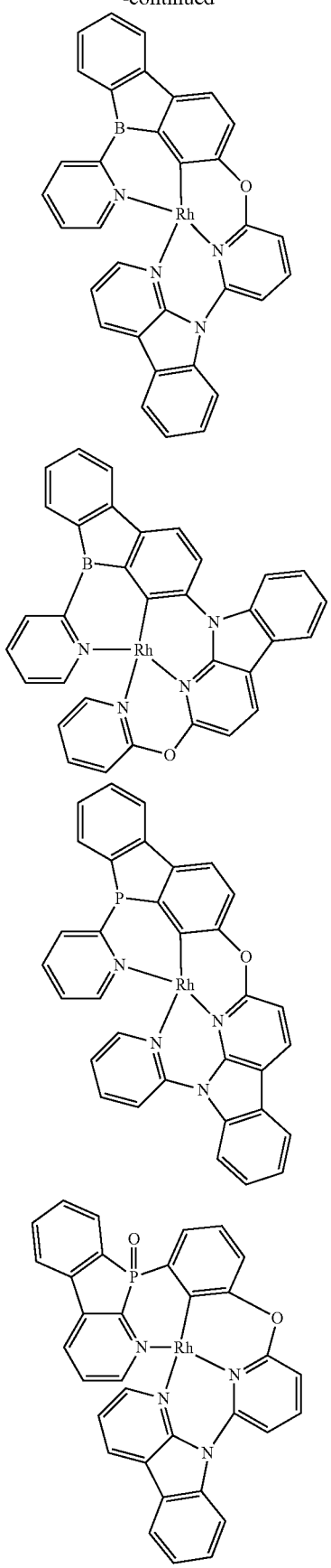

163
-continued
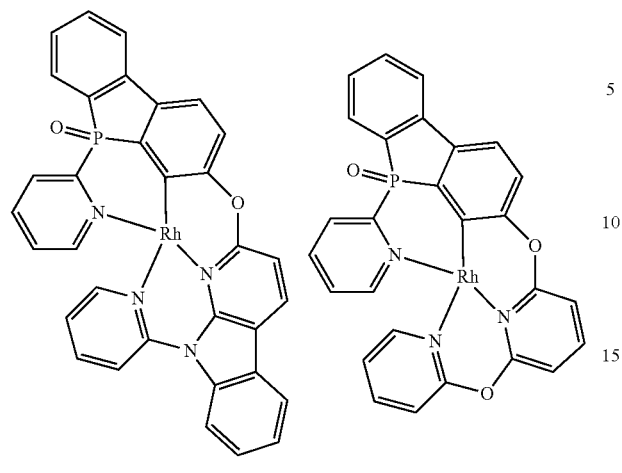
164
-continued
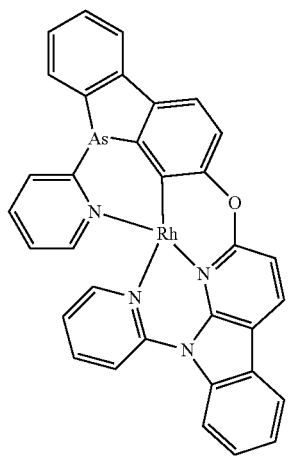
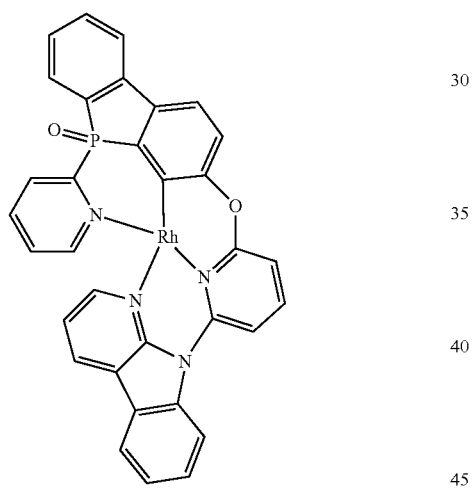
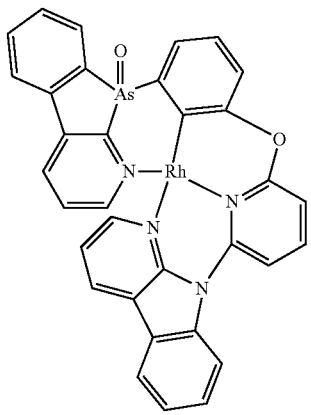
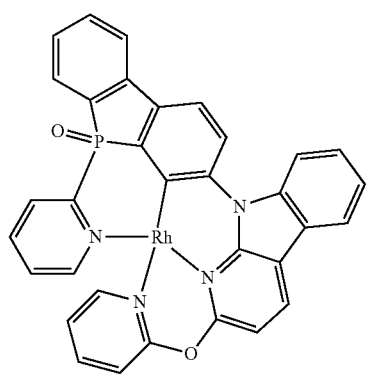
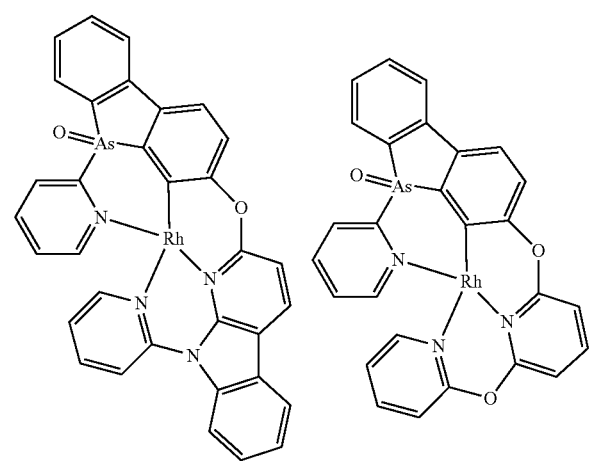

-continued
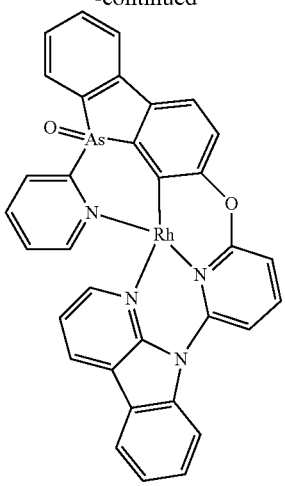
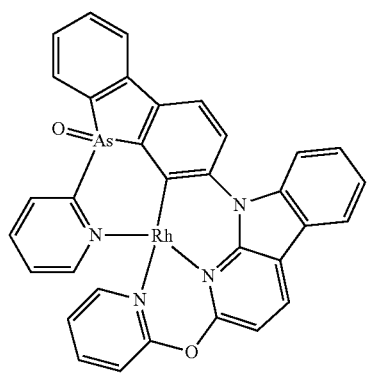
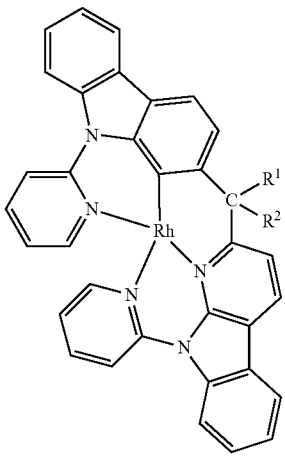
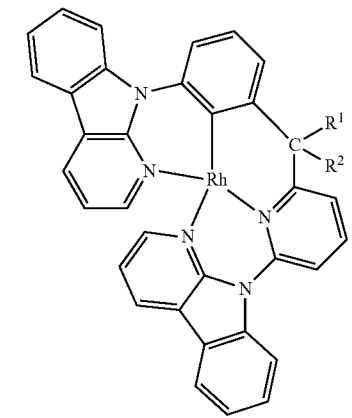
-continued
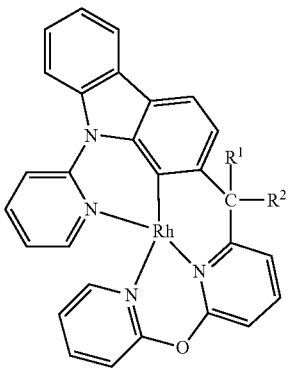
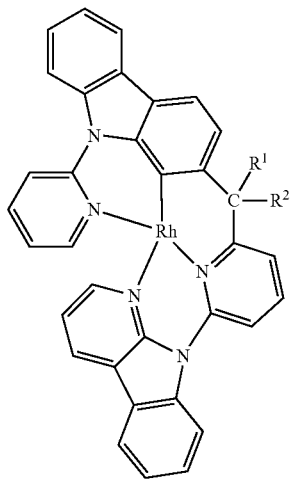
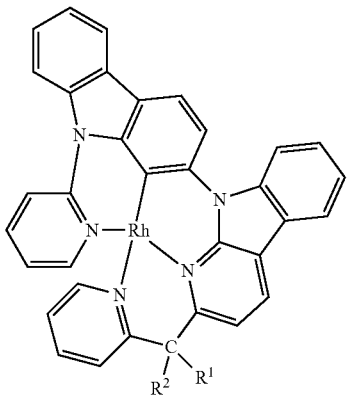
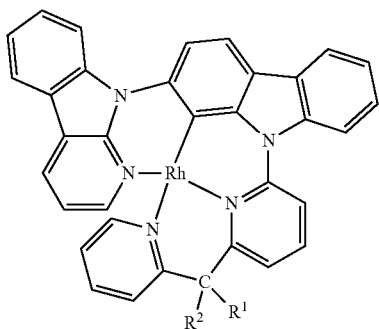

167
-continued
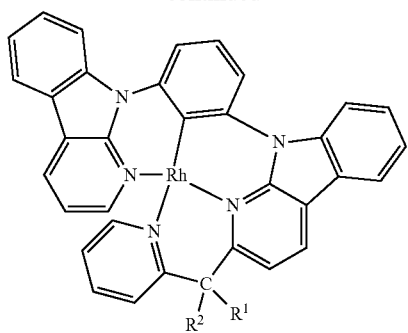
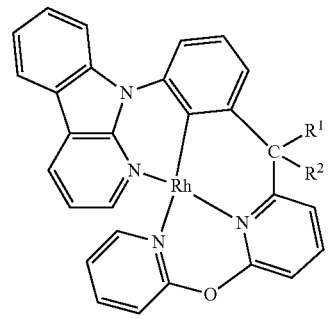
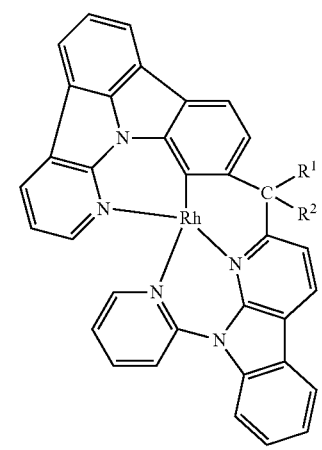
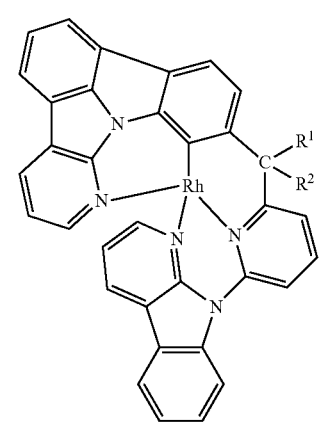
168
-continued
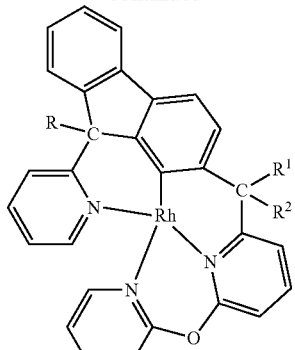
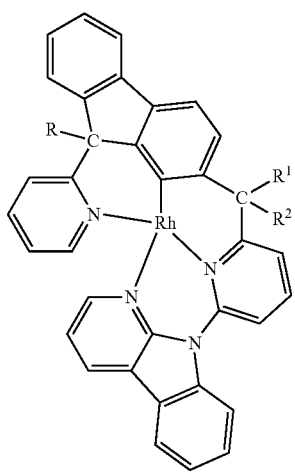
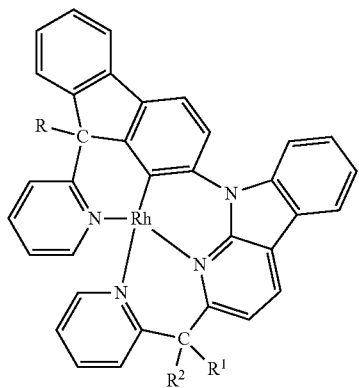
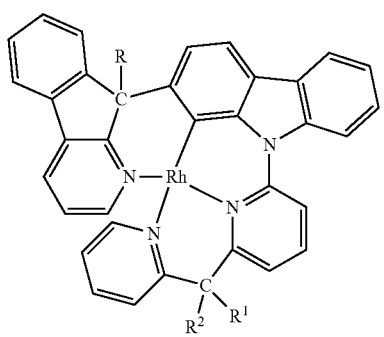

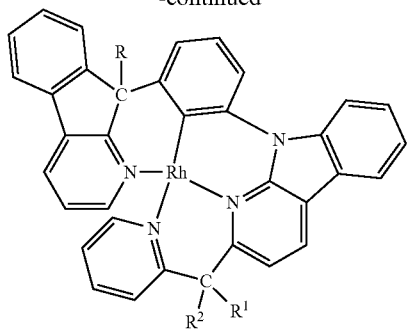
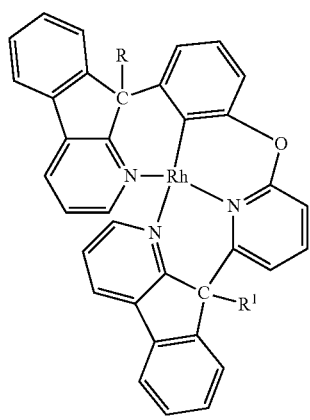
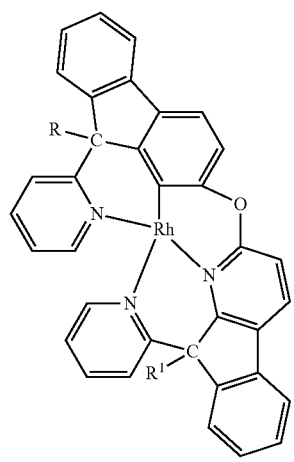
In one aspect, the compounds can have the structure:
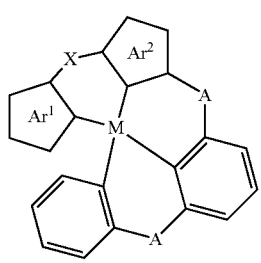
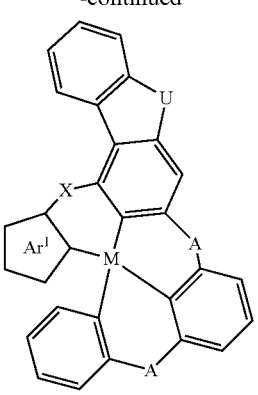
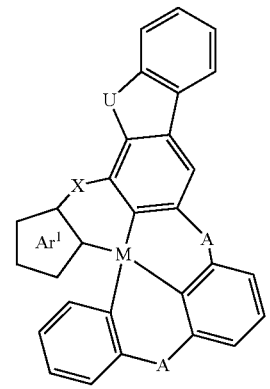
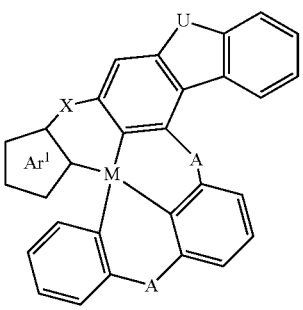
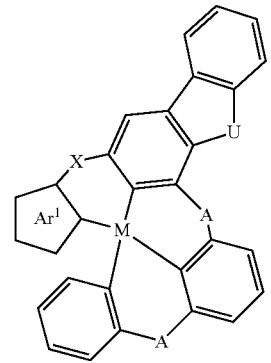
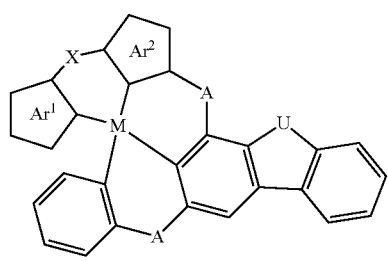

171
-continued
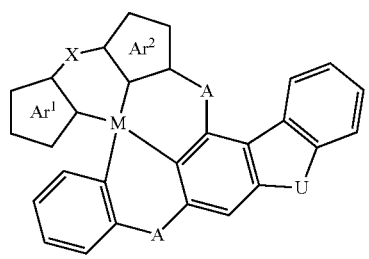
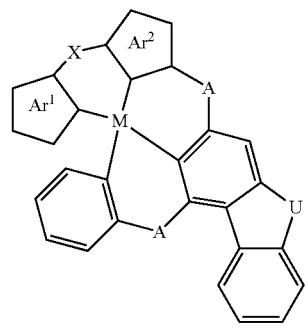
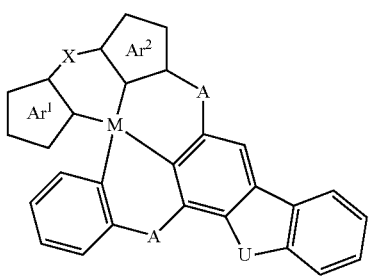
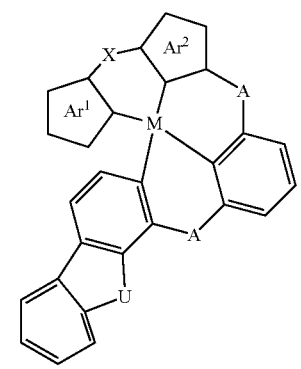
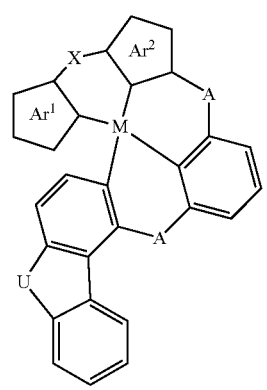
172
-continued
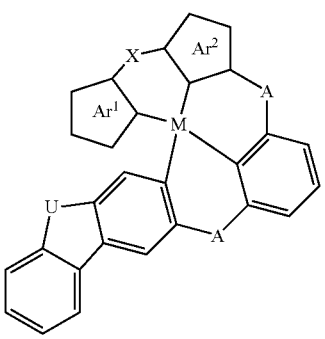
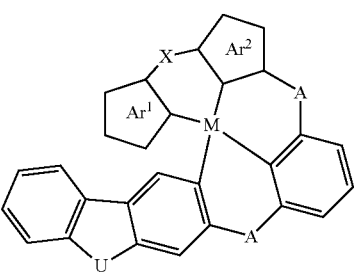
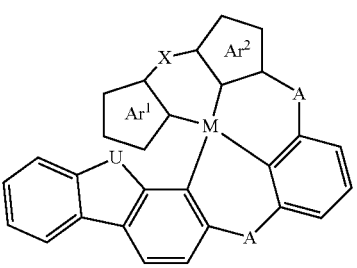
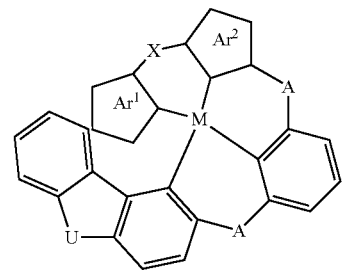
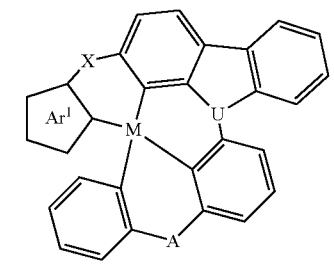
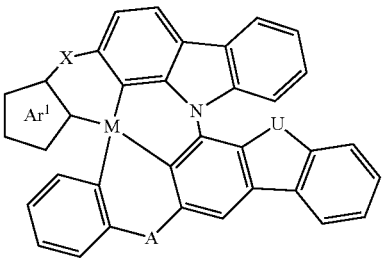

-continued
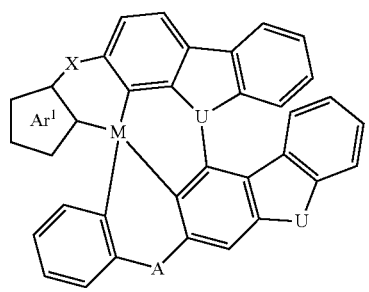
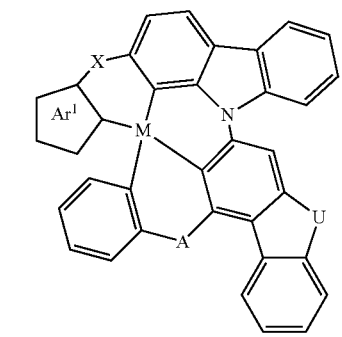
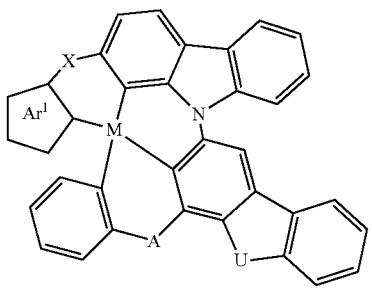
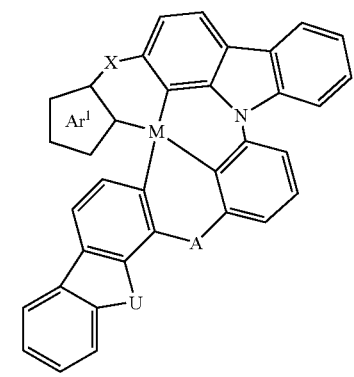
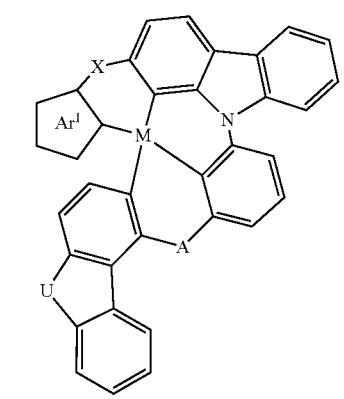
-continued
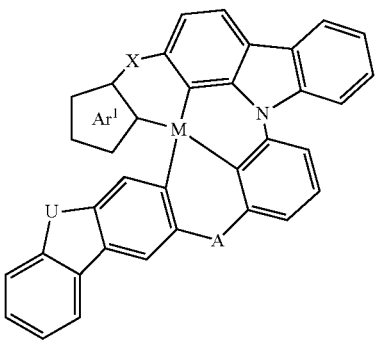
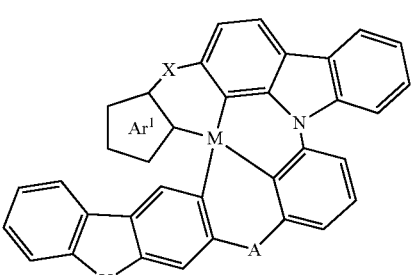
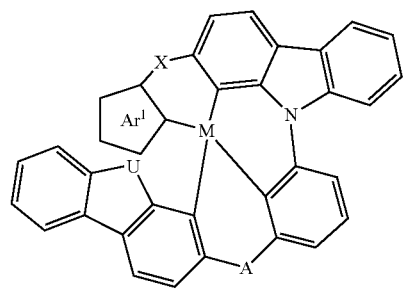
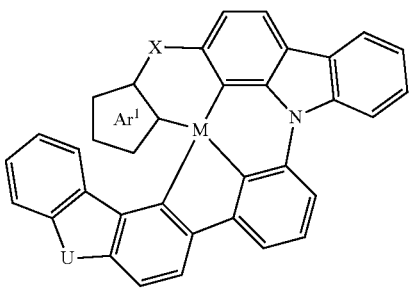
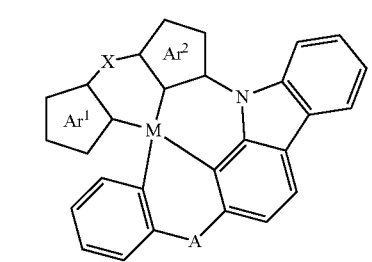

175
-continued
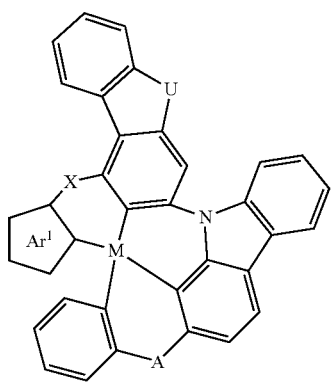
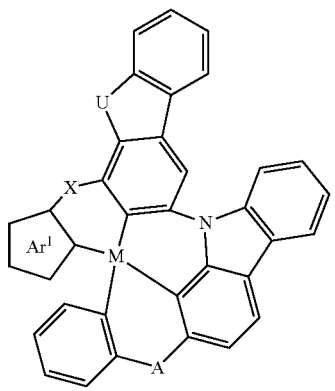
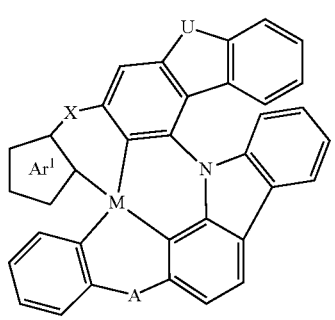
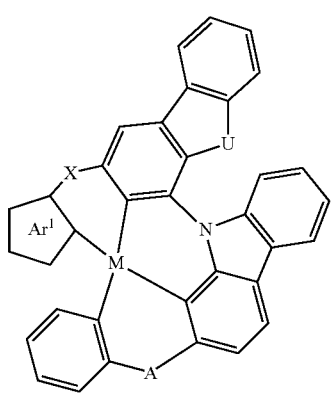
176
-continued
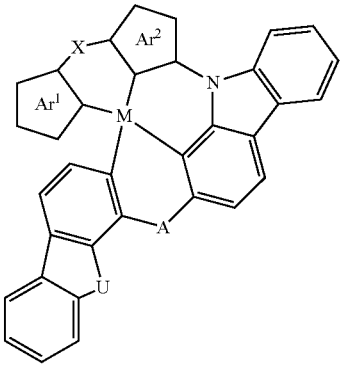
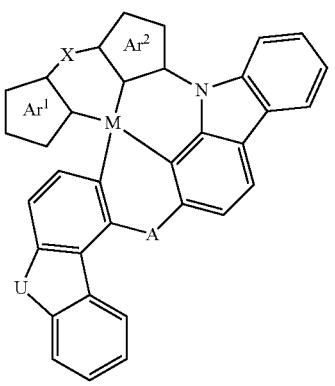
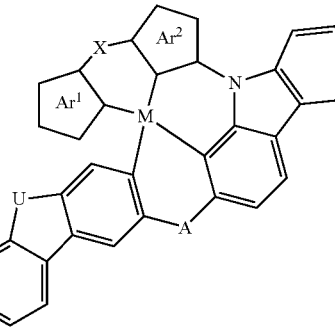
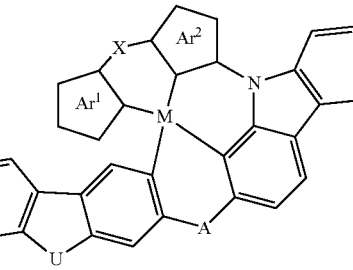
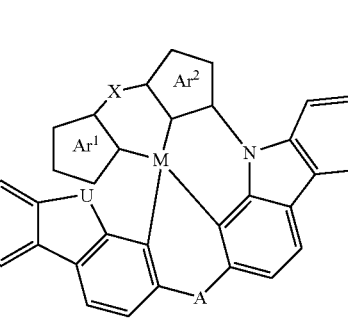

-continued
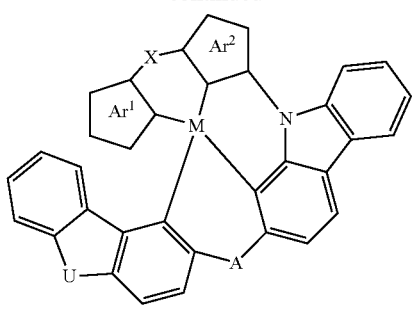
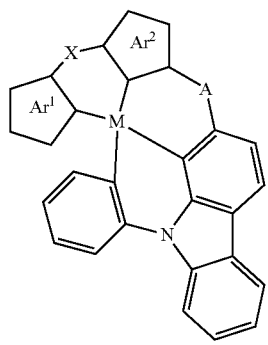
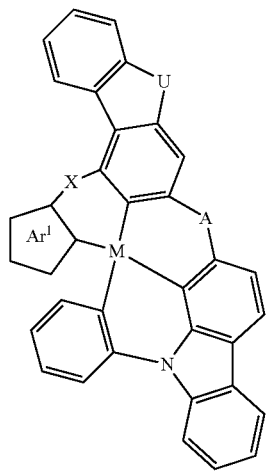
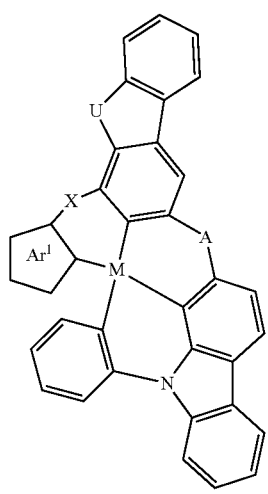
-continued
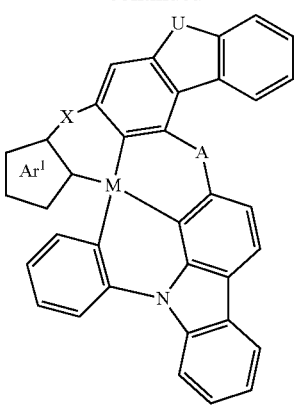
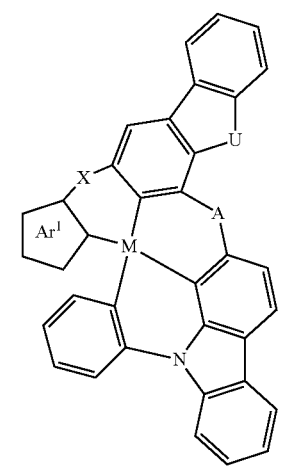
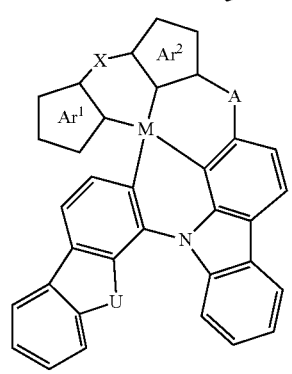
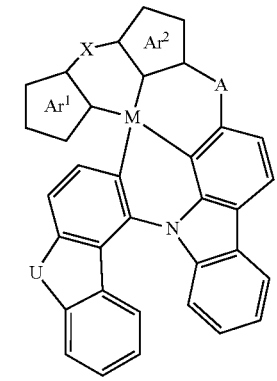

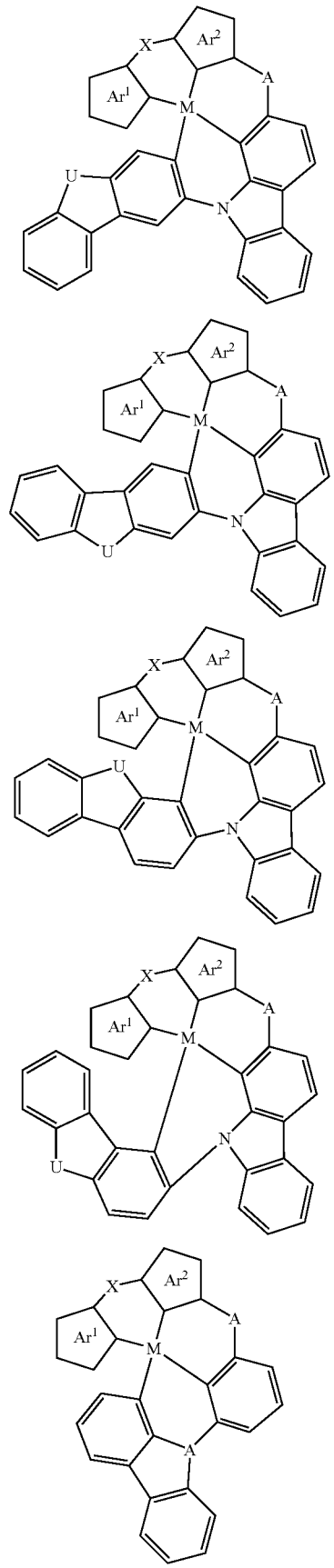
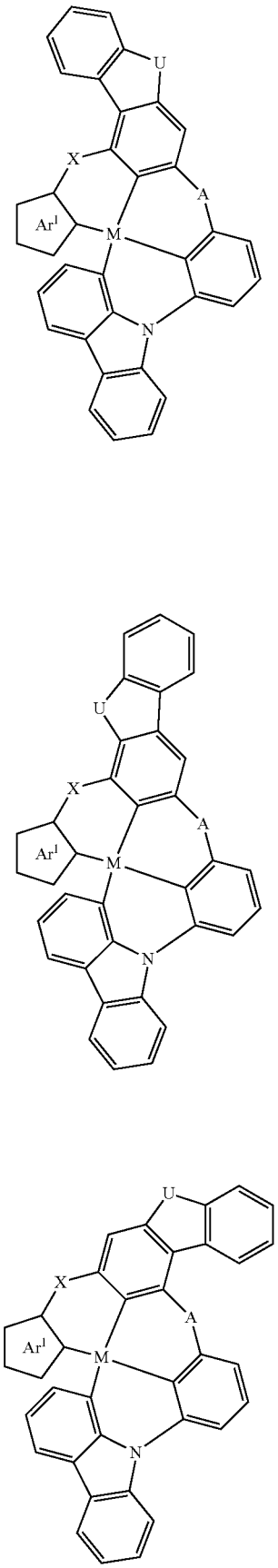

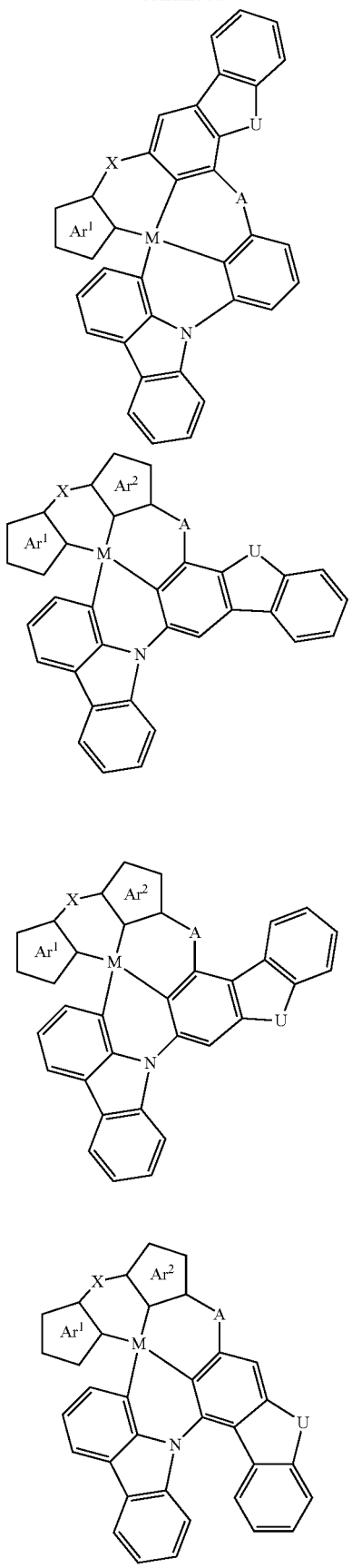
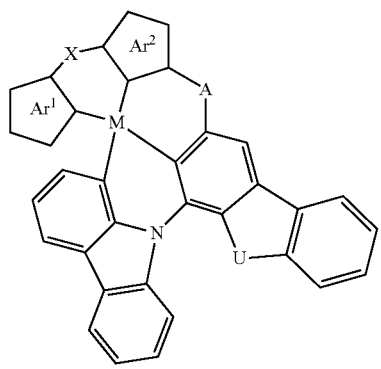
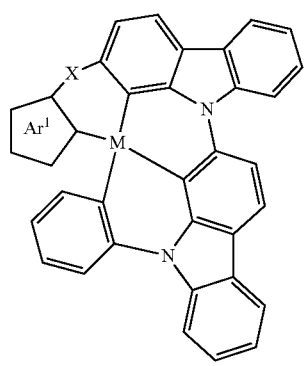
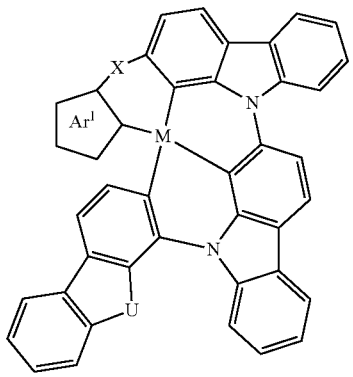
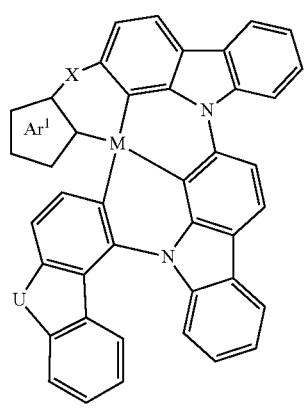

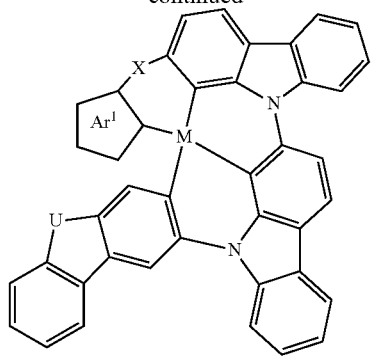
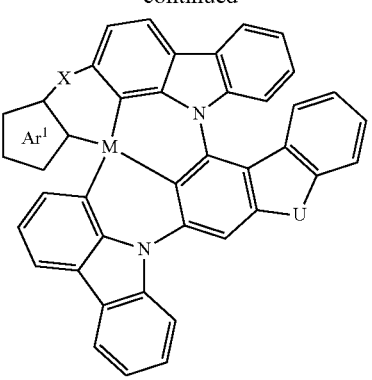
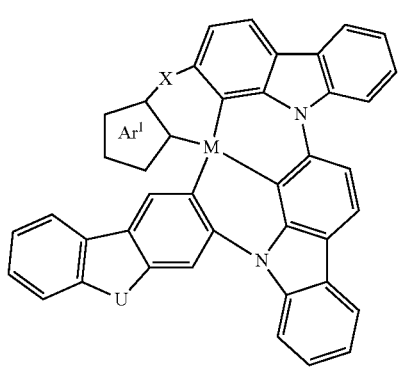
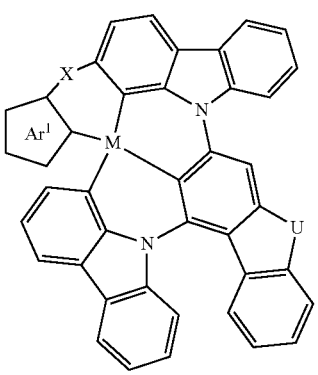
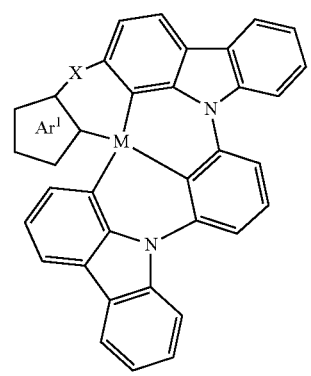
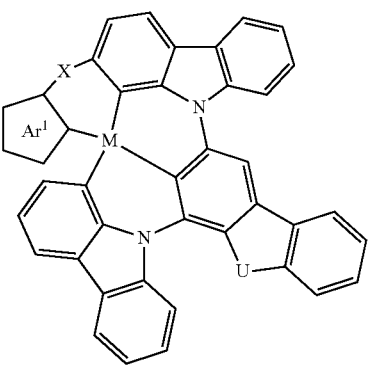
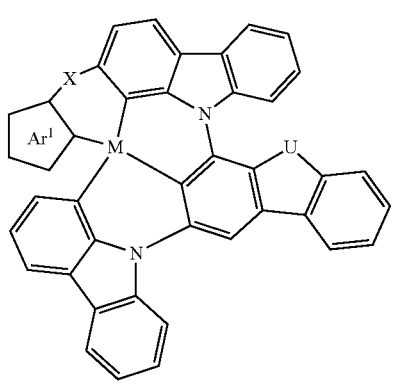
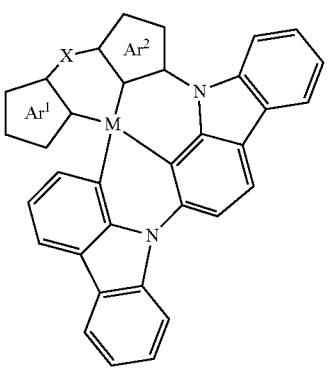

-continued
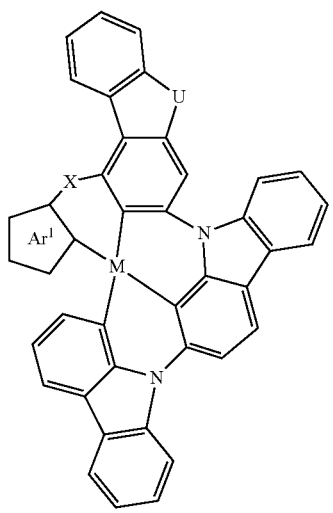
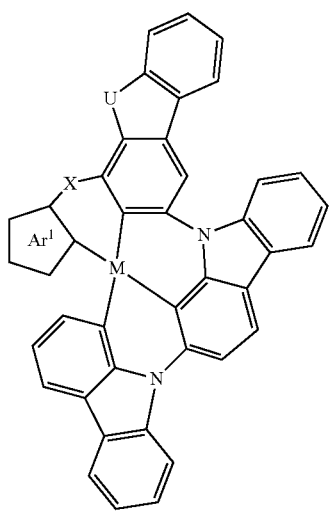
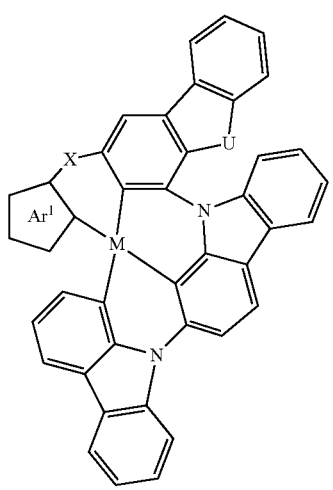
-continued
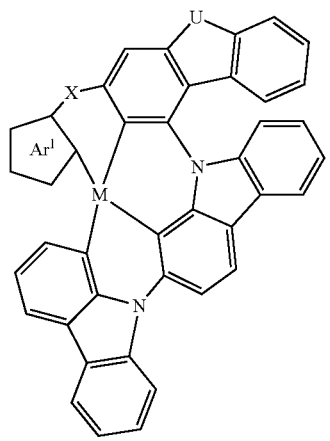
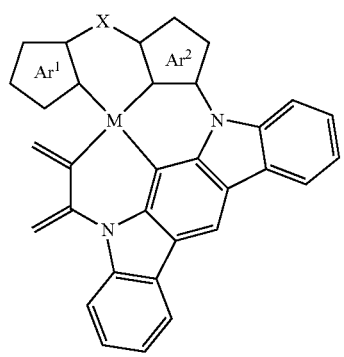
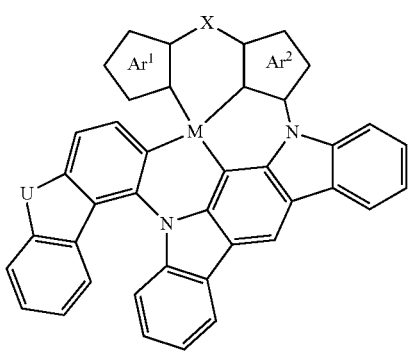
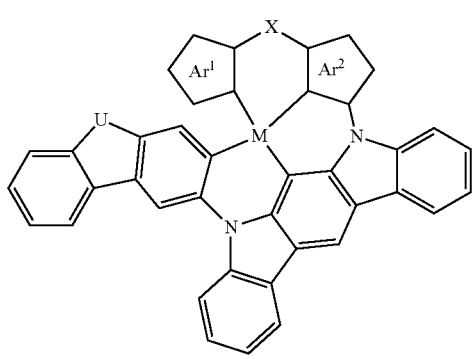

-continued
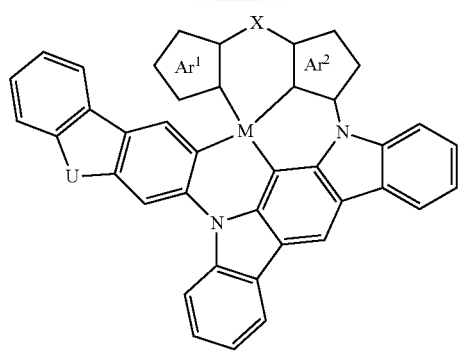
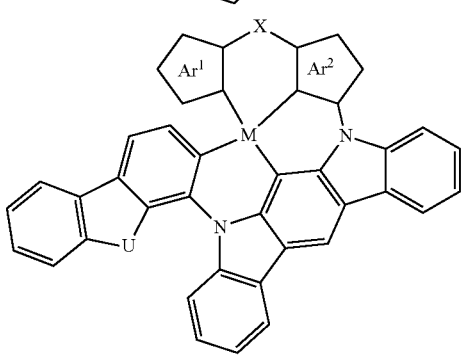
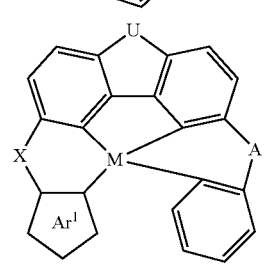
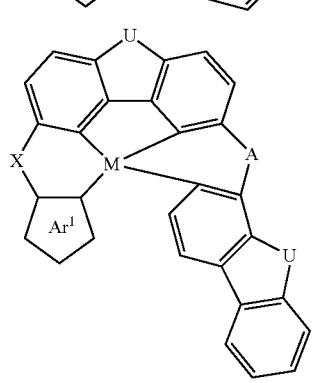
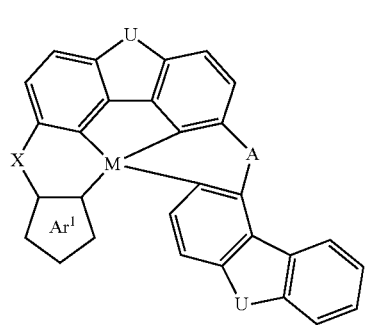
-continued
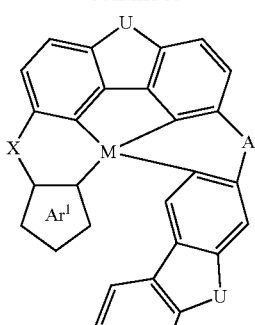
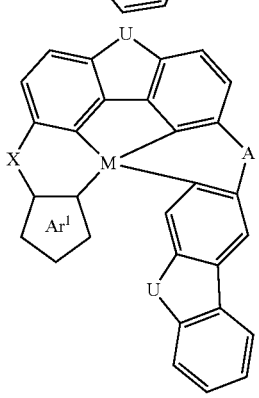
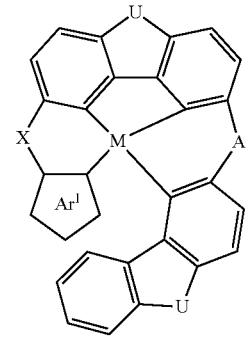
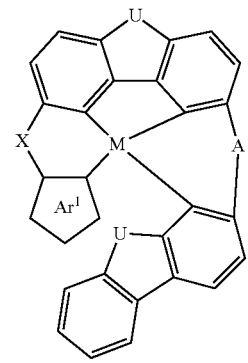
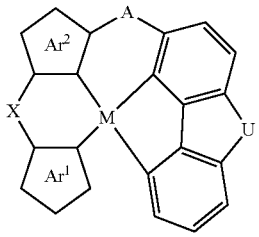

-continued
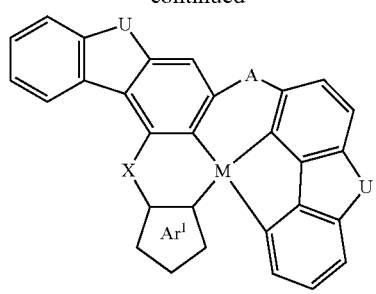
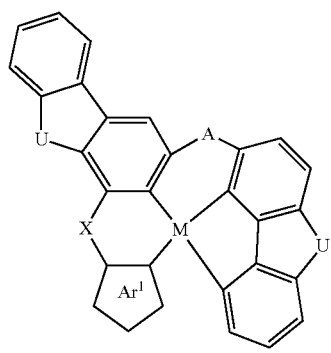
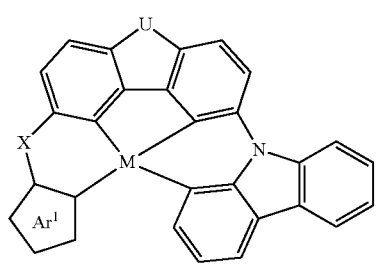
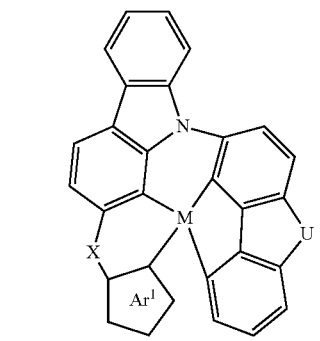
Specific compounds include, but are not limited to:
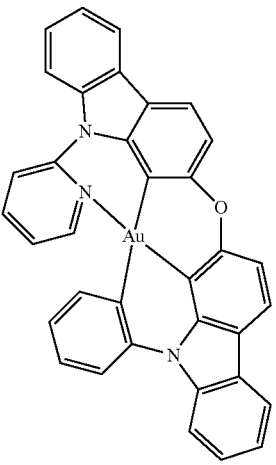
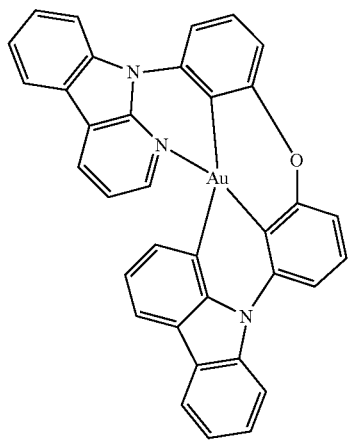
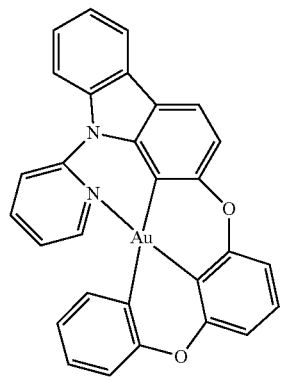

| 191 -continued | 192 -continued |
|---|---|
| 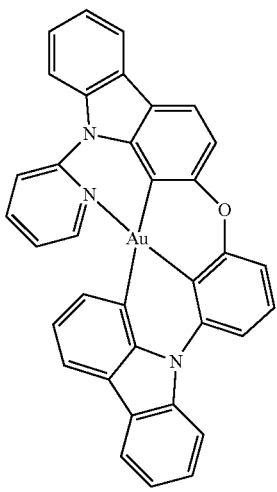 | 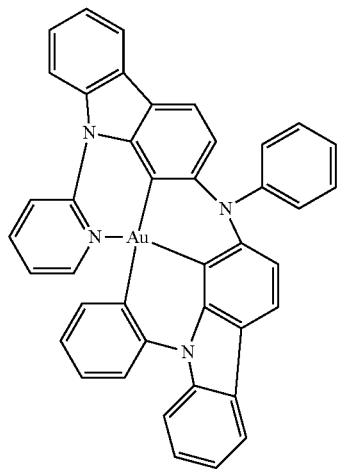 |
| 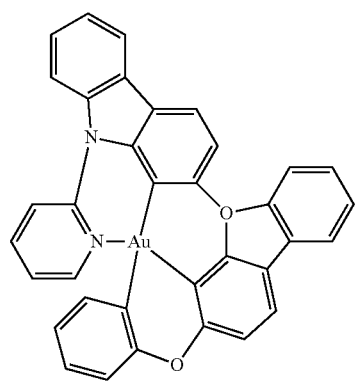 | 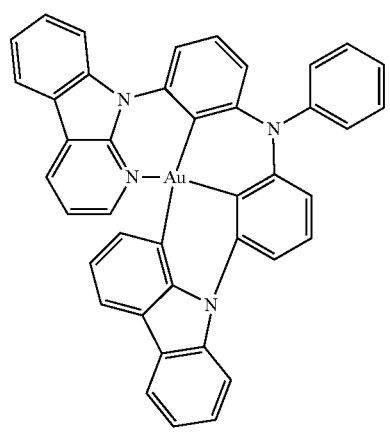 |
| 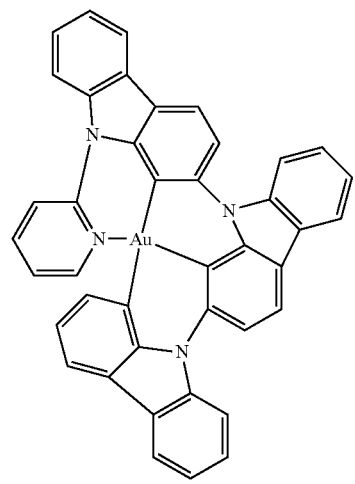 | 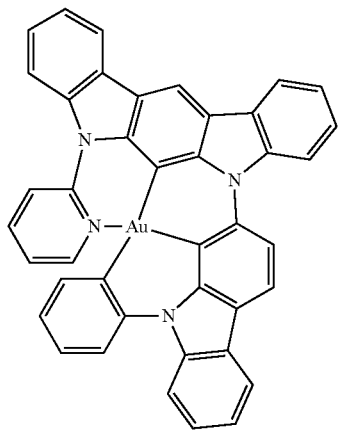 |

193
-continued
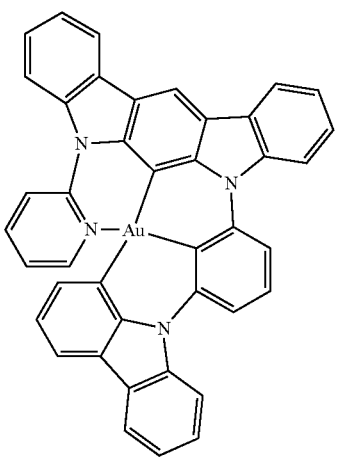
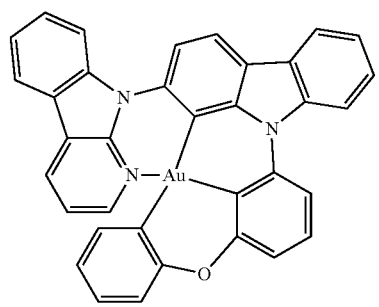
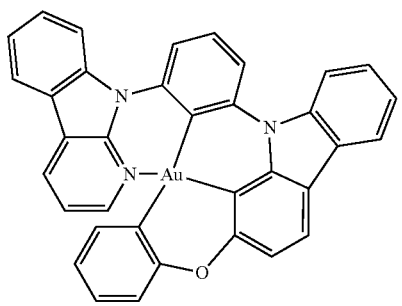
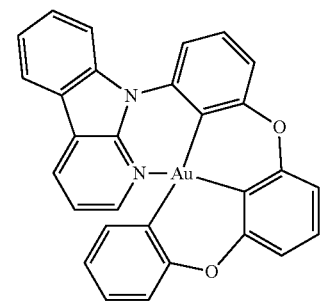
194
-continued
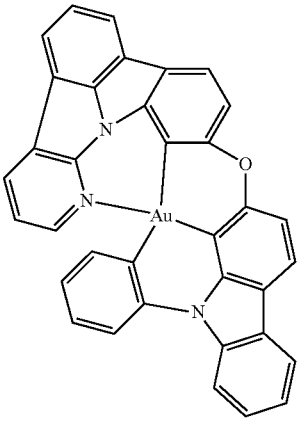
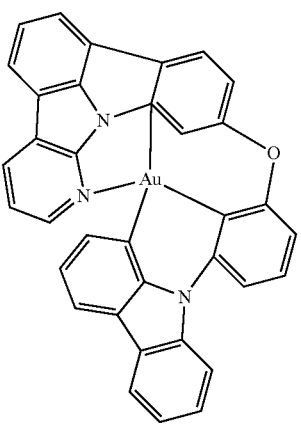
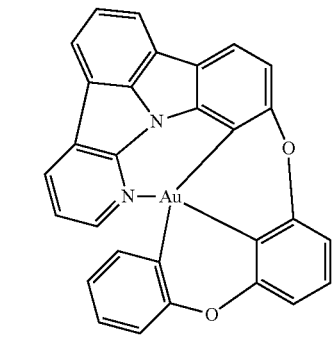
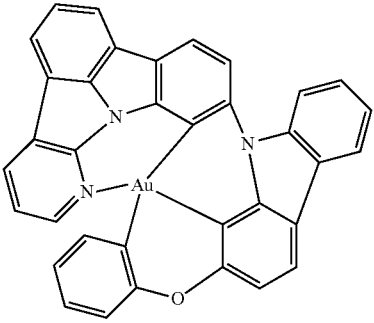

195
-continued
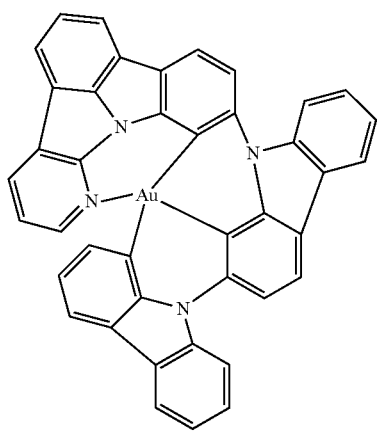
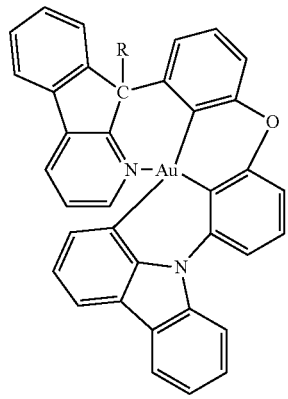
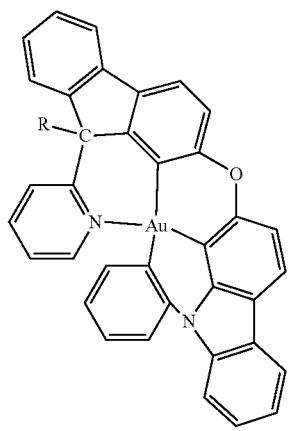
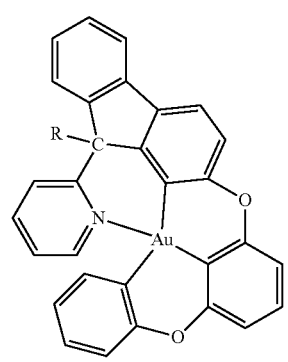
196
-continued
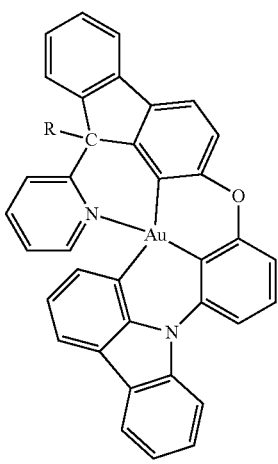
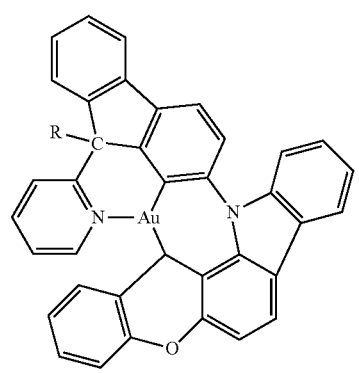
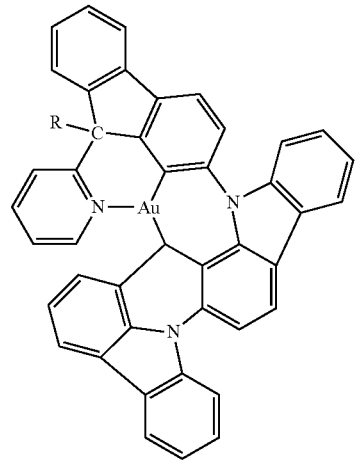
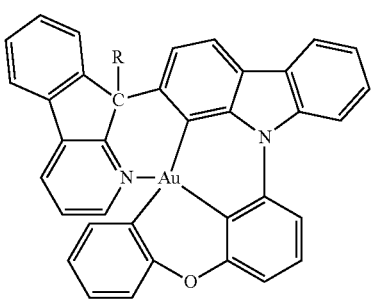

197
-continued
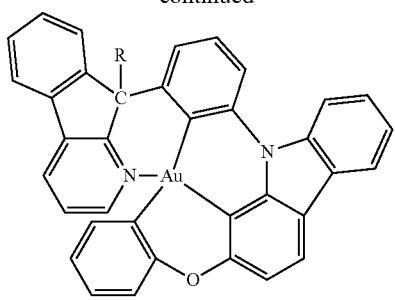
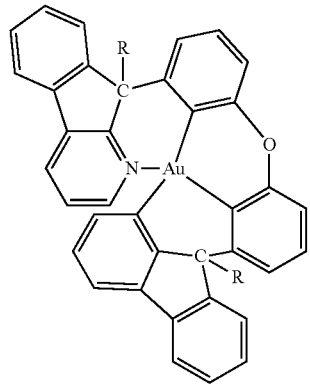
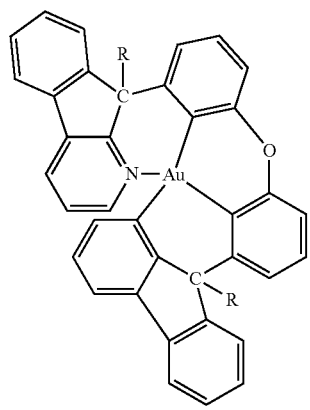
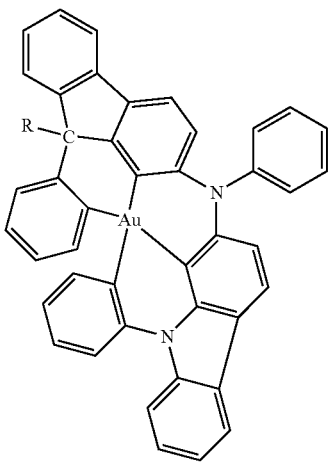
198
-continued
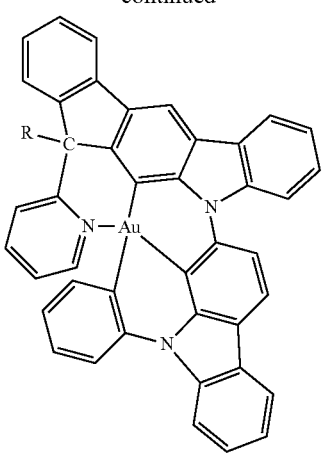
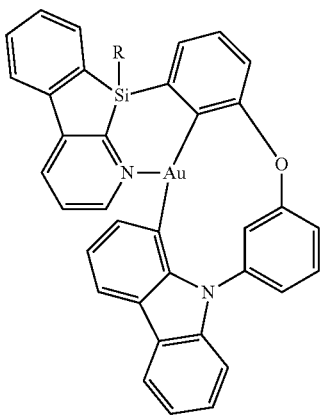
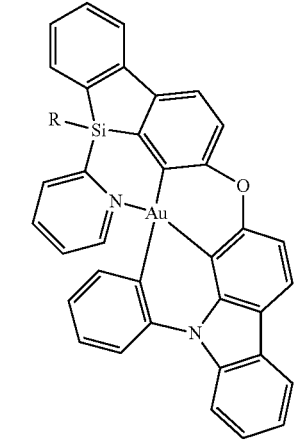
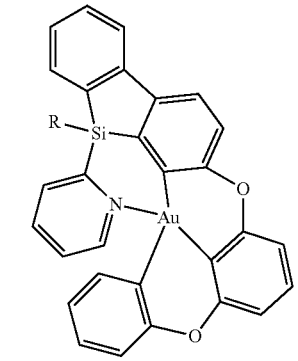

199
-continued
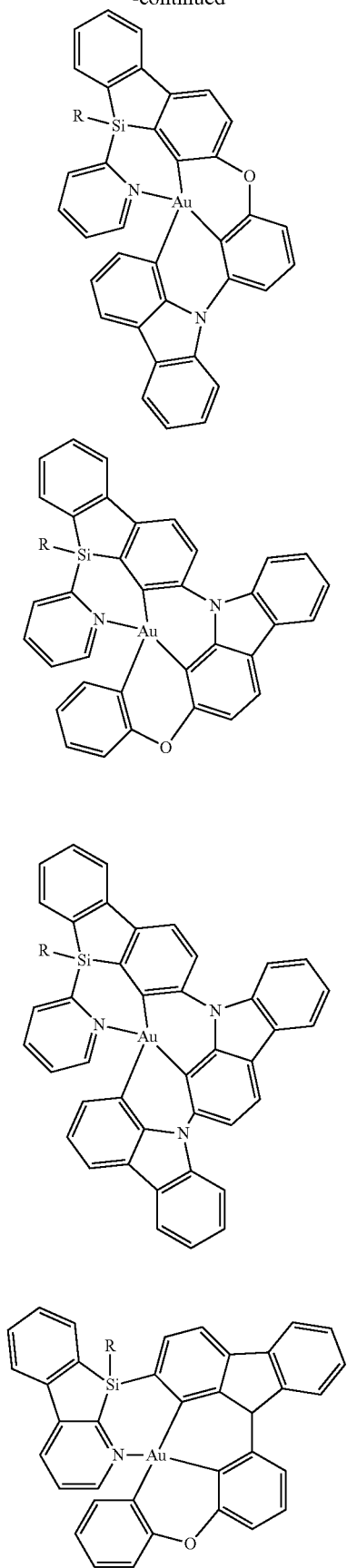
200
-continued
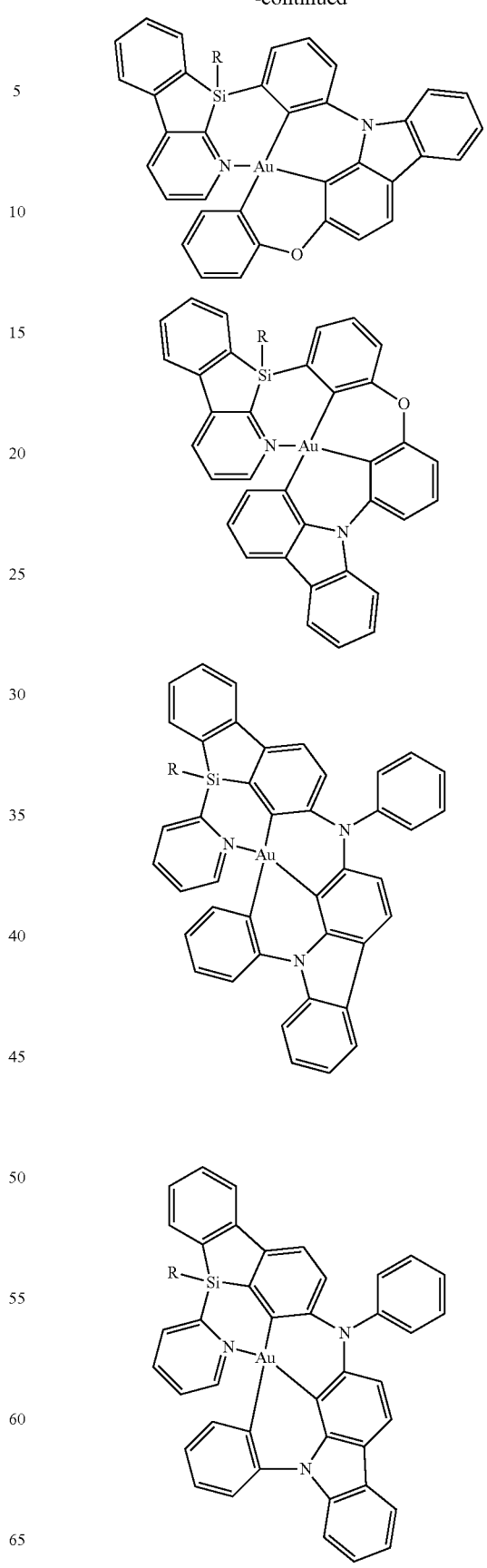

201
-continued
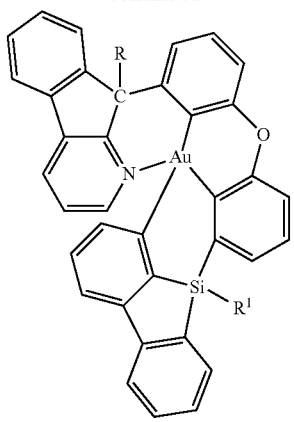
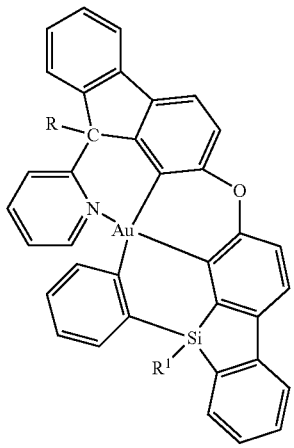
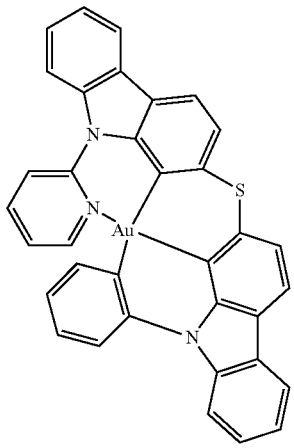
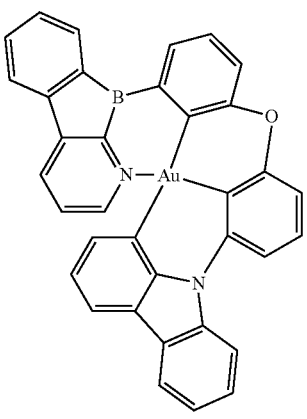
202
-continued
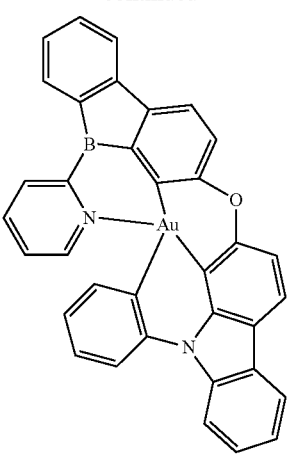
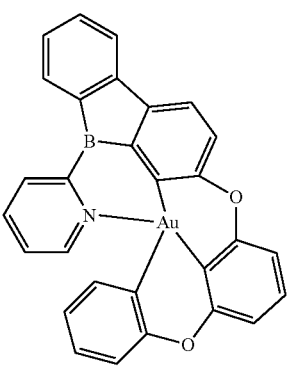
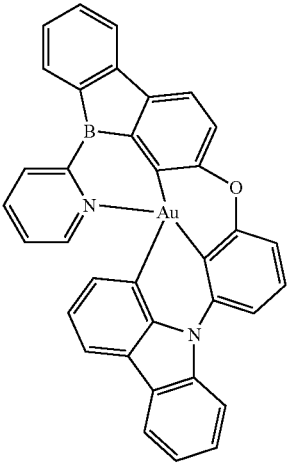
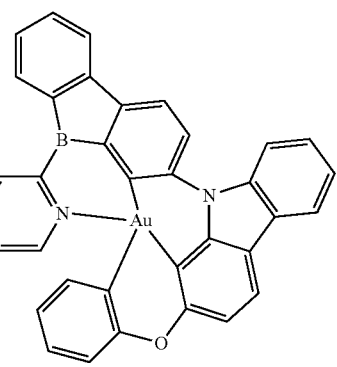

203
-continued
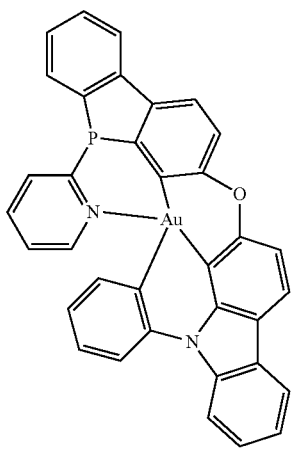
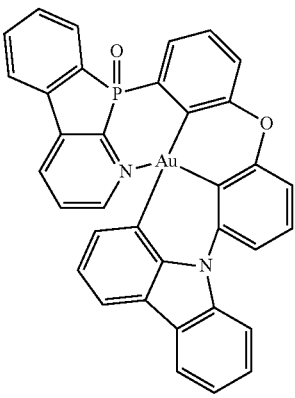
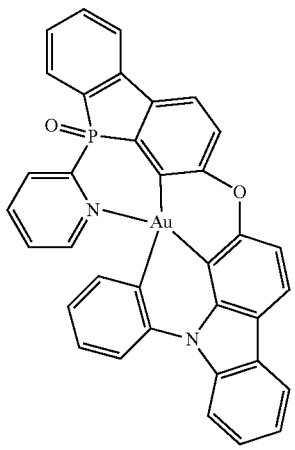
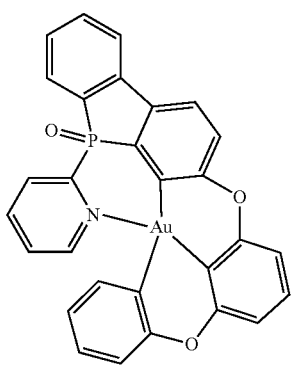
204
-continued
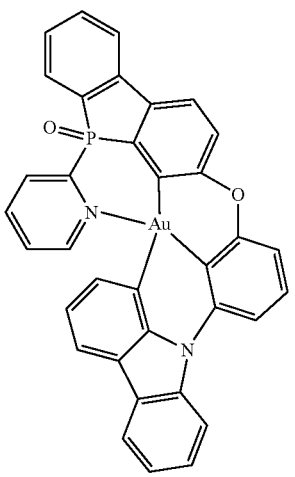
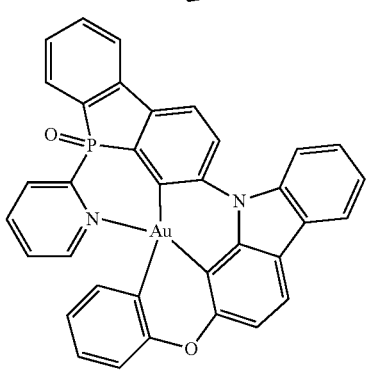
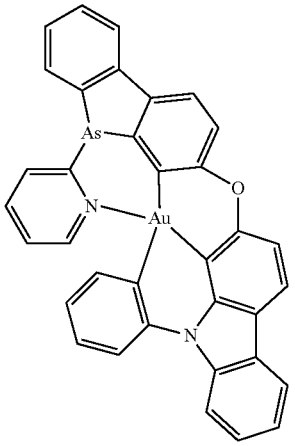
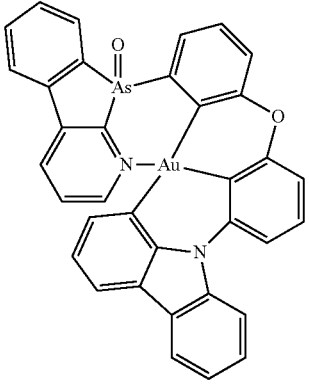

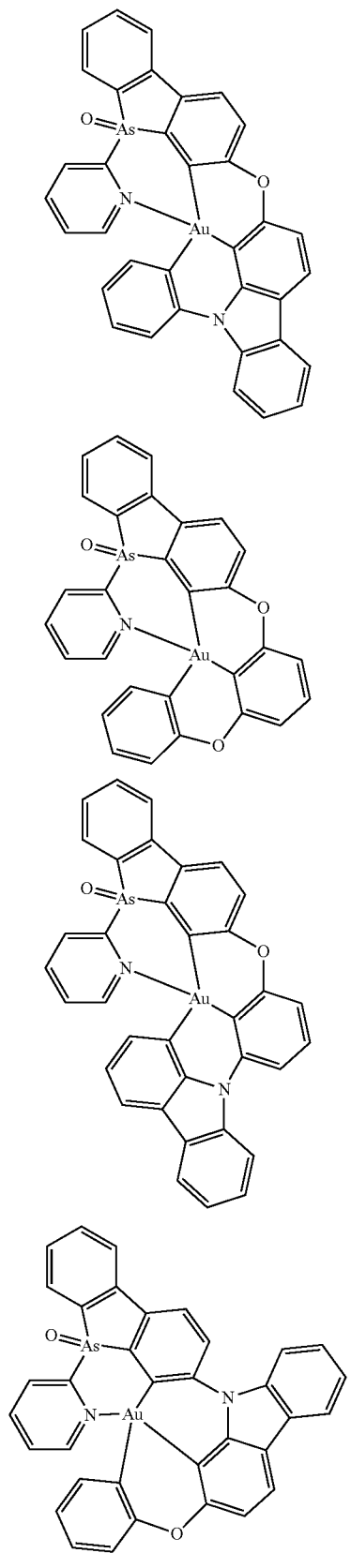

207
-continued
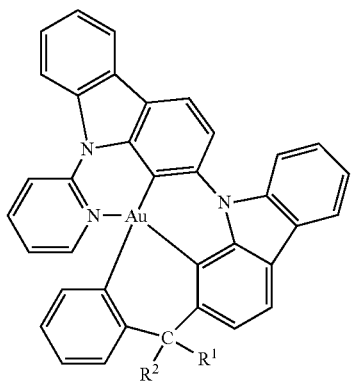
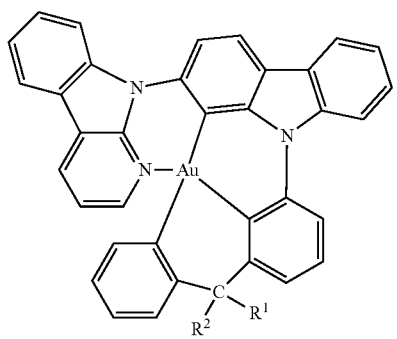
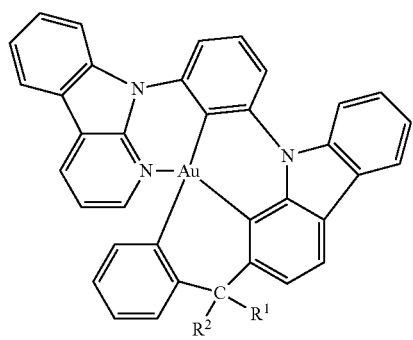
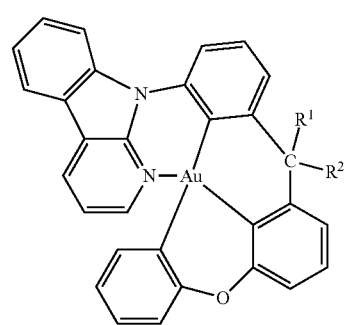
208
-continued
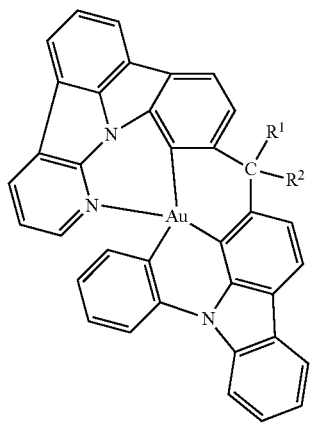
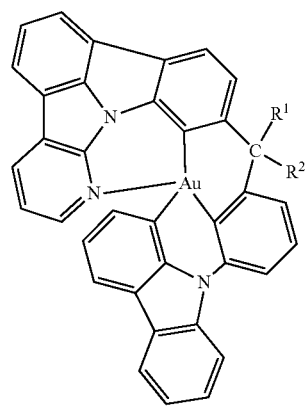
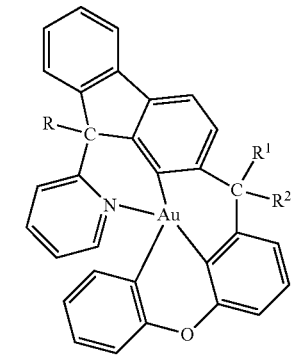
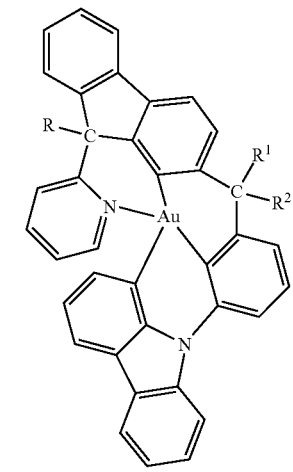

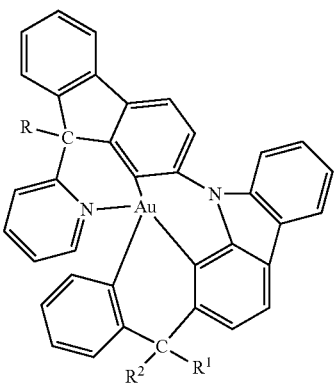
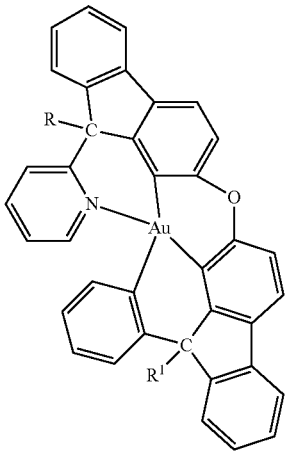
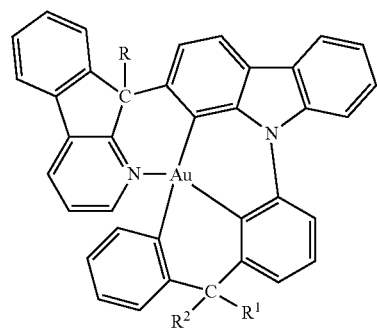
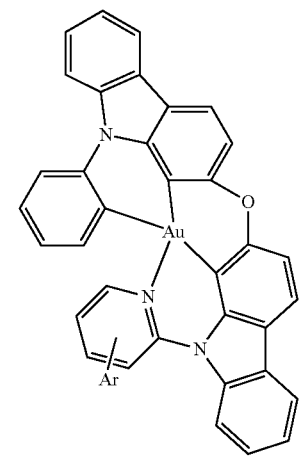
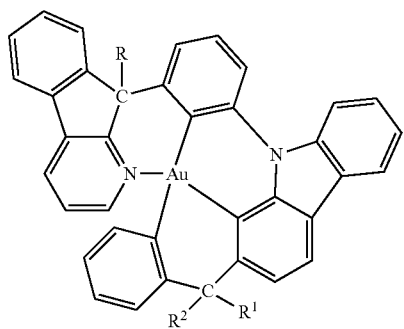
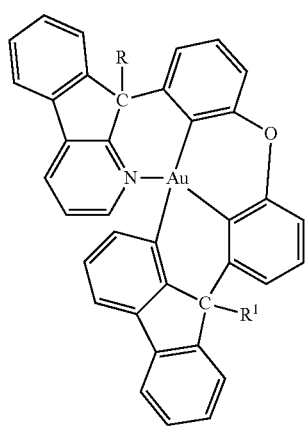
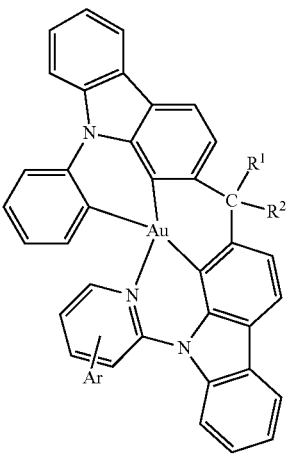

211
-continued
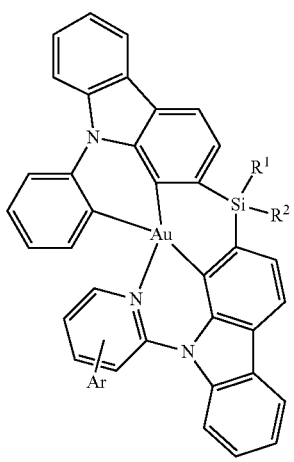
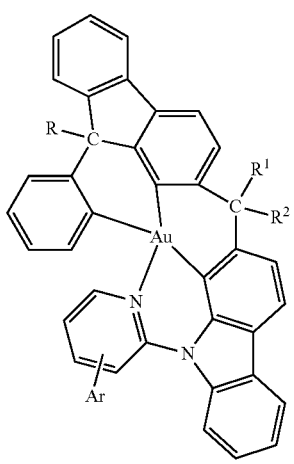
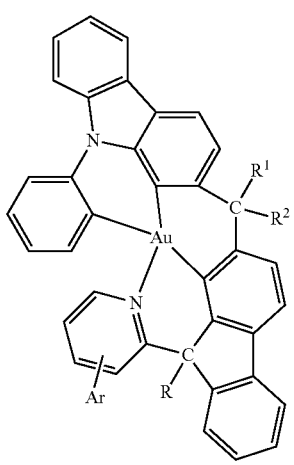
212
-continued
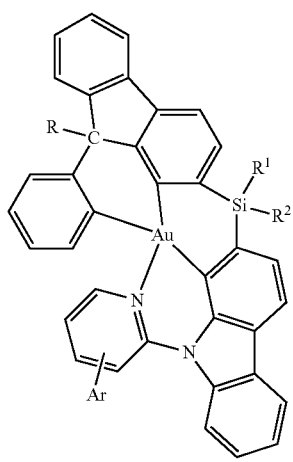
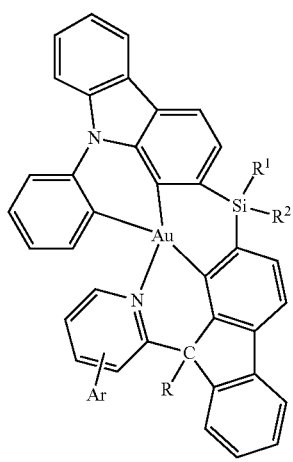
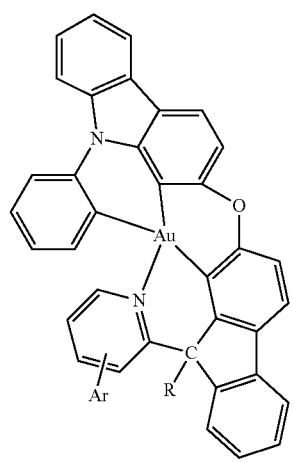

213
Where Ar is aryl functional group like
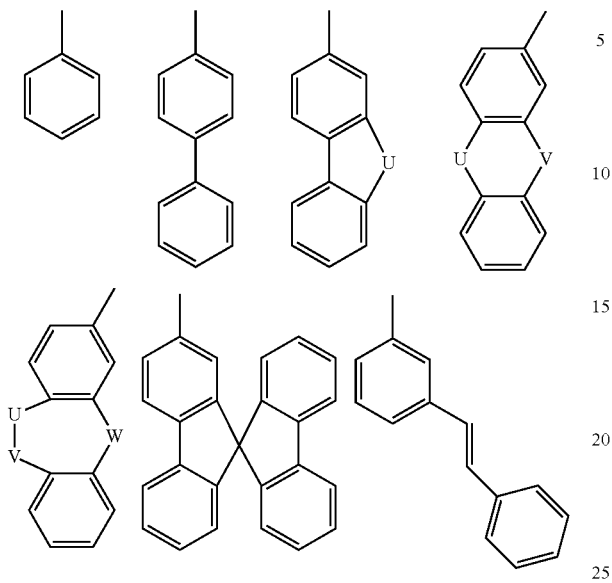
and their analogs.
Where U, V, W could be the same or different atoms like carbon (C), oxygen (O), nitrogen (N), phosphorus (P), silicon (Si), boron (B) and other atoms.
In one aspect, the compound can have the structure:
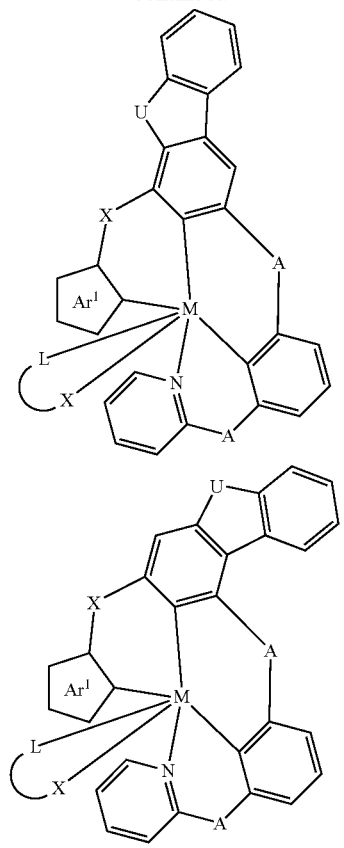
214
-continued
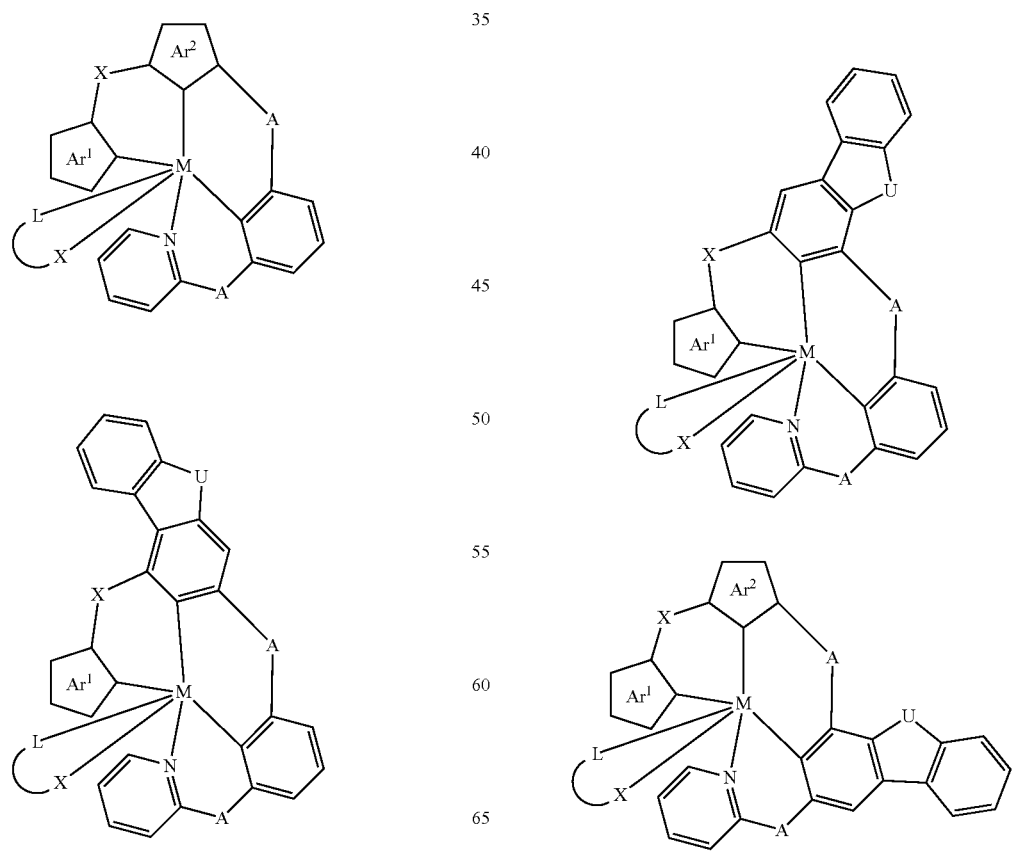

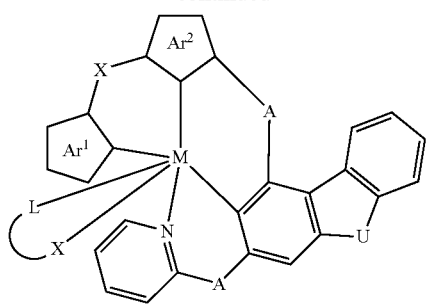
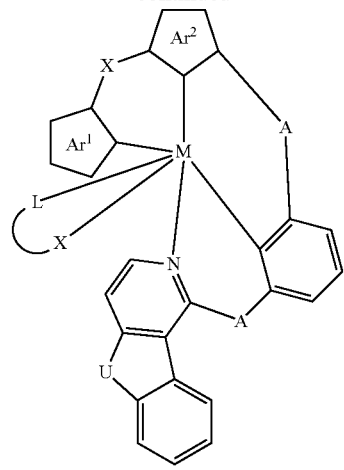
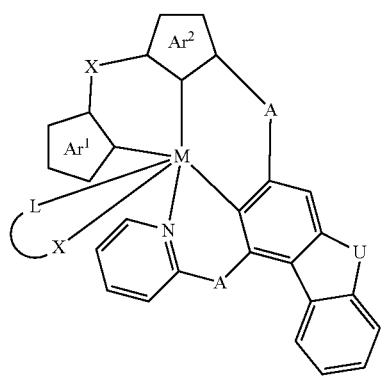
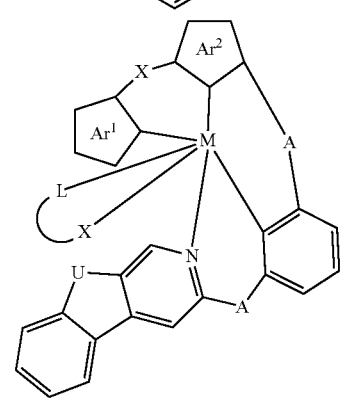
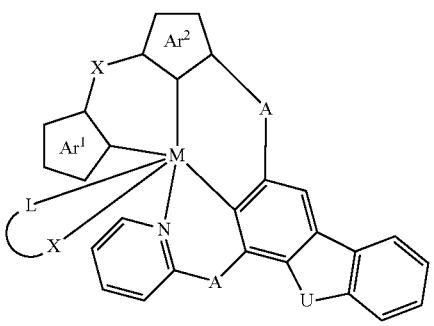
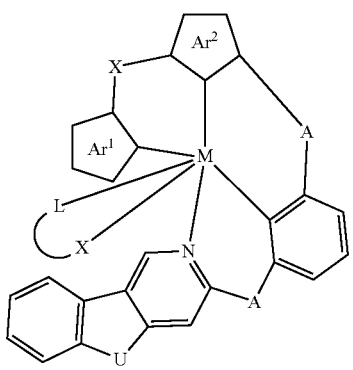
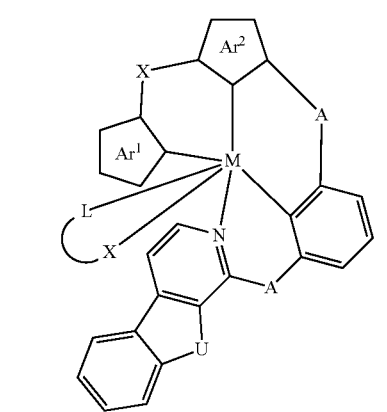
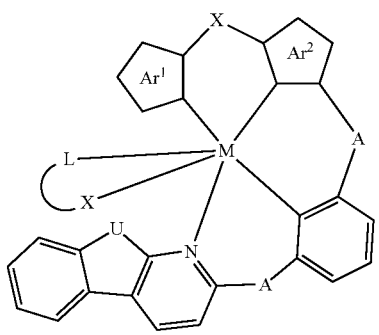

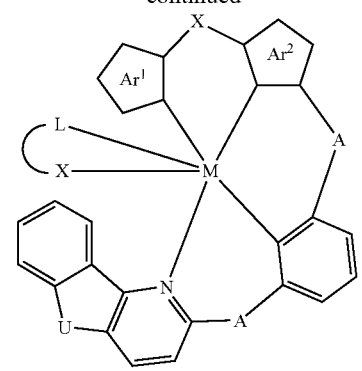
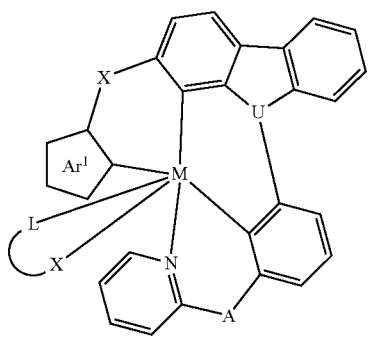
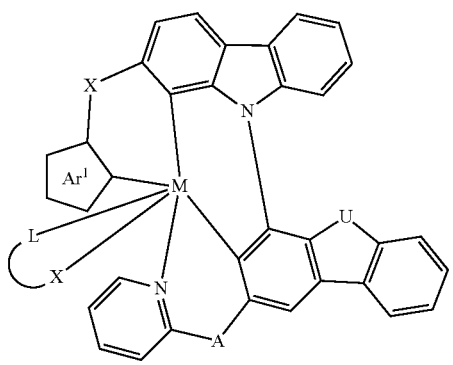
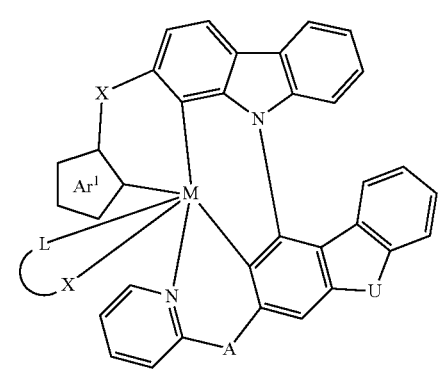
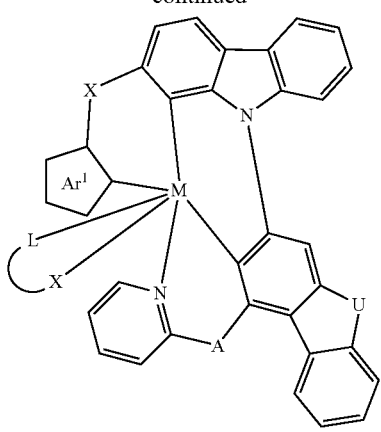
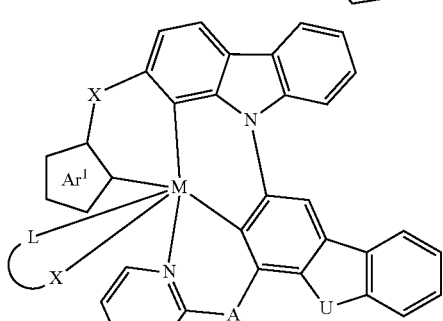
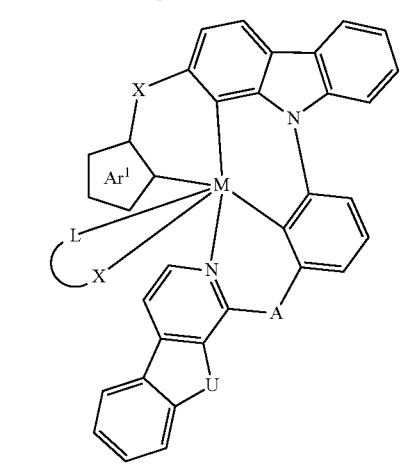
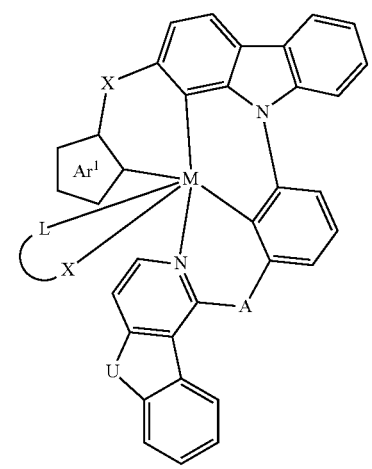

-continued
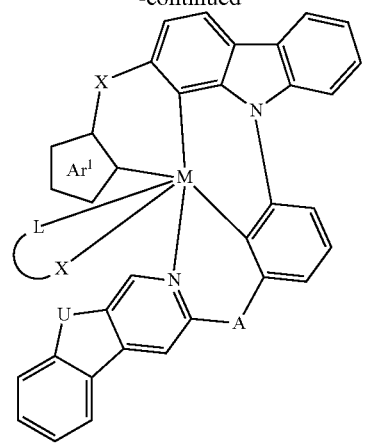
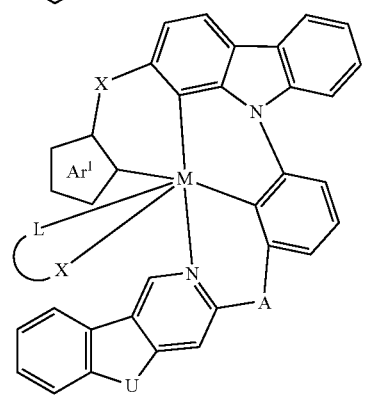
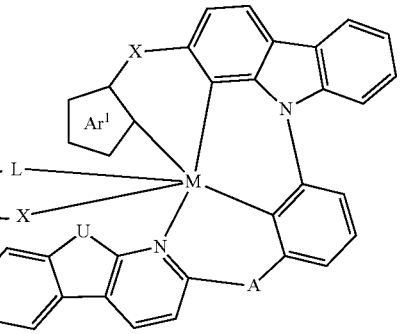
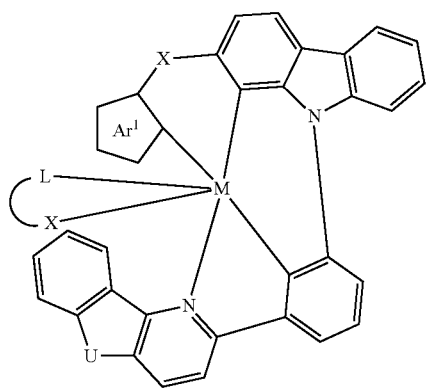
-continued
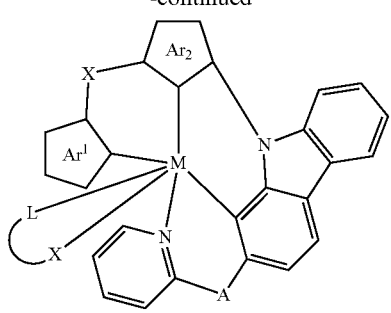
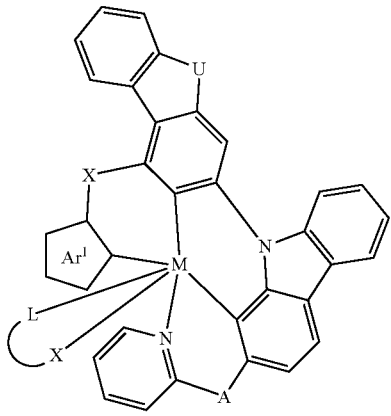
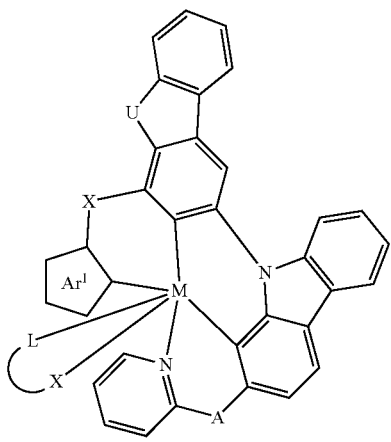
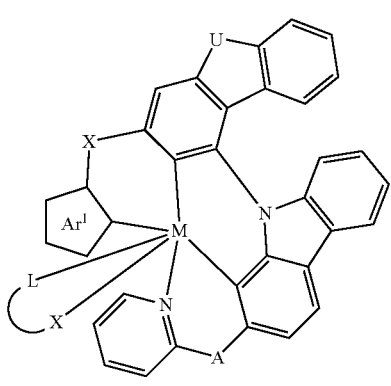

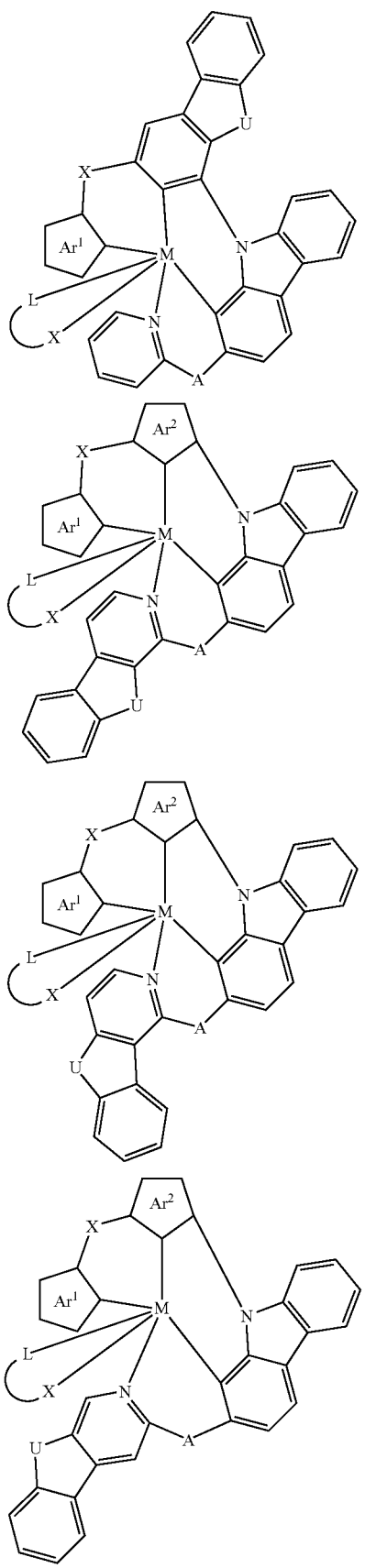
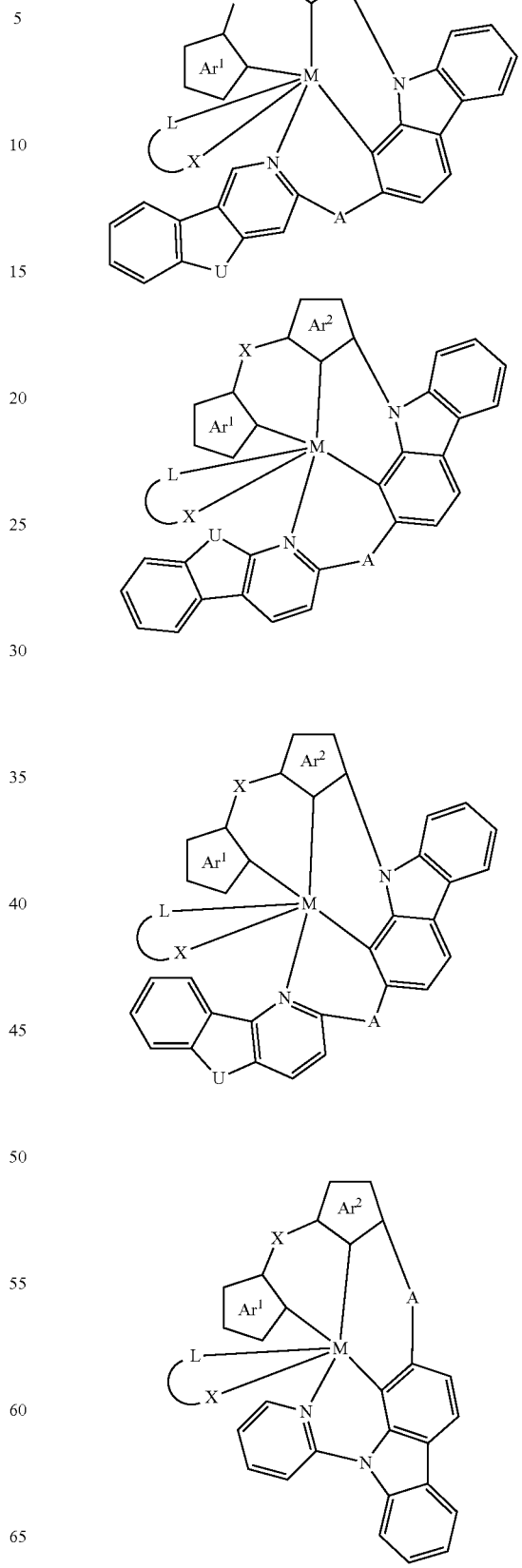

223
-continued
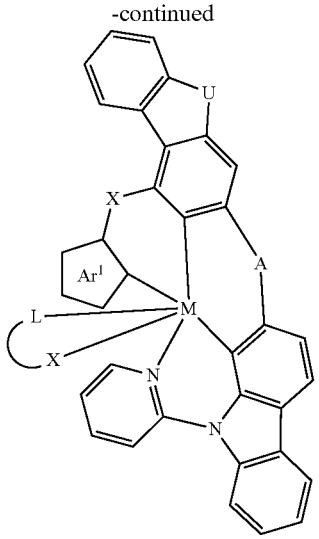
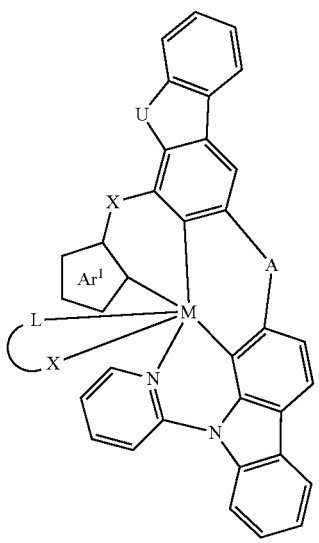
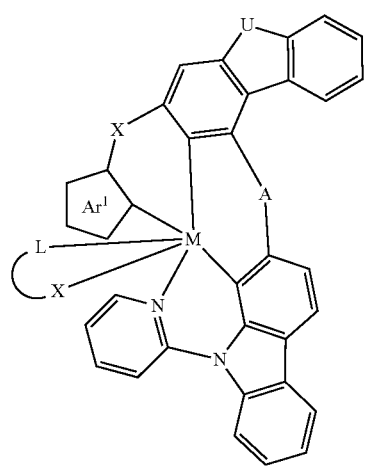
224
-continued
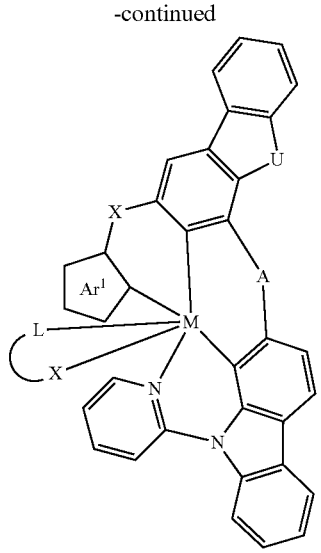
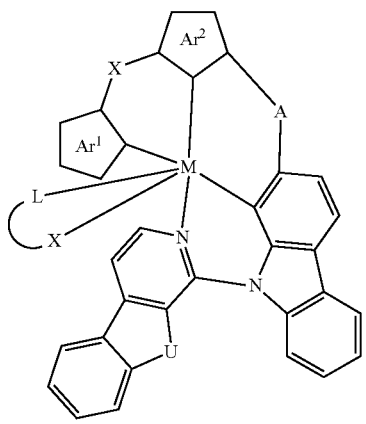
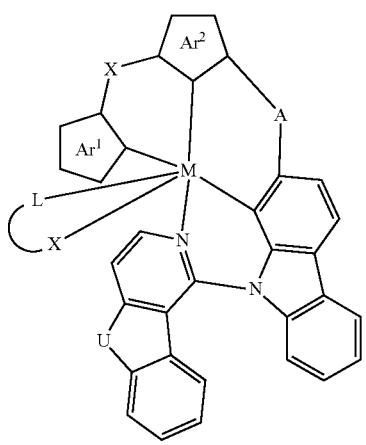

225
-continued
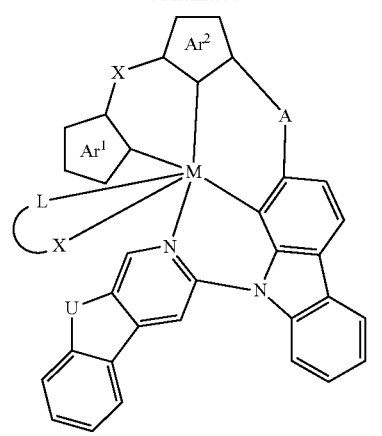
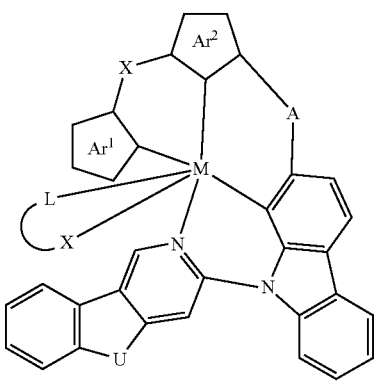
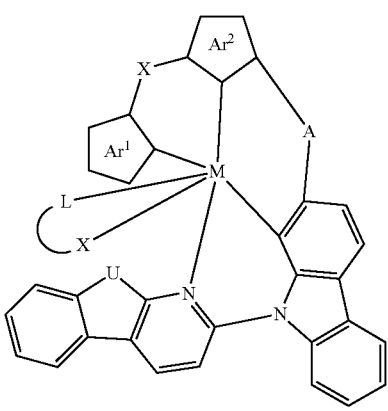
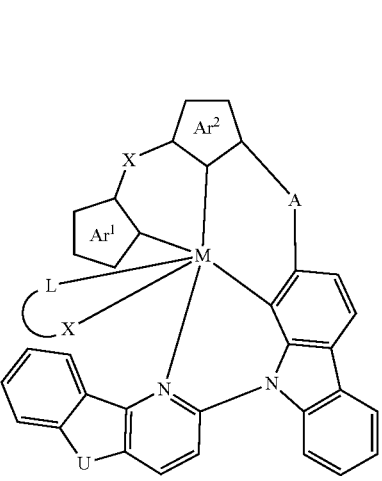
226
-continued
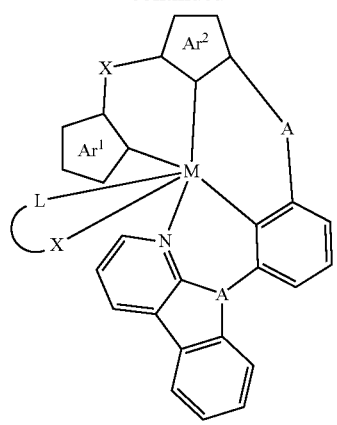
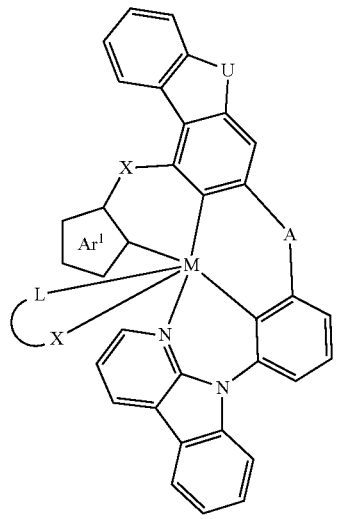
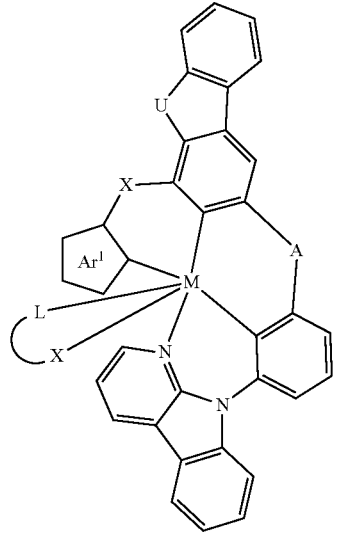

227
-continued
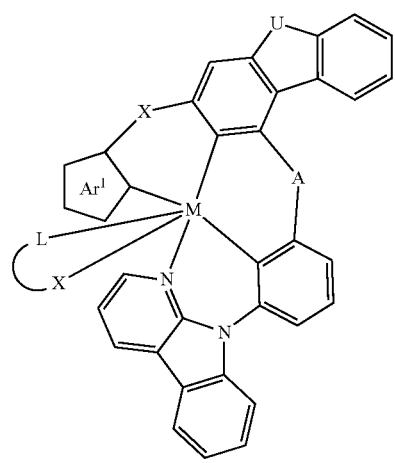
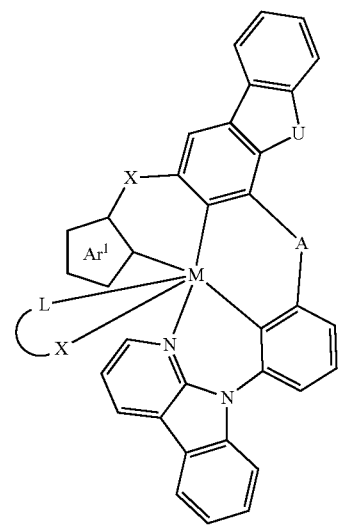
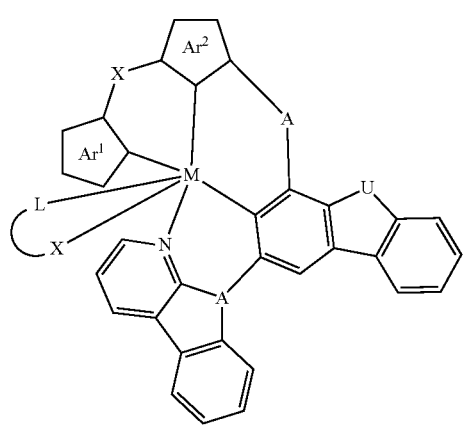
228
-continued
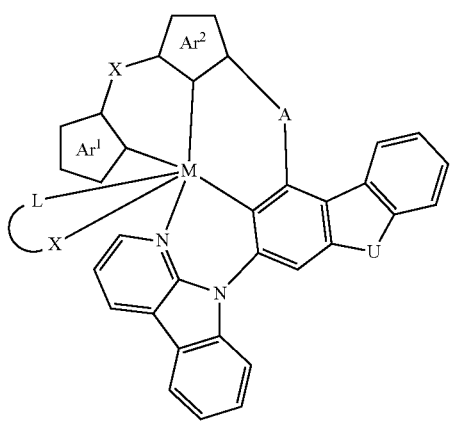
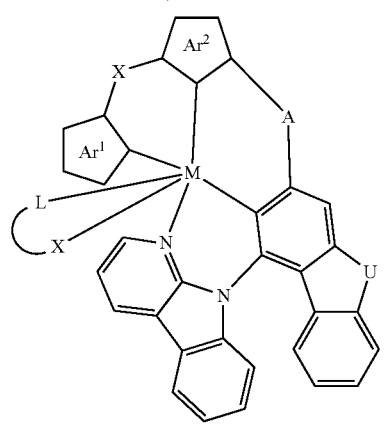
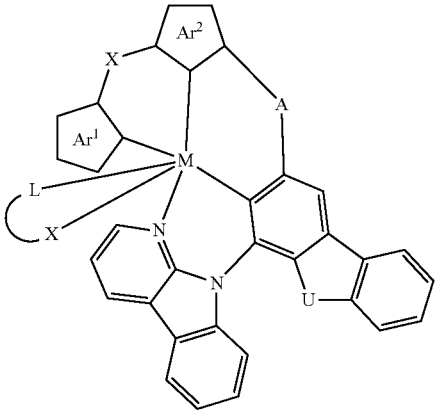
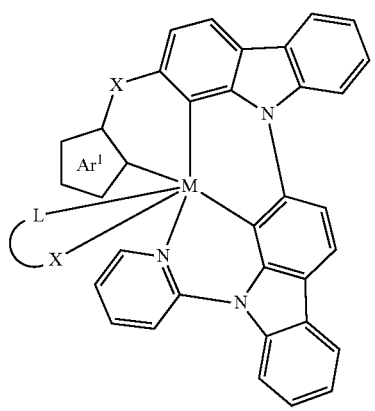

229
-continued
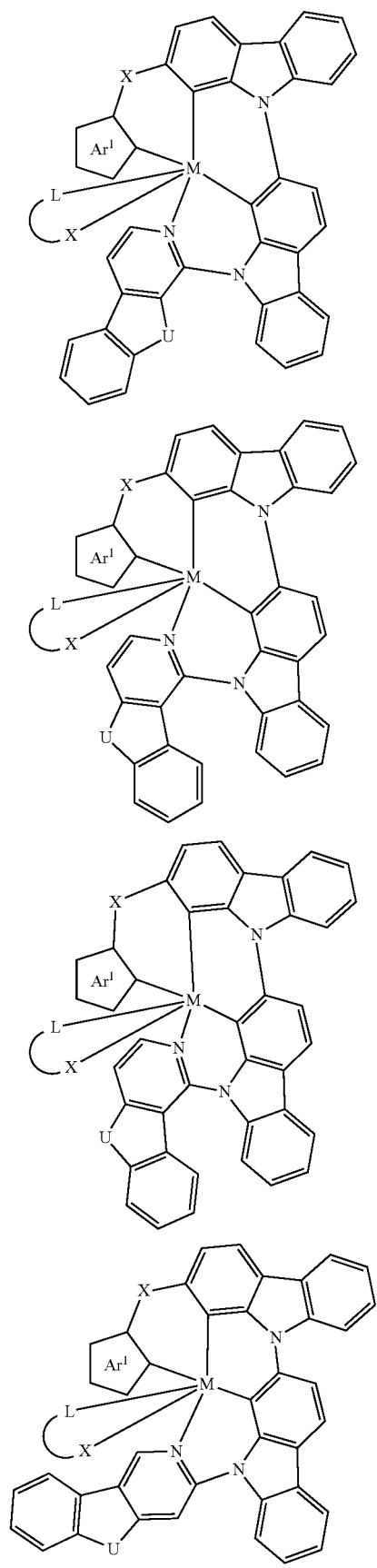
230
-continued
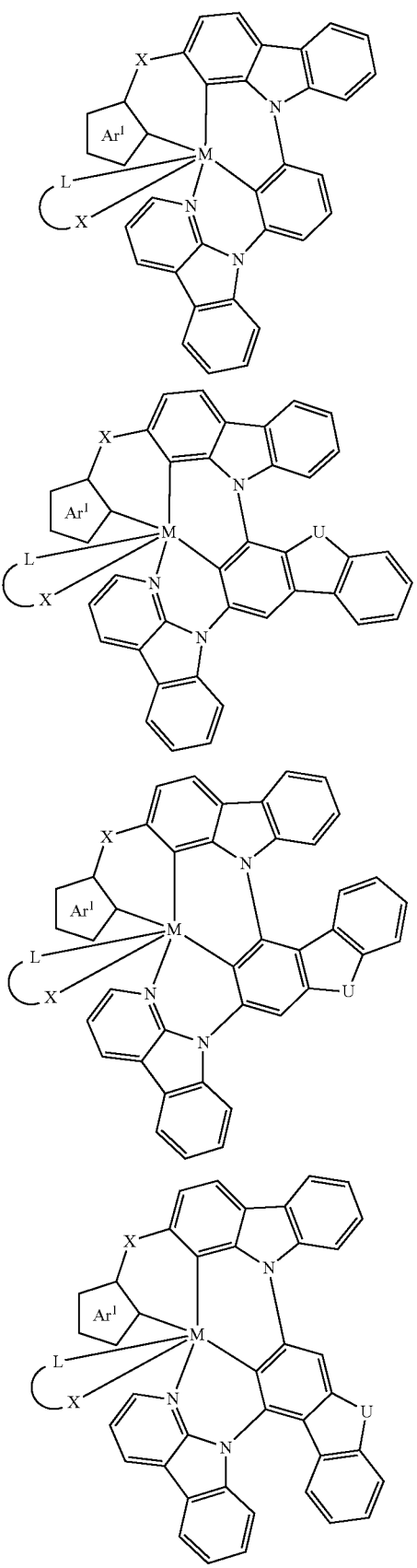

231
-continued
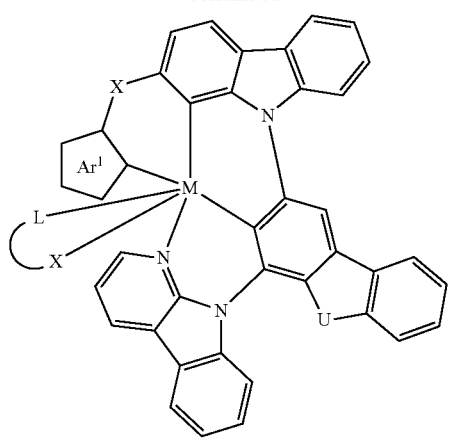
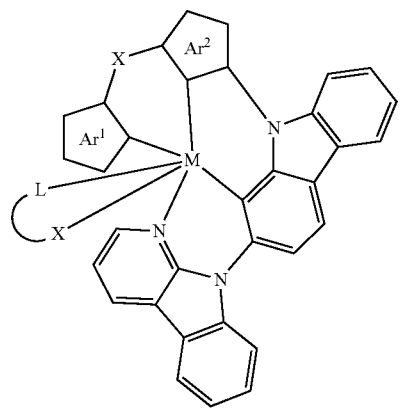
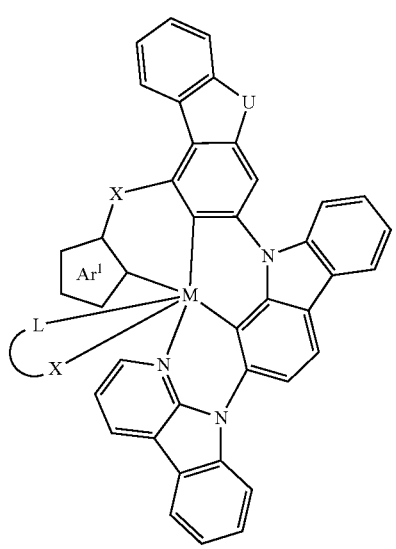
232
-continued
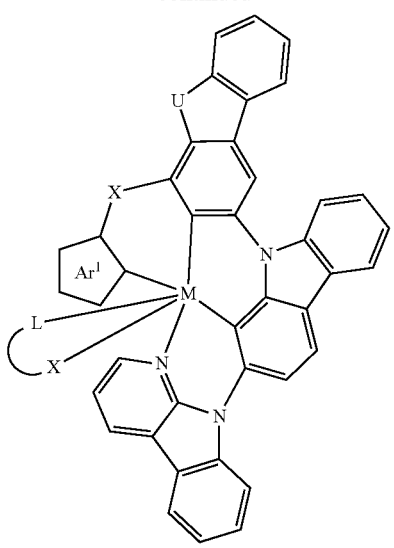
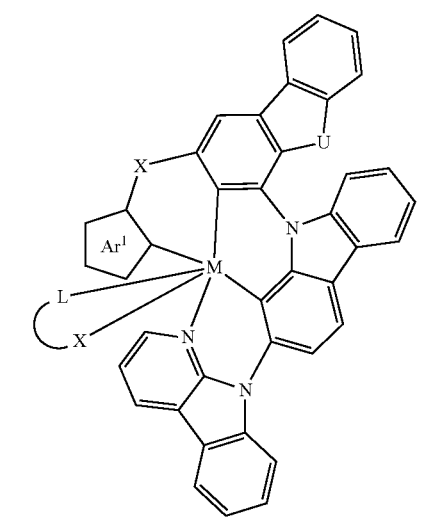
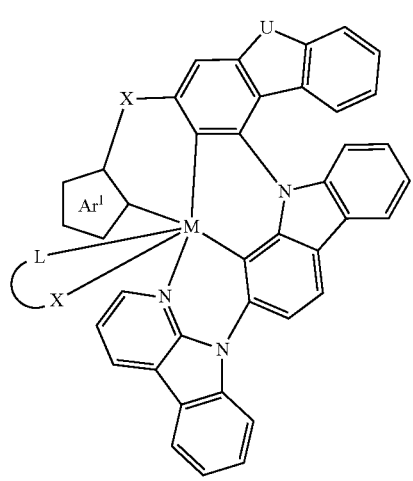

233
-continued
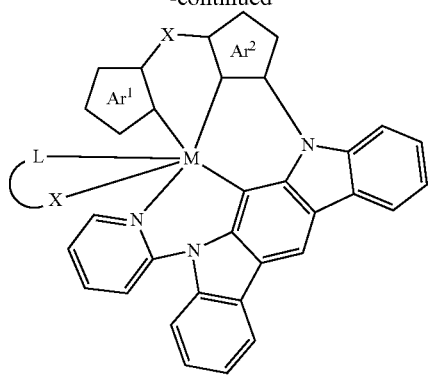
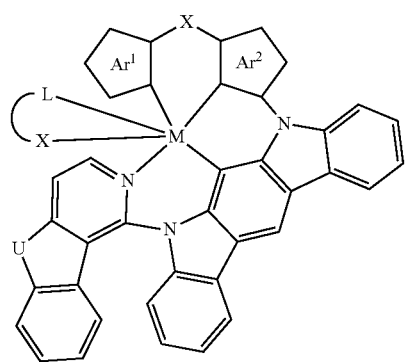
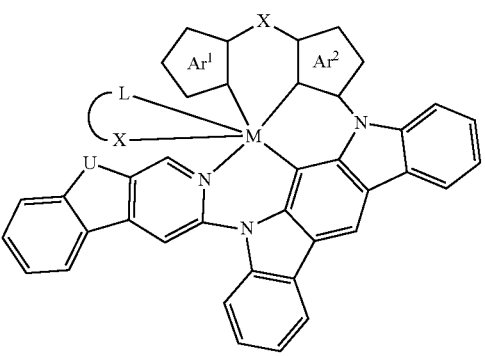
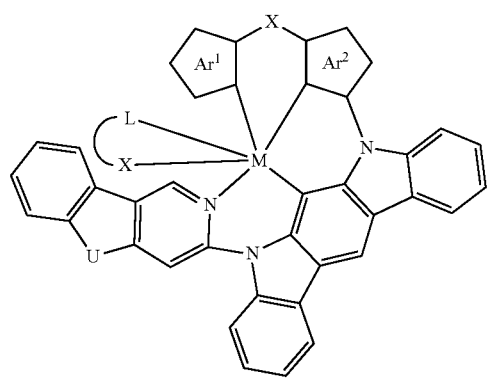
234
-continued
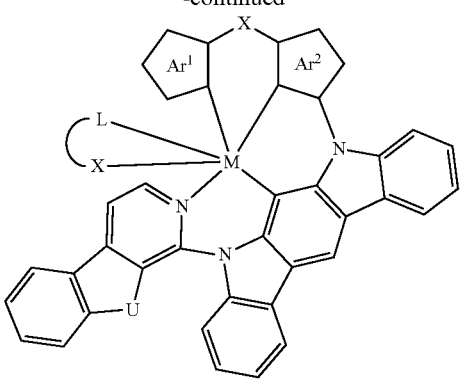
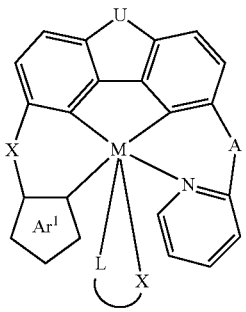
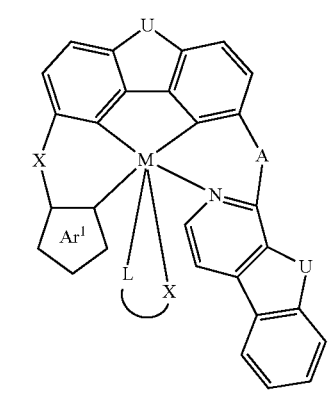
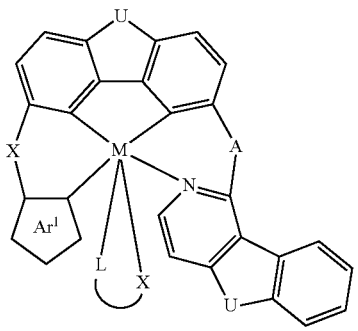

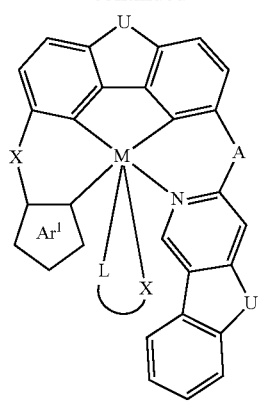
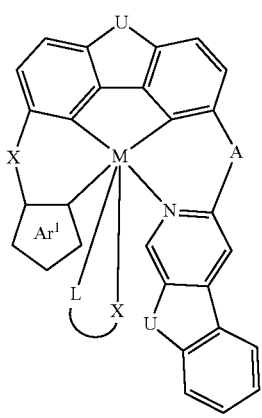
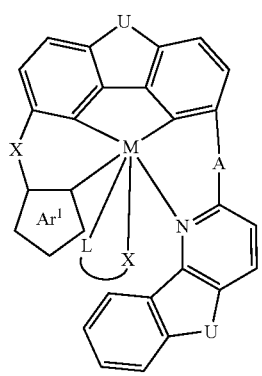
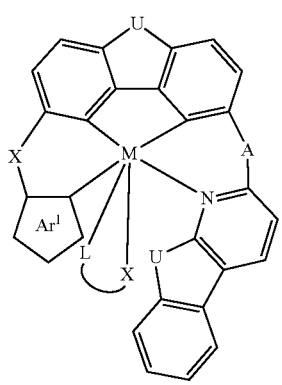
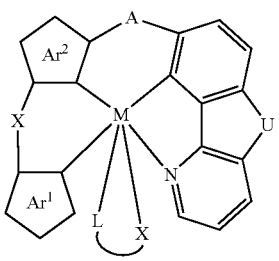
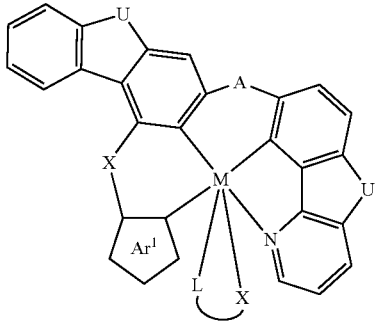
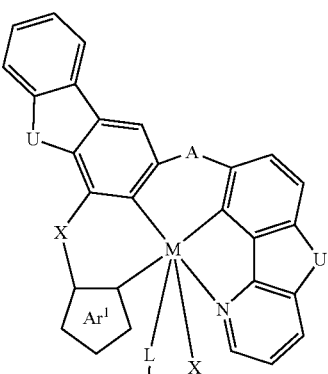
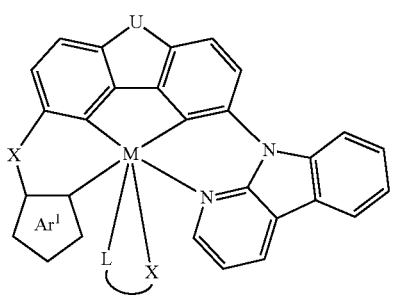
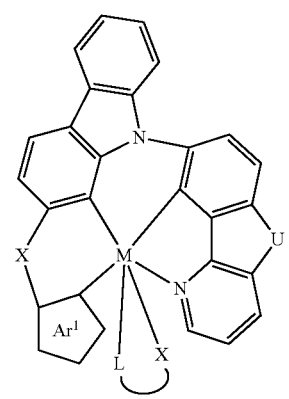

Specific compounds include, but are not limited to:
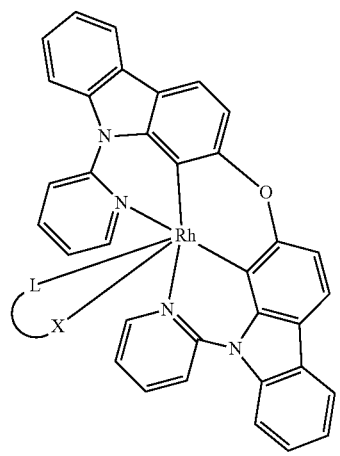
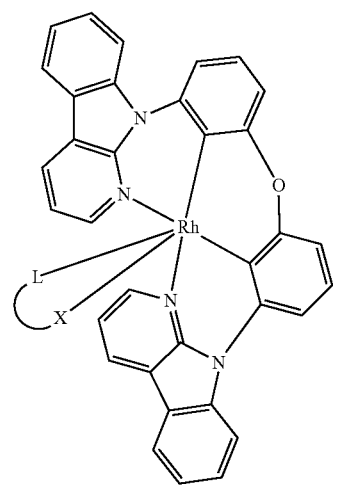
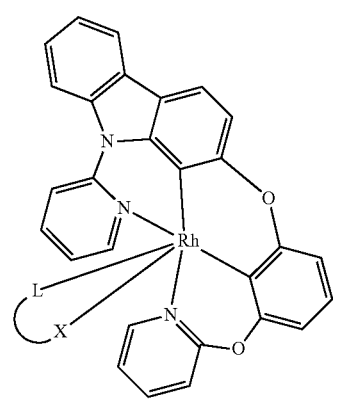
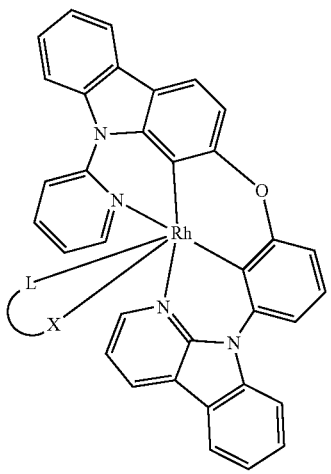
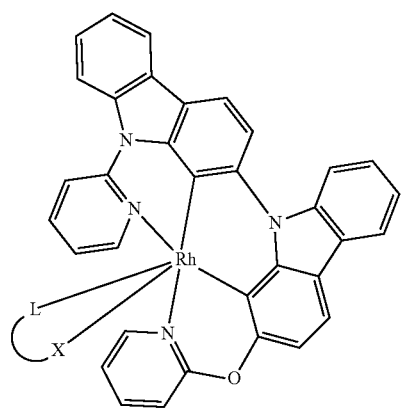
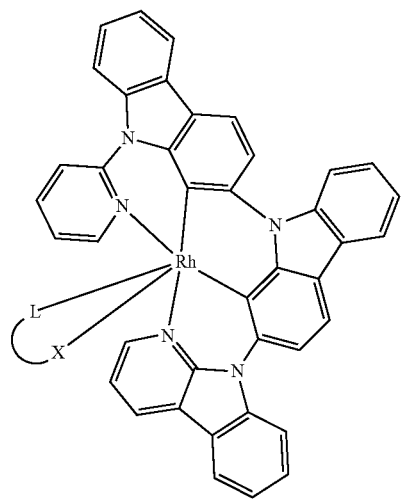

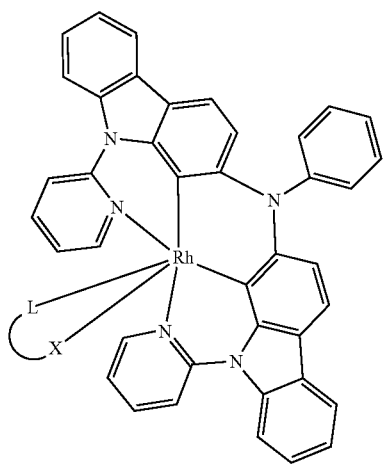
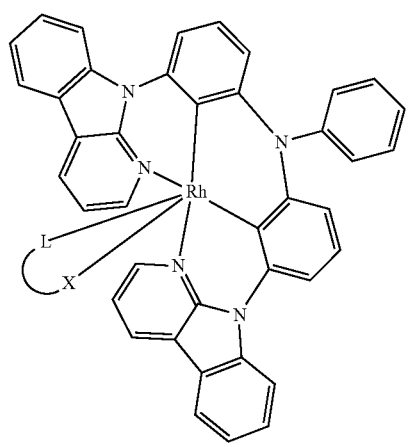
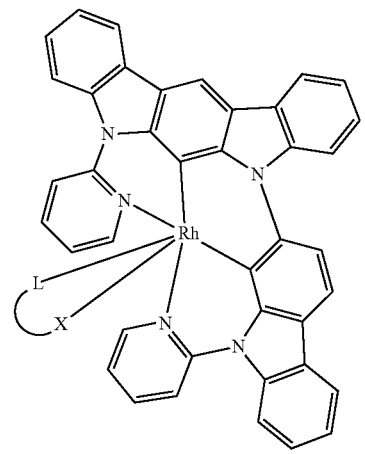
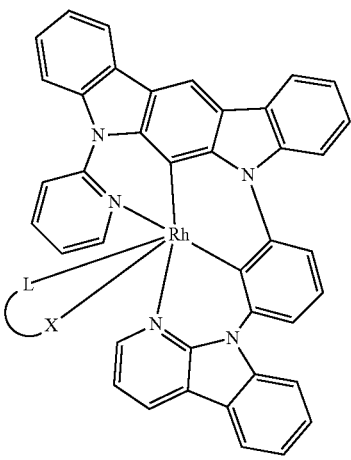
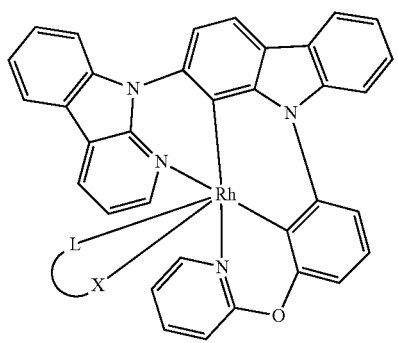
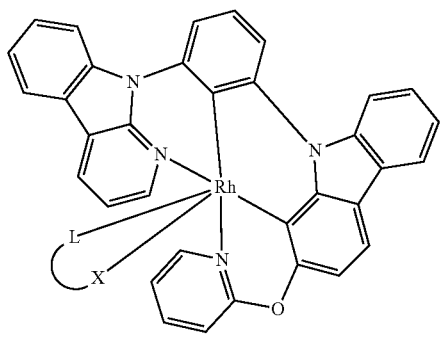
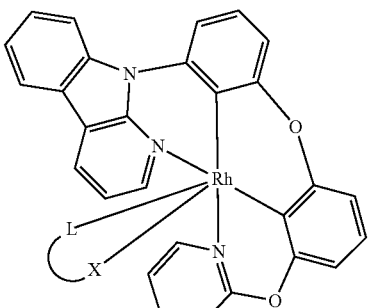

241
-continued
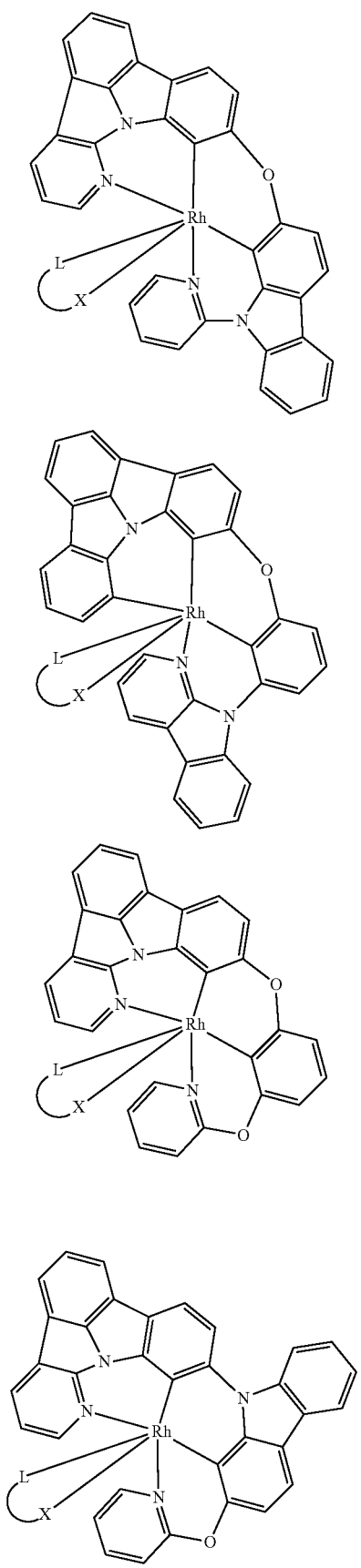
242
-continued
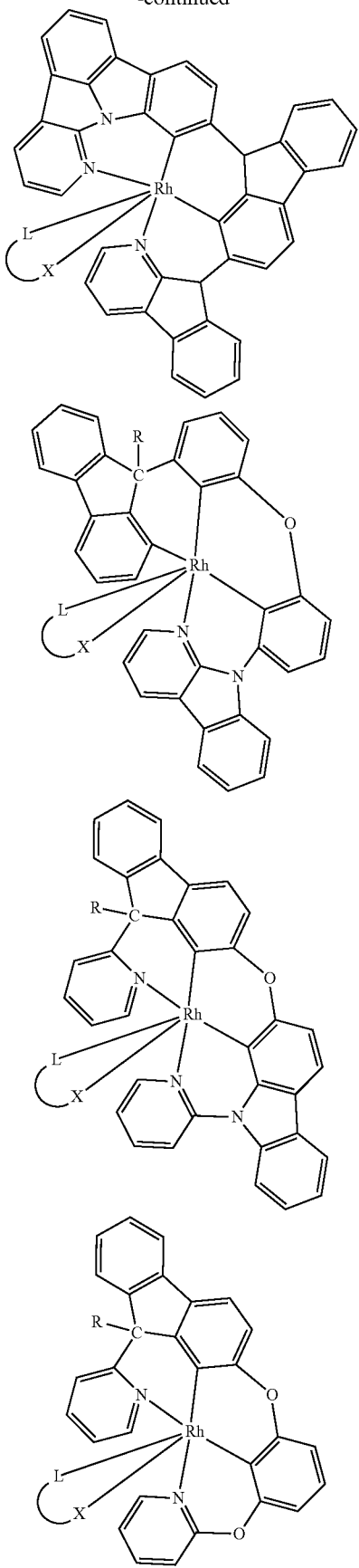

243
-continued
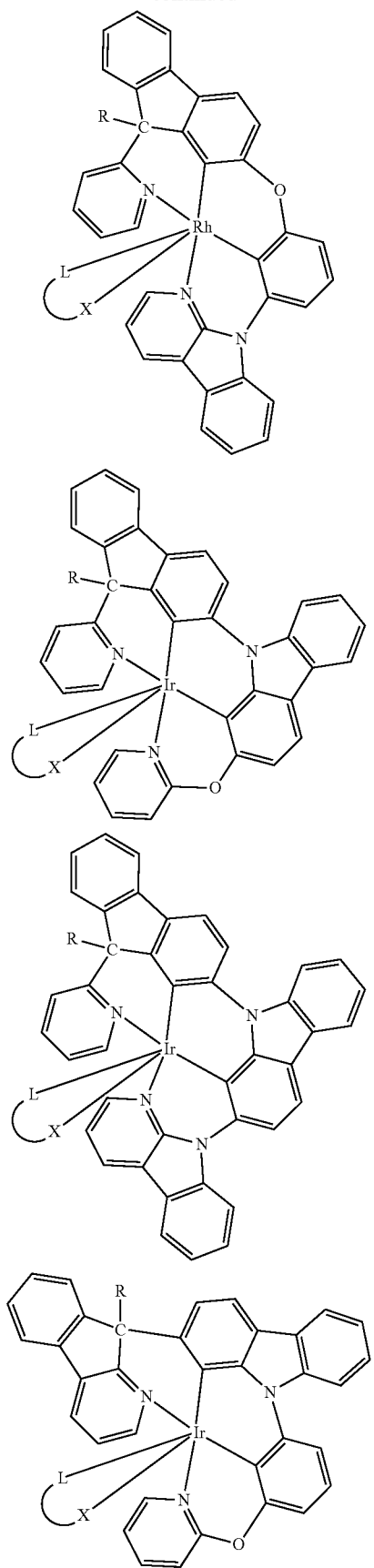
244
-continued
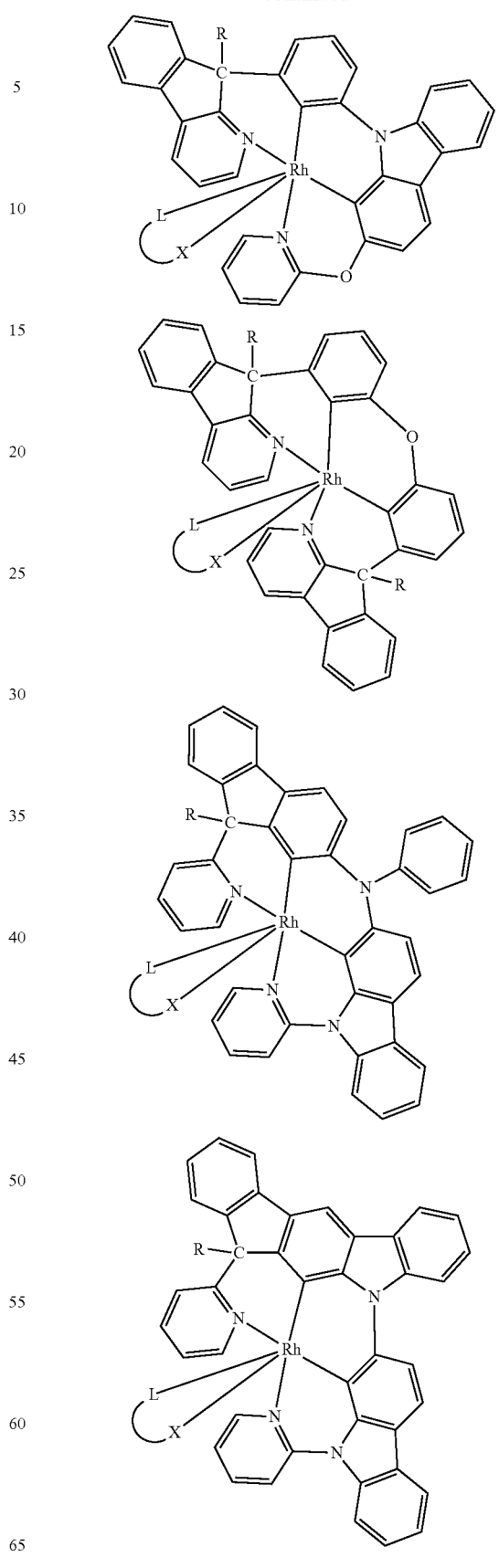

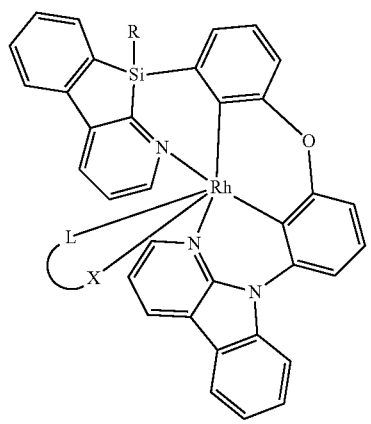
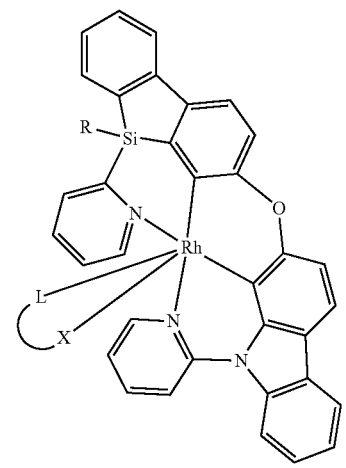
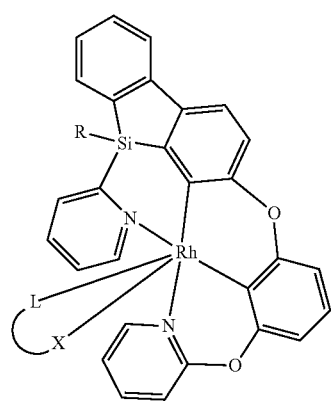
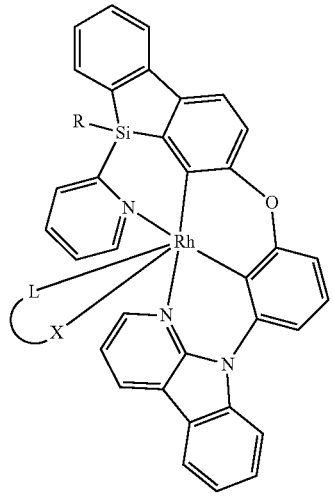
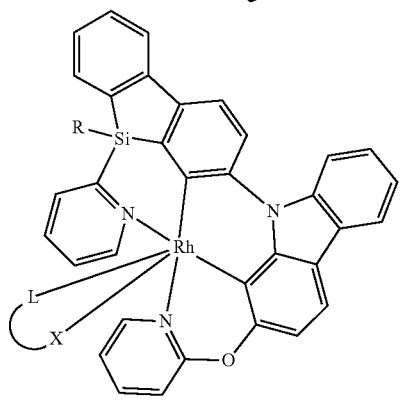
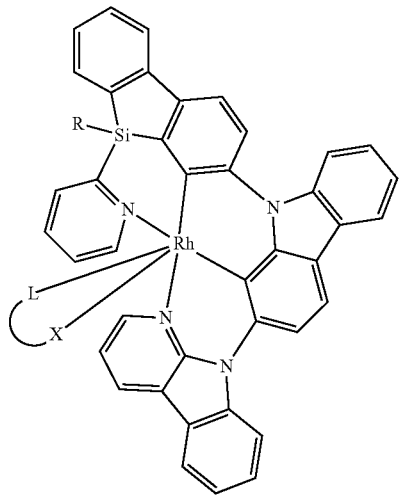
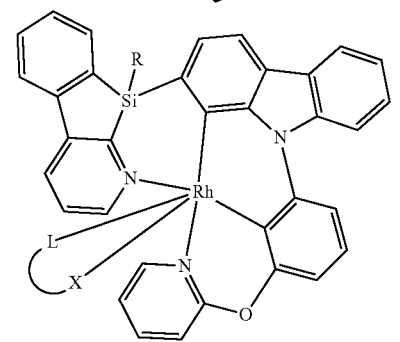

247
-continued
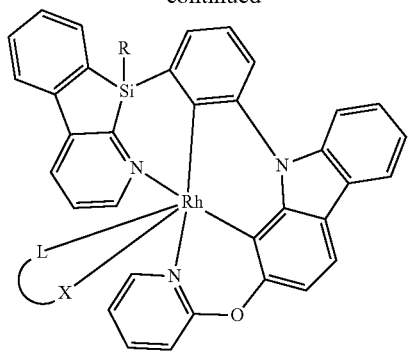
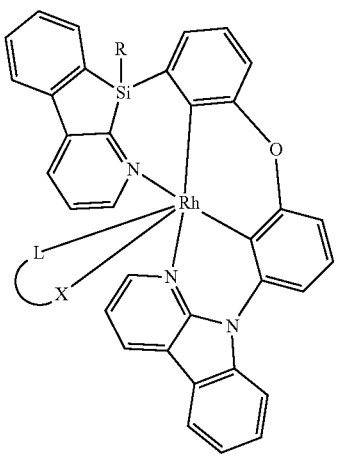
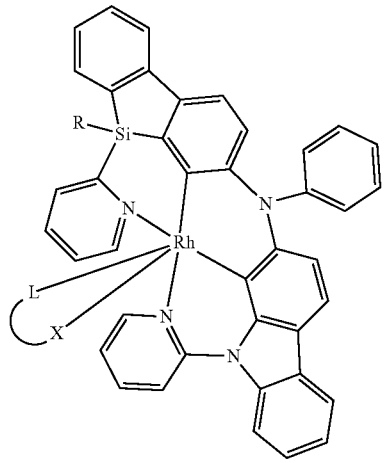
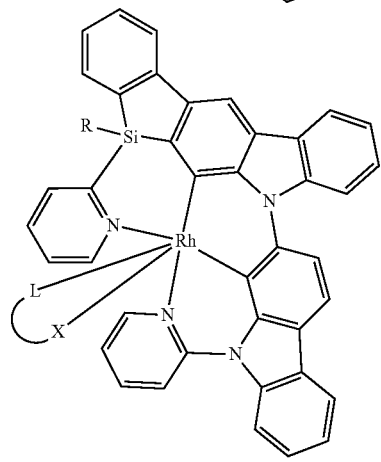
248
-continued
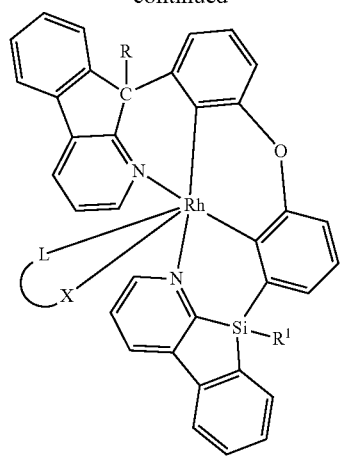
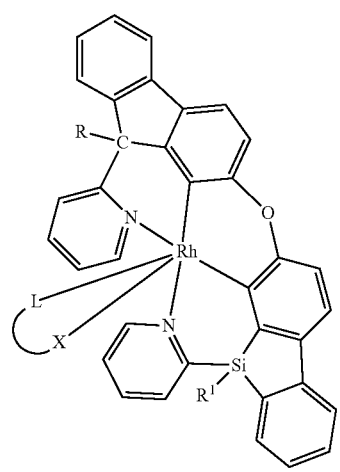
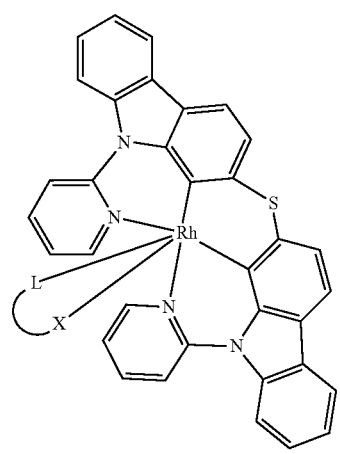

249
-continued
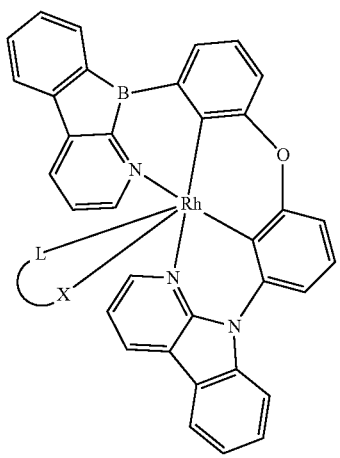
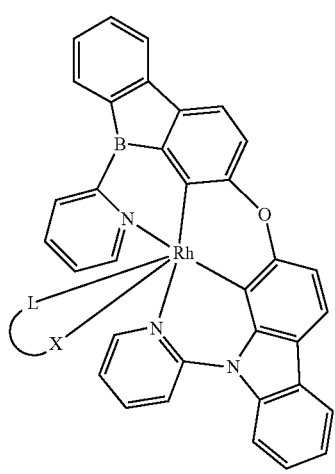
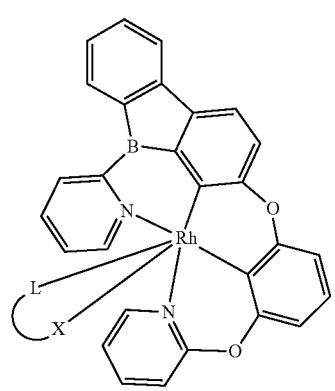
250
-continued
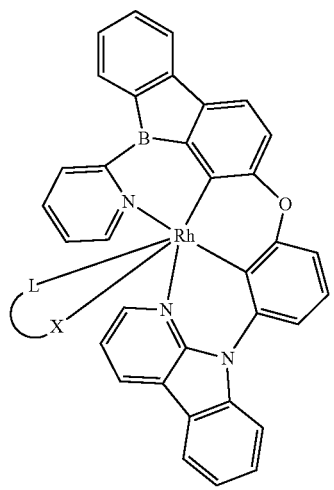
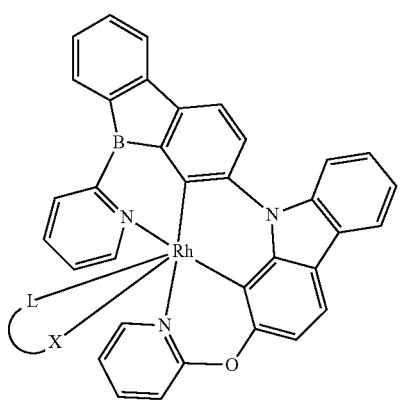
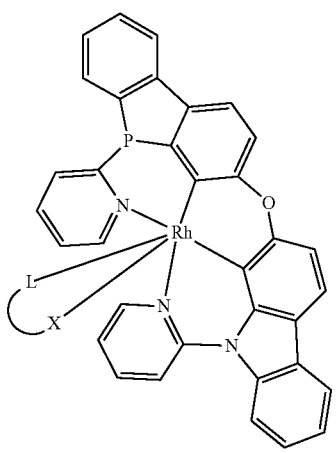

251
-continued
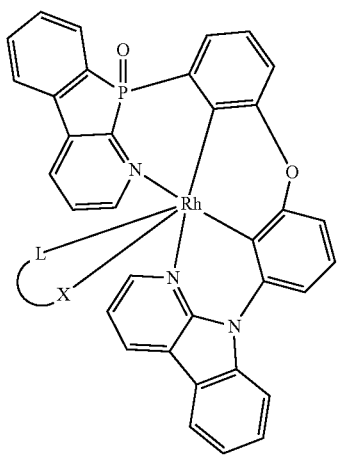
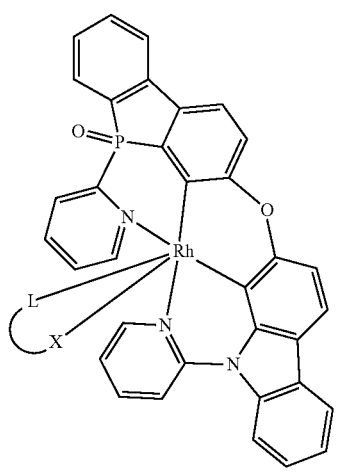
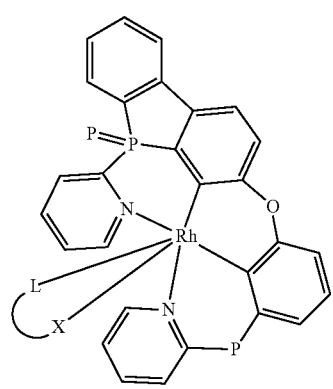
252
-continued
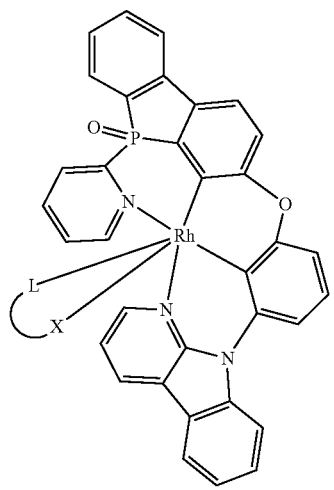
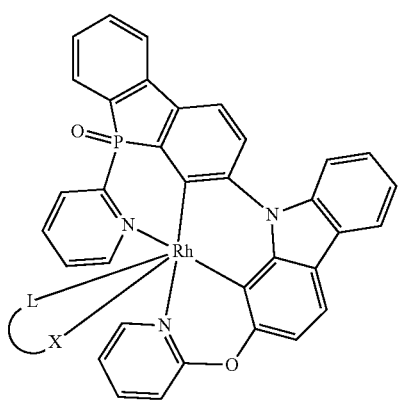
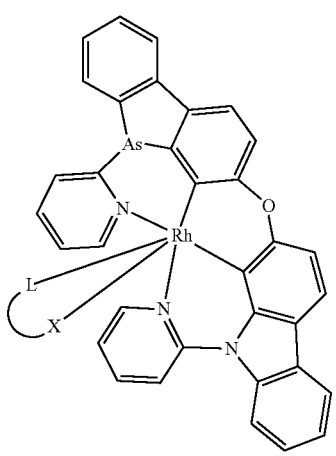

253
-continued
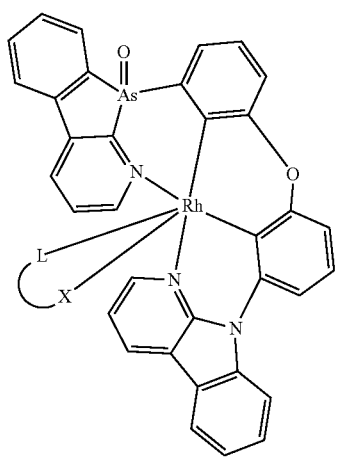
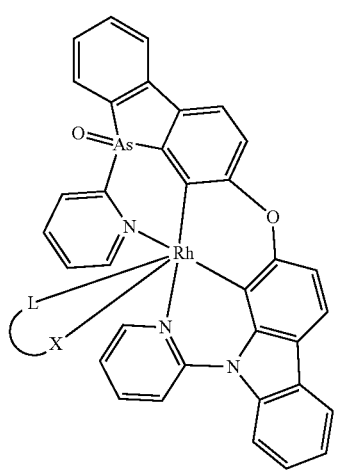
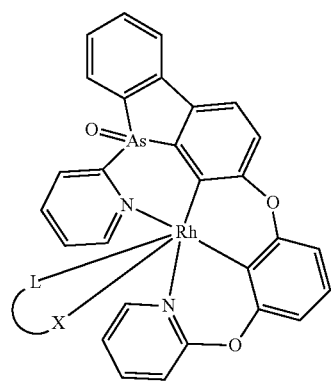
254
-continued
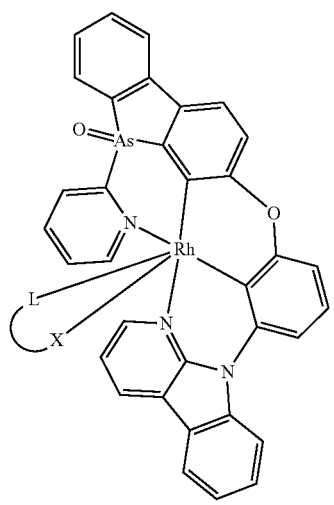
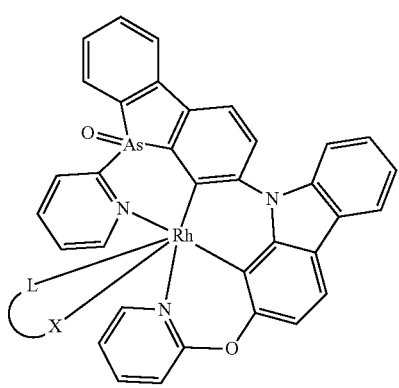
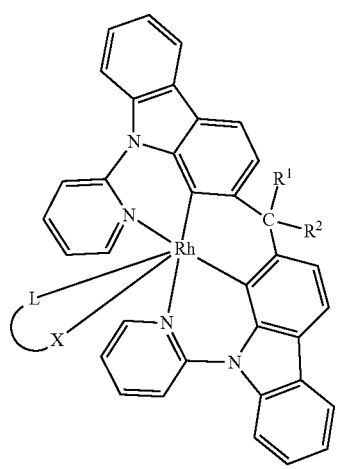

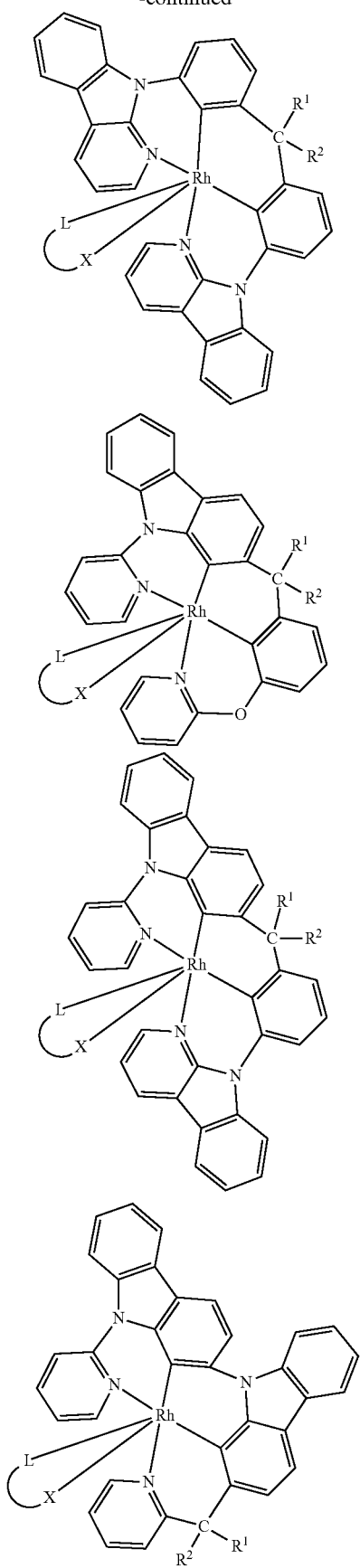
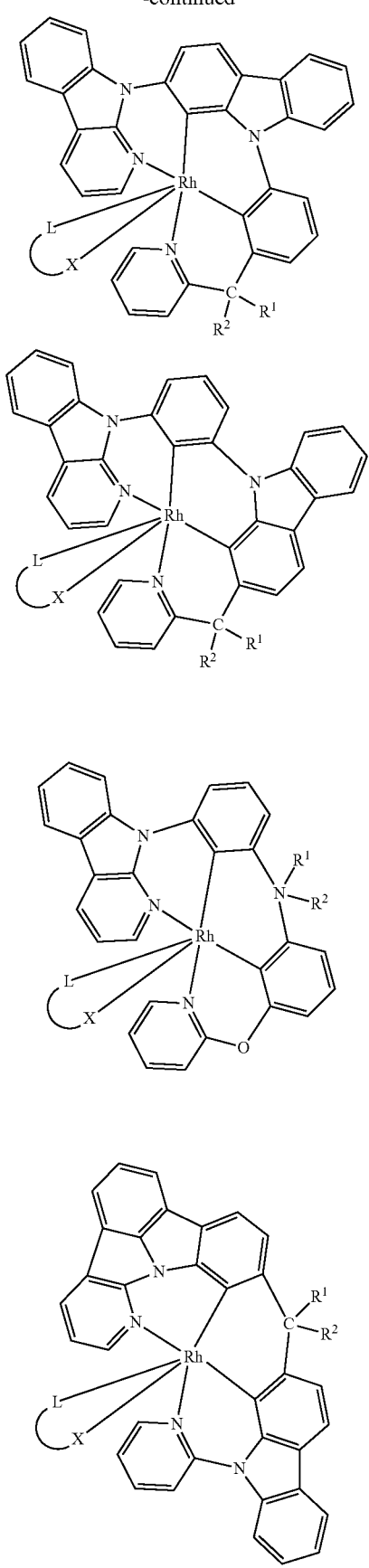

257
-continued
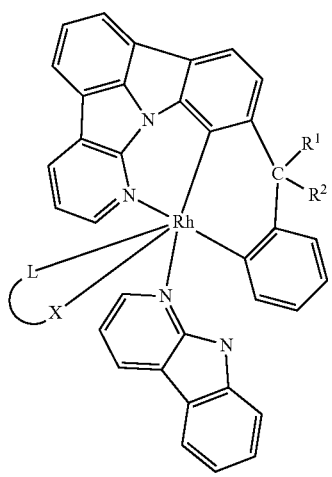
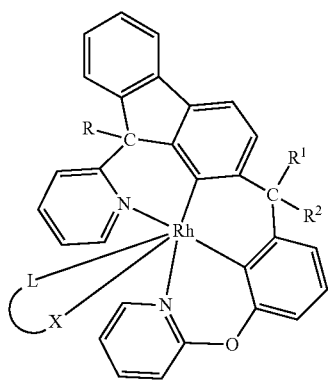
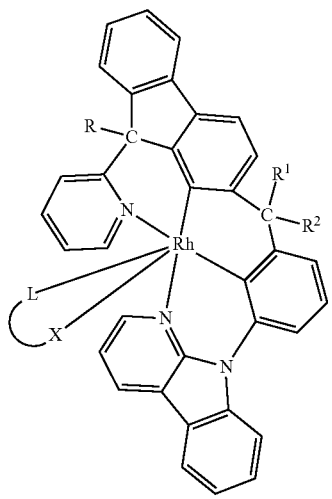
258
-continued
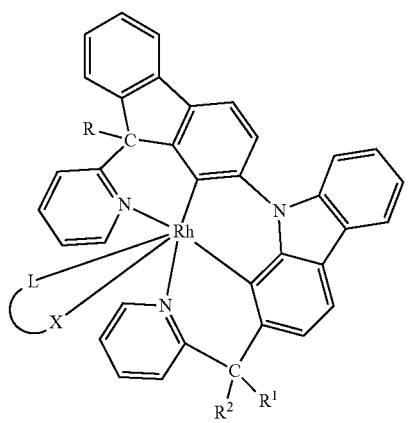
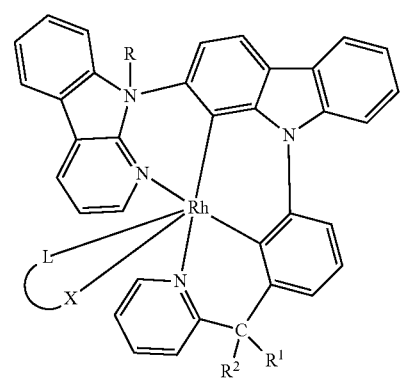
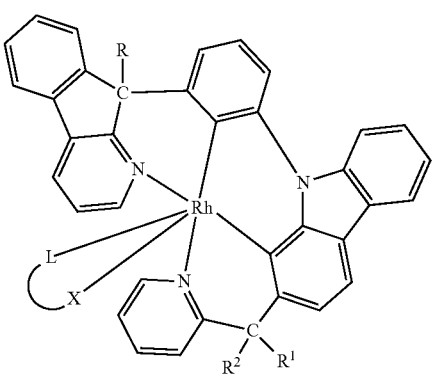
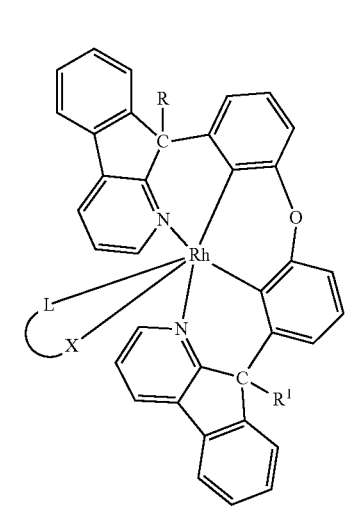

259
-continued
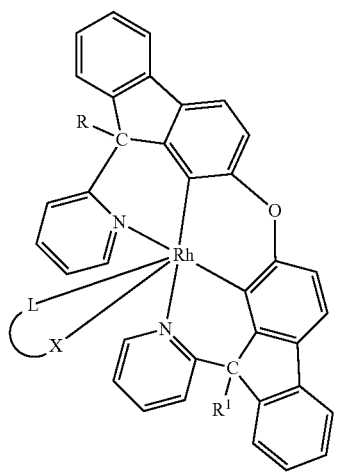
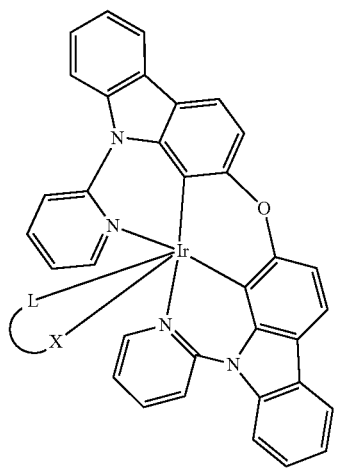
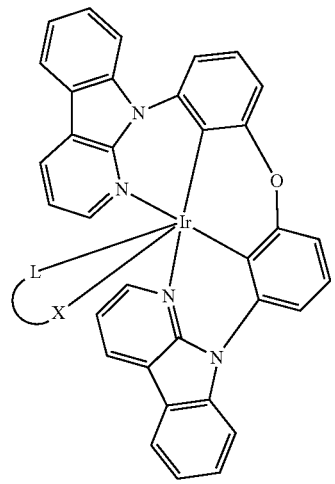
260
-continued
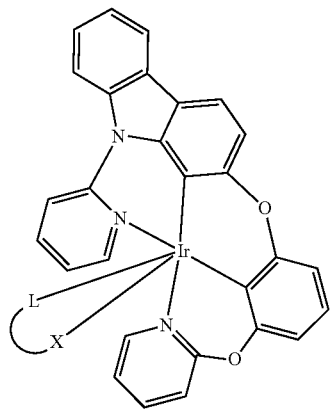
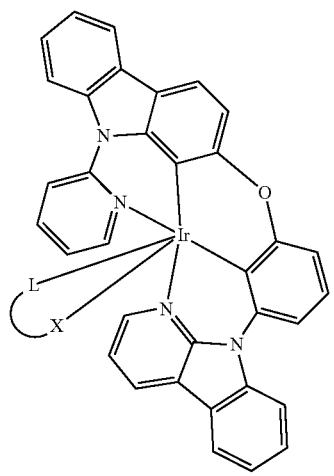
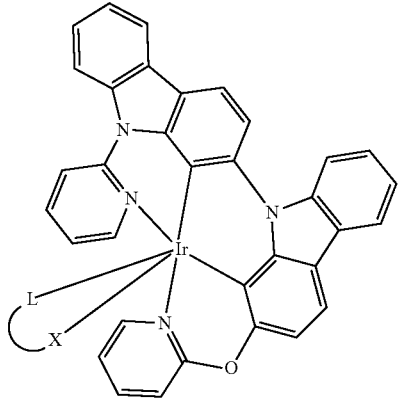

261
-continued
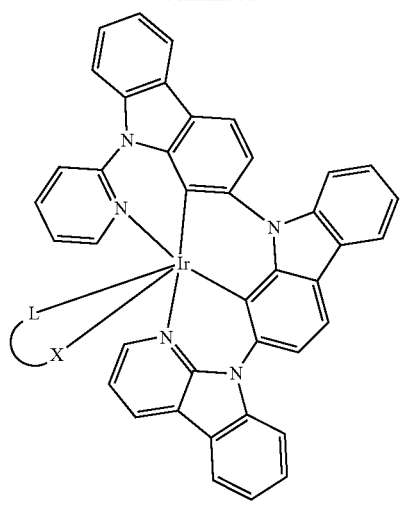
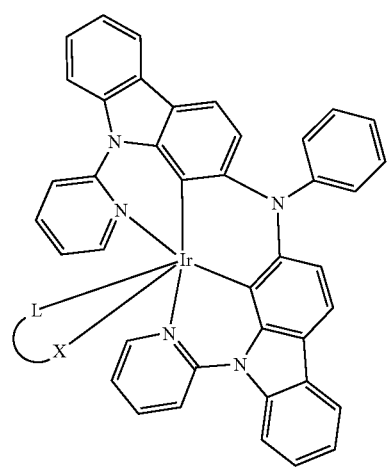
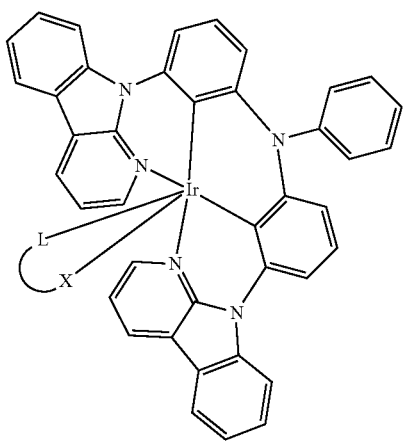
262
-continued
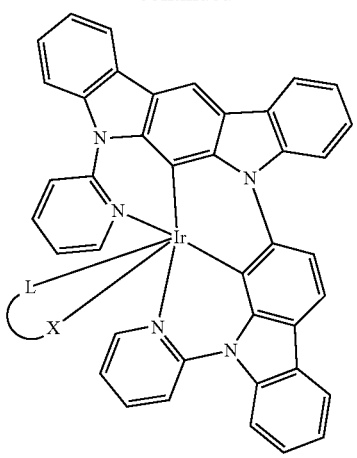
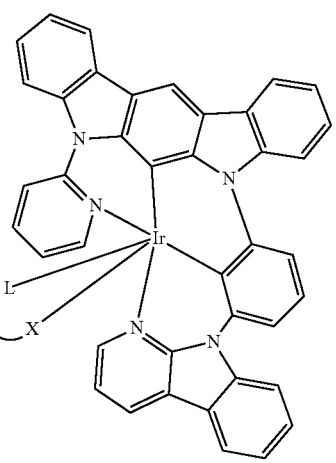
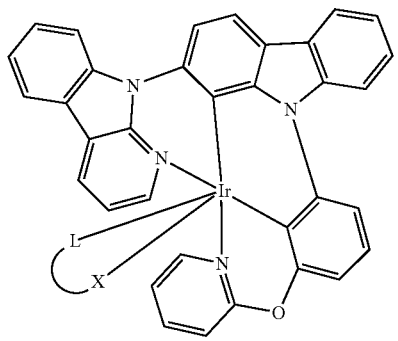

-continued
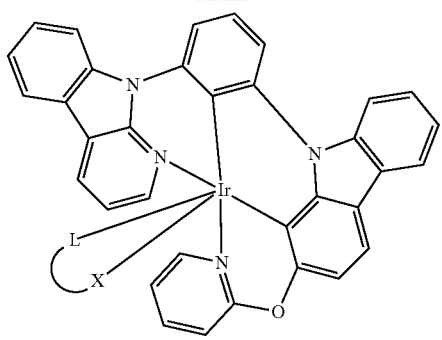
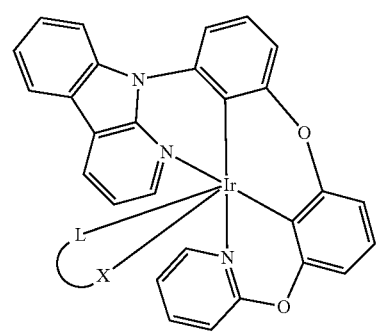
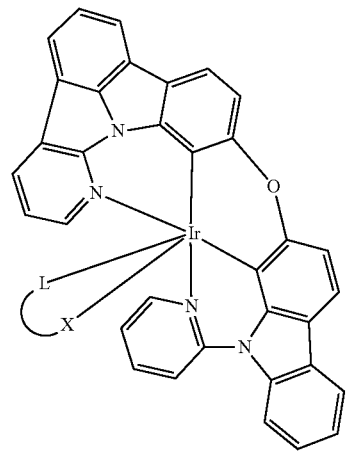
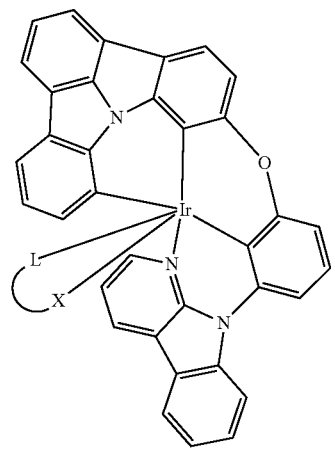
-continued
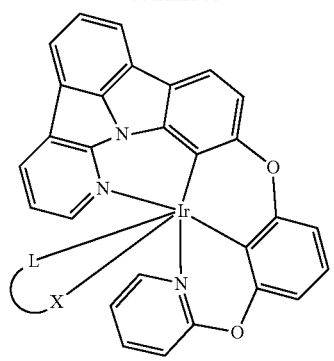
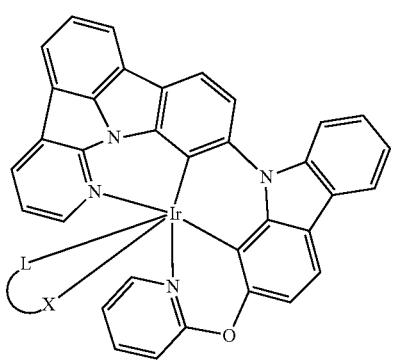
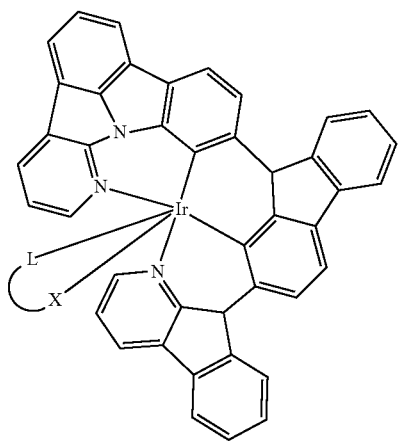
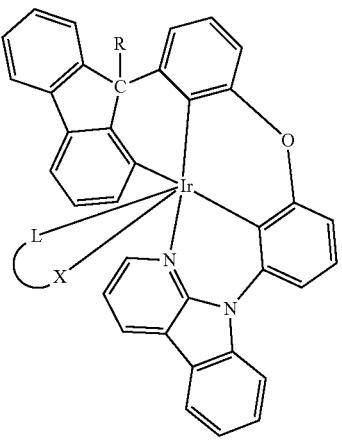

265
-continued
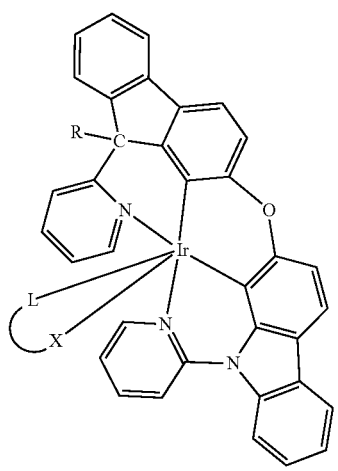
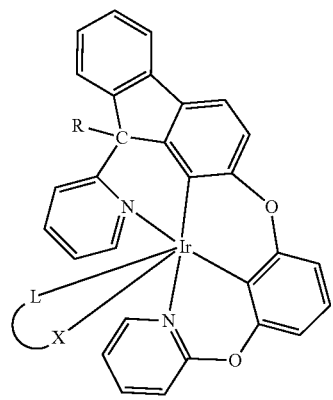
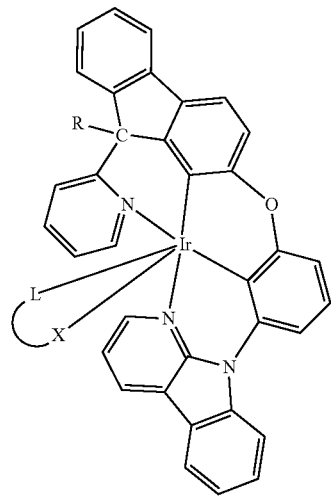
266
-continued
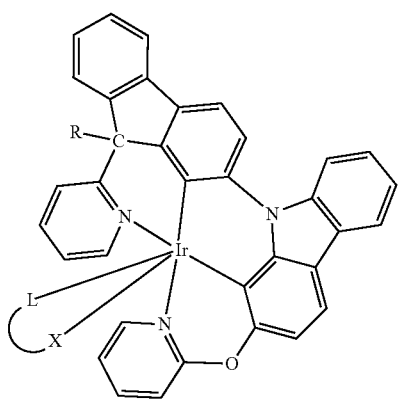
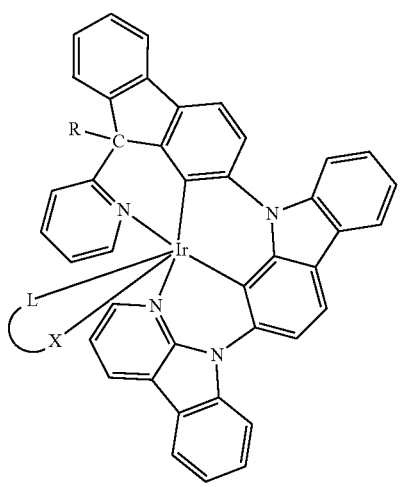
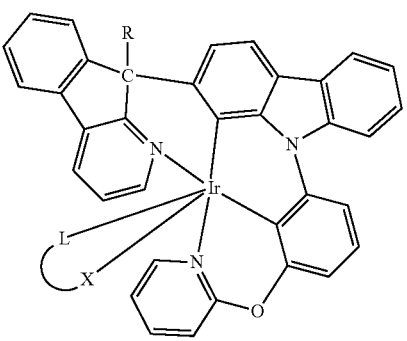
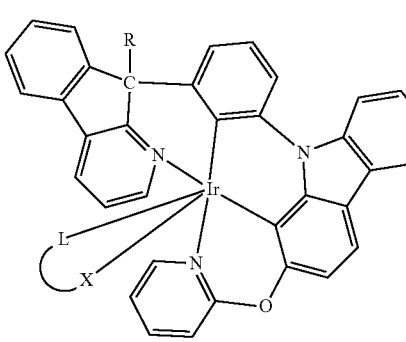

267
-continued
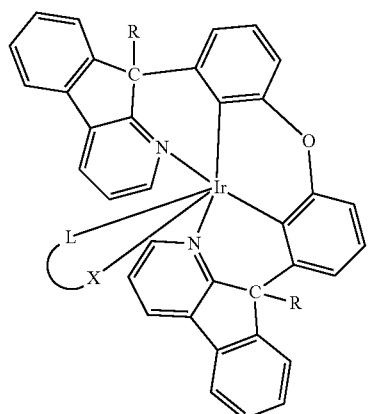
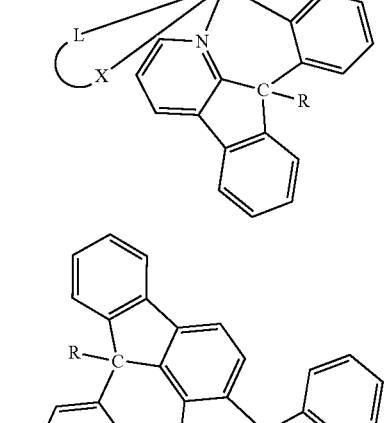
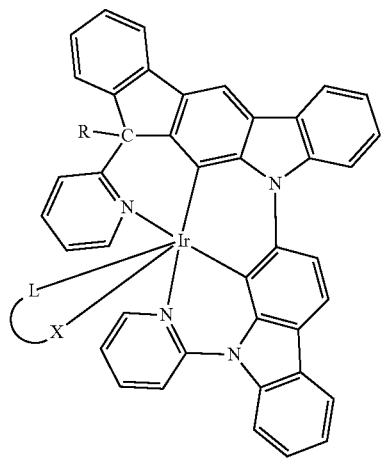
268
-continued
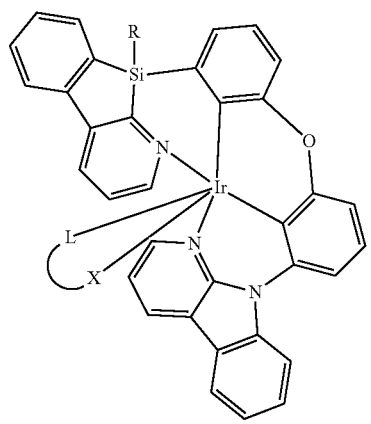
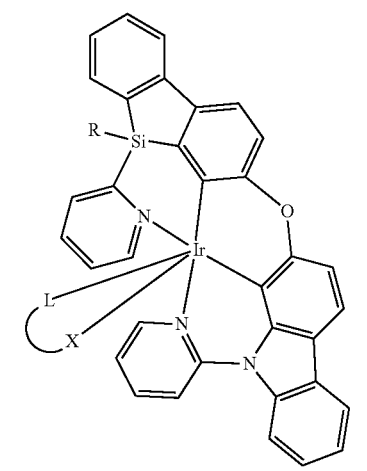
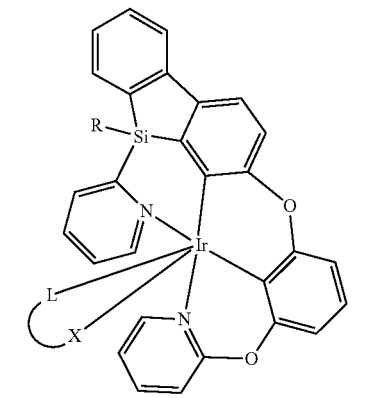

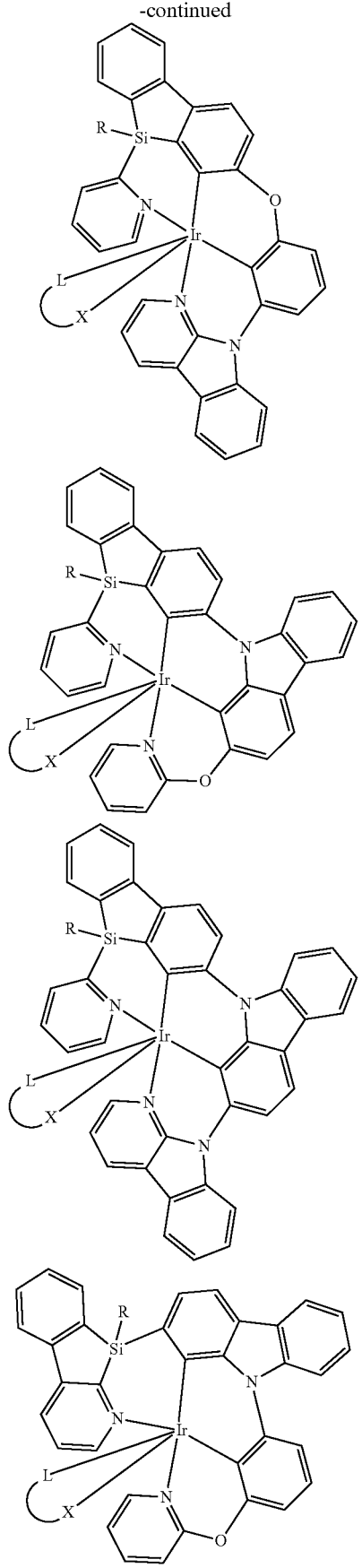
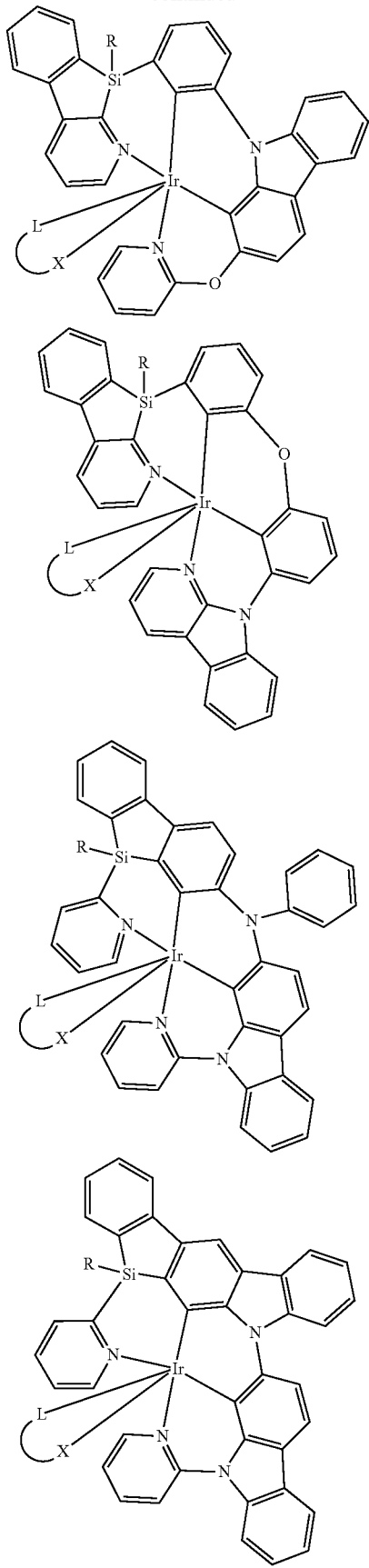

271
-continued
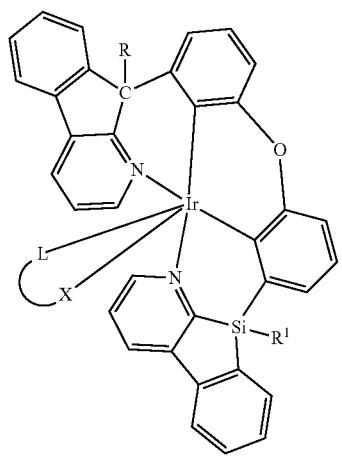
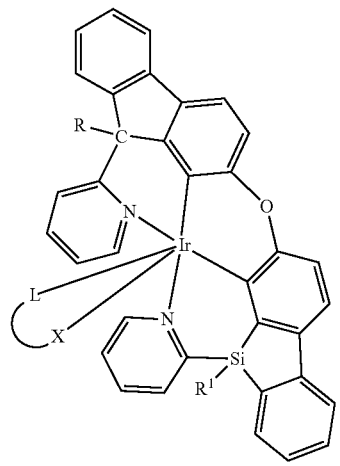
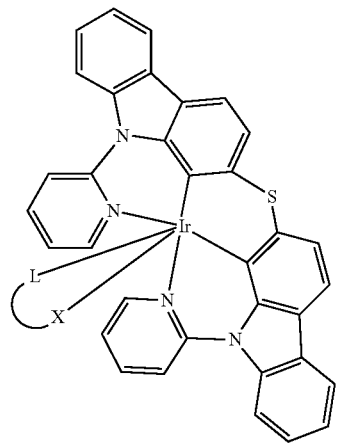
272
-continued
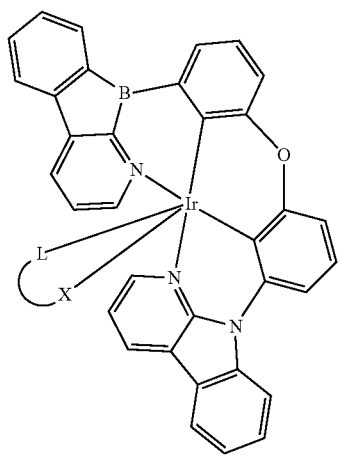
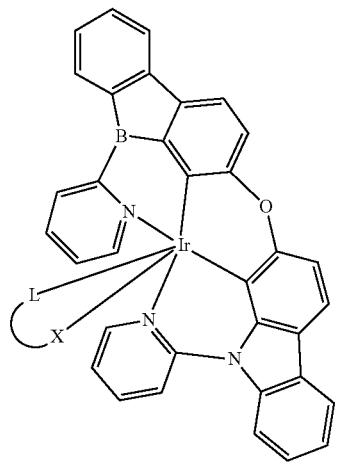
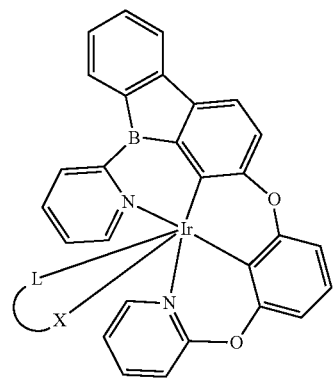

273
-continued
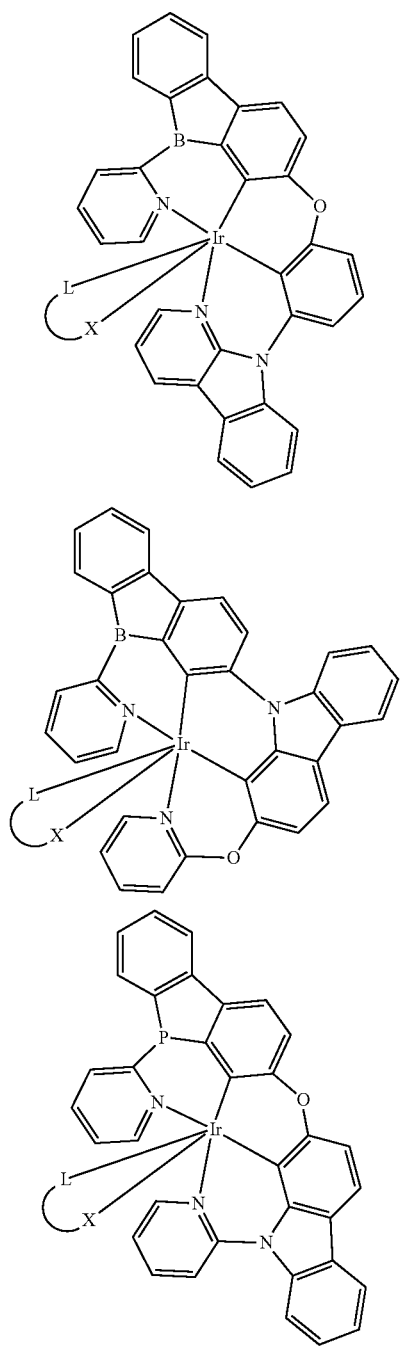
274
-continued
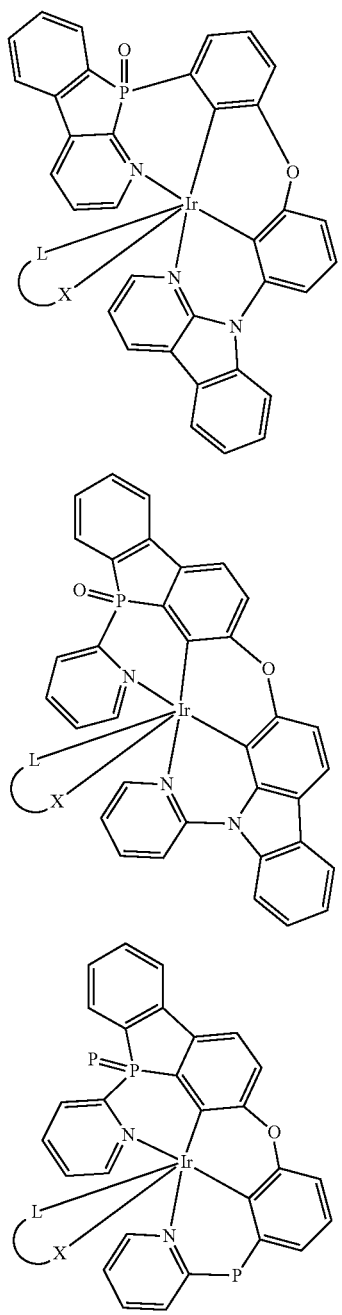

275
-continued
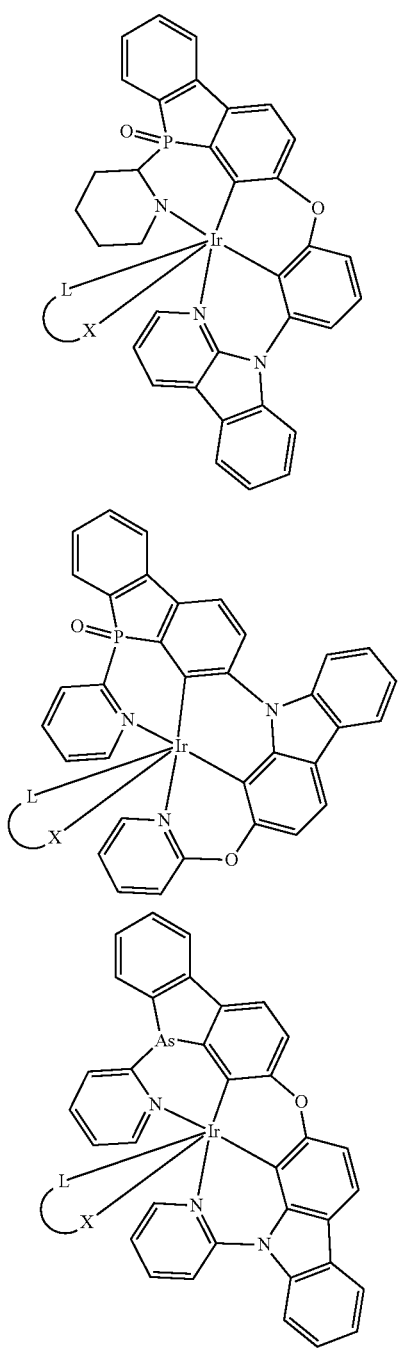
276
-continued
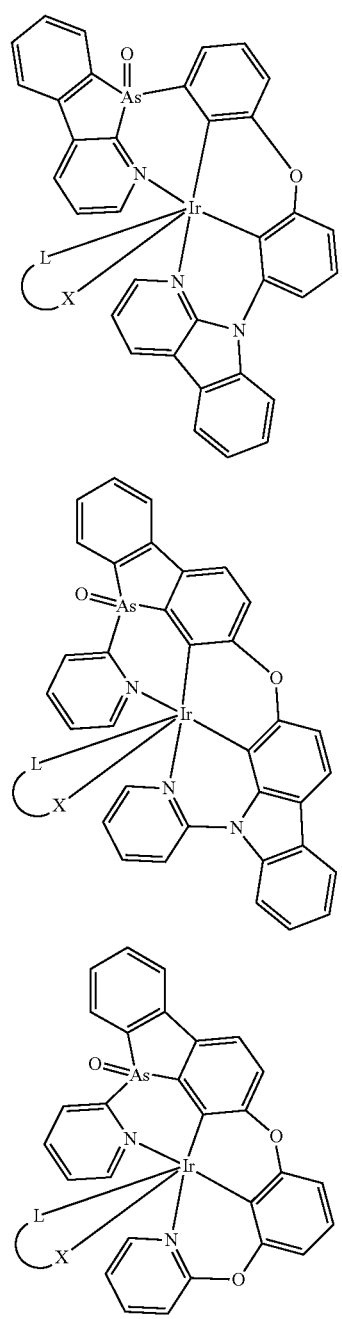

277
-continued
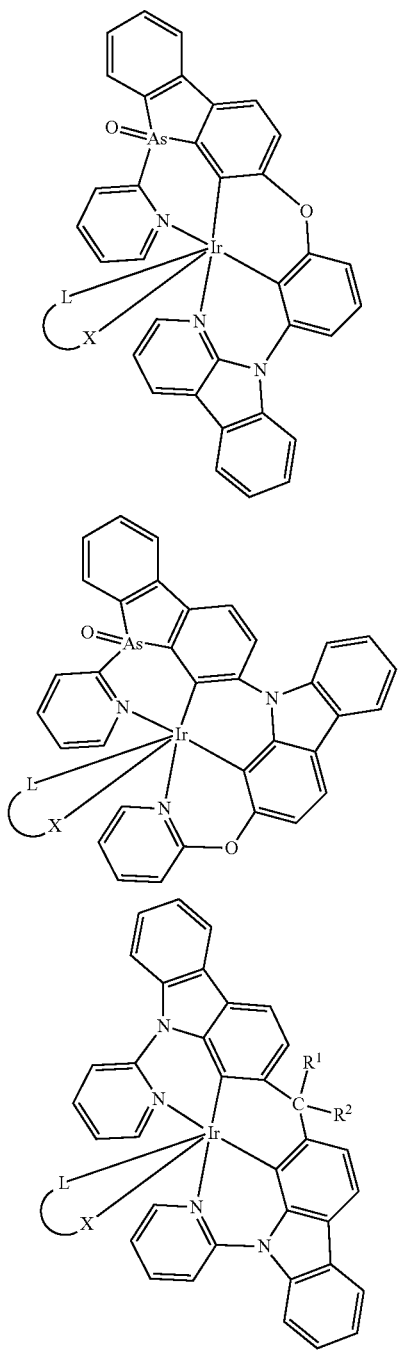
278
-continued
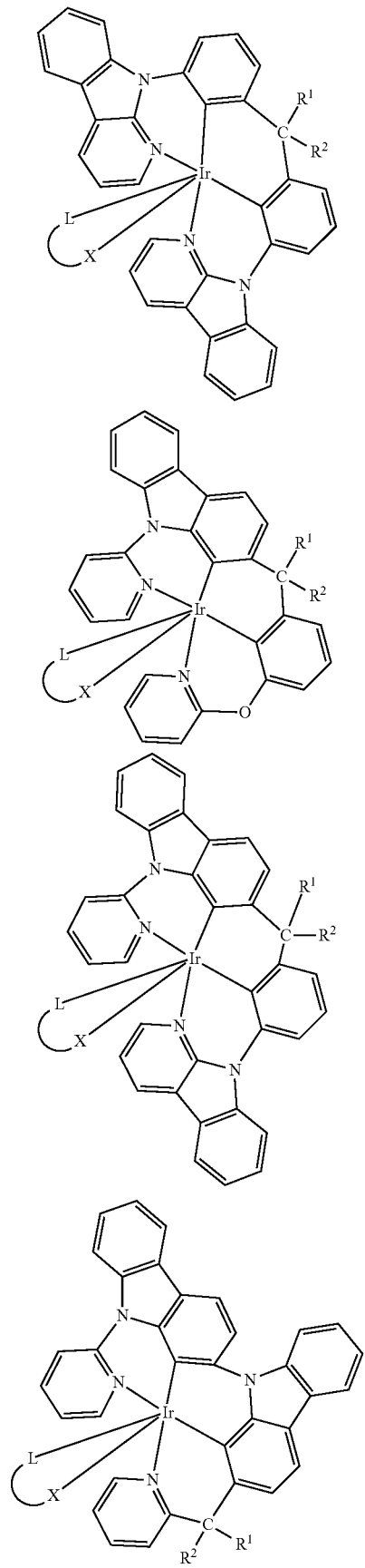

-continued
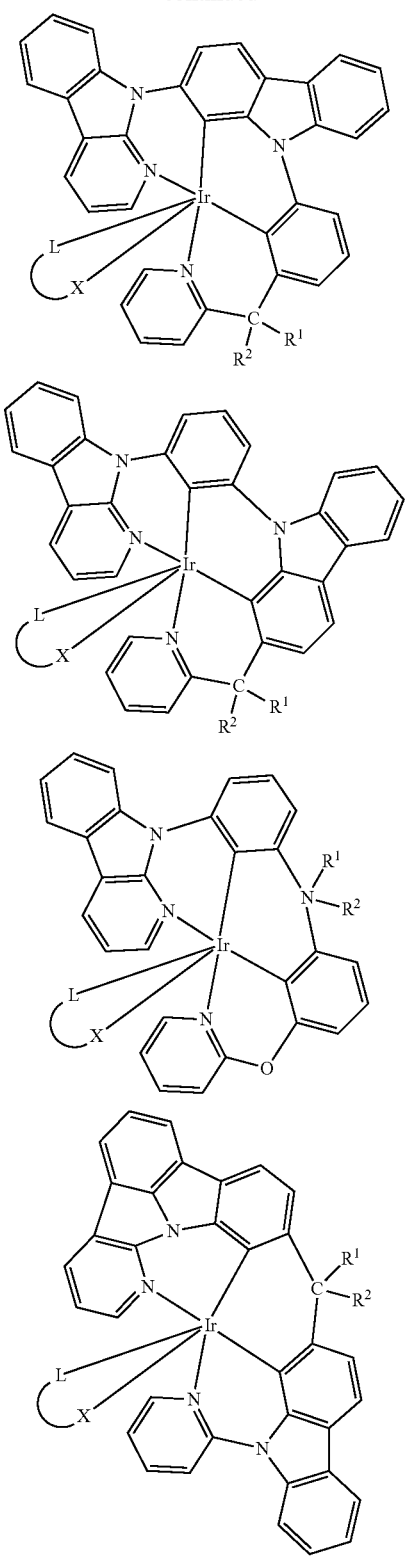
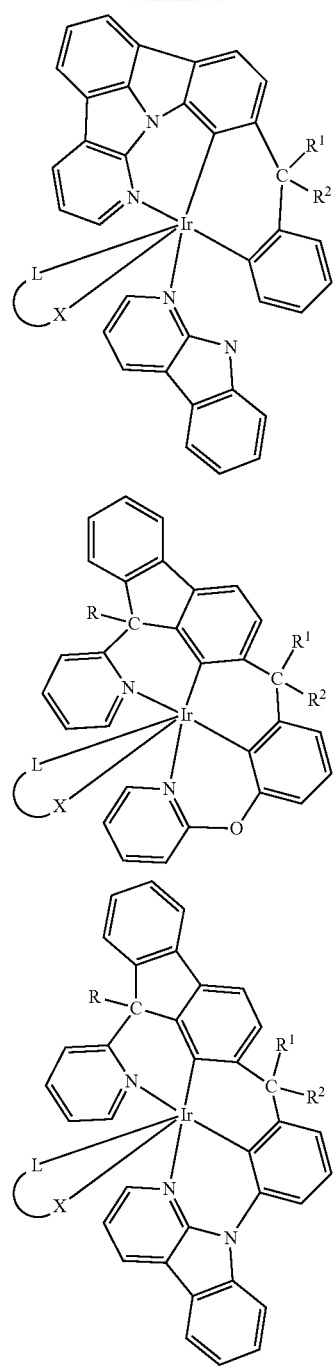

281
-continued

282
-continued

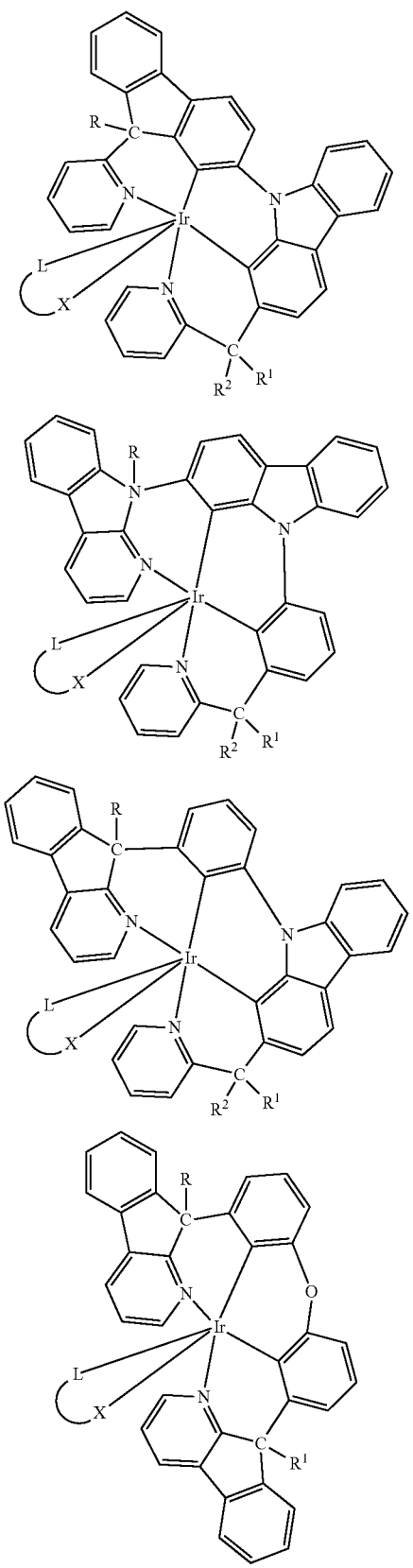

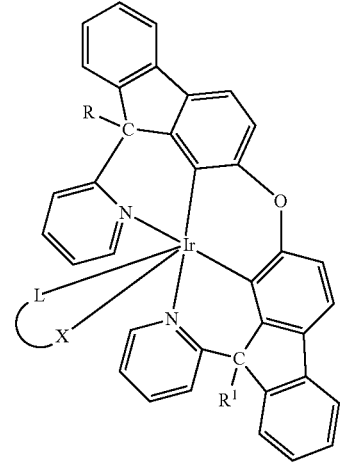

In one aspect,

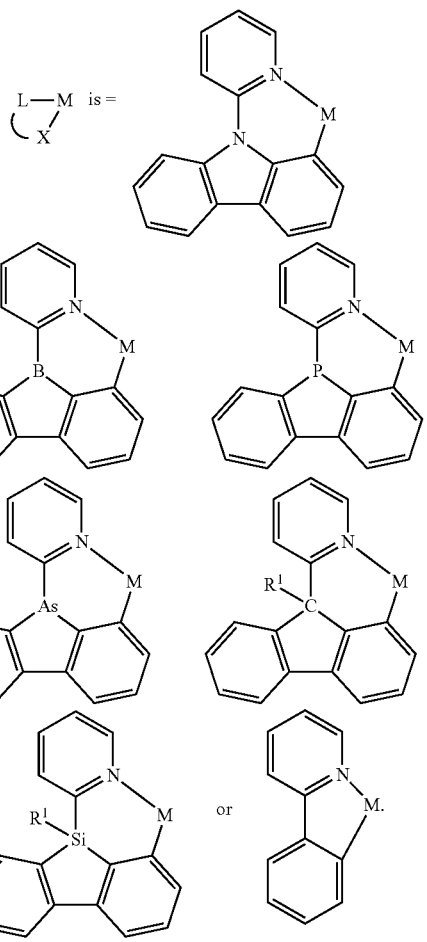

In one aspect, M can be Pt or Pd. In another aspect, each of X, A, and U independently can be O, $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or R² and R³ together form C=O, wherein each of R² and R³ independently is optionally linked to an adjacent ring structure, thereby forming a cyclic structure.

In one aspect,

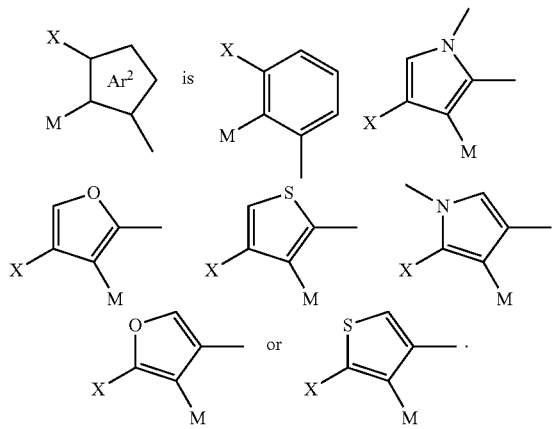

is

In one aspect,

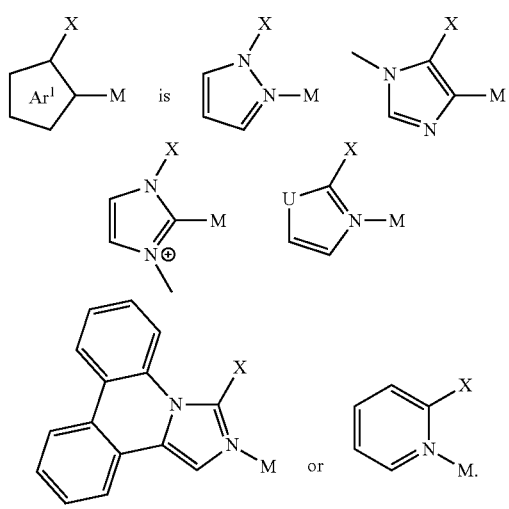

In one aspect,

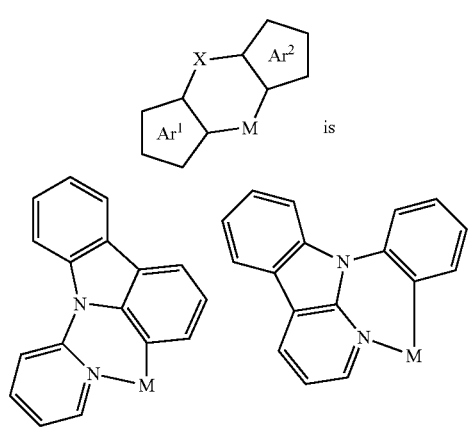

is

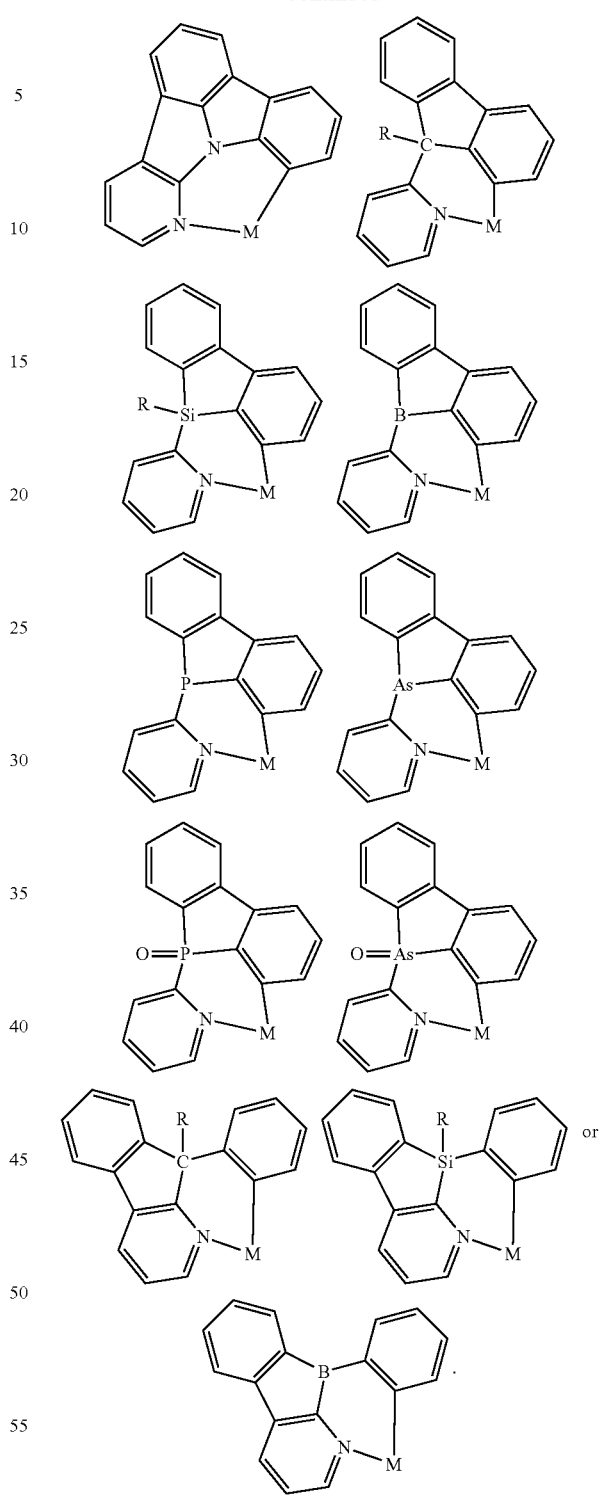

It is appreciated that some of the generic structures disclosed herein can be a subgenus of another generic structure disclosed herein. For example, a generic structure containing C, N, E¹, E², E³, E⁴, and/or E⁵ can in some cases, as appropriate and as recognized by those skilled in the art, be a subgenus of:

285

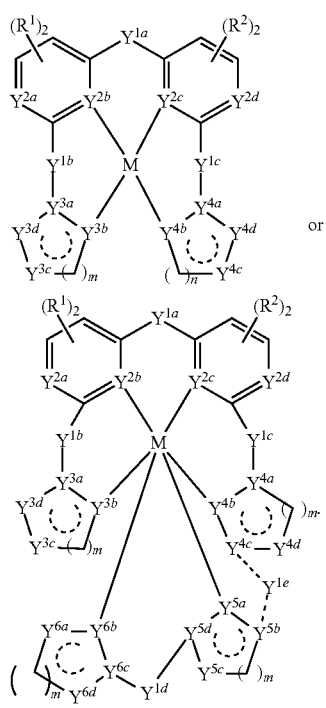

or

In one aspect, disclosed herein is a compound having the structure:

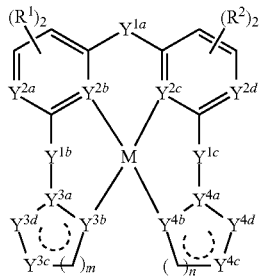

wherein M comprises Pt, Pd, Ir, Rh, or Au; wherein each of $R^1$ and $R^2$ independently are hydrogen, substituted or unsubstituted alkyl, alkenyl, alkynyl, aryl, heteroaryl, cycloalkane, cycloalkane, heterocyclyl, amino, nitro hydroxyl, halogen, thio, alkoxy, haloalkyl, arylalkane, or arylalkene; wherein each of $Y^{1a}$, $Y^{1b}$ and $Y^{1c}$ independently is O, $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to an adjacent ring structure, thereby forming a cyclic structure; wherein each of $Y^{2a}$, $Y^{2b}$, $Y^{2c}$ and $Y^{2d}$ independently is N, $NR^{6a}$, or $CR^{6b}$, wherein each of $R^{6a}$ and $R^{6b}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently is N, O, S, $NR^{6a}$, $CR^{6b}$, wherein each of $R^{6a}$ and $R^{6b}$ independently hydrogen,

286 substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; or $Z(R^{6c})_2$, wherein Z is C or Si, and wherein each $R^{6c}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; wherein each of m and n independently are an integer 1 or 2; wherein each of independently is partial or full unsaturation of the ring with which it is associated.

In one aspect, disclosed herein is a compound having the structure:

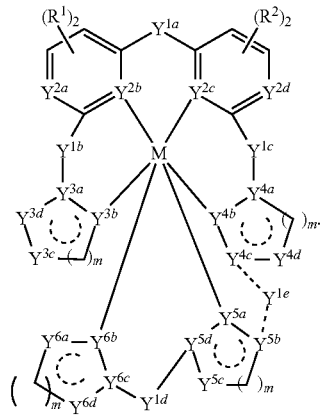

wherein M comprises Ir, Rh, Pt, Os, or Ru, wherein each of $R^1$ and $R^2$ independently are hydrogen, substituted or unsubstituted alkyl, alkenyl, alkynyl, aryl, heteroaryl, cycloalkane, cycloalkane, heterocyclyl, amino, nitro hydroxyl, halogen, thio, alkoxy, haloalkyl, arylalkane, or arylalkene; wherein each of $Y^{1a}$, $Y^{1b}$, $Y^{1c}$, $Y^{1d}$, and $Y^{1e}$ independently is O, $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to an adjacent ring structure, thereby forming a cyclic structure; wherein each of $Y^{2a}$, $Y^{2b}$, $Y^{2c}$ and $Y^{2d}$ independently is N, $NR^{6a}$, or $CR^{6b}$, wherein each of $R^{6a}$ and $R^{6b}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; wherein each of $Y^{3a}$, $Y^{3b}$, $Y^{3c}$, $Y^{3d}$, $Y^{3e}$, $Y^{4a}$, $Y^{4b}$, $Y^{4c}$ and $Y^{4d}$ independently is N, O, S, $NR^{6a}$, $CR^{6b}$, wherein each of $R^{6a}$ and $R^{6b}$ independently hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; or $Z(R^{6c})_2$, wherein Z is C or Si, and wherein each $R^{6c}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene; wherein in each of each of $Y^{5a}$, $Y^{5b}$, $Y^{5c}$, $Y^{5d}$, $Y^{6a}$, $Y^{6b}$, $Y^{6c}$ and $Y^{6d}$ independently is N, O, S, $NR^{6a}$, or $CR^{6b}$; wherein each of m and n independently are an integer 1 or 2; wherein each of

independently is partial or full unsaturation of the ring with which it is associated.

In one aspect, disclosed herein is a compound having the structure:

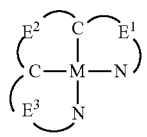

wherein the formula, M represent a metal cation with two positive charges, which include, but are not limited to Platinum(II) ($Pt^{2+}$), Palladium(II) ($Pd^{2+}$), wherein $E^1$, $E^2$, and $E^3$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, M can be Platinum (II). In one aspect, M can be Palladium (II).

In one aspect, the compound can be:

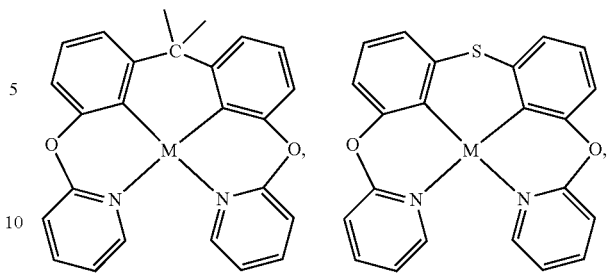

-continued

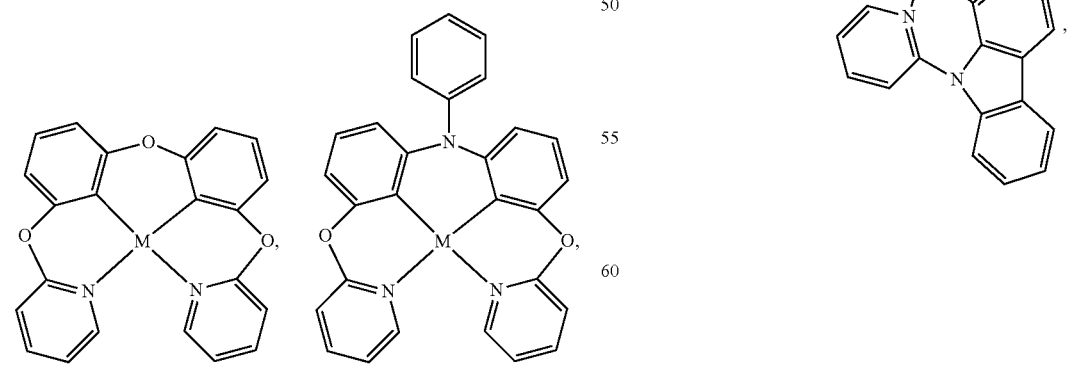

289
-continued
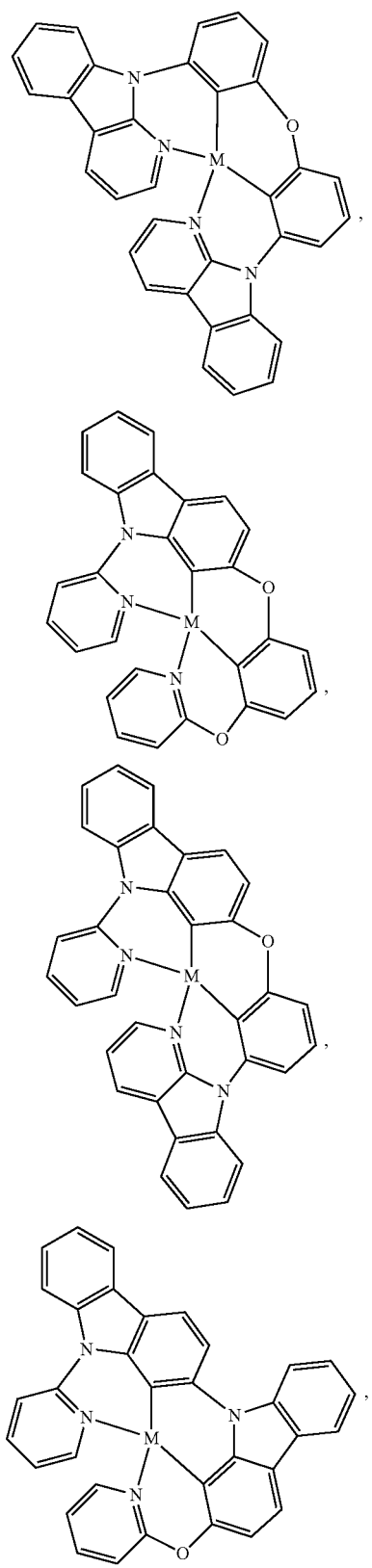
290
-continued
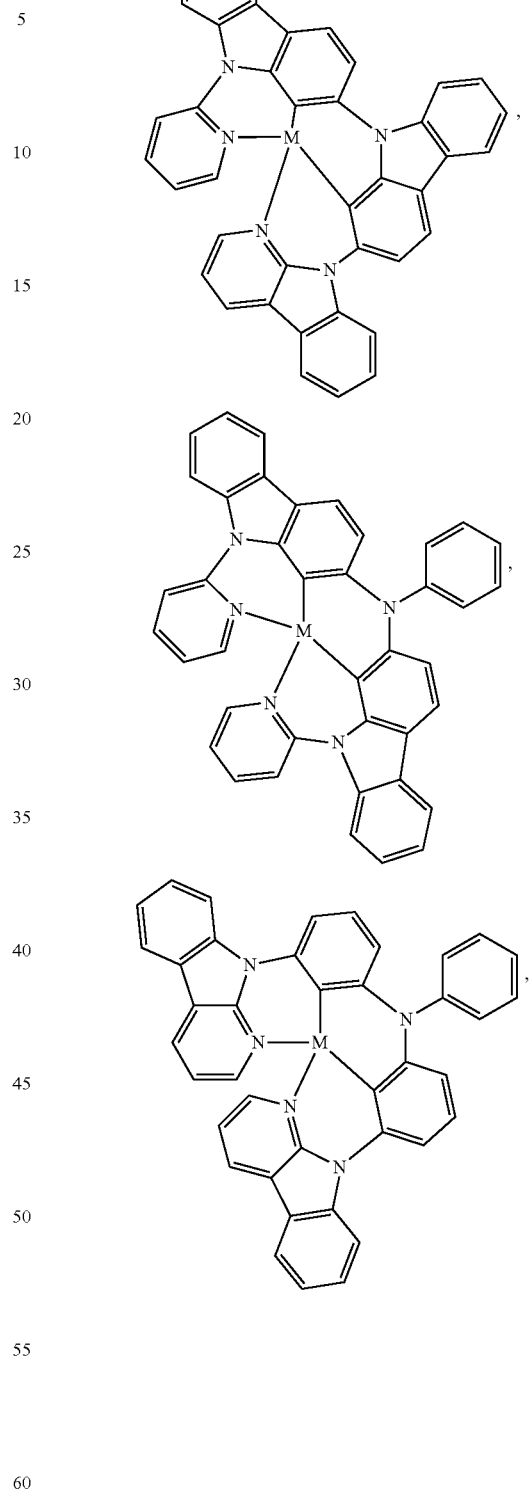

291
-continued
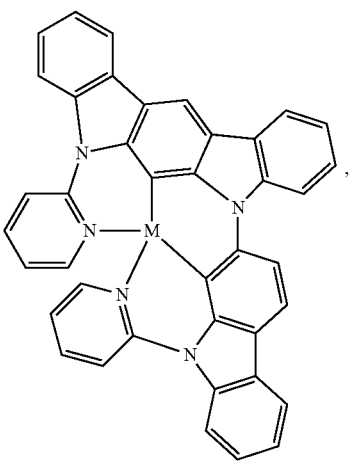
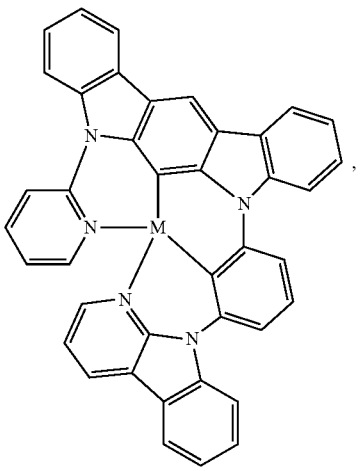
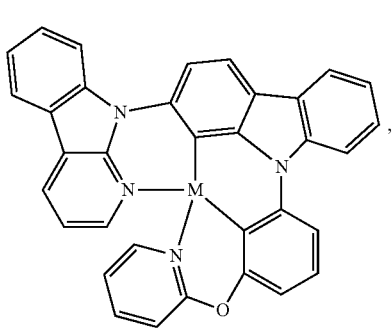
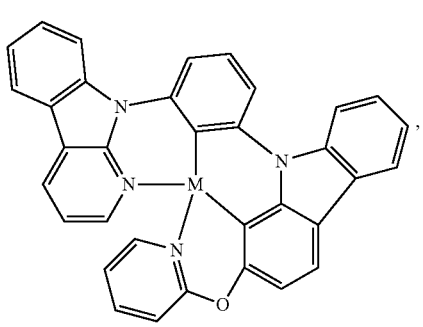
292
-continued
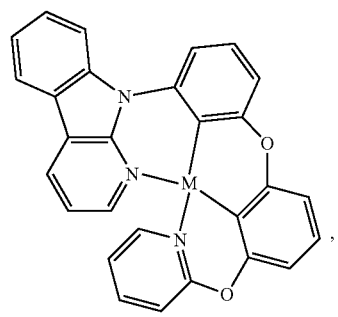
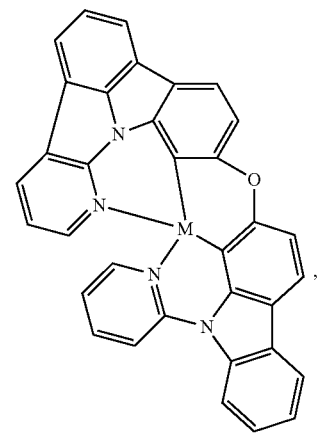
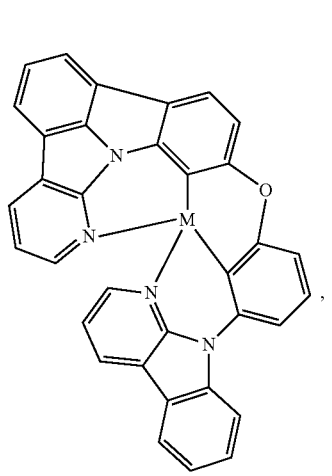
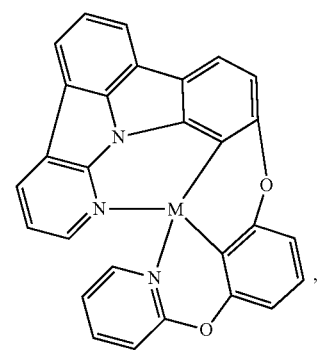

293
-continued
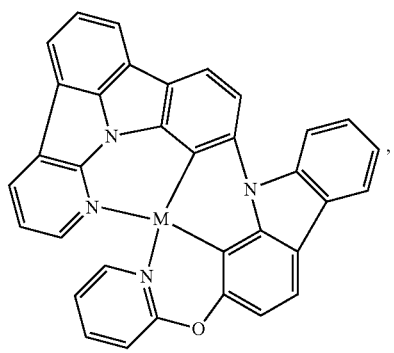,
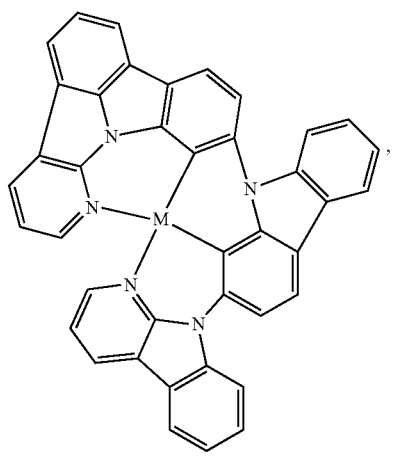,
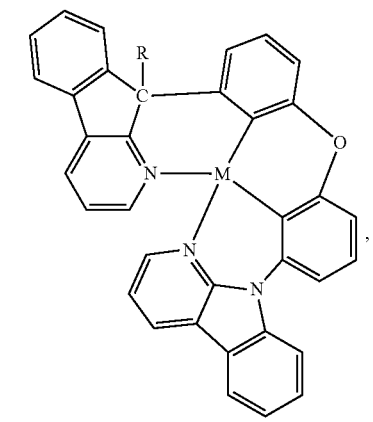,
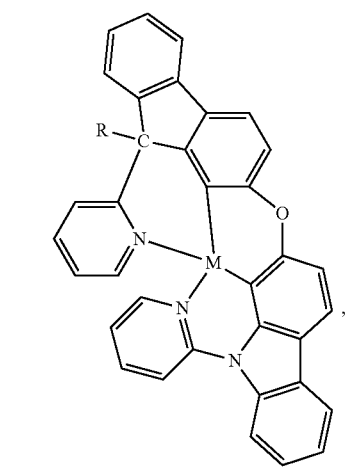,
294
-continued
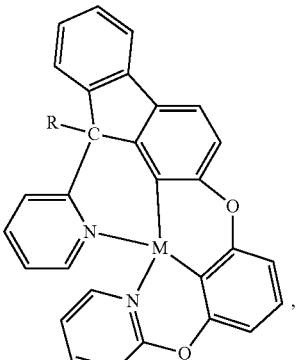,
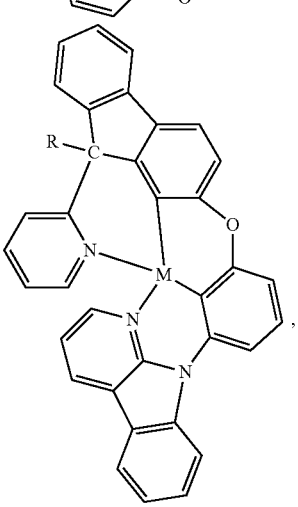,
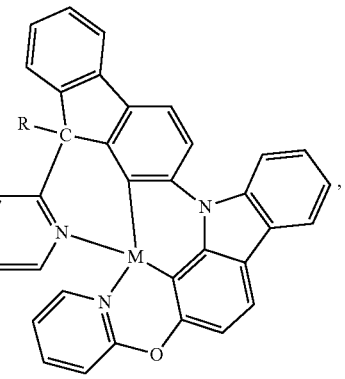,
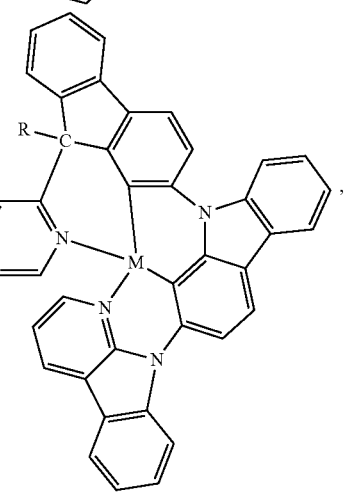, -continued

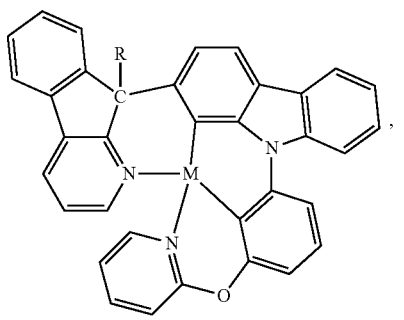

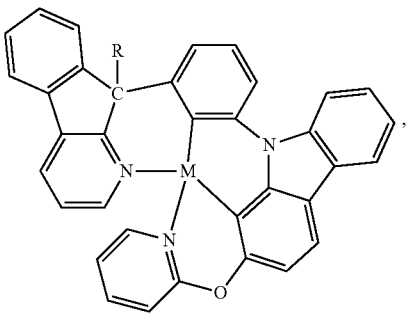

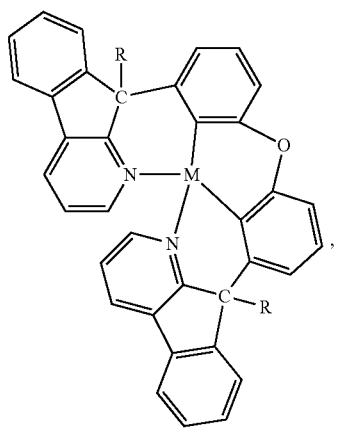

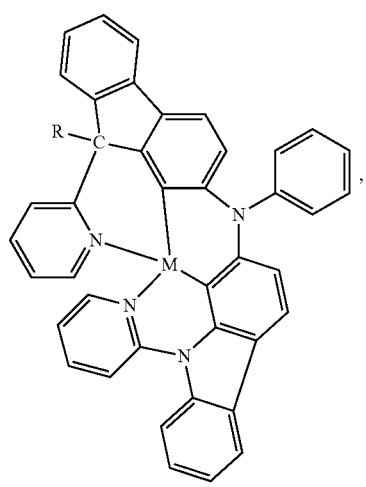

-continued

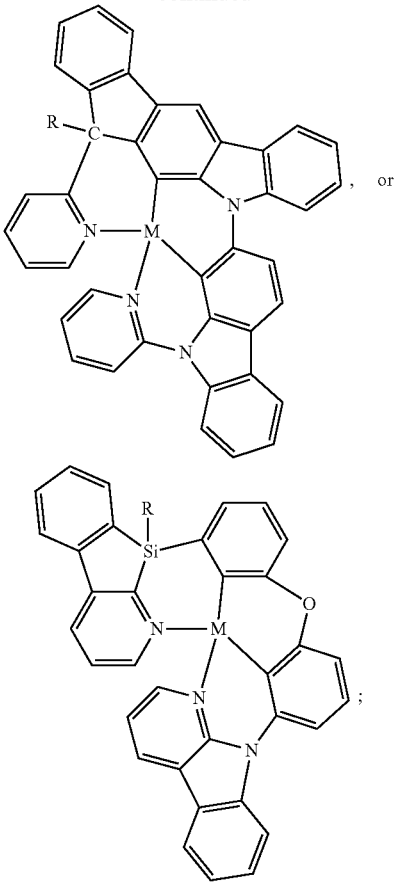

wherein each R independently is hydrogen, substituted or unsubstituted alkyl, alkenyl, alkynyl, aryl, cycloalkyl, cycloalkenyl, heterocyclyl, deuterium, halogen, hydroxyl, thiol, nitro, cyano, amino, a mono- or di-alkylamino, a mono- or diaryl amino, alkoxy, aryloxy, haloalkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, or substituted silyl.

In one aspect, disclosed herein is a compound having the structure:

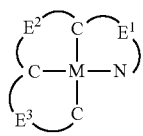

wherein M represents a metal cation with three positive charges, which include, but are not limited to Gold(III) ($Au^{3+}$), silver(III) ($Ag^{3+}$), wherein each $E^1$, $E^2$, and $E^3$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein N represents a substituted or unsubstituted aromatic ring or heterocyclic group with a nitrogen atom coordinated to the metal.

In one aspect, $E^1$, $E^2$, and $E^3$ can be oxygen. In one aspect, each of $E^1$, $E^2$, and $E^3$ can independently comprise O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure In another aspect, $E^1$ and $E^3$ can be oxygen. In yet another aspect, $E^2$ can be nitrogen, oxygen, carbon, silicon, phosphorous, or sulfur.

In one aspect, M can be Au (III). In one aspect, M can be Ag (III).

In one aspect, the compound can have the structure:

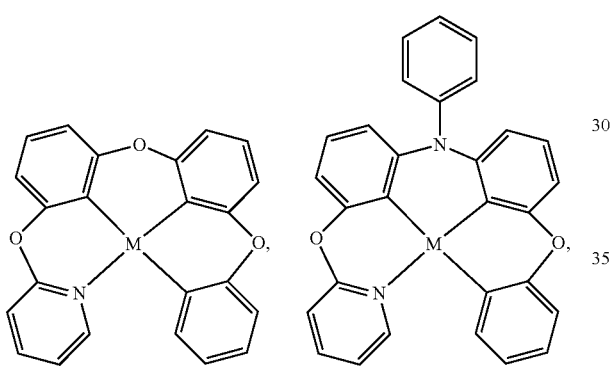

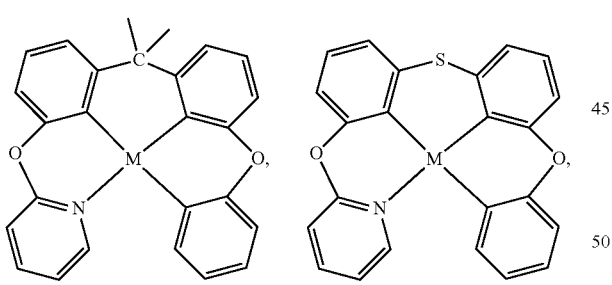

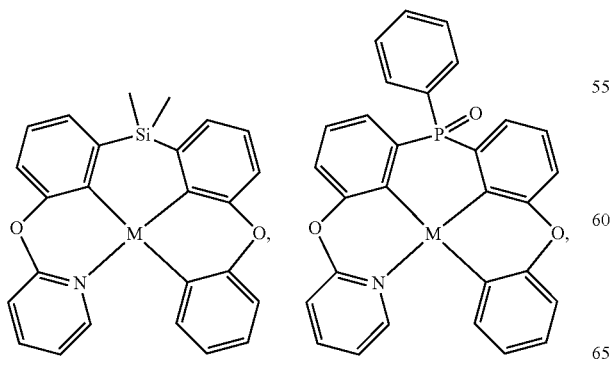

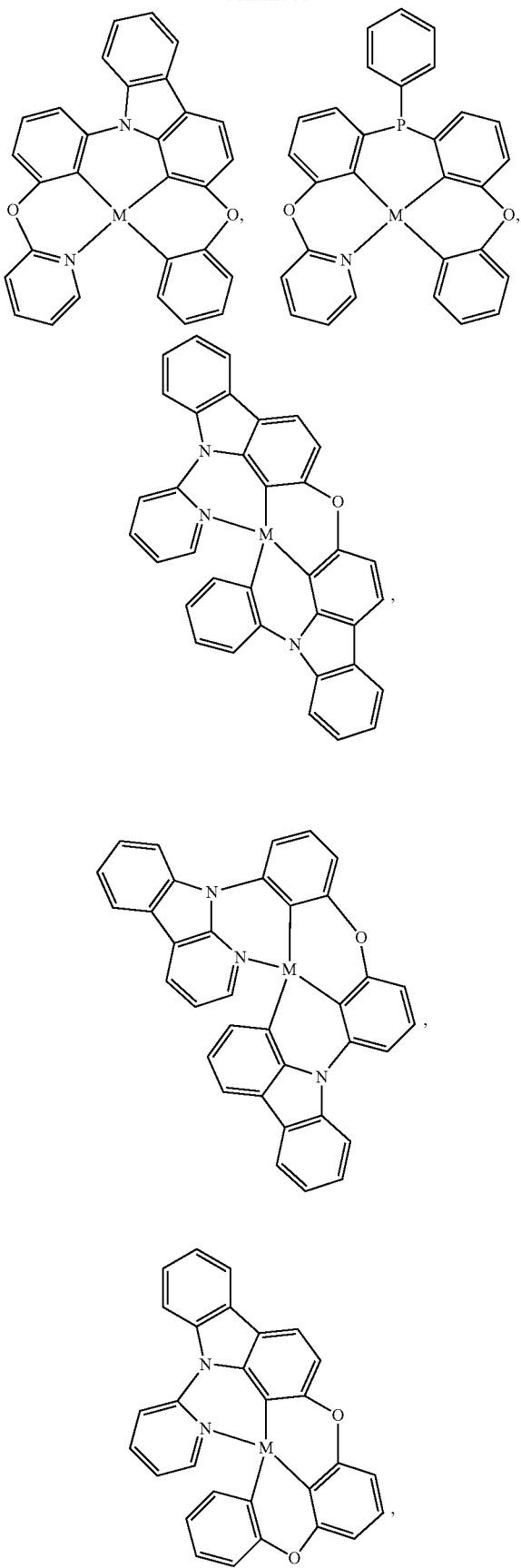

299
-continued
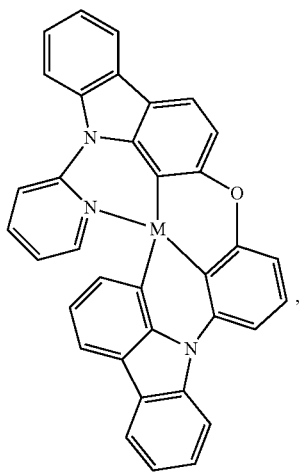
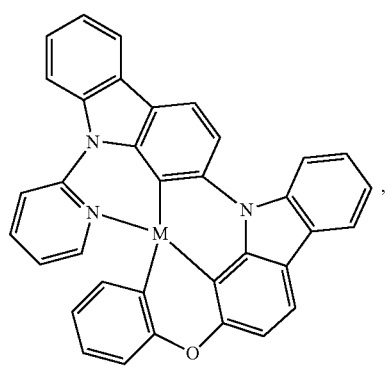
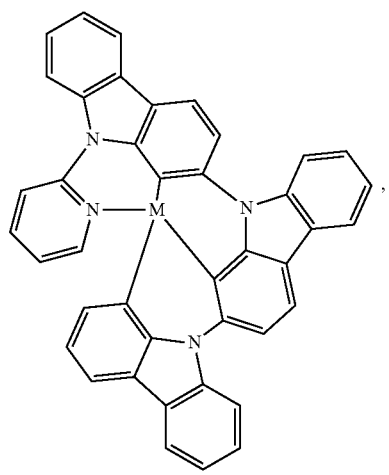
300
-continued
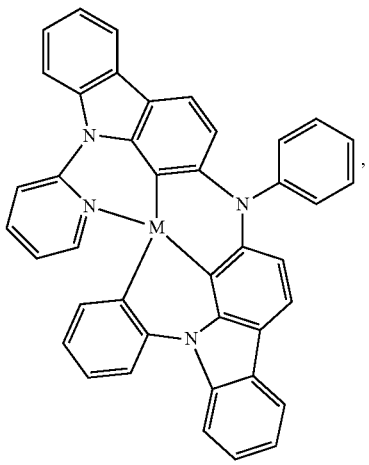
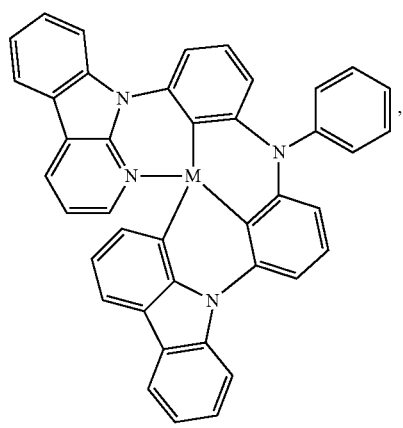
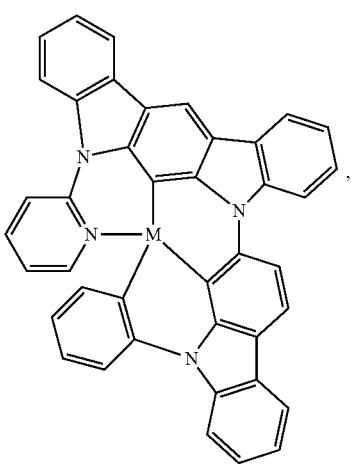

301
-continued
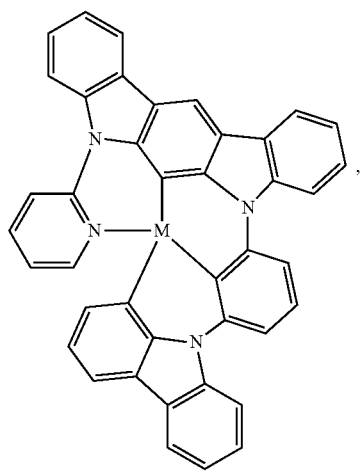
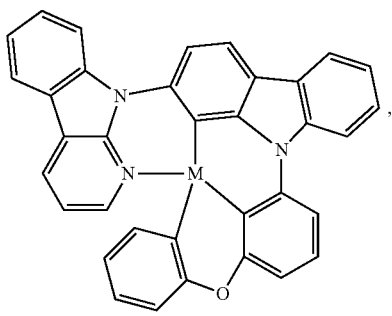
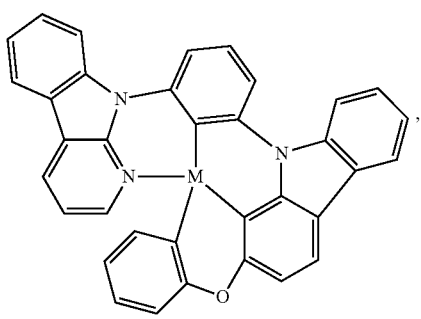
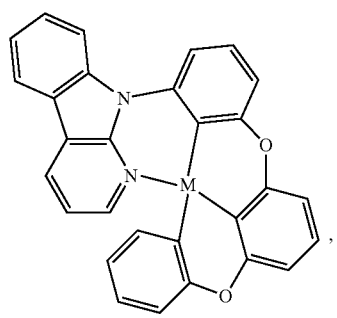
302
-continued
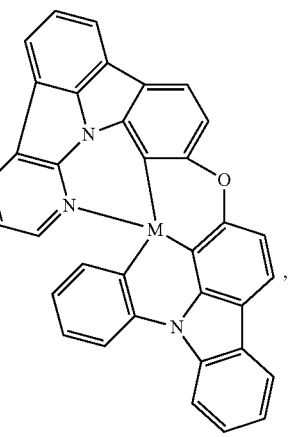
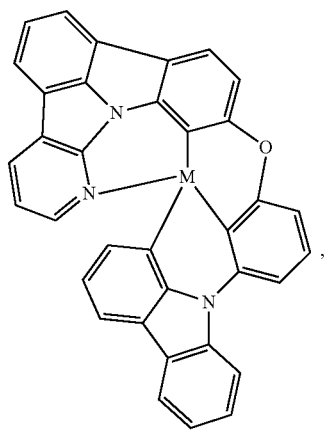
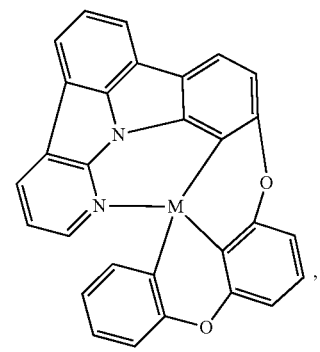
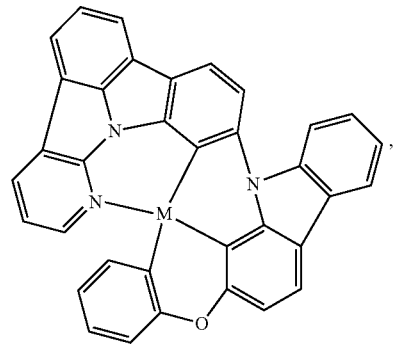

303
-continued
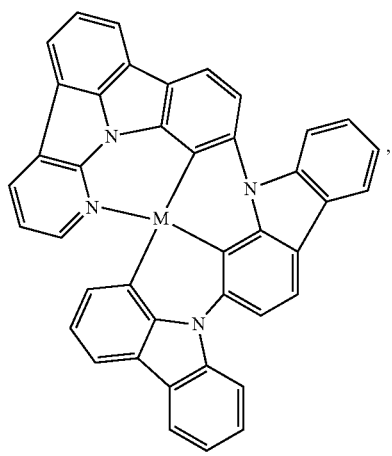
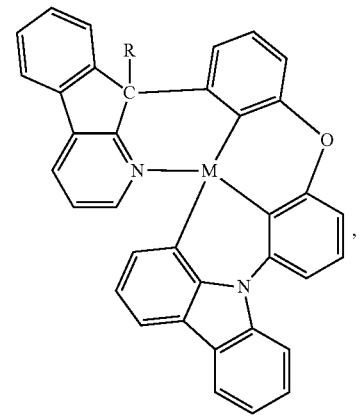
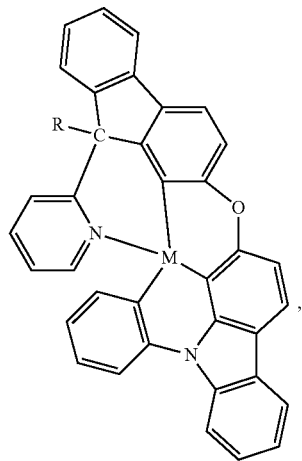
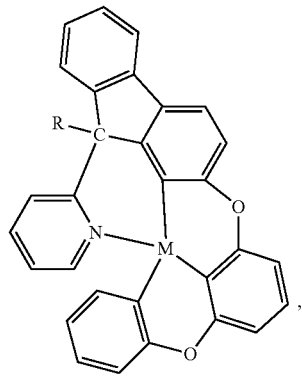
304
-continued
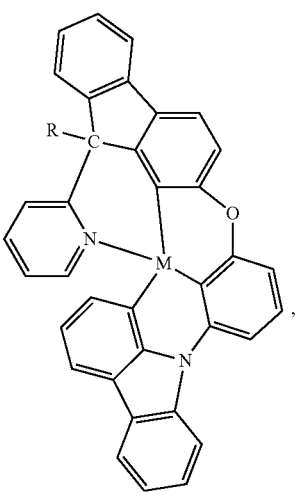
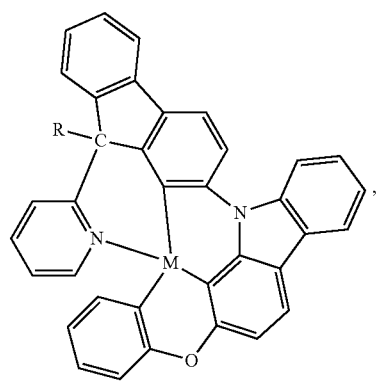
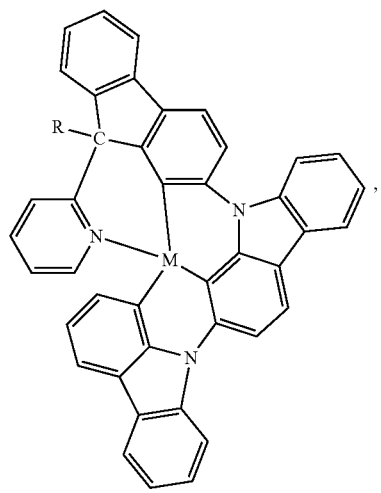
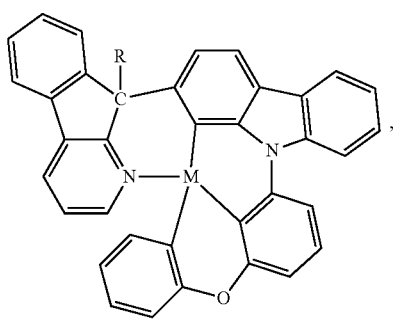

305
-continued

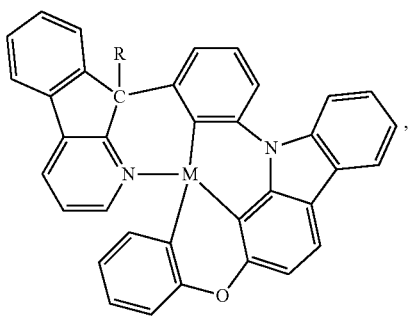,

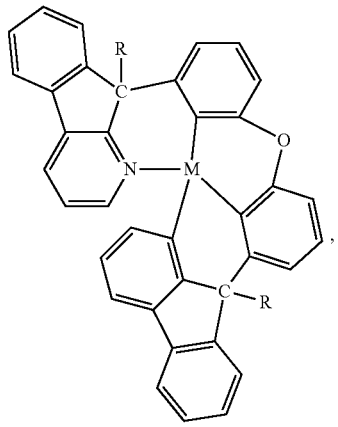,

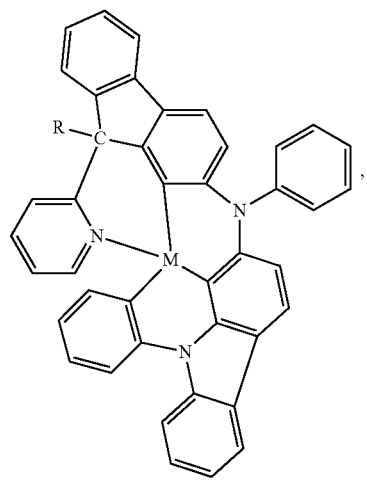,

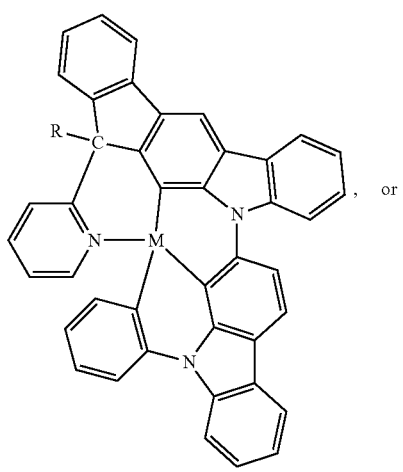, or

306
-continued

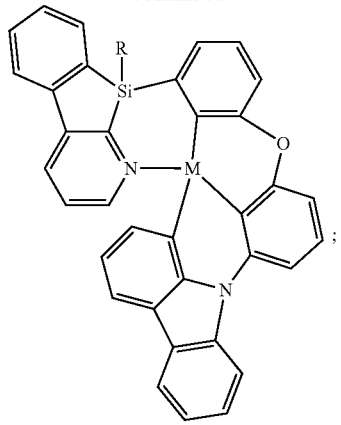;

wherein each R independently is hydrogen, substituted or unsubstituted alkyl, alkenyl, alkynyl, aryl, cycloalkyl, cycloalkenyl, heterocyclyl, deuterium, halogen, hydroxyl, thiol, nitro, cyano, amino, a mono- or di-alkylamino, a mono- or diaryl amino, alkoxy, aryloxy, haloalkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, or substituted silyl.

In one aspect, disclosed herein is a compound having the structure:

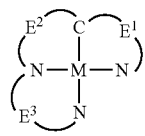

wherein M represent a metal cation with one positive charges, which include, but is not limited to, iridium (I) ($Ir^{1+}$), Rhodium (I) ($Rh^{1+}$), etc., wherein $E^1$, $E^2$, and $E^3$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein C represents a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, M can be Rhodium (I). In one aspect, M can be Iridium (I).

In one aspect, the compound can have the structure:
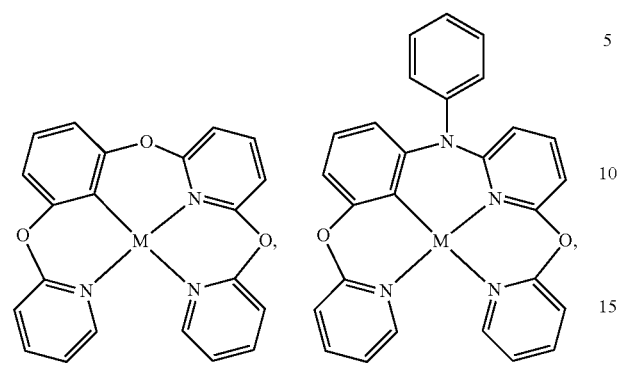
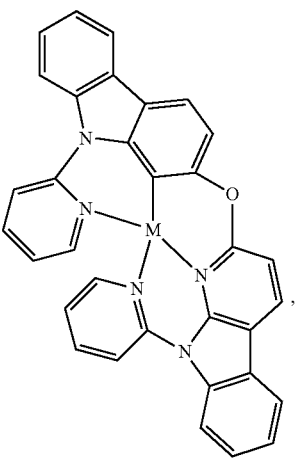
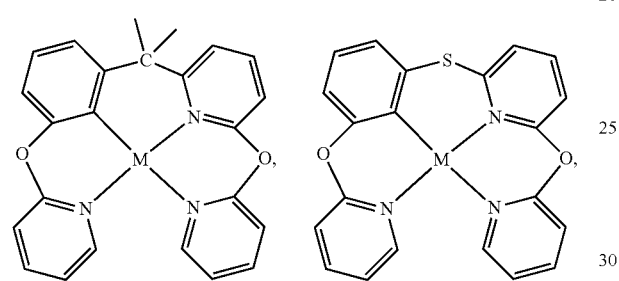
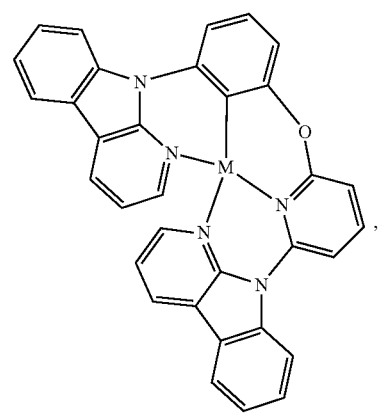
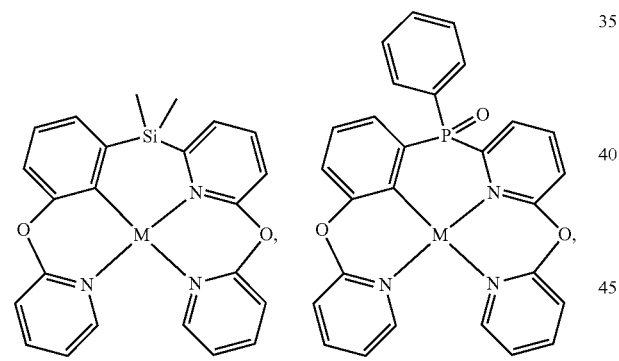
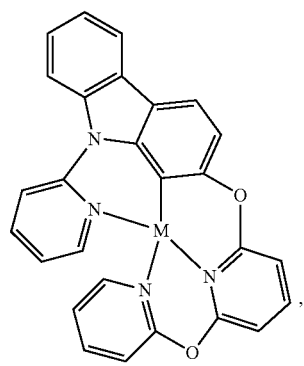
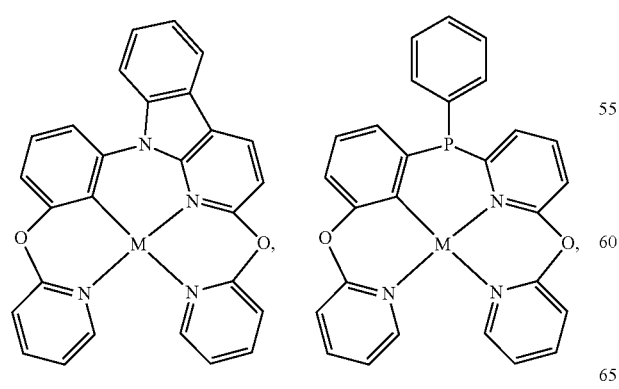
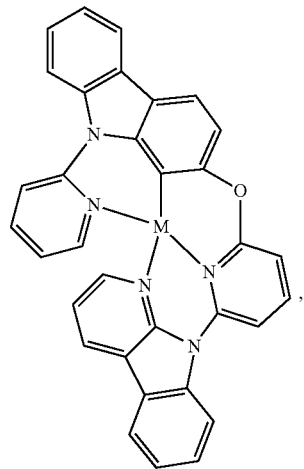

309
-continued
310
-continued
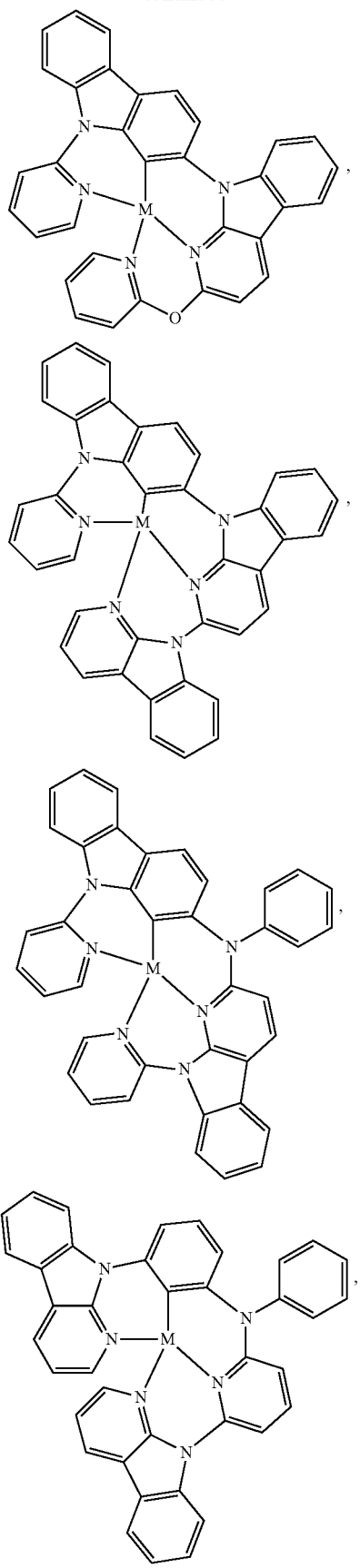
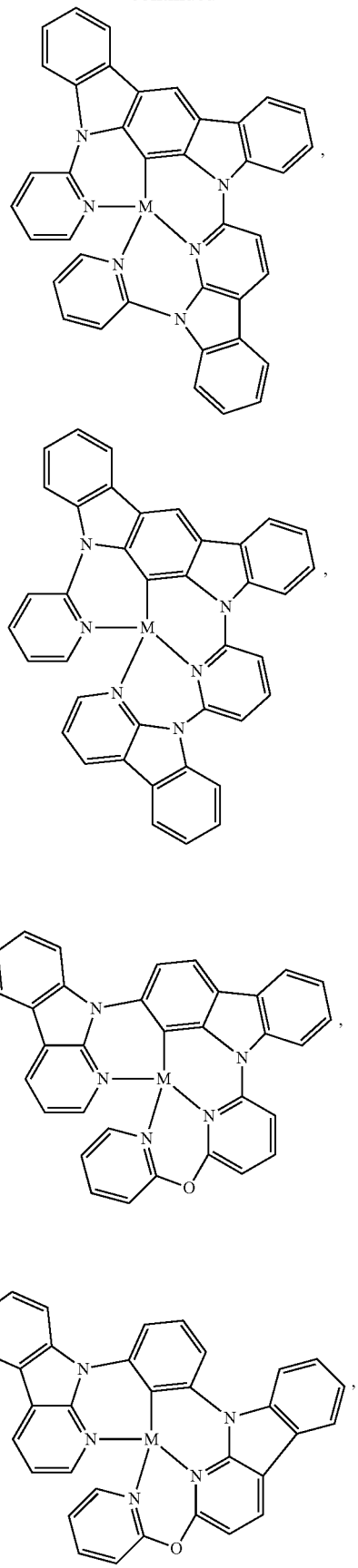

311
-continued
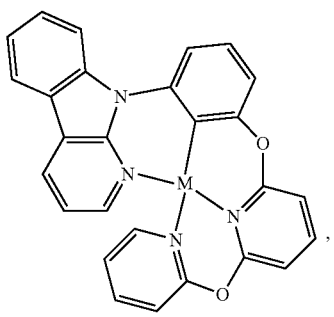
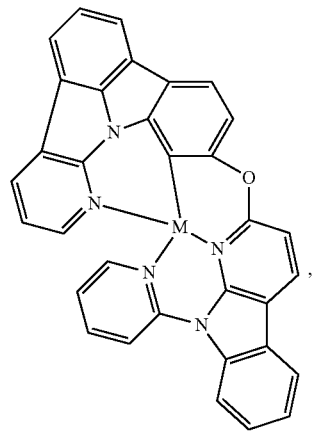
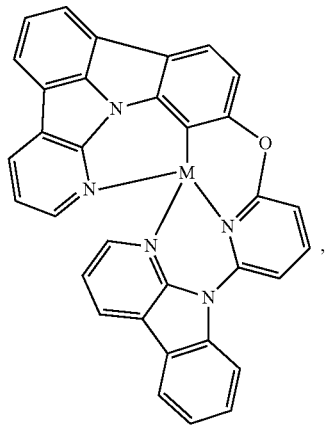
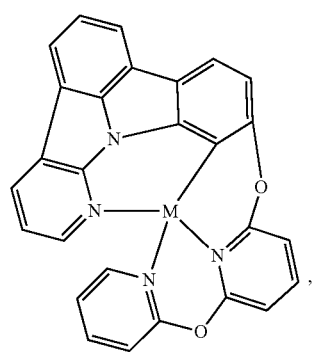
312
-continued
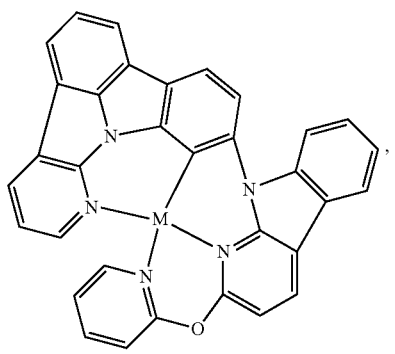
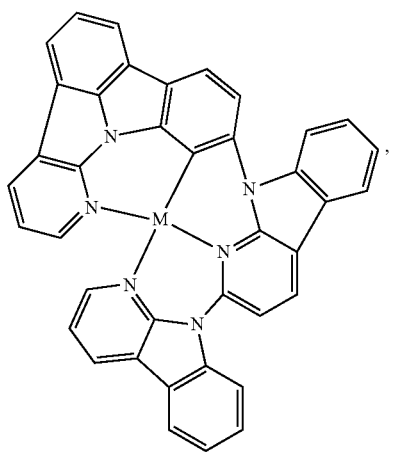
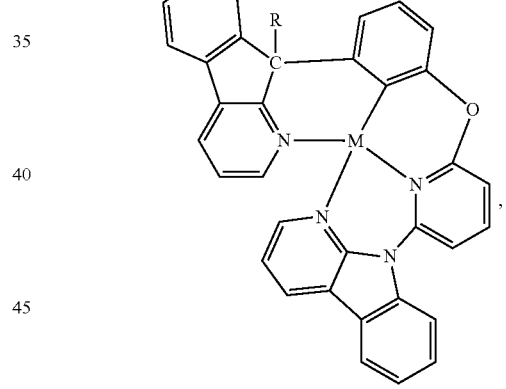
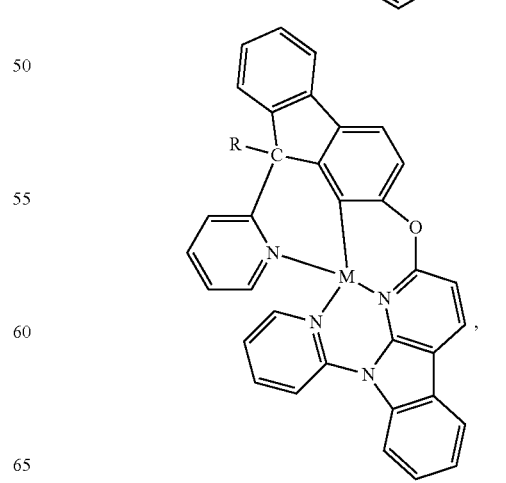

313
-continued
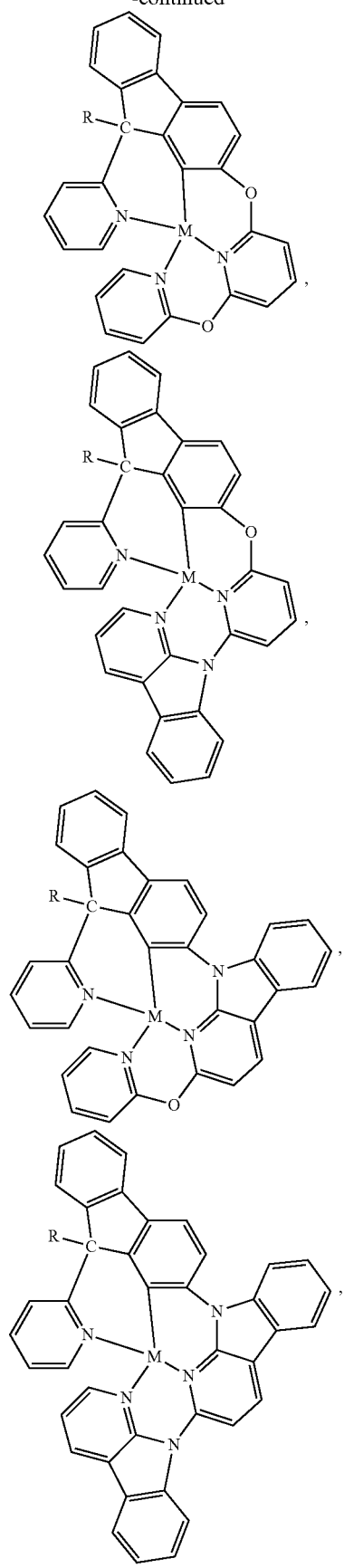
314
-continued
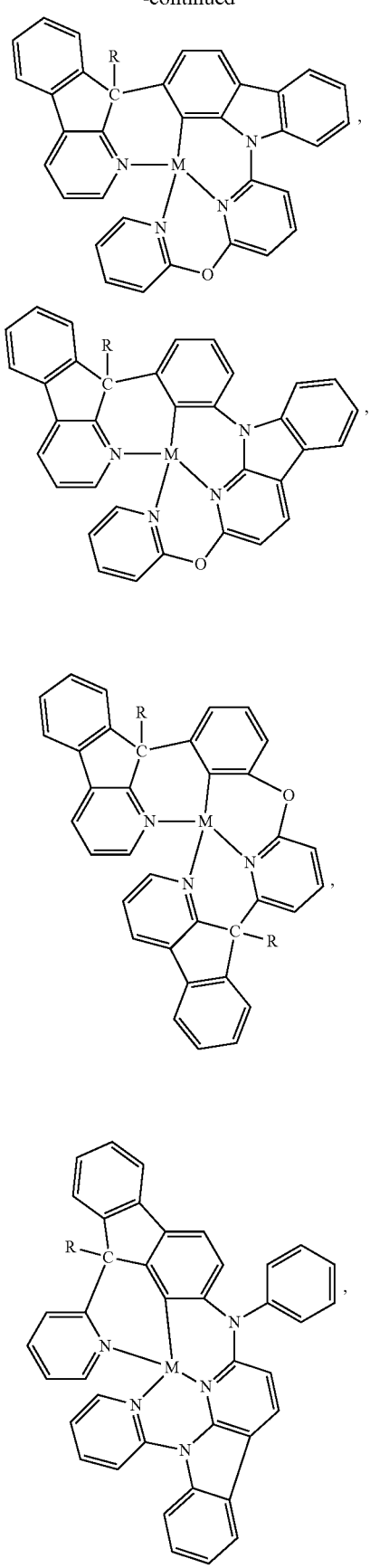

-continued

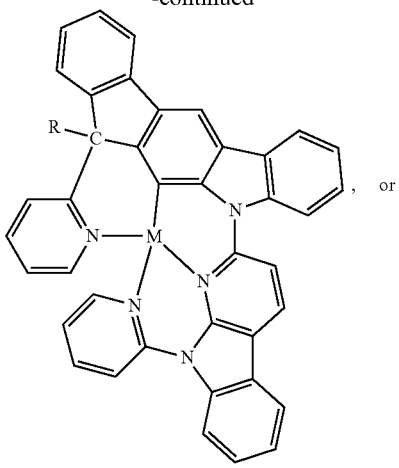, or

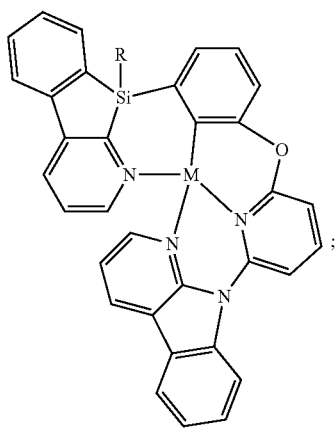;

wherein each R independently is hydrogen, substituted or unsubstituted alkyl, alkenyl, alkynyl, aryl, cycloalkyl, cycloalkenyl, heterocyclyl, deuterium, halogen, hydroxyl, thiol, nitro, cyano, amino, a mono- or di-alkylamino, a mono- or diaryl amino, alkoxy, aryloxy, haloalkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, or substituted silyl.

In one aspect, disclosed herein is a compound having the structure:

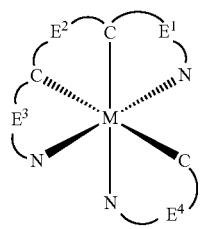

wherein M represent a metal cation with three positive charges, which include, but are not limited to, iridium (III) ($Ir^{3+}$), Rhodium(III) ($Rh^{3+}$), Cobalt (III) ($Co^{3+}$), Aluminum (III) ($Al^{3+}$), and Gallium(III) ($Ga^{3+}$), wherein $E^1$, $E^2$, $E^3$, and $E^4$ independently represent a linking atom, comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, M can be Iridium (III). In one aspect, M can be Rhodium (III). In another aspect, M can be Cobalt (III). In another aspect, M can be Aluminum (III). In another aspect, M can be gallium (III).

In one aspect, the compound can have the structure;

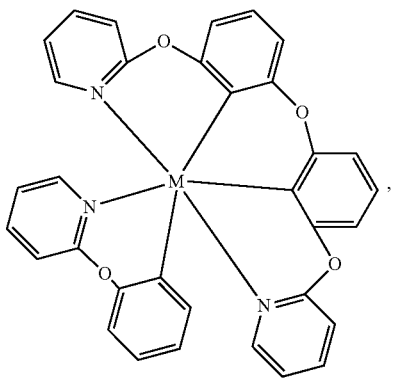,

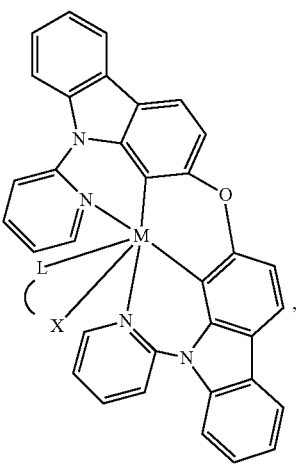,

317
-continued
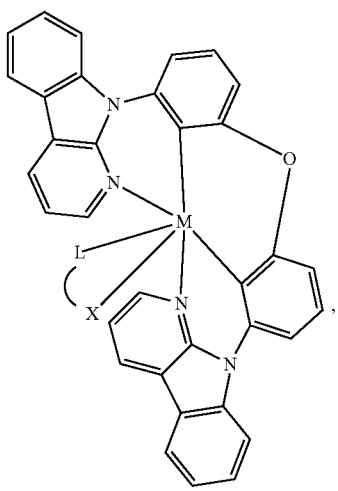
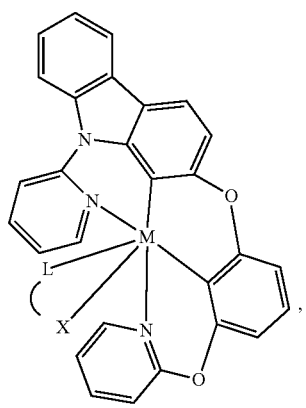
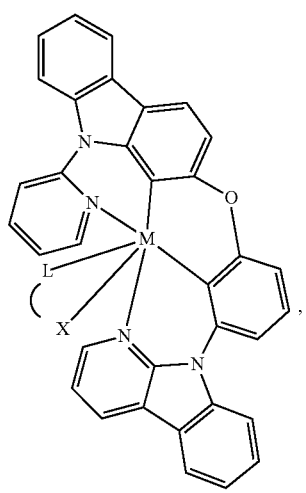
318
-continued
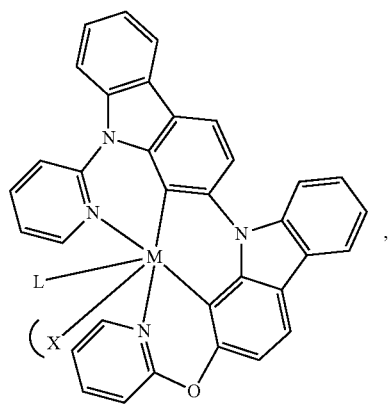
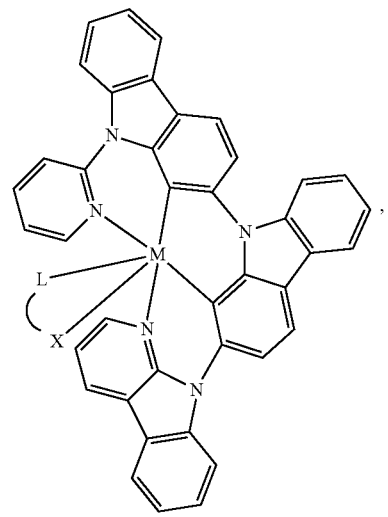
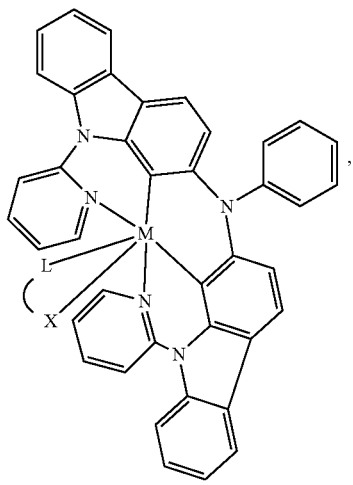

319
-continued
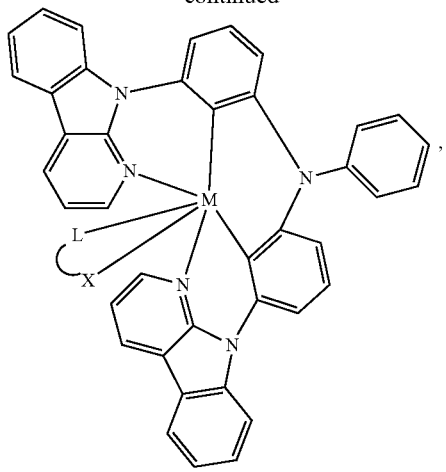
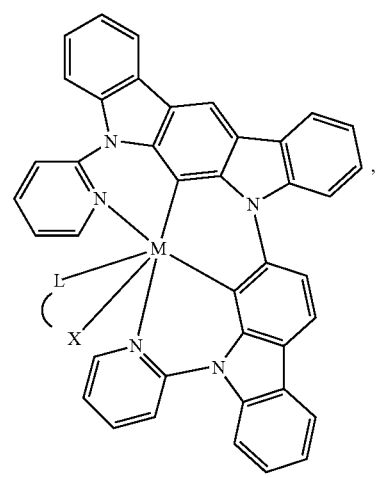
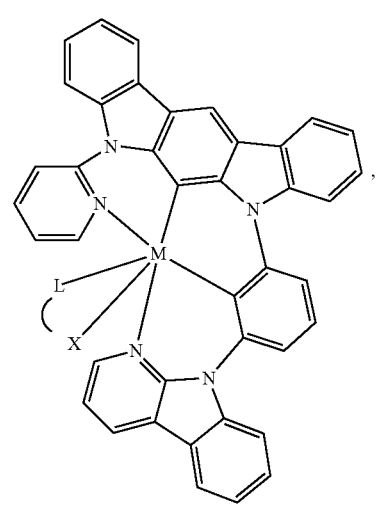
320
-continued
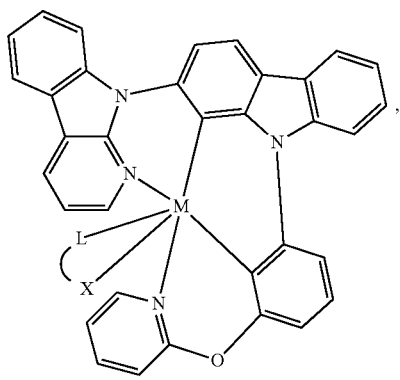
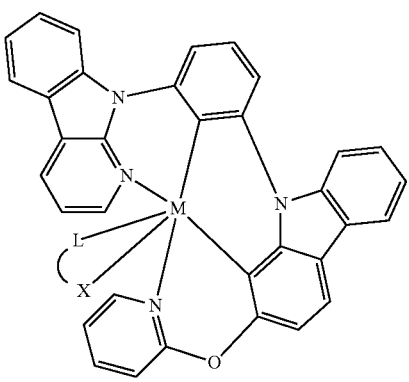
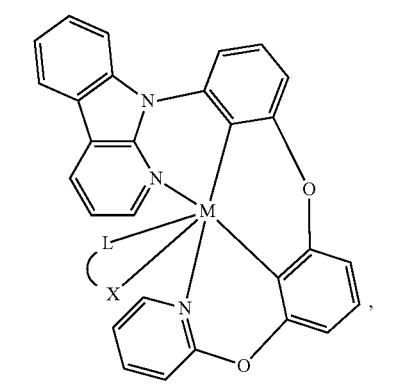
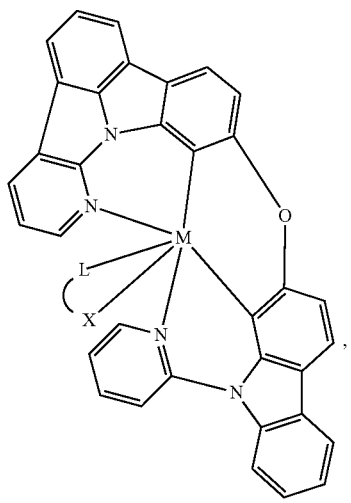

321
-continued
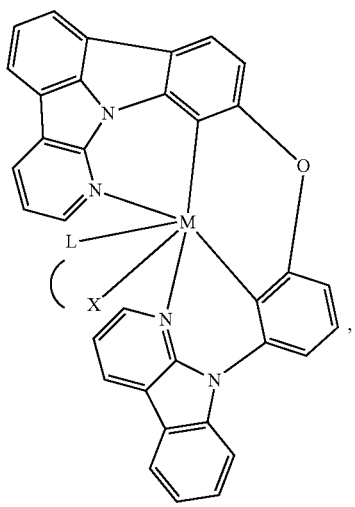
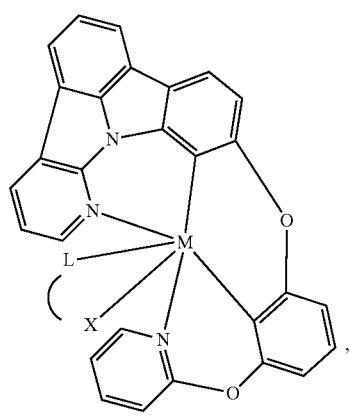
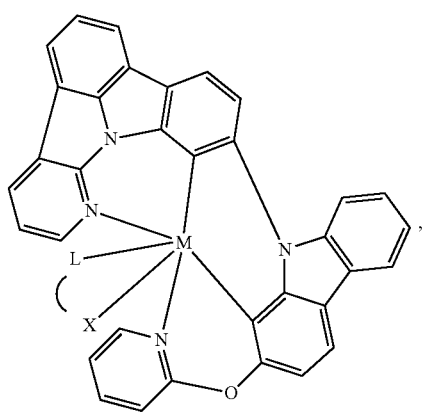
322
-continued
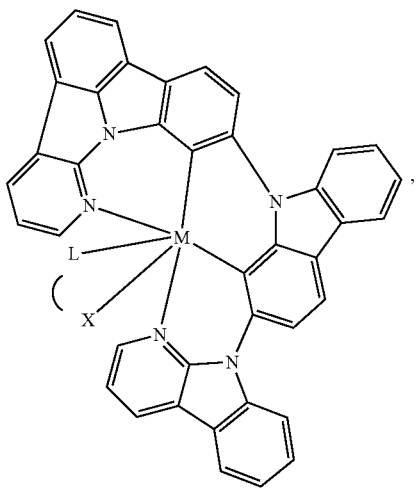
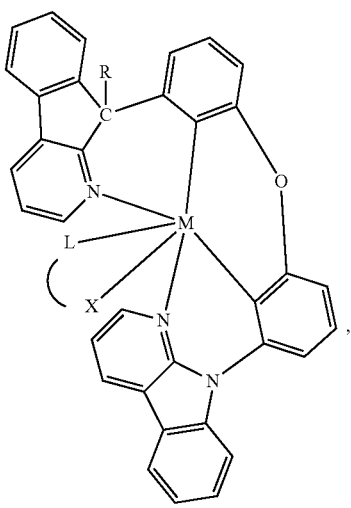
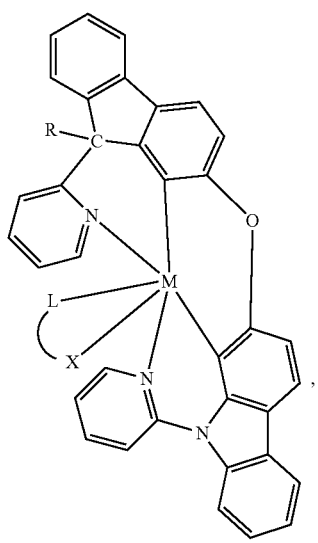

323
-continued
324
-continued
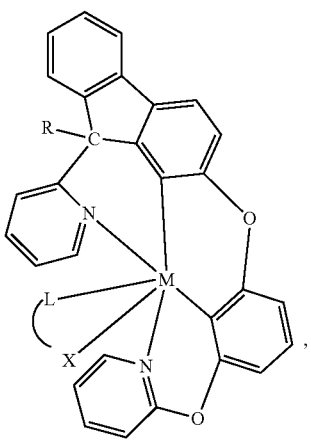
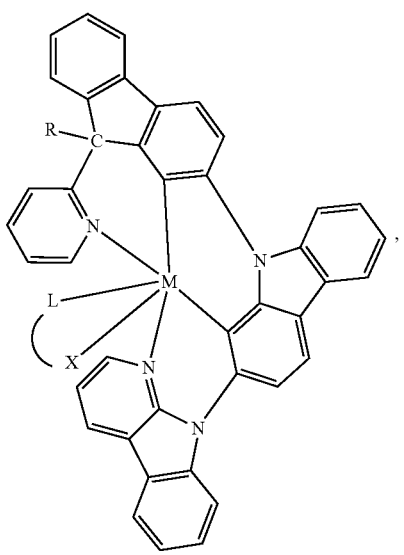
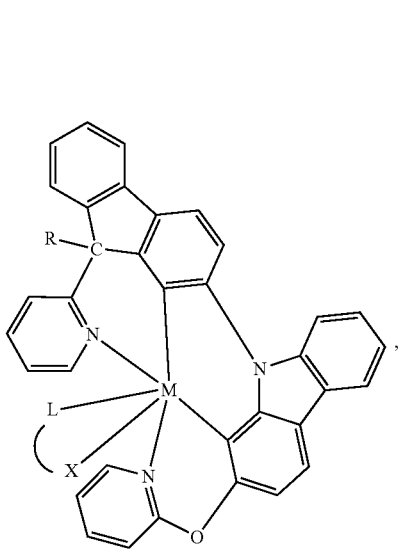
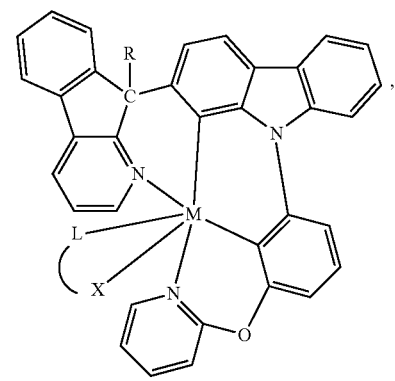
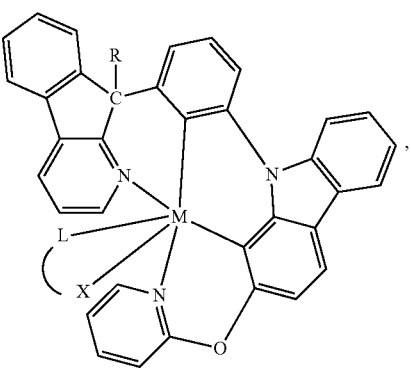

325
-continued

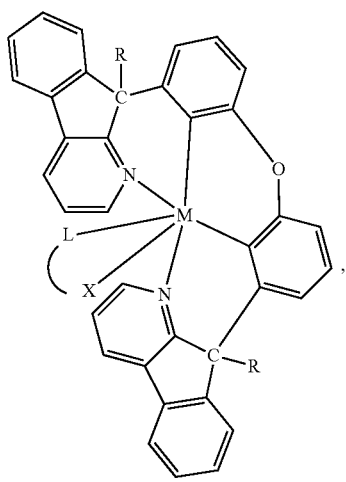

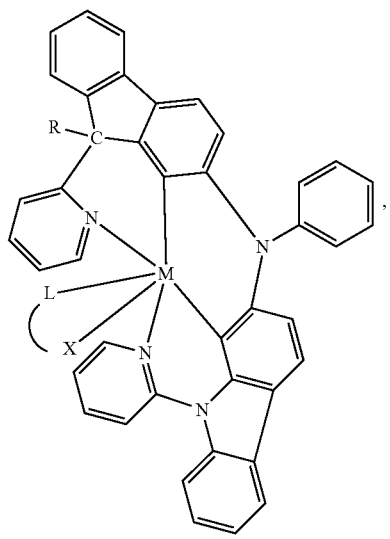
, or

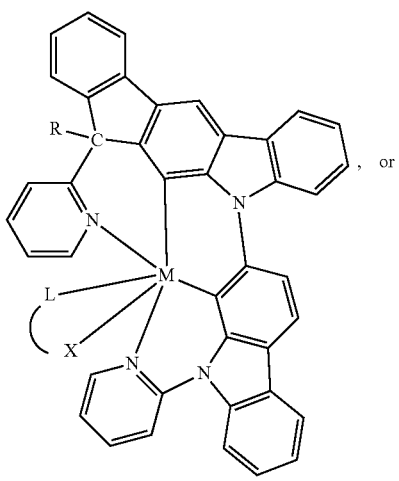

326
-continued

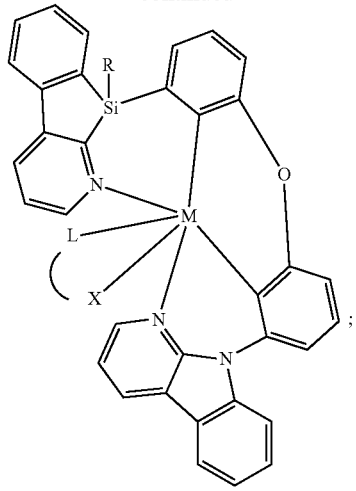
;

wherein each R independently is hydrogen, substituted or unsubstituted alkyl, alkenyl, alkynyl, aryl, cycloalkyl, cycloalkenyl, heterocyclyl, deuterium, halogen, hydroxyl, thiol, nitro, cyano, amino, a mono- or di-alkylamino, a mono- or diaryl amino, alkoxy, aryloxy, haloalkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, or substituted silyl, wherein

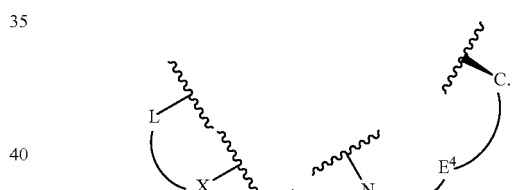

In one aspect, disclosed herein is a compound having the structure:

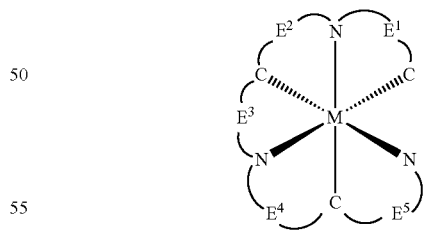

wherein M represent a metal cation with three positive charges, which include, but are not limited to, iridium (III) ($Ir^{3+}$), Rhodium(III) ($Rh^{3+}$), Cobalt (III) ($Co^{3+}$), Aluminum (III) ($Al^{3+}$), Gallium(III) ($Ga^{3+}$), wherein $E^1$, $E^2$, $E^3$, $E^4$, and $E^5$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, M can be Iridium (III). In one aspect, M can be Rhodium (III). In another aspect, M can be Cobalt (III). In another aspect, M can be Aluminum (III). In another aspect, M can be gallium (III).

In one aspect, the compound has the structure:

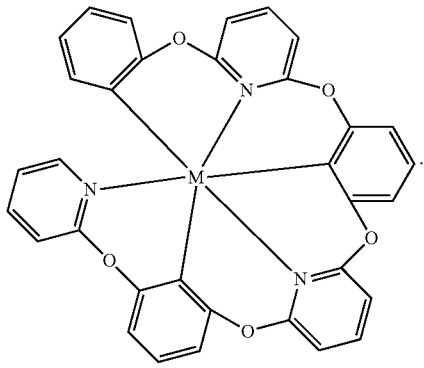

In one aspect, disclosed herein is a compound having the structure:

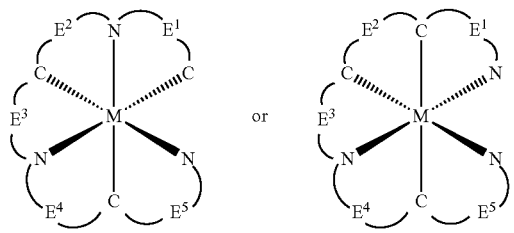

wherein M represent a metal cation with three positive charges, which include, but are not limited to, iridium (III) ($Ir^{3+}$), Rhodium(III) ($Rh^{3+}$), Cobalt (III) ($Co^{3+}$), Aluminum (III) ($Al^{3+}$), Gallium(III) ($Ga^{3+}$), wherein $E^1$, $E^2$, $E^3$, $E^4$, and $E^5$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, M can be Iridium (III). In one aspect, M can be Rhodium (III). In another aspect, M can be Cobalt (III). In another aspect, M can be Aluminum (III). In another aspect, M can be gallium (III).

In one aspect, the compound has the structure:

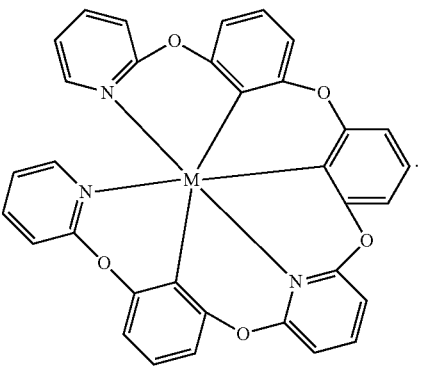

In one aspect, disclosed herein is a compound having the structure:

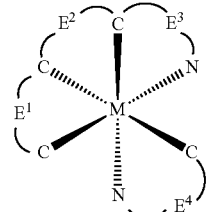

wherein M represent a metal cation with four positive charges, which include, but are not limited to, Palladium(IV) ($Pd^{4+}$), Platinum(IV) ($Pt^{4+}$), wherein $E^1$, $E^2$, $E^3$, and $E^4$, independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, M can be Platinum (VI). In one aspect, M can be Palladium (VI).

In one aspect, the compound can have the structure:
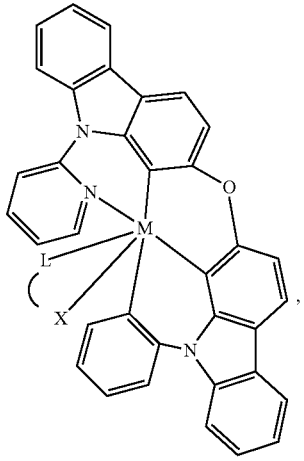
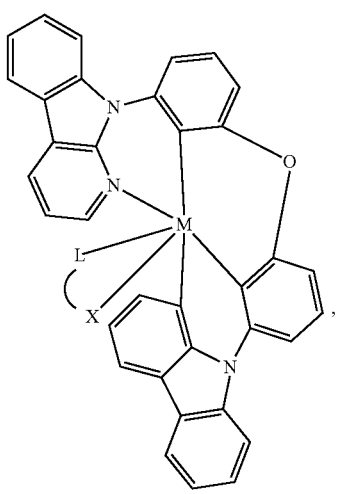
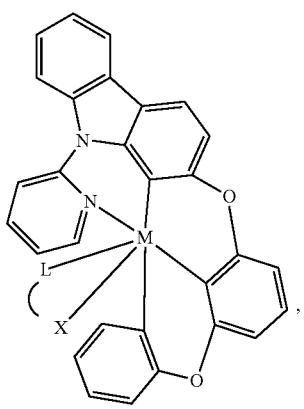
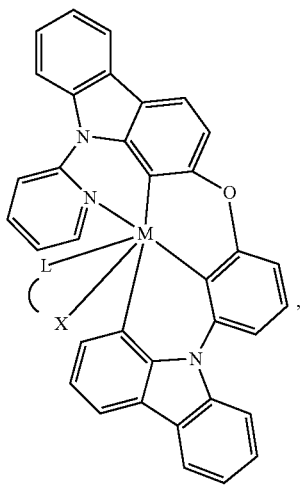
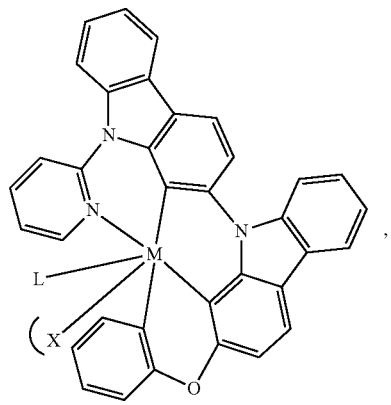
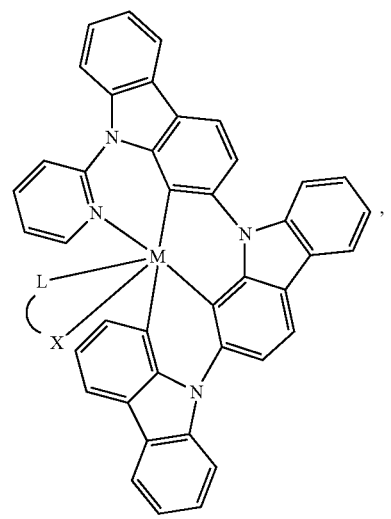

331
-continued
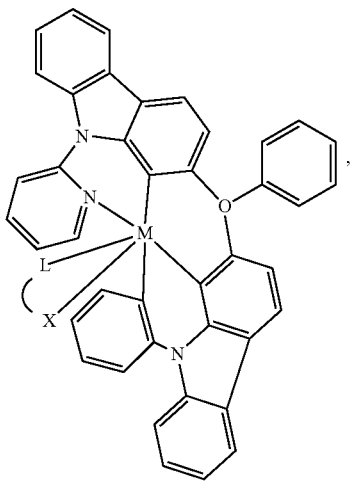
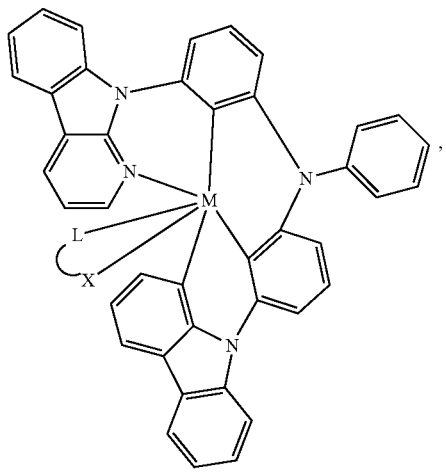
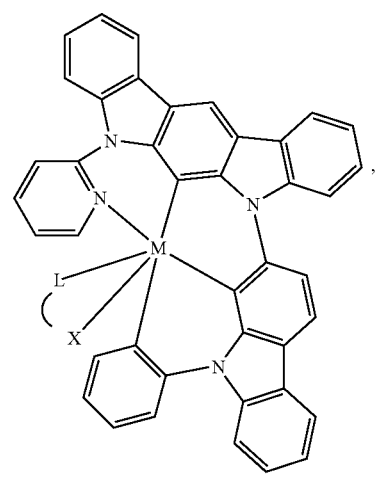
332
-continued
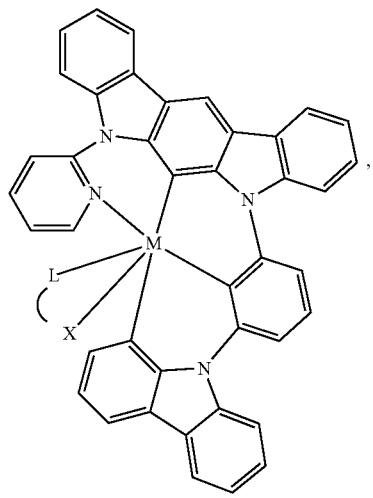
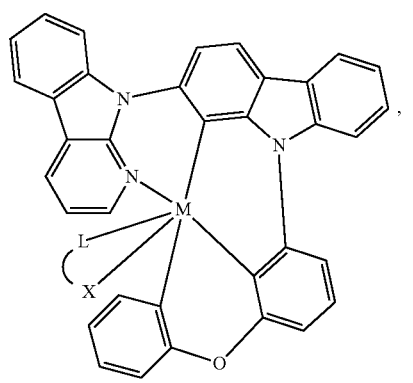
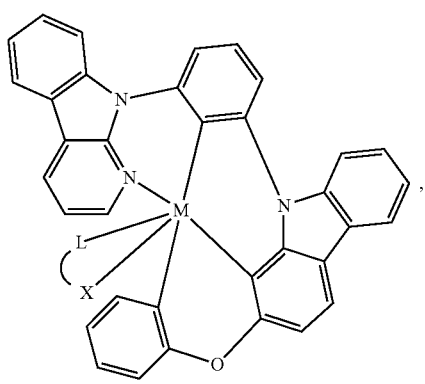
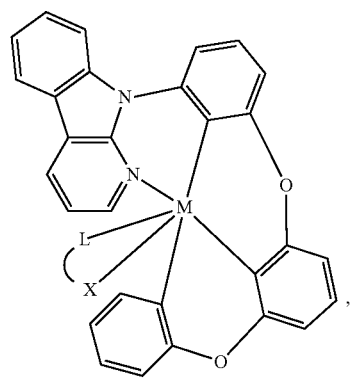

333
-continued
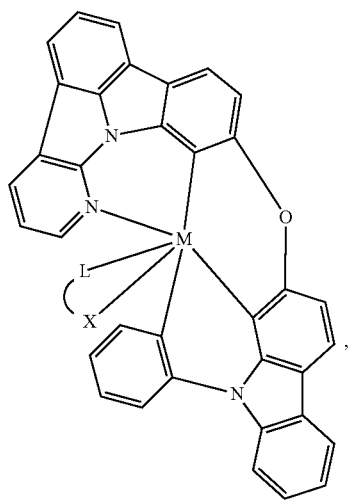
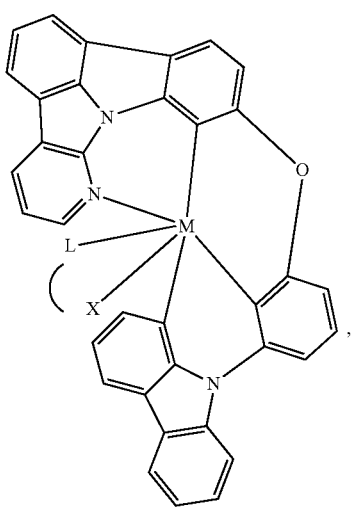
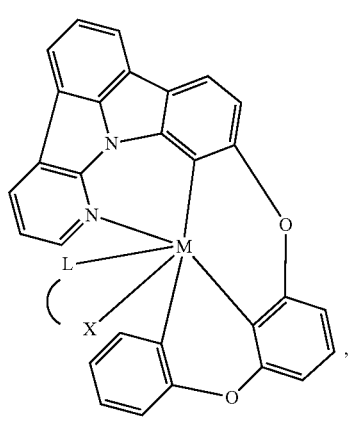
334
-continued
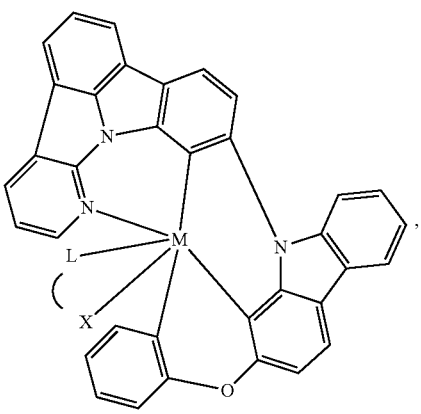
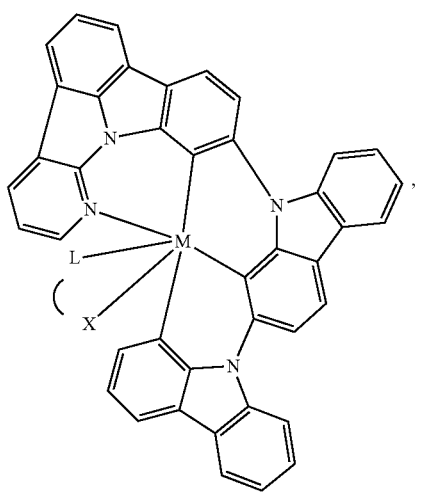
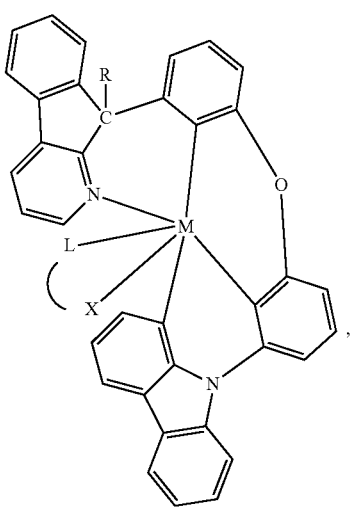

335
-continued
336
-continued
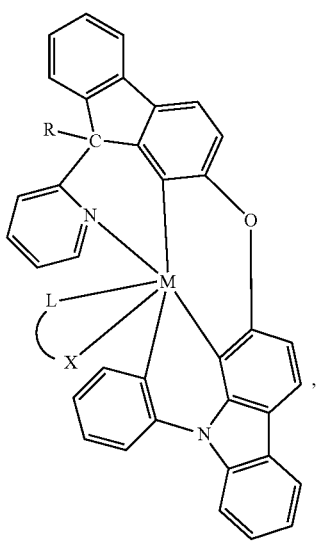
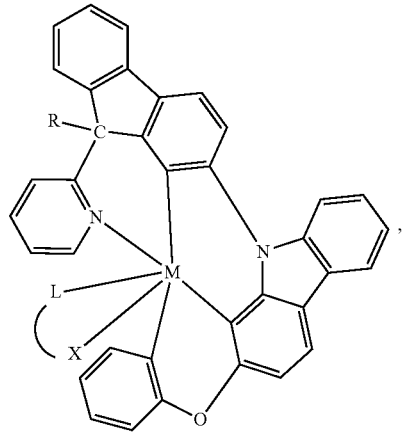
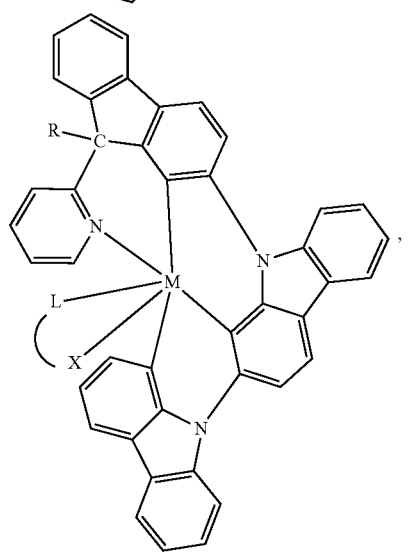
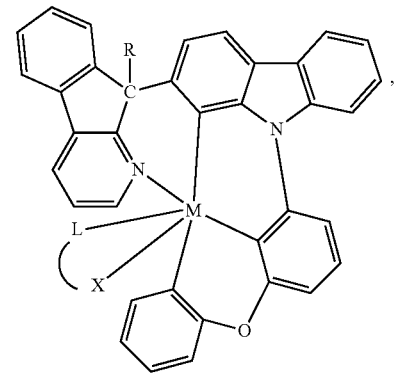
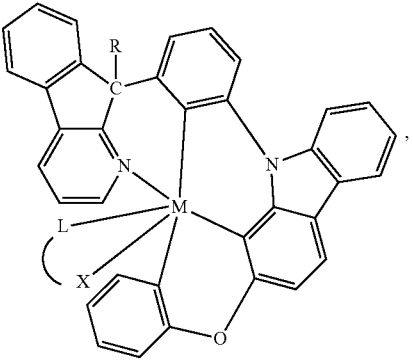

337
-continued

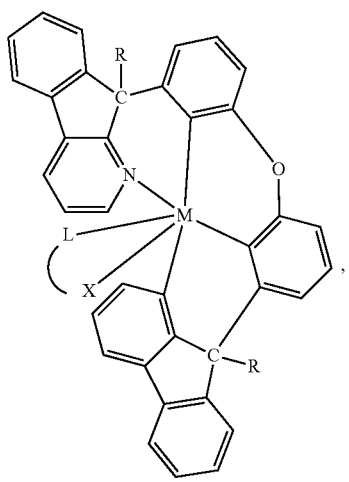

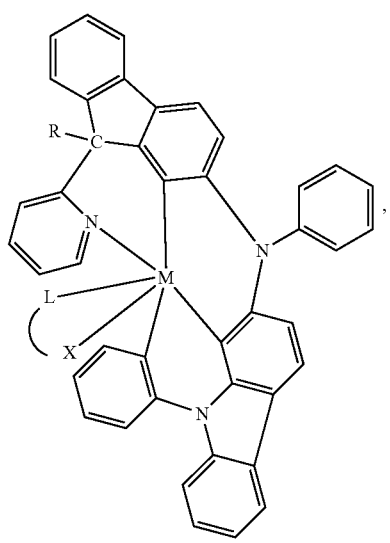

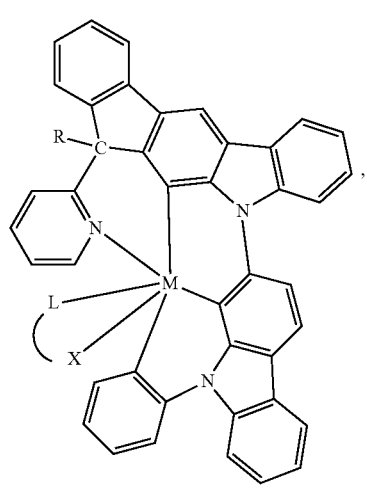

338
-continued

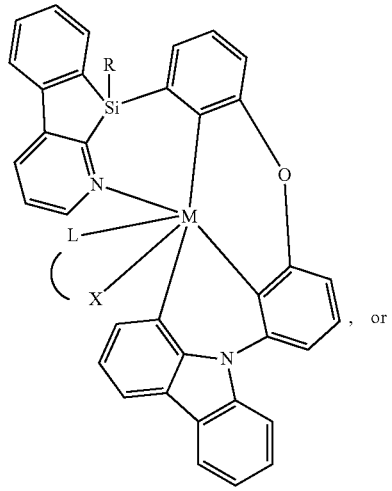

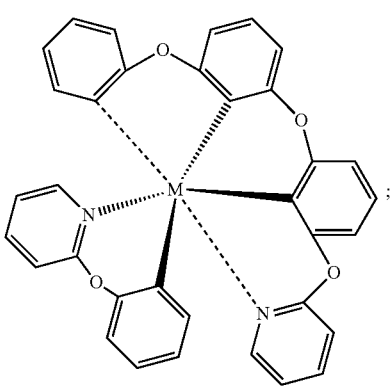

wherein each R independently is hydrogen, substituted or unsubstituted alkyl, alkenyl, alkynyl, aryl, cycloalkyl, cycloalkenyl, heterocyclyl, deuterium, halogen, hydroxyl, thiol, nitro, cyano, amino, a mono- or di-alkylamino, a mono- or diaryl amino, alkoxy, aryloxy, haloalkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, or substituted silyl, wherein

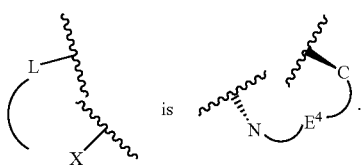

In one aspect, disclosed herein is a compound having the structure:

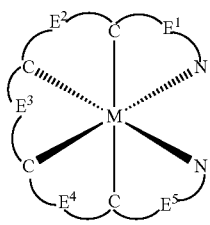

where M represent a metal cation with four positive charges, which include, but are not limited to, Palladium(IV) (Pd$^{4+}$), Platinum(IV) (Pt$^{4+}$), wherein $E^1$, $E^2$, $E^3$, $E^4$, and $E^5$ independently represent a linking atom comprising O, NR$^2$, CR$^2$R$^3$, S, BR$^2$, PR$^2$, P(O)R$^2$, or SiR$^2$R$^3$, or a combination thereof, wherein each of R$^2$ and R$^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or R$^2$ and R$^3$ together form C=O, wherein each of R$^2$ and R$^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, M can be Platinum (VI). In one aspect, M can be Palladium (VI).

In one aspect, the compound can have the structure:

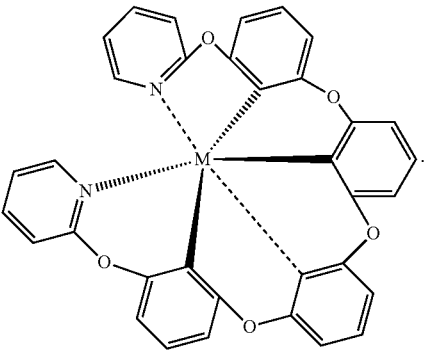

In one aspect, disclosed herein is a compound having the structure:

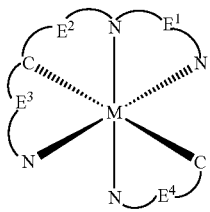

wherein M represent a metal cation with three positive charges, which include, but are not limited to, iridium (III) (Ir$^{3+}$), Rhodium(III) (Rh$^{3+}$), Cobalt (III) (Co$^{3+}$), Aluminum (III) (Al$^{3+}$), Gallium(III) (Ga$^{3+}$), wherein $E^1$, $E^2$, $E^3$, and $E^4$, independently represent a linking atom comprising O, NR$^2$, CR$^2$R$^3$, S, BR$^2$, PR$^2$, P(O)R$^2$, or SiR$^2$R$^3$, or a combination thereof, wherein each of R$^2$ and R$^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or R$^2$ and R$^3$ together form C=O, wherein each of R$^2$ and R$^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, the C groups can be phenyl. In another aspect, the N groups can be pyridine.

In one aspect, $E^1$, $E^2$, $E^3$, and $E^4$ can be oxygen.

In one aspect, M can be Iridium (III). In one aspect, M can be Rhodium (III). In another aspect, M can be Cobalt (III). In another aspect, M can be Aluminum (III). In another aspect, M can be gallium (III).

In one aspect, the compound has the structure:

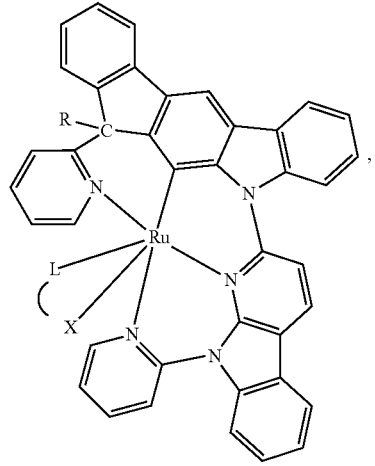

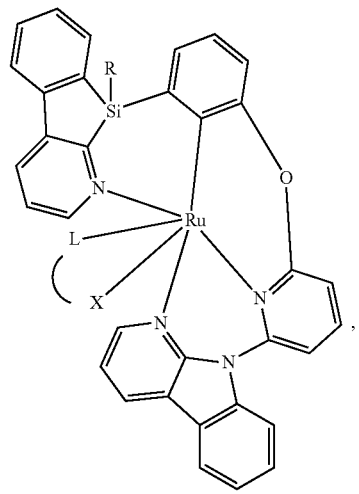

341
-continued
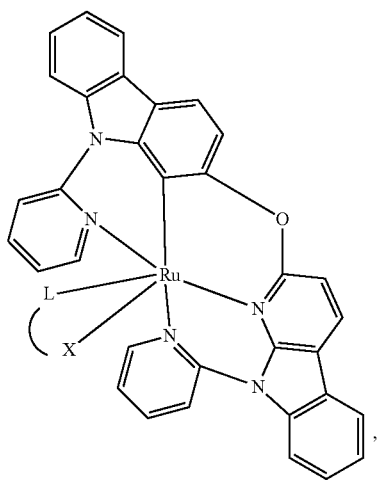
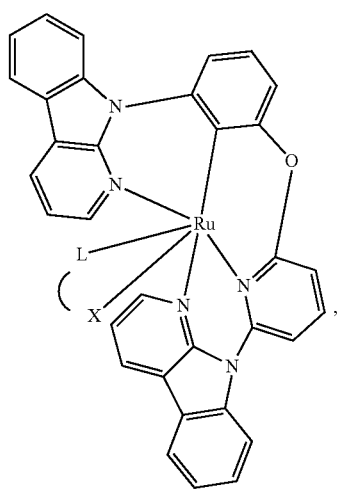
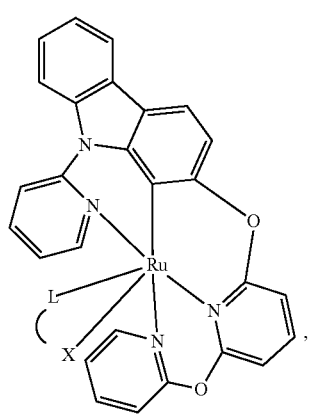
342
-continued
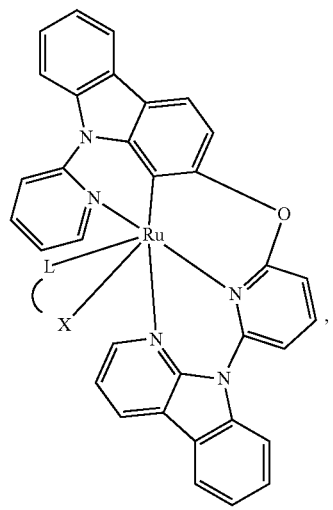
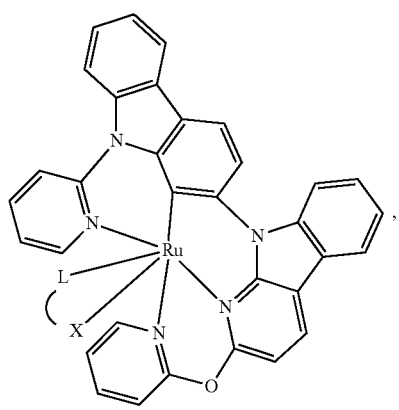
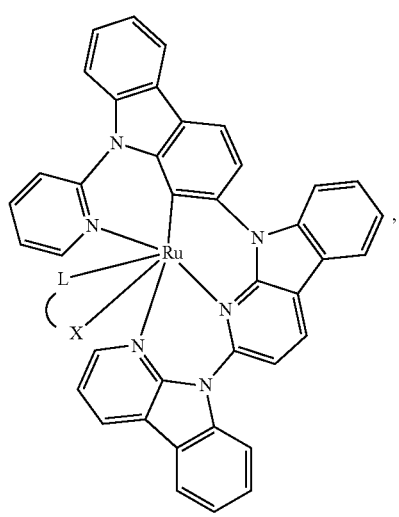

343
-continued
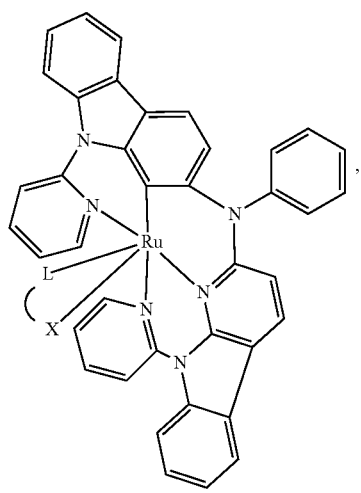
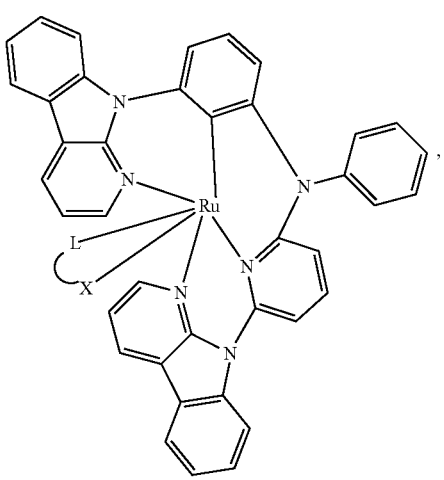
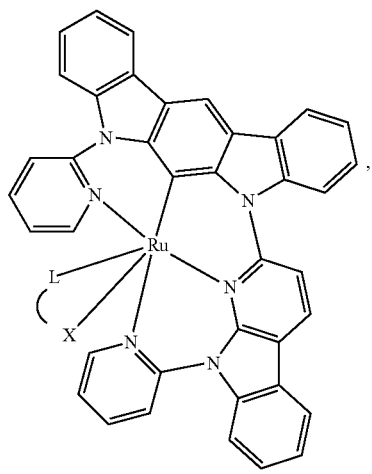
344
-continued
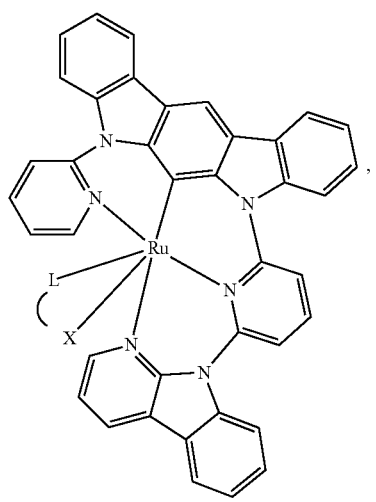
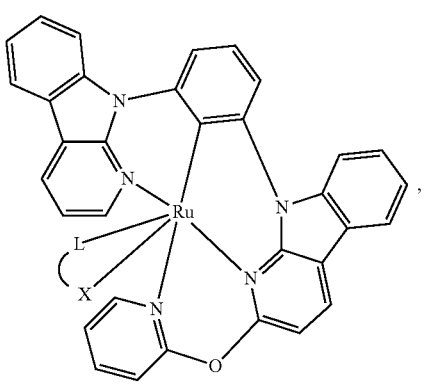
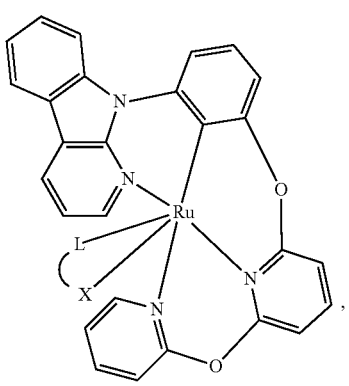

345
-continued
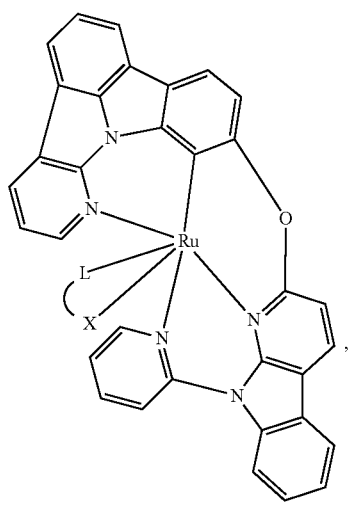
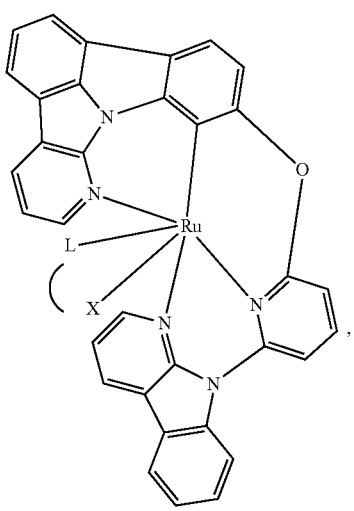
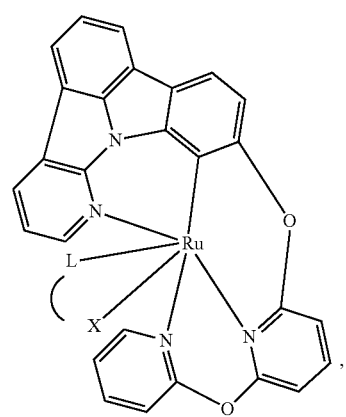
346
-continued
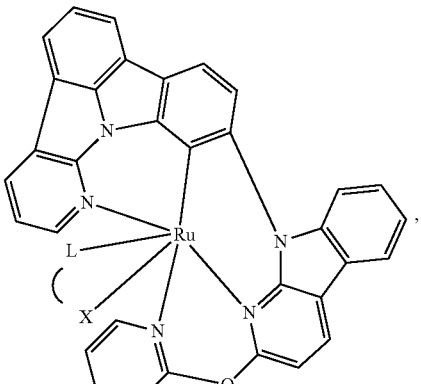
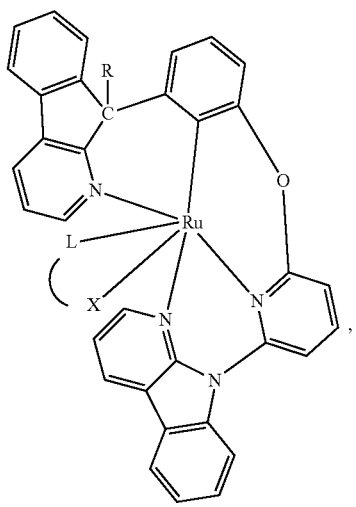
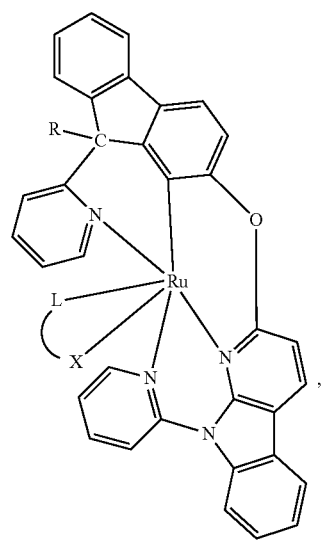

347
-continued
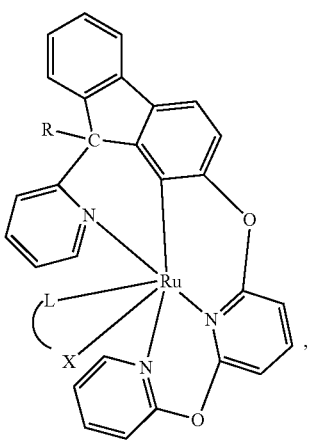
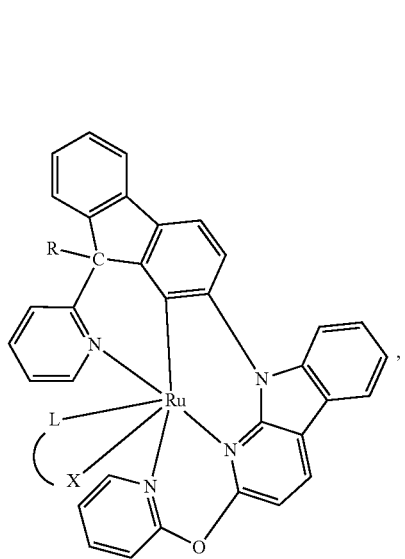
348
-continued
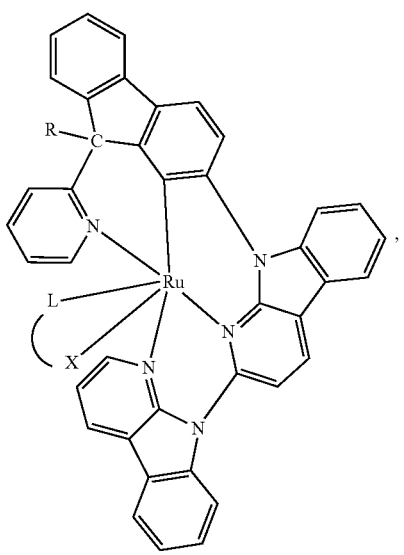
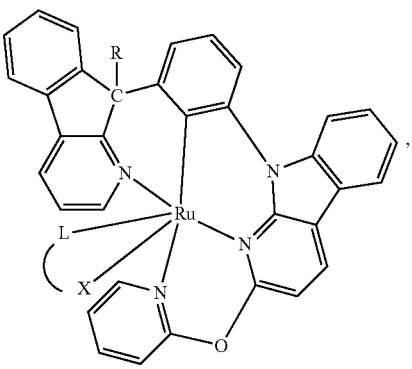
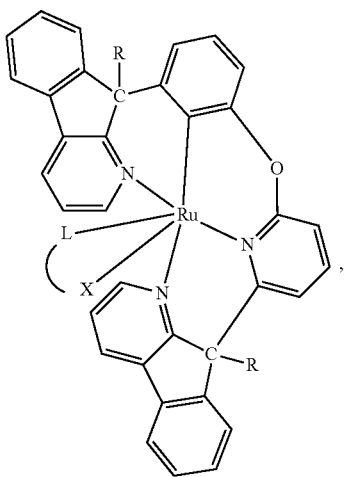

349
-continued
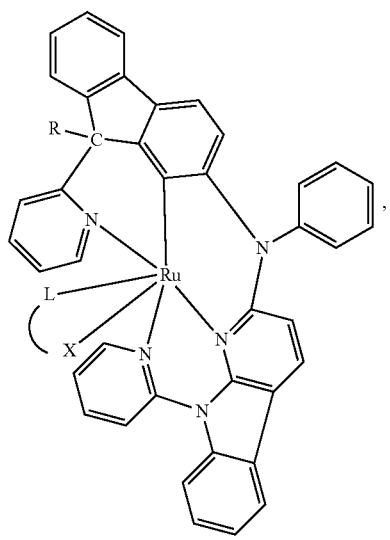
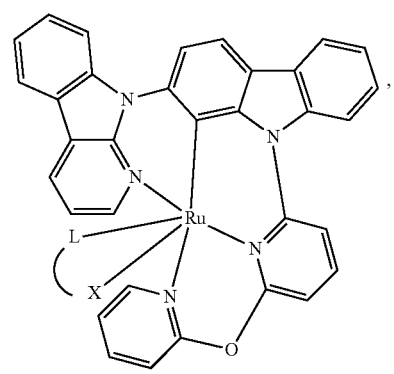
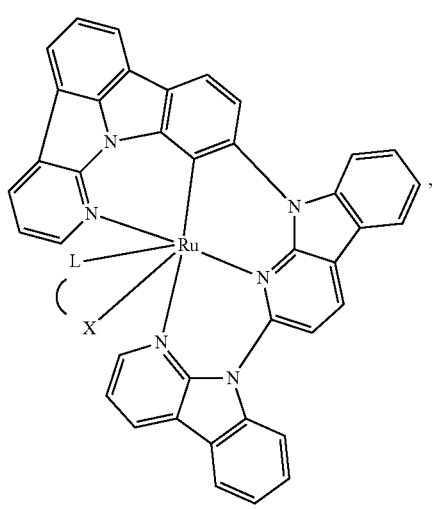
350
-continued
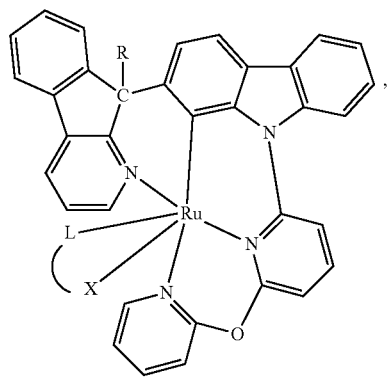
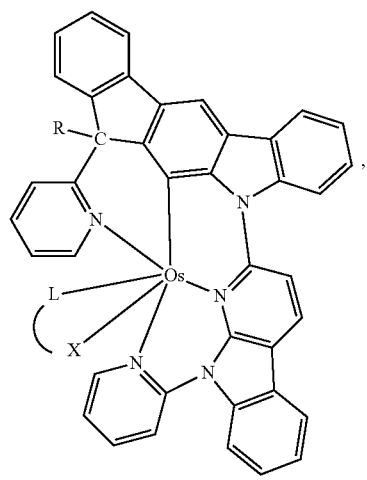
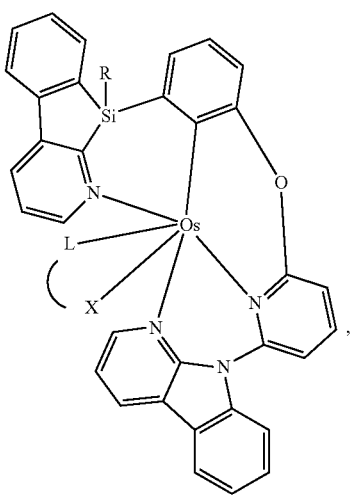

351
-continued
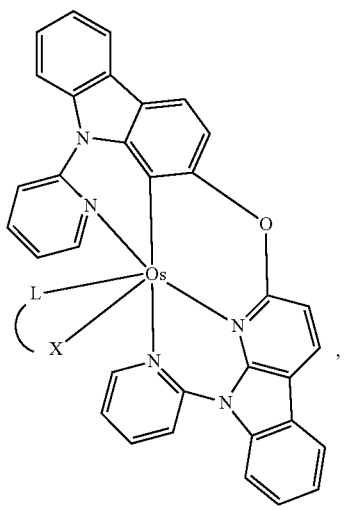
,
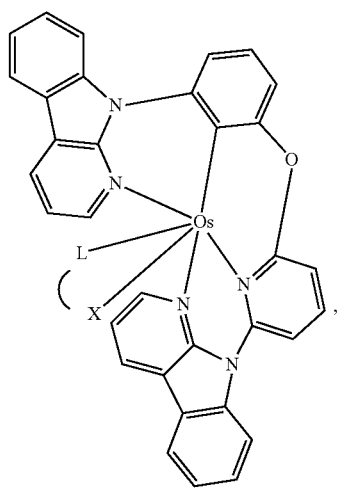
,
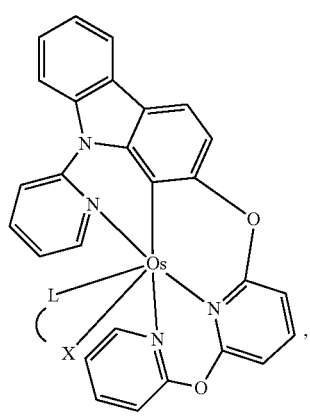
,
352
-continued
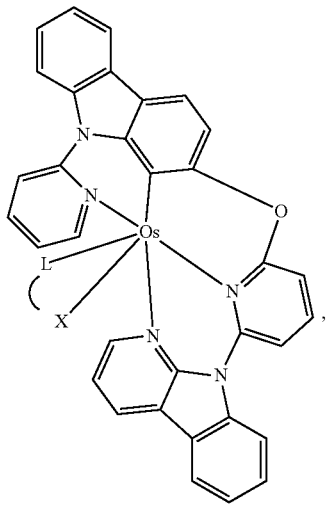
,
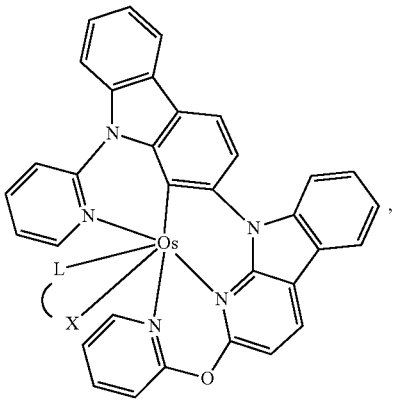
,
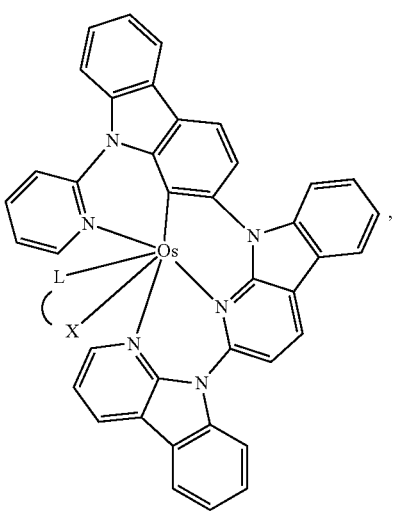
, 353
-continued
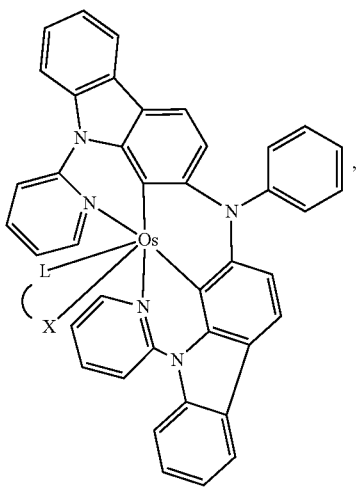
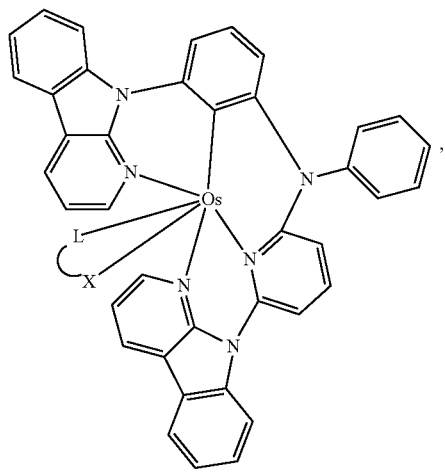
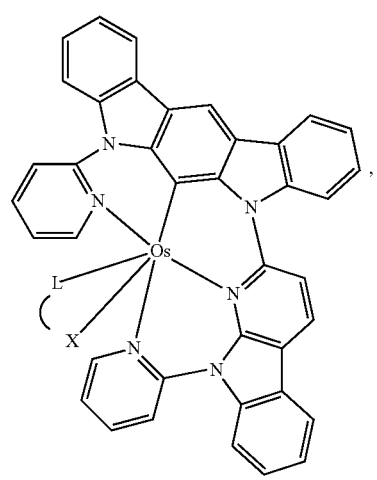
354
-continued
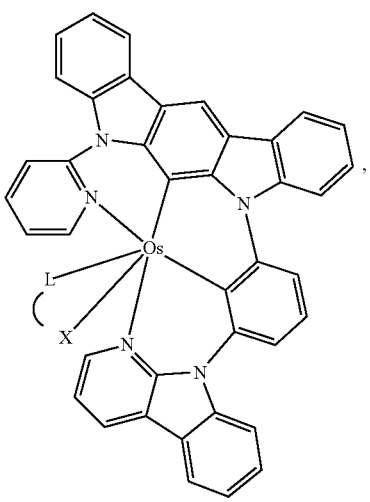
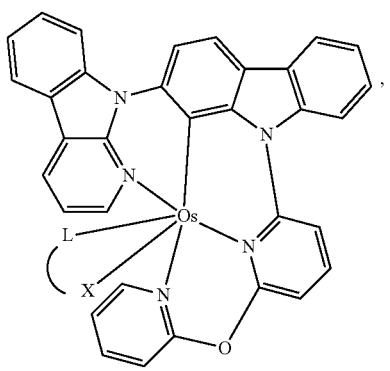
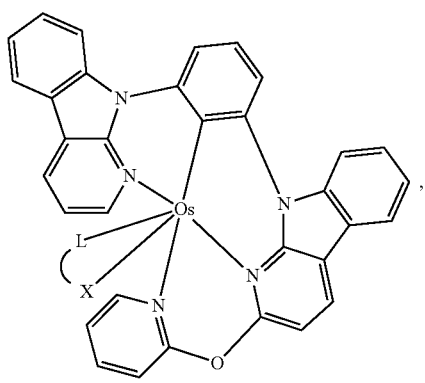
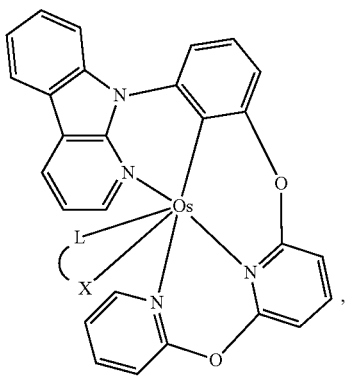

355
-continued
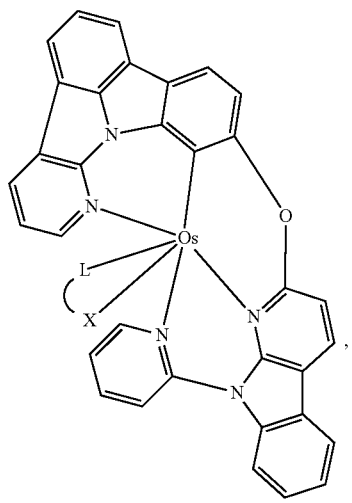
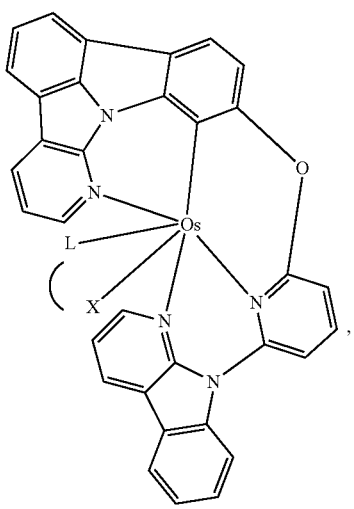
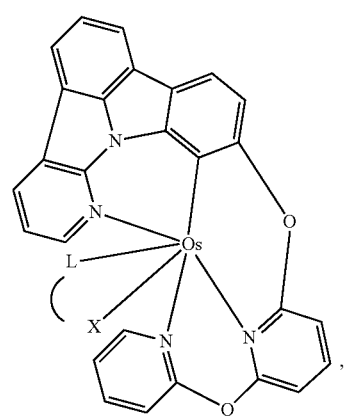
356
-continued
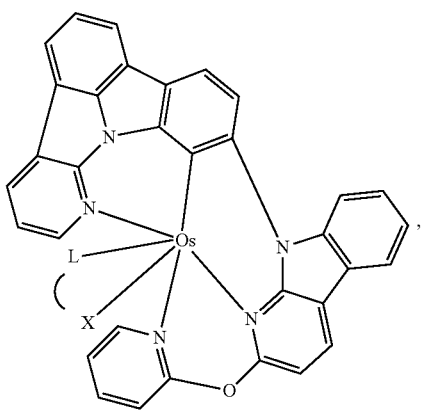
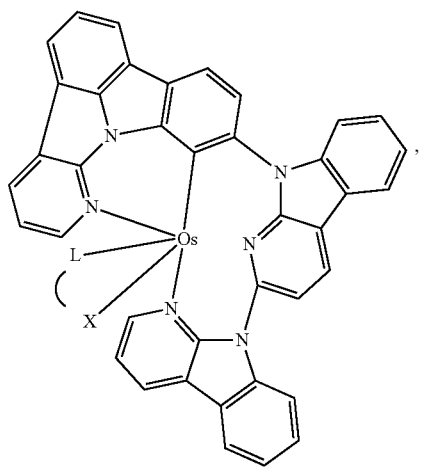
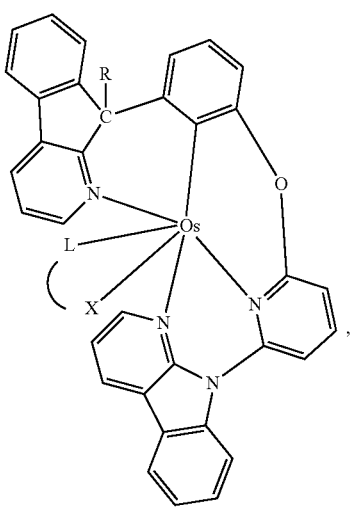

357
-continued
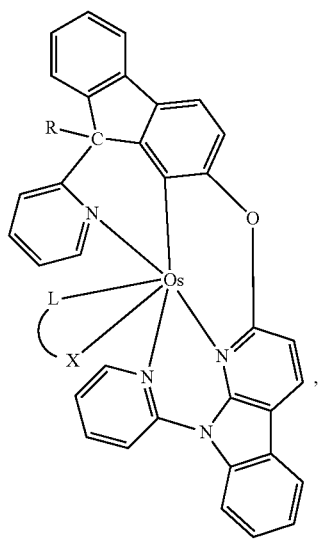
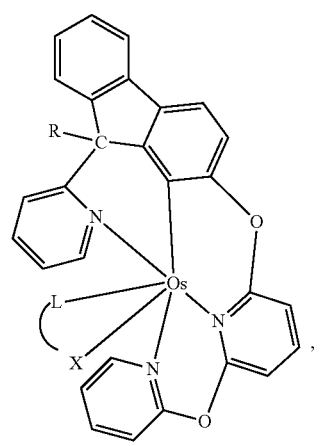
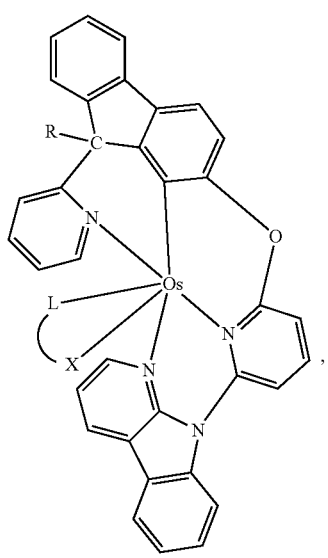
358
-continued
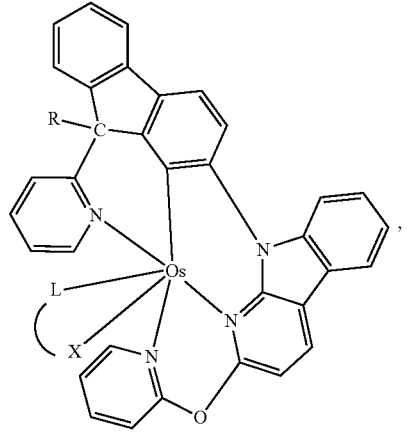
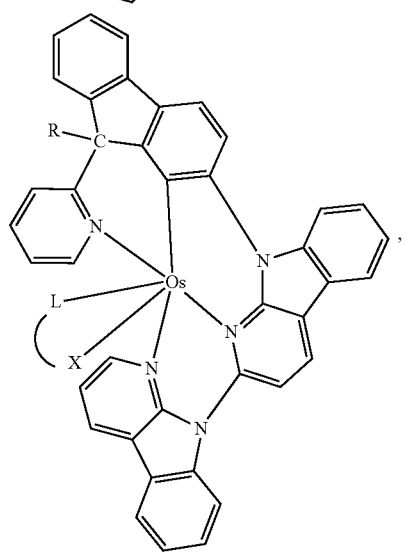
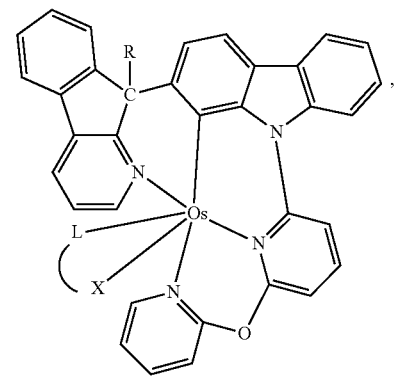
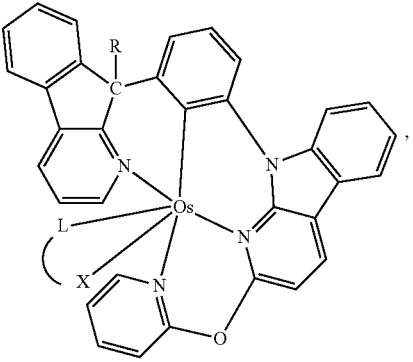

-continued

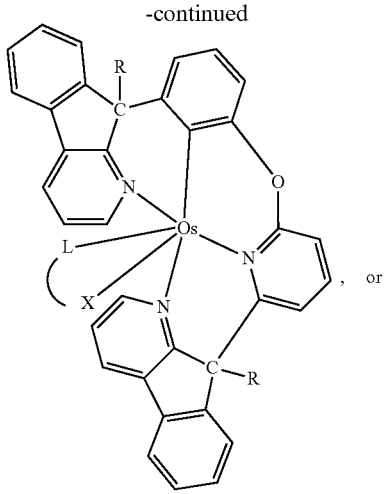

, or

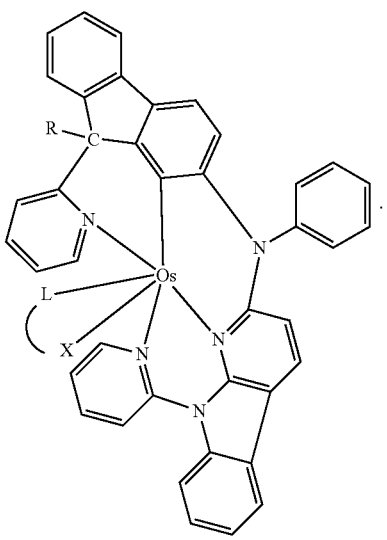

wherein R is hydrogen. alkyl, alkenyl, alkynyl, aryl, cycloalkyl, cycloalkenyl, heterocyclyl, deuterium, halogen, hydroxyl, thiol, nitro, cyano, amino, a mono- or di-alkylamino, a mono- or diaryl amino, alkoxy, aryloxy, haloalkyl, ester, nitrile, isonitrile, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrazino, or substituted silyl,
wherein

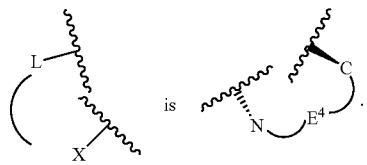

In one aspect, disclosed herein is a compound having the structure:

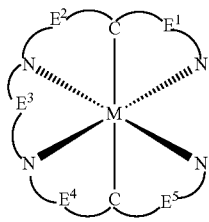

wherein M represent a metal cation with two positive charges, which include, but are not limited to, Ruthenium (II) ($Ru^{2+}$), Osmium (II) ($Os^{2+}$), wherein $E^1$, $E^2$, $E^3$, $E^4$, and $E^5$ independently represent a linking atom comprising O, $NR^2$, $CR^2R^3$, S, $BR^2$, $PR^2$, $P(O)R^2$, or $SiR^2R^3$, or a combination thereof, wherein each of $R^2$ and $R^3$ independently is hydrogen, alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is optionally linked to a C or N, thereby forming a cyclic structure; wherein each C independently represent a substituted or unsubstituted aromatic ring or heterocyclic group, wherein a carbon atom is coordinated to the metal, wherein each N independently represent a substituted or unsubstituted aromatic ring or heterocyclic group with a nitrogen atom coordinated to the metal.

In one aspect, the C groups can be phenyl. In another aspect, the N groups can be pyridine.

In one aspect, $E^1$, $E^2$, $E^3$, $E^4$, and $E^5$ can be oxygen.

In one aspect, M can be Iridium (III). In one aspect, M can be Rhodium (III). In another aspect, M can be Cobalt (III). In another aspect, M can be Aluminum (III). In another aspect, M can be gallium (III).

Compositions

As briefly described above, the present invention is directed to metal compounds. Also disclosed are compositions comprising one or more of the disclosed compounds.

Devices

As briefly described above, the present invention is directed to metal compounds. In one aspect, the compounds or compositions disclosed here can be used as host materials for OLED applications, such as full color displays. In another aspect, the compounds or compositions disclosed here can be used a emitter materials for OLED applications or displays.

In one aspect, the compounds can be the host material in the device. In another aspect, device can be a lighting device.

In one aspect, wherein the compound is used as a phosphorescent emitter in the device.

In one aspect, wherein the compound is used as a delayed fluorescent and phosphorescent emitter in the device.

The disclosed compounds of the present disclosure can be useful in a wide variety of applications, such as, for example, lighting devices. In a particular aspect, one or more of the compounds can be useful as host materials for an organic light emitting display device.

The disclosed compounds are useful in a variety of applications. As light emitting materials, the compounds can be useful in organic light emitting diodes (OLED)s, luminescent devices and displays, and other light emitting devices.

The energy profile of the compounds can be tuned by varying the structure of the ligand surrounding the metal center. For example, compounds having a ligand with electron withdrawing substituents will generally exhibit different properties, than compounds having a ligand with electron donating substituents. Generally, a chemical structural change affects the electronic structure of the compound, which thereby affects the electrical transport and transfer functions of the material. Thus, the compounds of the present invention can be tailored or tuned to a specific application that desires an energy or transport characteristic.

In another aspect, disclosed compound can provide improved efficiency and/or operational lifetimes in lighting devices, such as, for example, organic light emitting devices, as compared to conventional materials.

In other various aspects, the disclosed compounds can be useful as, for example, host materials for organic light emitting diodes, lighting applications, and combinations thereof.

In one aspect, the device is an electro-optical device. Electro-optical devices include, but are not limited to, photo-absorbing devices such as solar- and photo-sensitive devices, organic light emitting diodes (OLEDs), photo-emitting devices, or devices capable of both photo-absorption and emission and as markers for bio-applications. For example, the device can be an OLED.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art. Such devices are disclosed herein which comprise one or more of the compounds or composition disclosed herein.

The OLED can be produced by methods known to those skilled in the art. In general, the OLED is produced by successive vapor deposition of the individual layers onto a suitable substrate. Suitable substrates are, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof The disclosed compounds can be made using a variety of methods, including, but not limited to those recited in the examples provided herein. In other aspects, one of skill in the art, in possession of this disclosure, could readily determine an appropriate method for the preparation of an iridium compound as recited herein.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Synthesis of PtOOO

Scheme 1 shows the general scheme for the synthesis of the compounds disclosed herein.

Scheme 1

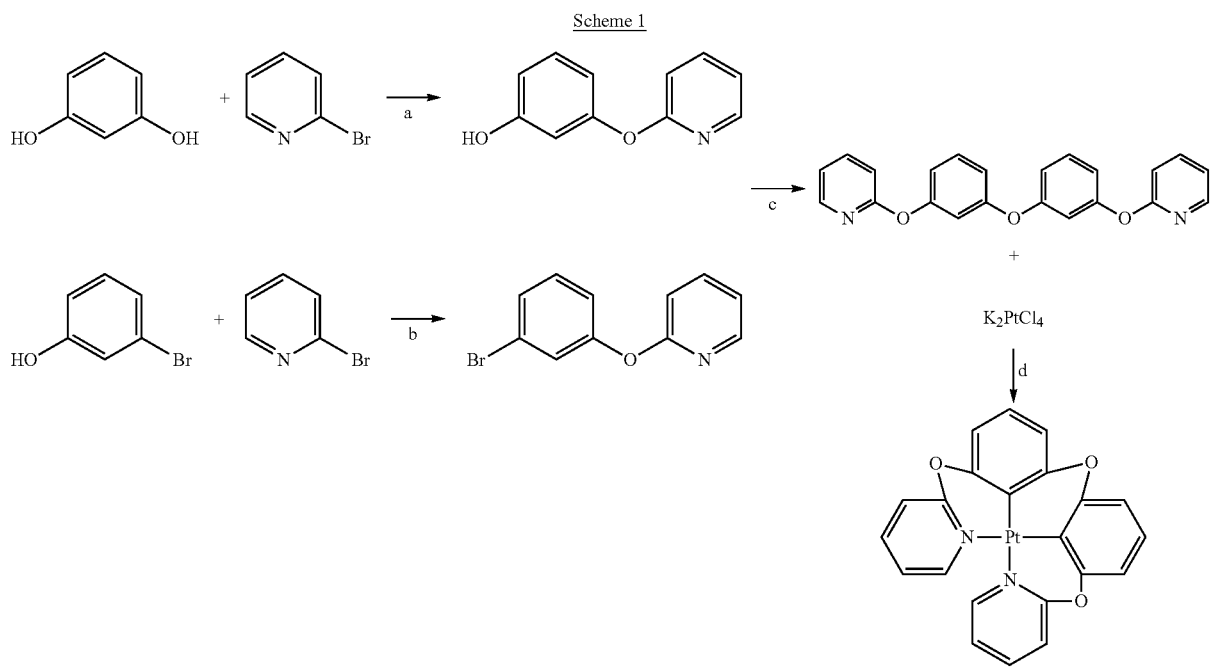

The reaction details for the synthesis is as follows:

(a) Resocinol (15 mmol), 2-bromopyridine (1 mmol), 1-methylimidazole (0.5 mmol), copper(I) iodide (0.1 mmol), potassium carbonate (2 mmol), dimethylformamide (15 mL). Sealed, degassed tube stirred at 130° C., 3 days. 3-(pyridin-2-yloxy)phenol produced in 40% yield.

(b) 3-bromophenol (1 mmol), 2-bromopyridine (2 mmol), 1-methylimidazole (0.5 mmol), copper(I) iodide (0.1 mmol), potassium carbonate (2 mmol), dimethylformamide (15 mL). Sealed, degassed tube stirred at 130° C., 3 days. 2-(3-bromophenoxyl)pyridine produced in 50% yield.

(c) 3-(pyridin-2-yloxy)phenol (1 mmol), 2-(3-bromophenoxyl)pyridine (1 mmol), 1-methylimidazole (0.5 mmol), copper(I) iodide (0.1 mmol), potassium carbonate (2 mmol), dimethylformamide (15 mL). Sealed, degassed tube stirred at 130° C., 3 days. 2,2'-(3,3'-oxybis(3,1-phenylene)bis(oxy))dipyridine produced in 50% yield.

(d) 2,2'-(3,3'-oxybis(3,1-phenylene)bis(oxy))dipyridine (1 mmol), potassium tetrachloroplatinate (1 mmol), and nBu4NBr (0.1 mmol) were charged into a 100 ml three necked flask, then 60 ml acetic acid was added. The mixture was degassed with Nitrogen and stirred at ambient temperature for 12 hours. The mixture was heated in an oil bath at a temperature of 110° C. for another 36 hours. 100 ml of water was added after the mixture was cooled down to room temperature. The precipitate was collected through filtration, washed with water for three times then dried in air and purified through column chromatography on silica gel using dichloromethane as eluent to obtain a crude product which was further purified by recrystallization in dichloromethane and ether at refrigerator to get the desired platinum compound PtOOO as a yellow solid in 82% yield. (DMSO-d6, 400 MHz): δ 6.82 (m, 4H), 7.02 (t, 2H), 7.24 (dd, 2H), 7.47 (d, 2H), 8.12 (dd, 2H), 8.34 (d, 2H)

Figure 2:
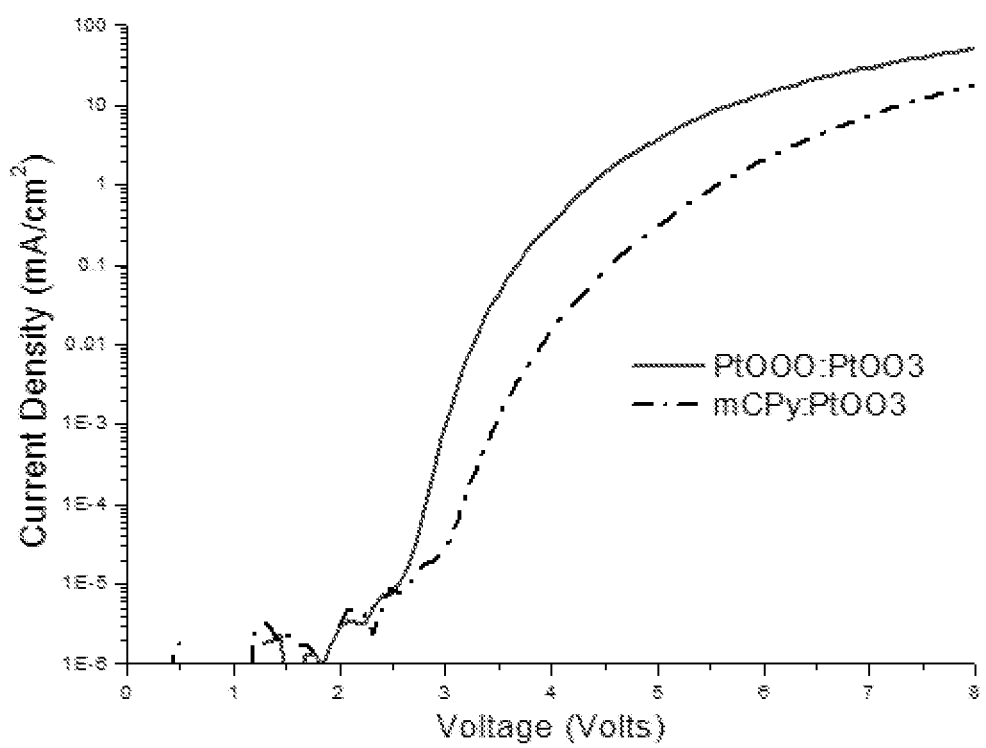
FIG. 2 shows the I-V curve of a device with PtOOO have the structure ITO/HATCN (10 nm)/NPD (40 nm)/TAPC (10 nm)/6% PtOO3: Host/DPPS (10 nm)/BmPyPB (40 nm)/LiF/Al.
Figure 3:
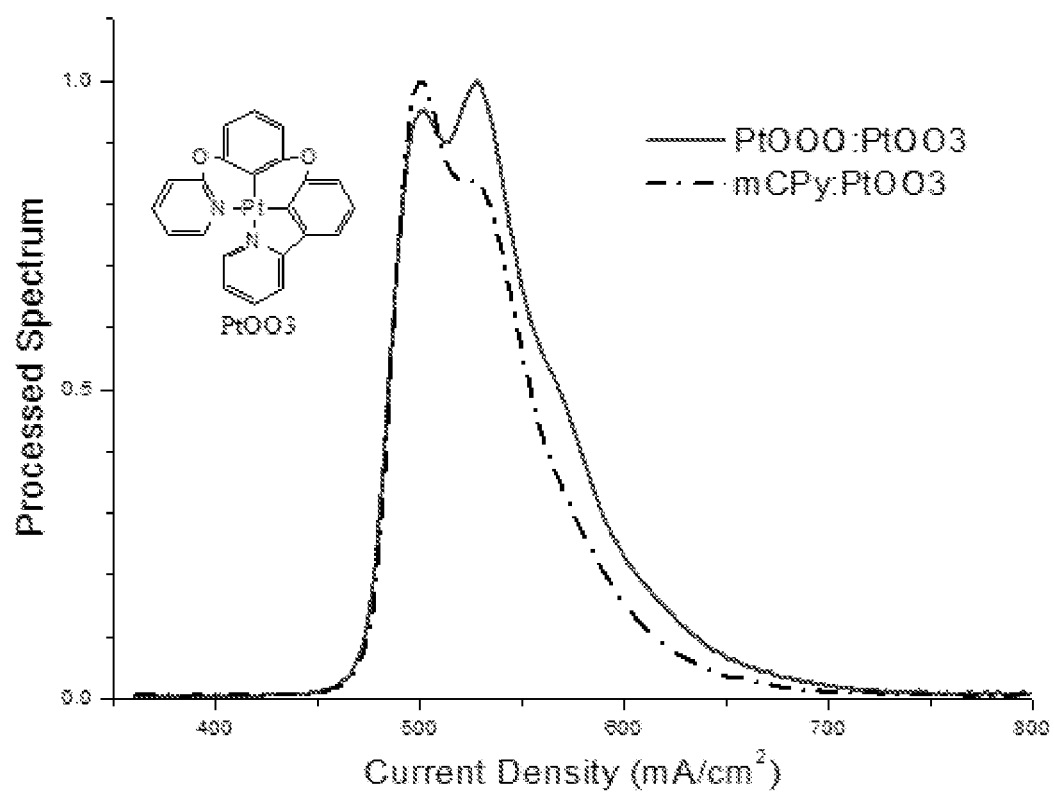
FIG. 3 shows the EL spectrum of devices using mCPy (dashed line) and PtOOO (solid line) as host materials.
Figure 4:
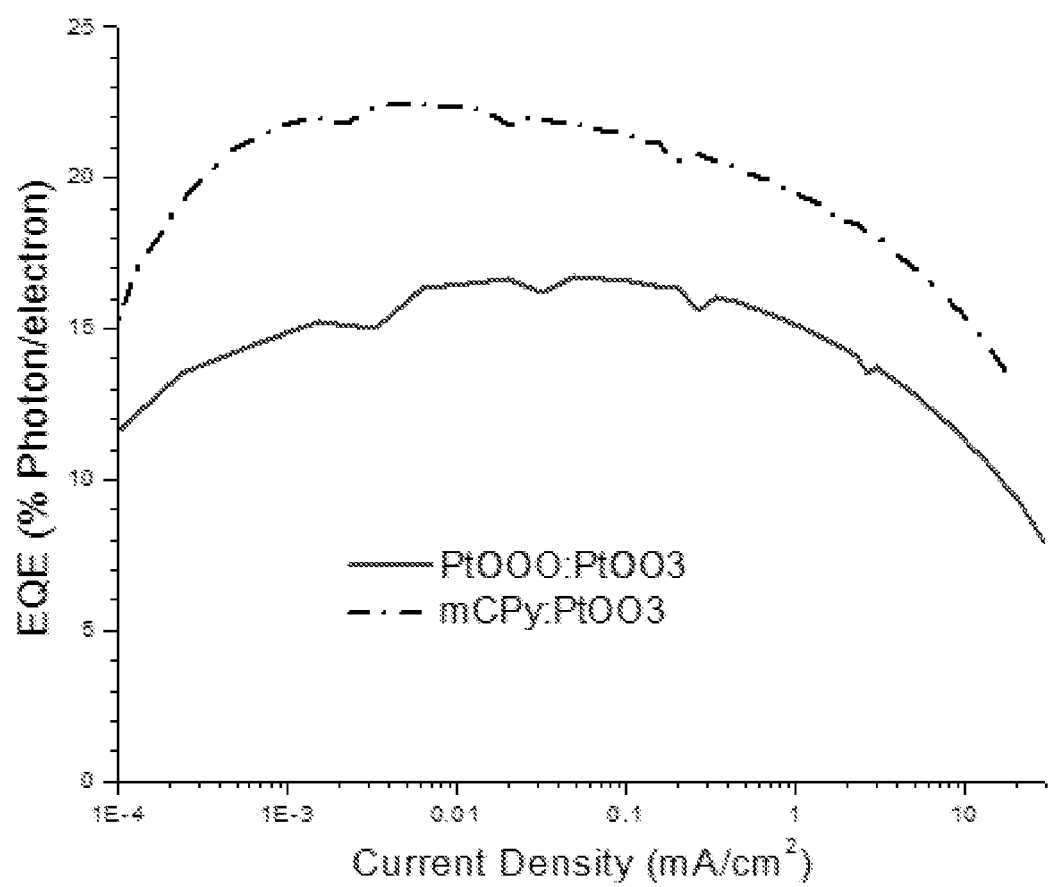
FIG. 4 shows the EQE of devices using mCPy (dashed line) and PtOOO (solid line) as host materials.
Figure 5:
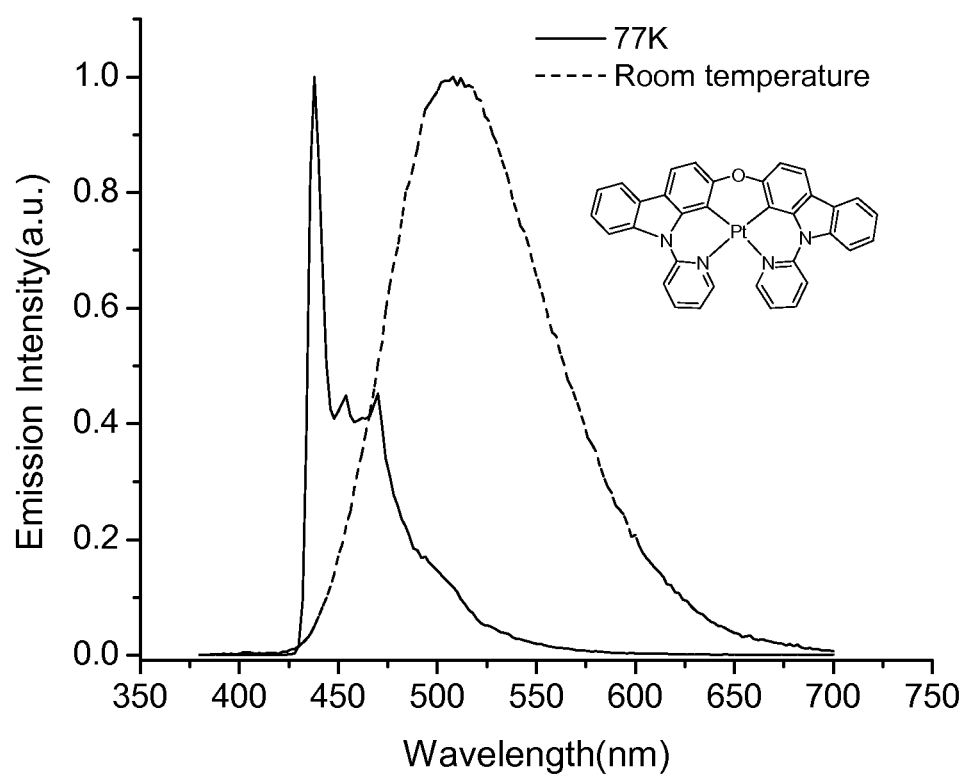
FIG. 5 shows the emission spectra of PtNON in dichloromethane at room temperature (solid line) and in 2-methyl THF at 77 K (dashed line).
Figure 6A:
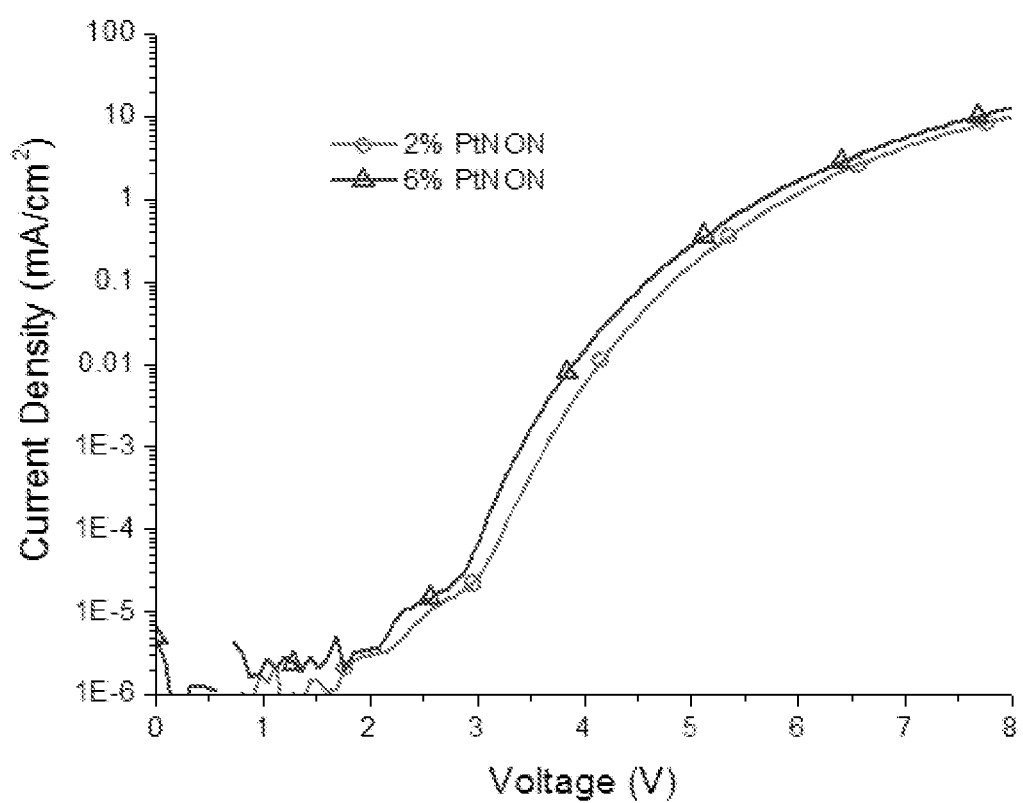
FIGS. 6A-6C show plots of (6A) current density vs. voltage, (6B) external quantum efficiency vs. brightness and (6C) EL spectra for the devices of ITO/HATCN (10 nm)/NPD (40 nm)/TAPC (10 nm)/x % PtNON:26mCPy (25 nm)/DPPS (10 nm)/BmPyPB (40 nm)/LiF/Al.
Figure 6B:
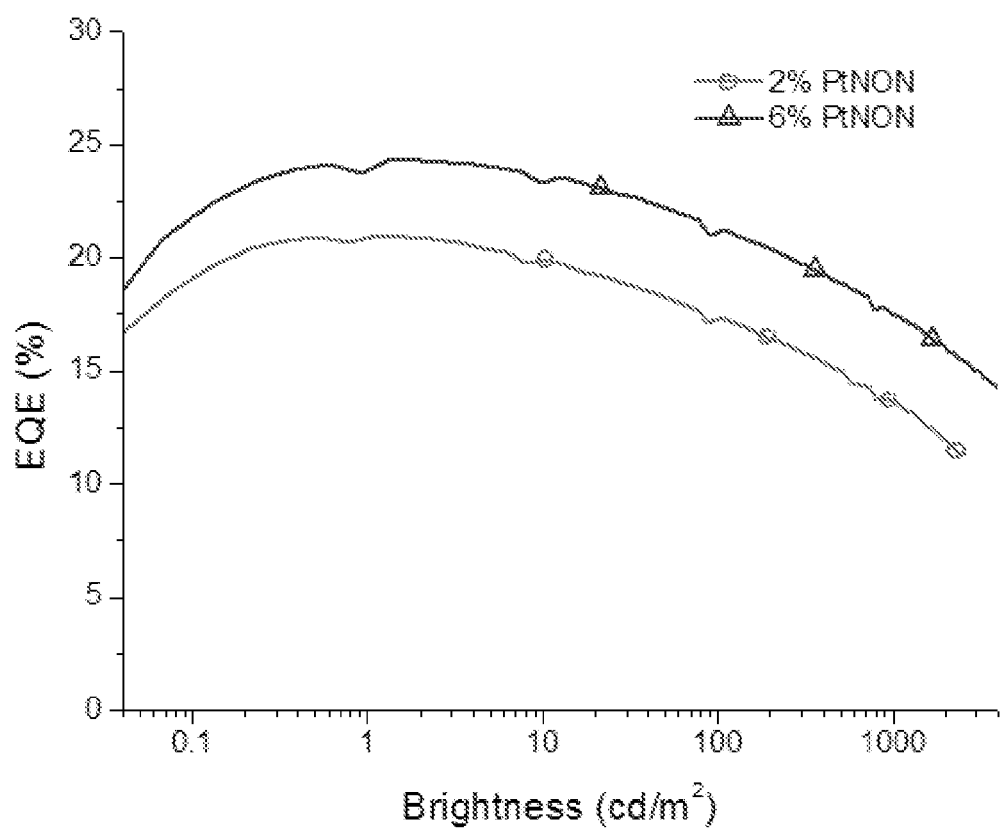
Figure 6C:
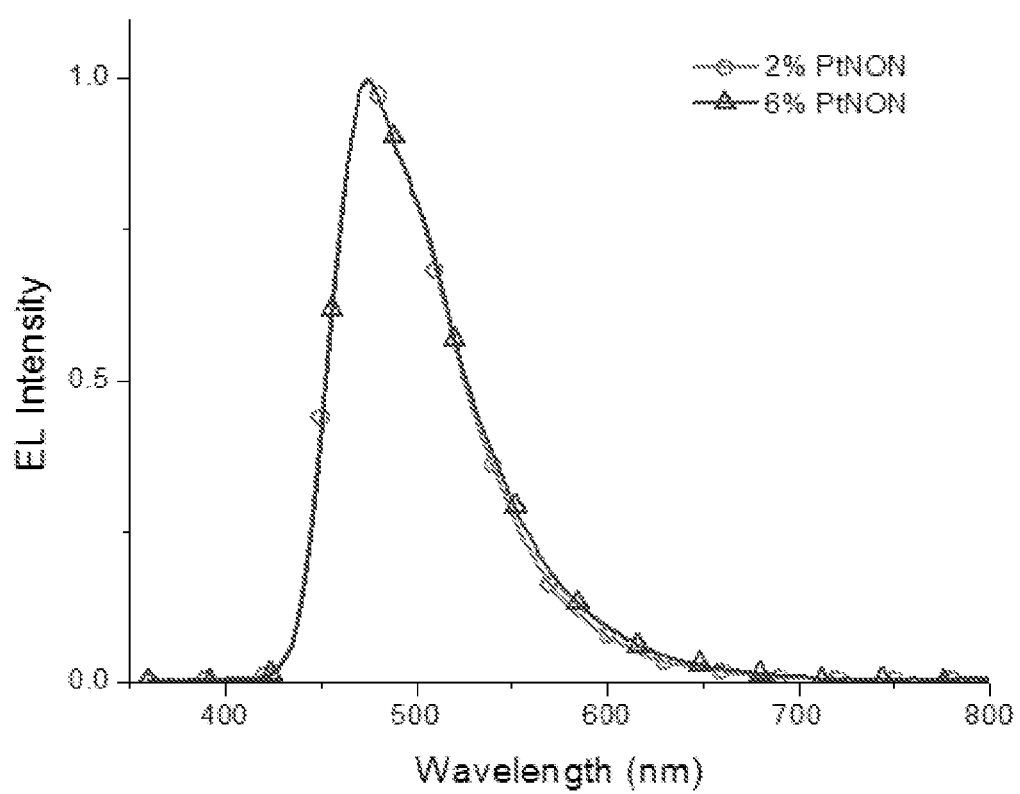
Figure 7:
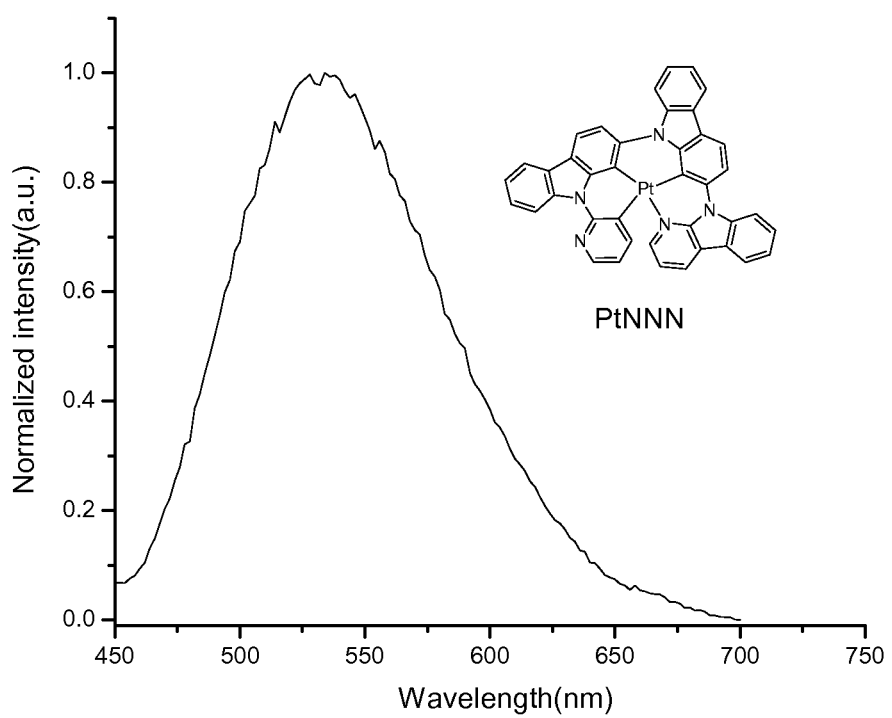
FIG. 7 shows the emission spectra of PtNNN in dichloromethane at room temperature.
Figure 8:
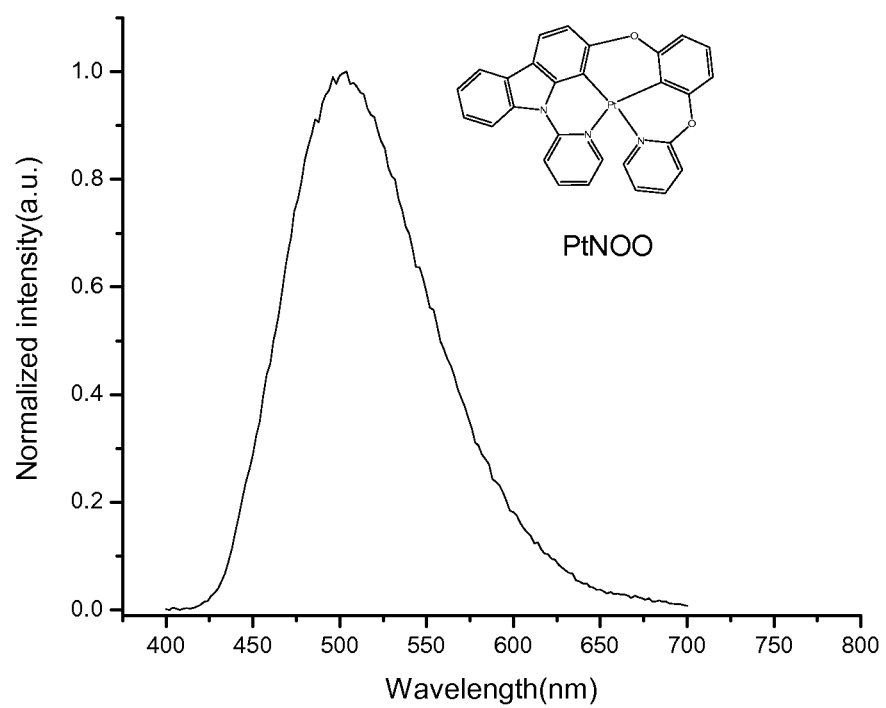
FIG. 8 shows the emission spectra of PtNOO in dichloromethane at room temperature.
Figure 9:
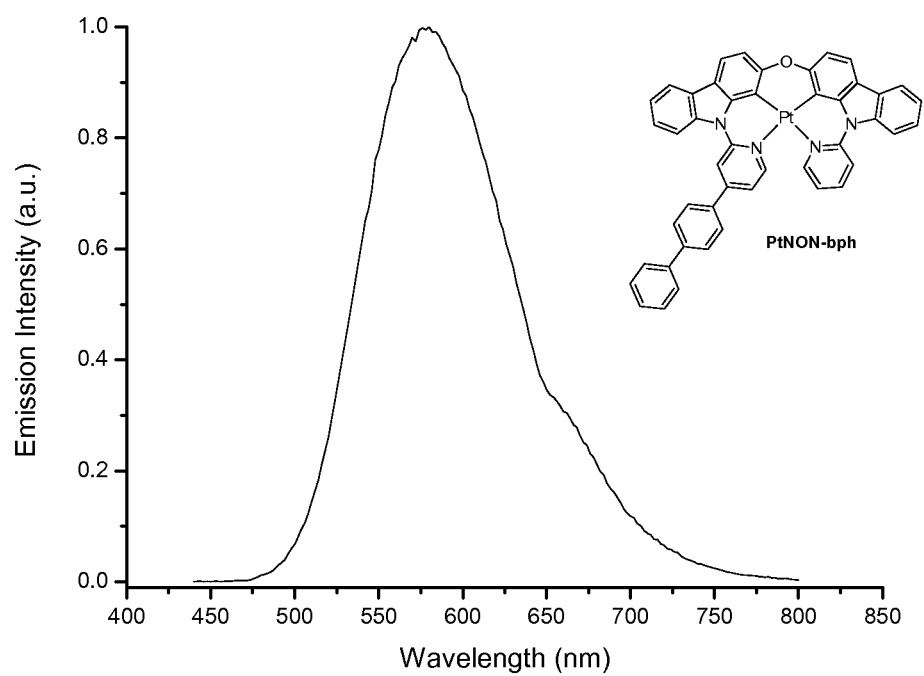
FIG. 9 shows the emission spectra of PtNON-bph in dichloromethane at room temperature.
Figure 10:
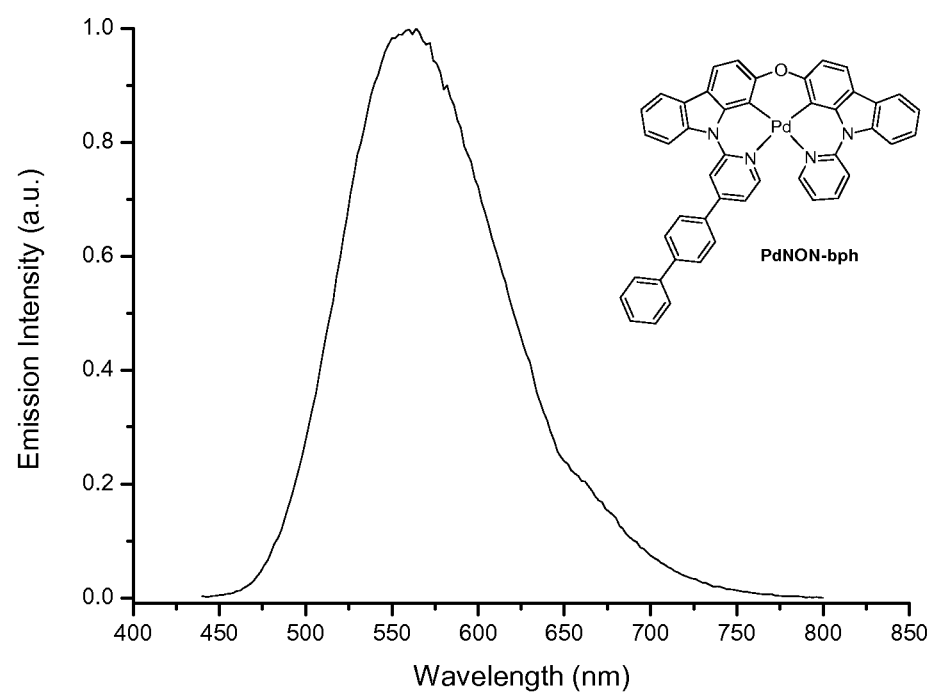
FIG. 10 shows the emission spectra of PdNON-bph in dichloromethane at room temperature.
Figure 11:
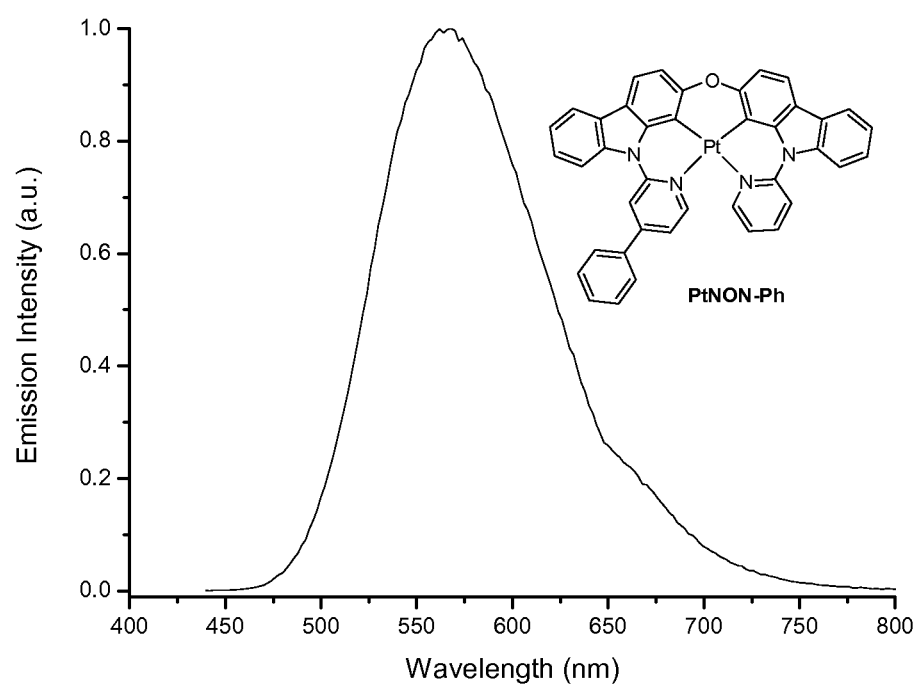
FIG. 11 shows the emission spectra of PtNON-ph in dichloromethane at room temperature.
Figure 12:
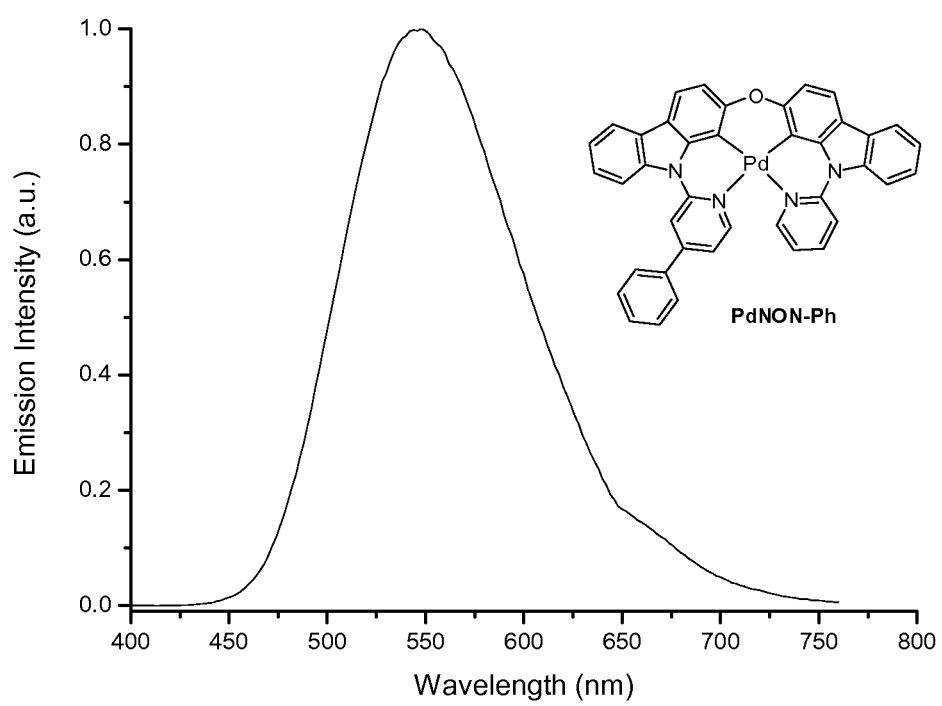
FIG. 12 shows the emission spectra of PdNON-ph in dichloromethane at room temperature.
Figure 13:
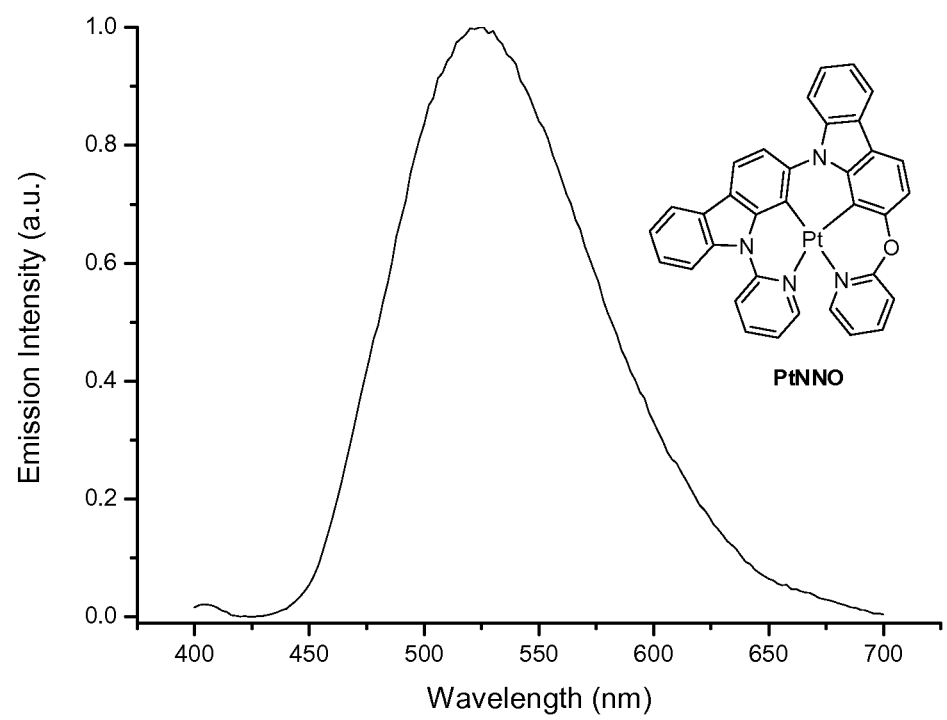
FIG. 13 shows the emission spectra of PtNNO in dichloromethane at room temperature.

PtOOO was tested as a host material in a device having the following structure: ITO/HATCN (10 nm)/NPD (40 nm)/TAPC (10 nm)/6% PtOO3: Host/DPPS (10 nm)/BmPyPB (40 nm)/LiF/Al. The I-V curve for this device compared to a device using mCPy as a host material is shown in FIG. 2. The EL spectrum this device compared to a device using mCPy as a host material is shown in FIG. 3. The EQE for this device compared to a device using mCPy as a host material is shown in FIG. 4.

Example 2

Synthesis of PdOOO

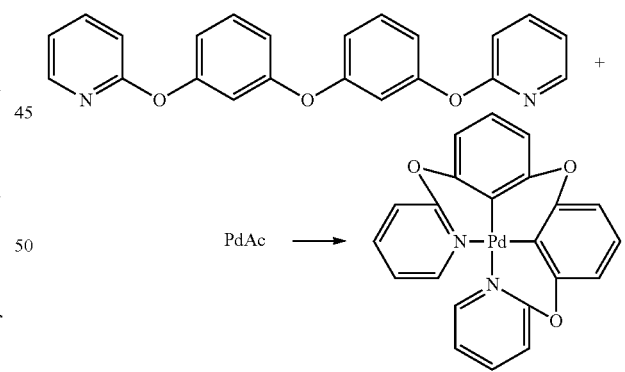

2,2'-(3,3'-oxybis(3,1-phenylene)bis(oxy))dipyridine (1 mmol), Palladium(II) acetate (1 mmol), and nBu4NBr (0.1 mmol) were charged into a 100 ml three necked flask, then 30 ml acetic acid was added. The mixture was degassed with Nitrogen and stirred at ambient temperature for 12 hours. The mixture was heated in an oil bath at a temperature of 110° C. for another 36 hours. 100 ml of water was added after the mixture was cooled down to room temperature. The precipitate was collected through filtration, washed with water for three times then dried in air and purified through column chromatography on silica gel using dichloromethane as eluent to obtain a crude product which was further purified by recrystallization in dichloromethane and ether at refrigerator to get the desired platinum compound PdOOO as a white solid in 80% yield. (DMSO-d6, 400 MHz): δ 6.83 (d, 2H), δ 6.88 (d, 2H), 7.07 (t, 2H), 7.31 (dd, 2H), 7.44 (d, 2H), 8.08 (dd, 2H), 8.42 (d, 2H).

Example 3

Synthesis of PtNON

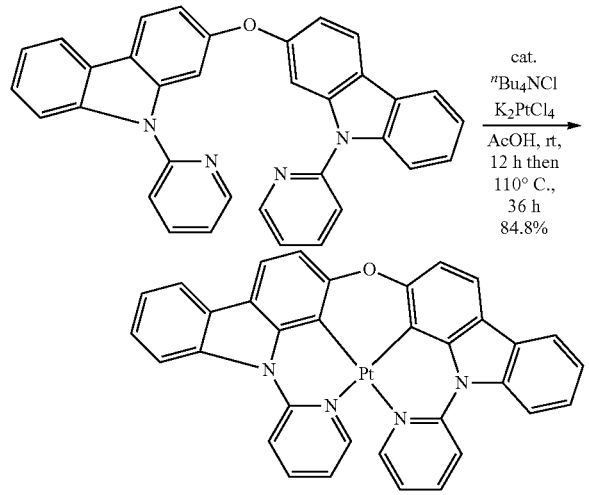

9-(pyridin-2-yl)-2-(9-(pyridin-2-yl)-9H-carbazol-2-yloxy)-9H-carbazole (240 mg, 0.48 mmol), K₂PtCl₄ (208 mg, 0.50 mmol), and nBu4NBr (15.4 mg, 0.048 mmol) were charged into a 100 ml three necked flask, then 30 ml acetic acid was added. The mixture was degassed with Nitrogen and stirred at ambient temperature for 12 hours. The mixture was heated in an oil bath at a temperature of 110° C. for another 36 hours. 100 ml of water was added after the mixture was cooled down to room temperature. The precipitate was collected through filtration, washed with water for three times then dried in air and purified through column chromatography on silica gel using dichloromethane as eluent to obtain a crude product which was further purified by recrystallization in dichloromethane and ether at refrigerator to get the desired platinum compound PtNON as a bright yellow solid 280 mg in 84.8% yield. 1H NMR (DMSO-d6, 400 MHz): δ 7.16 (d, 2H), 7.25-7.30 (m, 2H), 7.39 (t, 2H), 7.46 (t, 2H), 7.89 (d, 2H), 8.05 (d, 2H), 8.13-8.18 (m, 6H), 9.0 (d, 2H).

Example 4

Synthesis of PtNNN 9-(9-(9-(pyridin-2-yl)-9H-carbazol-2-yl)-9H-carbazol-2-yl)-9H-pyrido[2,3-b]indole (288 mg, 0.50 mmol), K₂PtCl₄ (228 mg, 0.55 mmol), and nBu₄NBr (16.1 mg, 0.05 mmol) were charged into a 100 ml three necked flask, then 30 ml acetic acid was added. The mixture was degassed with Nitrogen and stirred at ambient temperature for 12 hours. The mixture was heated in an oil bath at a temperature of 110° C. for another 36 hours. 100 ml of water was added after the mixture was cooled down to room temperature. The precipitate was collected through filtration, washed with water for three times then dried in air and purified through column chromatography on silica gel using dichloromethane as eluent to obtain a crude product which was further purified by recrystallization in dichloromethane and ether at refrigerator to get the desired platinum compound PtNNN as a bright yellow solid 100 mg in 26% yield. 1H NMR (DMSO-d6, 400 MHz): 9.17 (m, 1H), 9.04 (m, 1H), 8.78 (m, 1H), 8.43 (d, J=7.6 Hz 1H), 8.25-8.30 (m, 2H), 8.04-8.19 (m, 6H), 7.82-7.88 (m, 3H), 7.64 (M, 1H), 7.36-7.55 (m, 6H), 7.31 (dd, J=9.6 Hz, J=4.8 Hz, 1H).

Example 5

Synthesis of PtNOO 9-(pyridin-2-yl)-2-(3-(pyridin-2-yloxy)phenoxy)-9H-carbazole (215 mg, 0.50 mmol), K₂PtCl₄ (228 mg, 0.55 mmol), and nBu₄NBr (16.1 mg, 0.05 mmol) were charged into a 100 ml three necked flask, then 30 ml acetic acid was added. The mixture was degassed with Nitrogen and stirred at ambient temperature for 12 hours. The mixture was heated in an oil bath at a temperature of 110° C. for another 36 hours. 100 ml of water was added after the mixture was cooled down to room temperature. The precipitate was collected through filtration, washed with water for three times then dried in air and purified through column chromatography on silica gel using dichloromethane as eluent to obtain a crude product which was further purified by recrystallization in dichloromethane and ether at refrigerator to get the desired platinum compound PtNOO as a bright yellow solid 72 mg in 23% yield. 1H NMR (DMSO-d6, 400 MHz): 8.53-8.61 (m, 2H), 8.10-8.19 (m, 4H), 8.01 (d, J=8.4, 1H), 7.87 (d, J=8.4, 1H), 7.51 (d, J=8.4, 1H), 7.44 (m, 1H), 7.37 (dd, J=7.6 Hz, J=6.8 Hz, 1H), 7.28 (dd, J=6.0 Hz, J=6.8 Hz 1H), 7.21 (m, 1H), 7.05-7.10 (m, 2H), 6.87 (dd, J=7.2 Hz, J=7.6 Hz 2H).

Example 6

Synthesis of PtNON-bph

To a solution of NON-bph (52 mg) in HOAc (8 mL) were added K₂PtCl₄ (35 mg) and n-Bu₄NBr (3 mg). The mixture was heated to reflux for 3 days. The reaction mixture was cooled to rt, filtered through a pad of silica gel, and concentrated. Purification by column chromatography (hexanes: DCM=1:1 to 1:2) gave PtNON-bPh (49 mg, yield: 72%). ¹H NMR (400 MHz, DMSO-d₆) δ 9.13 (d, J=5.5 Hz, 1H), 9.07 (d, J=6.7 Hz, 1H), 8.38 (d, J=1.6 Hz, 1H), 8.26-8.17 (m, 5H), 8.12 (d, J=8.1 Hz, 1H), 8.01 (d, J=8.6 Hz, 2H), 7.96 (d, J=8.3 Hz, 1H), 7.94 (d, J=8.2 Hz, 1H), 7.87 (d, J=8.1 Hz, 2H), 7.79-7.73 (m, 2H), 7.69 (dd, J=6.3, 1.6 Hz, 1H), 7.58-7.39 (m, 7H), 7.35 (td, J=5.9, 2.8 Hz, 1H), 7.21 (dd, J=8.2, 2.7 Hz, 2H).

Example 7

Synthesis of PdNON-bph

To a solution of NON-bPh (39 mg) in HOAc (6 mL) were added Pd(OAc)₂ (14 mg) and n-Bu₄NBr (2 mg). The mixture was heated to reflux for 2 days. The reaction mixture was cooled to rt, filtered through a pad of silica gel, and concentrated. Purification by column chromatography (hexanes: DCM=1:1 to 1:2) gave PdNON-bPh (32 mg, yield: 70%). ¹H NMR (400 MHz, DMSO-d₆) δ 9.00 (d, J=5.9 Hz, 1H), 8.94 (d, J=6.5 Hz, 1H), 8.33 (d, J=1.5 Hz, 1H), 8.24-8.14 (m, 5H), 8.10 (d, J=8.2 Hz, 1H), 8.03-7.97 (m, 4H), 7.87 (d, J=8.2 Hz, 2H), 7.79-7.71 (m, 3H), 7.57-7.36 (m, 8H), 7.23 (dd, J=8.2, 2.7 Hz, 2H).

Example 8

Synthesis of PtNON-ph

To a solution of NON-Ph (65 mg) in HOAc (5 mL) were added $K_2PtCl_4$ (44 mg) and n-$Bu_4NBr$ (3 mg). The mixture was heated to reflux for 2 days. The reaction mixture was cooled to rt, filtered through a pad of silica gel, and concentrated. Purification by column chromatography (hexanes:DCM=1:1 to 1:2) gave PtNON-Ph (65 mg, yield: 84%).

Example 9

Synthesis of PdNON-ph

To a solution of NON-Ph (58 mg) in HOAc (5 mL) were added $Pd(OAc)_2$ (24 mg) and n-$Bu_4NBr$ (3 mg). The mixture was heated to reflux for 2 days. The reaction mixture was cooled to room temperature, filtered through a pad of silica gel, and concentrated. Purification by column chromatography (hexanes:DCM=1:1 to 1:2) gave PdNON-Ph (50 mg, yield: 73%).

Example 10

Synthesis of PdNNO

To a solution of NNO (75 mg) in HOAc (10 mL) were added $K_2PtCl_4$ (65 mg) and n-$Bu_4NBr$ (5 mg). The mixture was heated to reflux for 2 days. The reaction mixture was cooled to room temperature, filtered through a pad of silica gel, and concentrated. Purification by column chromatography (hexanes:DCM=1:1 to 1:2) gave PtNON-Ph (42 mg, yield: 40%).

What is claimed is:

1. A compound having the structure:

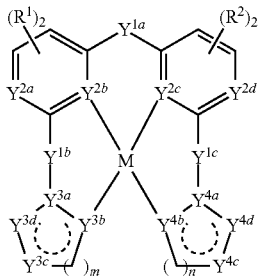

wherein M comprises Pt, Pd, Ir, Rh, or Au;
wherein each of $R^1$ and $R^2$ independently are hydrogen, substituted or unsubstituted alkyl, alkenyl, alkynyl, aryl, heteroaryl, cycloalkane, cycloalkane, heterocyclyl, amino, nitro hydroxyl, halogen, thio, alkoxy, haloalkyl, arylalkane, or arylalkene;
wherein each $Y^{1a}$ independently is O, $NR^2$, or S, or a combination thereof, wherein each $R^2$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene;
wherein each of $Y^{1b}$ and $Y^{1c}$ independently is O or S, or a combination thereof;
wherein each of $Y^{2a}$, $Y^{2b}$, $Y^{2c}$, and $Y^{2d}$ independently is $CR^{6b}$, wherein each $R^{6b}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene;
each of $Y^{3a}$, $Y^{3c}$, $Y^{3d}$, $Y^{4a}$, $Y^{4c}$ and $Y^{4d}$ independently is $CR^{6b}$, wherein each $R^{6b}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene;
wherein each of $Y^{3b}$ and $Y^{4b}$ are N or $NR^{6a}$, wherein each $R^{6a}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene;
wherein each of m and n independently are 2;
wherein each of independently is partial or full unsaturation of the ring with which it is associated.

2. The compound of claim 1,
wherein m is 2,
wherein n is 2,
wherein $Y^{2b}$ and $Y^{2c}$ is CH,
wherein $Y^{3b}$ and $Y^{4b}$ is N,
and
wherein M is Pt or Pd.

3. The compound of claim 2,
wherein at least of one of $Y^{2a}$, $Y^{2d}$, $Y^{3d}$ and $Y^{4d}$ is C, and
wherein M is Pt or Pd.

4. A compound having the structure:

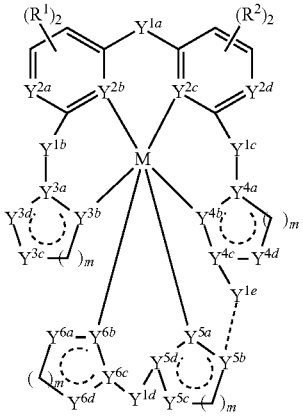

wherein M comprises Ir, Rh, Pt, Os, or Ru;
wherein each of $R^1$ and $R^2$ independently are hydrogen, substituted or unsubstituted alkyl, alkenyl, alkynyl, aryl, heteroaryl, cycloalkane, cycloalkane, heterocyclyl, amino, nitro hydroxyl, halogen, thio, alkoxy, haloalkyl, arylalkane, or arylalkene;

wherein each $Y^{1a}$ independently is O, $NR^2$, or S, wherein $Y^{1d}$, and $Y^{1e}$ independently is, $NR^2$, $CR^2R^3$, S, $AsR^2$, $BR^2$, $PR^2$, $P(O)R^2$, or $SiR^2R^3$, or a combination thereof, wherein each of $R^2$ and $R^3$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, arylalkene, or $R^2$ and $R^3$ together form C=O, wherein each of $R^2$ and $R^3$ independently is linked to an adjacent ring structure, thereby forming a cyclic structure;

wherein each of $Y^{1b}$ and $Y^{1c}$ independently is O or S, or a combination thereof;

wherein each of $Y^{2a}$, $Y^{2b}$, $Y^{2c}$, and $Y^{2d}$ independently is $CR^{6b}$, wherein each $R^{6b}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene;

wherein each of $Y^{3a}$, $Y^{3c}$, $Y^{3d}$, $Y^{4a}$, $Y^{4c}$, and $Y^{4d}$ independently is $CR^{6b}$, wherein each $R^{6b}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene;

wherein each of $Y^{3b}$ and $Y^{4b}$ are N or $NR^{6a}$, wherein each $R^{6a}$ independently is hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene;

wherein in each of each of $Y^{5a}$, $Y^{5b}$, $Y^{5c}$, $Y^{5d}$, $Y^{6a}$, $Y^{6b}$, $Y^{6c}$, and $Y^{6d}$ independently is N, O, S, $NR^{6a}$, or $CR^{6b}$; wherein each of $R^{6a}$ and $R^{6b}$ independently hydrogen, substituted or unsubstituted alkyl, alkenyl, alkynyl, aryl, heteroaryl, cycloalkane, cycloalkane, heterocyclyl, amino, hydroxyl, halogen, thio, alkoxy, haloalkyl, arylalkane, or arylalkene;

wherein each m independently is 2;
wherein each of

independently is partial or full unsaturation of the ring with which it is associated.

5. The compound of claim 4,
wherein m is 2,
wherein $Y^{2b}$ and $Y^{2c}$ is CH,
wherein $Y^{3b}$ and $Y^{4b}$ is N,
and
wherein M is Ir or Rh.

6. The compound of claim 5,
wherein at least of one of $Y^{2a}$, $Y^{2d}$, $Y^{3d}$ and $Y^{4d}$ is C, and
wherein M is Ir or Rh.

7. A device comprising the compound of claim 1.

8. The device of claim 7, wherein the device is an organic light emitting diode.

9. The device of claim 7, wherein the device comprises a full color display.

10. The device of claim 7, wherein the one or more compounds is used as a host material.

11. The device of claim 7, wherein the device can be a lighting device.

12. A device comprising the compound of claim 1, wherein the compound is used as a phosphorescent emitter in the device.

13. A device comprising the compound of claim 1, wherein the compound is used as a delayed fluorescent and phosphorescent emitter in the device.

14. A composition comprising the compound of claim 1.

* * * * *